United States Patent
Wu et al.

(10) Patent No.: US 11,530,268 B2
(45) Date of Patent: Dec. 20, 2022

(54) TRISPECIFIC ANTI-CD38, ANTI-CD28, AND ANTI-CD3 BINDING PROTEINS AND METHODS OF USE FOR TREATING VIRAL INFECTION

(71) Applicant: Sanofi, Paris (FR)

(72) Inventors: Lan Wu, Cambridge, MA (US); Ling Xu, Cambridge, MA (US); Edward Seung, Cambridge, MA (US); Ronnie Wei, Needham, MA (US); Gary Nabel, Cambridge, MA (US); Zhi-Yong Yang, Cambridge, MA (US); Tarik Dabdoubi, Paris (FR); Béatrice Cameron, Paris (FR); Cendrine Lemoine, Paris (FR); Catherine Prades, Paris (FR)

(73) Assignee: Sanofi, Paris (FR)

(*) Notice: Subject to any disclaimer, the term of this patent is extended or adjusted under 35 U.S.C. 154(b) by 6 days.

(21) Appl. No.: 16/596,474

(22) Filed: Oct. 8, 2019

(65) Prior Publication Data

US 2020/0140552 A1 May 7, 2020

Related U.S. Application Data

(60) Provisional application No. 62/831,572, filed on Apr. 9, 2019, provisional application No. 62/831,608, filed on Apr. 9, 2019.

(30) Foreign Application Priority Data

Sep. 11, 2019 (EP) .................................. 19306097

(51) Int. Cl.
| | |
|---|---|
| *C07K 16/28* | (2006.01) |
| *A61P 31/16* | (2006.01) |
| *A61P 31/18* | (2006.01) |
| *A61P 31/22* | (2006.01) |
| *C12N 5/0783* | (2010.01) |

(52) U.S. Cl.
CPC .......... *C07K 16/2818* (2013.01); *A61P 31/16* (2018.01); *A61P 31/18* (2018.01); *A61P 31/22* (2018.01); *C07K 16/2809* (2013.01); *C07K 16/2896* (2013.01); *C12N 5/0636* (2013.01); *C07K 2317/31* (2013.01); *C07K 2317/33* (2013.01); *C07K 2317/51* (2013.01); *C07K 2317/515* (2013.01); *C07K 2317/522* (2013.01); *C07K 2317/524* (2013.01); *C07K 2317/526* (2013.01); *C07K 2317/53* (2013.01); *C07K 2317/73* (2013.01); *C07K 2317/92* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 9,181,349 B2 | 11/2015 | Baurin | |
| 9,221,917 B2 | 12/2015 | Baurin | |
| 10,882,922 B2 | 1/2021 | Yang | |
| 11,186,649 B2 | 11/2021 | Wu et al. | |
| 2010/0226923 A1 | 9/2010 | Rao | |
| 2012/0076782 A1 | 3/2012 | Tesar | |
| 2012/0201827 A1 | 8/2012 | Elias | |
| 2012/0251541 A1 | 10/2012 | Baurin | |
| 2013/0345404 A1 | 12/2013 | Baurin | |
| 2014/0213772 A1 | 7/2014 | Ghayur | |
| 2014/0322217 A1 | 10/2014 | Moore | |
| 2016/0200811 A1 | 7/2016 | Baurin | |
| 2017/0320967 A1 | 11/2017 | Yang | |
| 2019/0054182 A1 | 2/2019 | Yang | |
| 2019/0106504 A1 | 4/2019 | Wu | |
| 2020/0054765 A1 | 2/2020 | Yang | |
| 2020/0399369 A1 | 12/2020 | Asokan | |
| 2021/0061925 A1 | 3/2021 | Yang et al. | |

FOREIGN PATENT DOCUMENTS

| | | |
|---|---|---|
| CN | 105837688 A | 8/2016 |
| EP | 0308936 A2 | 2/1989 |
| EP | 1378520 A1 | 1/2004 |
| EP | 1736484 A1 | 12/2006 |
| WO | WO199627011 A1 | 9/1996 |
| WO | WO199951642 A1 | 10/1999 |
| WO | WO2005000899 A2 | 1/2005 |
| WO | WO2005000899 A3 | 8/2005 |
| WO | WO2009149189 A2 | 12/2009 |
| WO | WO2009149189 A3 | 3/2010 |
| WO | WO2011038290 A2 | 3/2011 |
| WO | WO2011154453 A1 | 12/2011 |
| WO | WO2012092612 A1 | 7/2012 |
| WO | WO2012135345 A1 | 10/2012 |
| WO | WO2012154312 A1 | 11/2012 |

(Continued)

OTHER PUBLICATIONS

Mariuzza, R.A. et al. (Jun. 1987). "The Structural Basis of Antigen-Antibody Recognition," Annu. Rev. Biophys. Biophys. Chem. 16(1):139-159.

(Continued)

*Primary Examiner* — Nicole Kinsey White
(74) *Attorney, Agent, or Firm* — Morrison & Foerster LLP

(57) ABSTRACT

The disclosure provides methods of treating viral infection using trispecific binding proteins comprising four polypeptide chains that form three antigen binding sites that specifically bind a CD38 polypeptide (e.g., human and/or cynomolgus monkey CD38 polypeptides), a CD28 polypeptide, and a CD3 polypeptide.

34 Claims, 24 Drawing Sheets

Specification includes a Sequence Listing.

(56) References Cited

FOREIGN PATENT DOCUMENTS

| WO | WO2012158948 A1 | 11/2012 |
|---|---|---|
| WO | WO2013070776 A1 | 5/2013 |
| WO | WO2013086533 A1 | 6/2013 |
| WO | WO2013163427 A1 | 10/2013 |
| WO | WO2014089152 A1 | 6/2014 |
| WO | WO2014116846 A2 | 7/2014 |
| WO | WO2014144299 A2 | 9/2014 |
| WO | WO2014116846 A3 | 10/2014 |
| WO | WO2014144299 A3 | 12/2014 |
| WO | WO2015063339 A1 | 5/2015 |
| WO | WO2015149077 A1 | 10/2015 |
| WO | WO2016033690 A1 | 3/2016 |
| WO | 2016105450 A2 | 6/2016 |
| WO | WO2016116626 A1 | 7/2016 |
| WO | WO2016196740 A1 | 12/2016 |
| WO | WO2017074878 A1 | 5/2017 |
| WO | WO2017180913 A2 | 10/2017 |
| WO | WO2017180913 A3 | 2/2018 |
| WO | WO2018120842 A1 | 7/2018 |
| WO | WO2018151841 A1 | 8/2018 |
| WO | 2020076853 A1 | 4/2020 |

OTHER PUBLICATIONS

Alegre, M. et al. (Jun. 1994). "A Non-Activating "Humanized" Anti-CD3 Monoclonal Antibody Retains Immunosuppressive Properties In Vivo," Transplantation, 57(11):1537-1543.

Almeida, J. et al. (1999). "High-Sensitive Immunophenotyping and DNA Ploidy Studies for the Investigation of Minimal Residual Disease in Multiple Myeloma," British J of Haematol. 107:121-131.

Altschul, S.F. et al. (Sep. 1, 1997). "Gapped BLAST and PSI-BLAST: A New Generation of Protein Database Search Programs," Nucleic Acids Res. 25(17):3389-3402.

Atwell, S. et al. (1997). "Stable Heterodimers From Remodeling the Domain Interface of a Homodimer Using a Phage Display Library," J. Mol. Biol. 270 (1):26-35.

Brandsma, A.M. et al. (Oct. 1, 2017; e-pub. Aug. 16, 2017). "Single Nucleotide Polymorphisms of the High Affinity IgG Receptor FcγRI Reduce Immune Complex Binding and Downstream Effector Functions," The Journal of Immunology 199(7):2432-2439.

Chai, J.G. et al. (1997). "Immobilized Anti-CD3 mAb Induces Anergy in Murine Naive and Memory CD4+ T Cells," Int Immunol. 9(7):935-944.

Chen, H.W. et al. (Apr. 1, 2006). "Ex Vivo Expansion of Dendritic-Cell-Activated Antigenspecific CD41\+ T Cells With Anti-CD3/CD28, Interleukin-? and Interleukin-15: Potential for Adoptive T Cell Immunotherapy," Clinical Immunology 119(1):21-31.

Chothia, C. et al. (1989). "Conformations of Immunoglobulin Hypervariable Regions," Nature 342(6252): 877-883.

Chothia, C. et al. (Aug. 20, 1987). "Canonical Structures for the Hypervariable Regions of Immunoglobulins," J. Mol. Biol. 196(4):901-917.

Chu, S.Y et al. (Dec. 4, 2014). "Immunotherapy with Long-Lived Anti-CD38 × Anti-CD3 Bispecific Antibodies Stimulates Potent T Cell-Mediated Killing of Human Myeloma Cell Lines and CD38+ Cells in Monkeys: A Potential Therapy for Multiple Myeloma," Blood 124(21): 4727, 6 pages.

Colombian Opposition dated Mar. 15, 2019 for CO Application No. NC2018/0012107 filed on Nov. 9, 2018, twenty-one pages.

Deckert, J. et al. (2014; e-pub. Jul. 1, 2014). "SAR650984, a Novel Humanized CD38-Targeting Antibody, Demonstrates Potent Anti-Tumor Activity in Models of Multiple Myeloma and Other CD38+ Hematologic Malignancies," Clin. Cancer Res 20:4574-4583.

Digiammarino, E. et al. (Sep.-Oct. 2011, e-pub. Sep. 1, 2011). "Ligand Association Rates to the Inner-Variable-Domain of a Dual-Variable-Domain Immunoglobulin are Significantly Impacted by Linker Design," MAbs. 3(5):487-494.

Esensten, J.H. et al. (May 17, 2016). "CD28 Costimulation: From Mechanism to Therapy," Immunity 44:973-988.

Findlay, L. et al. (2010; e-pub. Nov. 4, 2009). "Improved In Vitro Methods to Predict the In Vivo Toxicity in Man of Therapeutic Monoclonal Antibodies Including TGN1412," J Immunol Methods 352:1-12.

Fournier, P. et al. (Jan. 2010). "Tumor Antigen-Dependent and Tumor Antigen-Independent Activation of Antitumor Activity in T Cells by a Bispecific Antibody-Modified Tumor Vaccine," Clinical & Developmental Immunology 2010(1):Article IDS 423781, 12 pages.

Garfall, A.L. et al. (Nov. 21, 2019). "Three is a Charm for anAntibody to Fight Cancer," Nature 575:450-451.

Gratama, J,W. et al. (Sep. 1, 2001). "Tetramer-Based Quantification of Cytomegalovirus (CMV)-Specific DD81 T Lymphocytes In T-Cell-Depleted Stem Cell Grafts and After Transplantation May Identify Patients at Risk for Progressive CMV Infection," Blood 98(5):1358-1364.

Haas, C. et al. (Mar. 31, 2005; e-pub. Nov. 25, 2004). "T-cell Triggering by CD3- and CD28-Binding Molecules Linked to a Human Virus-Modified Tumor Cell Vaccine," Vaccine 23(19):2439-2453.

Hartman, W.R. et al. (May 17, 2010). "CD38 Expression, Function, and Gene Resequencing in a Human Lymphoblastoid Cell Line-Based Model System," Leukemia and Lymphoma 51(7):1315-1325, 20 pages.

Hinton, P.R. et al. (Jan. 1, 2006). "An Engineered Human IgG1 Antibody With Longer Serum Half-Life," J. Immunol. 176(1):346-356.

Hitoshi, N. et al. (Dec. 15, 1991). "Efficient Selection for High-Expression Transfectants with a Novel Eukaryotic Vector," Gene 108(2):193-199.

Hui, E. et al. (Mar. 31, 2017). "T Cell Costimulatory Receptor CD28 is a Primary Target for PD-1-Mediated Inhibition," Science 355(6332):1428-1433, 13 pages.

International Preliminary Report on Patentability dated May 11, 2018 for PCT Application No. PCT/US2016/058540 filed on Oct. 24, 2016, seven pages.

International Preliminary Report on Patentability dated Oct. 25, 2018 for PCT Application No. PCT/US2017/027488, filed on Apr. 13, 2017, thirty one pages.

International Search Report and Written Opinion dated Jan. 2, 2018 for PCT Application No. PCT/US2017/027488, filed on Apr. 13, 2017, forty four pages.

International Search Report and Written Opinion of the International Searching Authority dated Mar. 10, 2017 for PCT Application No. PCT/US2016/058540 filed on Oct. 24, 2016, fifteen pages.

International Search Report dated Dec. 17, 2019, for PCT Application No. PCT/US2019/055232, filed on Oct. 8, 2019, seven pages.

International Search Report dated May 17, 2019, for PCT Application No. PCT/US2018/055084, filed on Oct. 9, 2018, twelve pages.

Invitation to Pay Additional Fees and, Where Applicable, Protest Fee dated Feb. 20, 2019, for PCT Application No. PCT/US2018/055084, filed on Oct. 9, 2018, twenty three pages.

Invitation to Pay Additional Fees and, Where Applicable, Protest Fee dated Oct. 16, 2017, for PCT Application No. PCT/US2017/027488, filed on Apr. 13, 2017, twenty eight pages.

Jakob, C.G. et al. (May 1, 2013, e-pub. Apr. 2, 2013). "Structure Reveals Function of the Dual Variable Domain Immunoglobulin (DVD-Ig™) Molecule," MAbs. 5(3)1358-363.

Kalim, M. et al. (2017; e-pub. Aug. 2, 2017). "Intracellular Trafficking of New Anticancer Therapeutics: Antibody-Drug Conjugates," Drug Des. Devel. Ther. 11:2265-2276.

Kilpatrick, K.E. et al. (Aug. 1997). "Rapid Development of Affinity Matured Monoclonal Antibodies Using RIMMS," Hybridoma 16(4):381-389.

Lefranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.

Li, T. et al. (Jun. 2, 2016). "Immuno-Targeting the Multifunctional CD38 Using Nanobody," Scientific Reports 6(1):27055, 11 pages.

Liu, Q. et al. (Sep. 2005). "Crystal Structure of Human CD38 Extracellular Domain," Structure 13(9):1331-1339.

(56) References Cited

OTHER PUBLICATIONS

MacCallum, R.M. et al. (1996). "Antibody-Antigen Interactions: Contact Analysis and Binding Site Topography," J. Mol. Biol. 262:732-745.

Masui, S. et al. (Mar. 1, 2005). "An Efficient System to Establish Multiple Embryonic Stem Cell Lines Carrying an Inducible Expression Unit," Nucleic Acids Res. 33(4):e43, pp. 1-8.

Mateo, G. et al. (May 15, 2005). "Genetic Abnormalities and Patterns of Antigenic Expression in Multiple Myeloma," Clin. Cancer Res. 11(10):3661-3667.

McDermott, S.P. et al. (Jul. 15, 2010, e-published as Apr. 19, 2010). "Comparison of Human Cord Blood Engraftment Between Immunocompromised Mouse Strains," Blood 116(2):193-200.

McKeage, K. (Feb. 2016). "Daratumumab: First Global Approval," Drugs. 76(2):275-281.

Merchant, A. M. et al. (Jul. 1998). "An Efficient Route to Human Bispecific IgG," Nature Biotechnology 16:677-681.

Moore, G. et al. (Dec. 5, 2015). "1798 Tuning T Cell Affinity Improves Efficacy and Safety of Anti-CD38 × Anti-CD3 Bispecific Antibodies in Monkeys—a Potential Therapy for Multiple Myeloma," American Society of Hematology, Poster Abstract presented at 57th Annual Meeting & Exposition, Orlando, FL, three pages.

Morphosys. (Nov. 25, 2010). "R&D Day 2010," 102 pages, (as cited in 299.41)—Rojkjaer, L. (Nov. 29, 2010). "Morphosys R&D 2010," URL:https://www.morphosys.de/sites/default/files/phoneconferences/downloads/101125mar_rd_nov_2010_ nyc_ final.pdf.

Nair, J.R. et al. (2011; e-pub. Jun. 29, 2011). "CD28 Expressed on Malignant Plasma Cells Induces a Prosurvival and Immunosuppressive Microenvironment," J Immunol. 187:1243-1253.

Padlan, E.A. et al. (Jan. 1995). "Identification of Specificity-Determining Residues in Antibodies," FASEB J. 9(1):133-139.

Parslow, A.C. et al. (2016). "Antibody-Drug Conjugates for Cancer Therapy," Biomedicines 4:14, pp. 1-17.

Penaranda, C.I. et al. (Aug. 15, 2011). "Anti-CD3 Therapy Promotes Tolerance by Selectively Depleting Pathogenic Cells While Preserving Regulatory T Cells," J Immunol. 187(4):2015-2022, 19 pages.

Peters, B. et al. (Mar. 2005; e-pub. Mar. 15, 2005). "The Immune Epitope Database and Analysis Resource: From Vision to Blueprint," PLos Biol. 3(3):e91, pp. 0379-0381.

Ridgway, J.B.B. et al. (1996). "Knobs-Into-Holes' Engineering of Antibody CH3 Domains for Heavy Chain Heterodimerization," Protein Engineering 9(7):617-621.

Robillard, N. et al. (Jun. 1998). "CD28, a Marker Associated with Tumoral Expansion in Multiple Myeloma," Clin Cancer Res. 4:1521-1526.

Rudikoff, S. et al. (Mar. 1982). "Single Amino Acid Substitution Altering Antigen-Binding Specificity," Proc. Natl. Acad. Sci USA 79:1979-1983.

Sarzotti-Kelsoe, M. et al. (Jul. 2014; e-published on Dec. 1, 2013). "Optimization and Validation of the TZM-BI Assay for Standardized Assessments of Neutralizing Antibodies Against HIV-1," J. Immunological Methods 409:131-146, 37 pages.

Sharma, P. et al. (Apr. 3, 2015). "The Future of Immune Checkpoint Therapy," Science 348(6230):56-61.

Shields, R.L. et al. (Mar. 2, 2001). "High Resolution Mapping of the Binding Site on Human IgG1 for FcγRI, FcγII. FcγIII, and FcRn and Design of IgG1 Variants With Improved Binding to the FcγR," J. Biol. Chem. 276(9):6591-6604.

Shultz, L.D. et al. (Jul. 2014). "Human Cancer Growth and Therapy In NOD/SCID/IL2Rynull (NSG) Mice," Cold Spring Harb. Protoc. 2014(7):694-708, 24 pages.

Smith, E.J. et al. (Dec. 11, 2015). "A Novel, Native-Format Bispecific Antibody Triggering T-cell Killing of B-cells is Robustly Active in Mouse Tumor Models and Cynomolgus Monkeys," Sci Rep 5(17943):1-12.

Song, Li-Ping et al. (Jun. 1, 2003). "A New Model of Trispecific Antibody with Cytotoxicity Against Tumor Cells," Acta Biochimica Etbiophysica Sinica 35(6):503-510.

Spiess, C. et al. (Sep. 2013). "Development of a Human IgG4 Bispecific Antibody for Dual Targeting of Interleukin-4 (IL-4) and Interleukin-13 (IL-13) Cytokines," The Journal of Biological Chemistry 288(37):26583-26593.

Spiess, C. et al. (2015, e-pub. Jan. 27, 2015). "Alternative Molecular Formats and Therapeutic Applications for Bispecific Antibodies," Mol. Immunol. 67:95-106.

Stebbings, R. et al. (Sep. 1, 2007). ""Cytokine Storm" In The Phase I Trial of Monoclonal Antibody TGN1412: Better Understanding the Causes to Improve Preclinical Testing of Immunotherapeutics," J. Immunol. 179(5):3325-3331.

Steinmetz, A. et al. (Mar. 16, 2016). "CODV-Ig, A Universal Bispecific Tetravalent and Multifunctional Immunoglobulin Format for Medical Applications," MABS 8(5):867-878, with Supplementary material, 59 pages.

Stevenson, G.T. (Nov.-Dec. 2006). "CD38 as a Therapeutic Target," Mol. Med. 12(11-12):345-346.

Suntharalingam, G. et al. (Sep. 7, 2006). "Cytokine Storm in a Phase 1 Trial of the Anti-CD28 Monoclonal Antibody TGN1412," N Engl J Med 355(10):1018-1028.

Tabares, P. et al. (Apr. 2014; e-pub. Feb. 1, 2014). "Human Regulatory T Cells are Selectively Activated by Low-Dose Application of the CD28 Superagonist TGN1412/TAB08," Eur J Immunol. 44:1225-1236.

Thompson, J.D. (Nov. 11, 1994). "Clustal W: Improving the Sensitivity of Progressive Multiple Sequence Alignment Through Sequence Weighting, Position-Specific Gap Penalties and Weight Matrix Choice," Nucleic Acids Res. 22(22):4673-4680.

Tiller, T. et al. (Oct. 2009, e-pub. Aug. 27, 2009). "Cloning and Expression of Murine Ig Genes From Single B Cells," J. Immunol. Methods 350(1-2):183-193.

Waibler, Z. et al. (Mar. 5, 2008). "Signaling Signatures and Functional Properties of Anti-Human CD28 Superagonistic Antibodies," PLoS One 3(3):e1708, pp. 1-13.

Wang, X. (Apr. 1, 2004). "A New Recombinant Single Chain Trispecific Antibody Recruits T Lymphocytes to Kill CEA (Carcinoma Embryonic Antigen) Positive Tumor Cells In Vitro Efficiently," Journal of Biochemistry 135(4):555-565.

Wang, X. et al. (Jan. 2018; e-pub. Oct. 6, 2017). "IgG Fc Engineering to Modulate Antibody Effector Functions," Protein & Cell 9(1):63-73.

Wennerberg, A.E. et al. (Oct. 1993). "Hepatocyte Paraffin 1: A Monoclonal Antibody that Reacts with Hepatocytes and can be Used for Differential Diagnosis of Hepatic Tumors," Am J Pathol. 143(4):1050-1054.

Willems, A. et al. (Nov. 1, 2005; e-pub. May 13, 2005). "CD3 × CD28 Cross-Interacting Bispecific Antibodies Improve Tumor Cell Dependent T-Cell Activation," Cancer Immunology, Immunotherapy 54(11):1059-1071.

Written Opinion of the International Searching Authority dated Dec. 17, 2019, for PCT Application No. PCT/US2019/055232, filed on Oct. 8, 2019, six pages.

Written Opinion of the International Searching Authority dated May 17, 2019, for PCT Application No. PCT/US2018/055084, filed on Oct. 9, 2018, fifteen pages.

Wu, L. et al. (Nov. 18, 2019). "Trispecific Antibodies Enhance the Therapeutic Efficacy of Tumor-Directed T Cells Through T Cell Receptor Co-Stimulation," Nat Cancer 1:86-98.

Xu, L. et al. (Oct. 6, 2017; e-pub. Sep. 20, 2017). "Trispecific Broadly Neutralizing HIV Antibodies Mediate Potent SHIV Protection in Macaques," Science 358(6359):85-90, 17 pages.

International Preliminary Report on Patentability dated Apr. 8, 2021 for PCT Application No. PCT/US2019/055232, filed on Oct. 8, 2019, 7 pages.

U.S. Appl. No. 17/503,038, filed Oct. 15, 2021, for Cameron et al.(Copy not submitted herewith pursuant to the waiver of 37 C.F.R. 1.98(a)(2)(iii) issued by the Office on Sep. 21, 2004).

U.S. Appl. No. 17/737,814, filed May 5, 2022, for Cameron et al.

Affinity of WT TsAbs for individual targets ($K_D$ round up to integer)

| TsAbs | CD38 | CD28 | CD3 | Affinity order ranking |
|---|---|---|---|---|
| CD38$_{SB19}$CD28$_{sup}$CD3$_{mid}$ | 2 nM | 3 nM | 23 nM | • CD38 binding: MsAb ≈ TsAbs |
| CD38$_{SB19}$CD28$_{cvn}$CD3$_{mid}$ | 2 nM | 17 nM | 19 nM | |
| CD38$_{VH1}$CD28$_{sup}$CD3$_{mid/low}$ | 4/6 nM | 2/4 nM | 21/76 nM | • CD28 binding: MsAb > TsAb ≥ BsAbs |
| CD38$_{VH1}$CD28$_{cvn}$CD3$_{mid/low}$ | 4/6 nM | 18/34 nM | 23/59 nM | |
| CD38$_{HHY1370}$CD28$_{sup}$CD3$_{mid}$ | 1 nM | 5 nM | 48 nM | • CD3 binding: MsAb ≈ BsAb ≈ TsAb |
| CD38$_{HHY1370}$CD28$_{cvn}$CD3$_{mid}$ | 1 nM | 19 nM | 44 nM | |

Impact of multi-target binding to CD38$_{SB19}$CD28$_{sup}$CD3$_{mid}$

| State of TsAb | CD38 | CD28 | CD3 | Comments |
|---|---|---|---|---|
| Single target | 2 nM | 3 nM | 23 nM | Fast kinetics of CD3 binding when all targets are present |
| All targets | 2 nM | 4 nM | 19 nM | |

FIG. 2

| TsAbs | $^1$KD value against rec. protein by SPR (nM) | $^2$Apparent KD value against rec. cells by FACS (nM) |
| --- | --- | --- |
| CD38$_{SB19}$CD28$_{sup}$CD3$_{mid}$ | 2 | 4 |
| CD38$_{VH1}$CD28$_{sup}$CD3$_{mid/low}$ | 4/6 | 11 |
| CD38$_{VH1}$CD28$_{syn}$CD3$_{mid/low}$ | 4/6 | 4.4 |
| CD38$_{MOR13178}$CD28$_{sup}$CD3$_{mid}$ | 1 | no accurate EC50 value could be estimated (no saturation) |

FIG. 3

TRISPECIFIC ANTI-CD38, ANTI-CD28, AND ANTI-CD3 BINDING PROTEINS AND METHODS OF USE FOR TREATING VIRAL INFECTION

CROSS REFERENCES TO RELATED APPLICATIONS

This application claims the priority benefit of International Application No. PCT/US2018/055084, filed Oct. 9, 2018; U.S. Provisional Application Ser. No. 62/831,572, filed Apr. 9, 2019; U.S. Provisional Application Ser. No. 62/831,608, filed Apr. 9, 2019; and EP Application No. 19306097.7, filed Sep. 11, 2019; all of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952032100SEQLIST.TXT, date recorded: Oct. 2, 2019, size: 144 KB).

FIELD

The disclosure relates to methods of using trispecific binding proteins comprising four polypeptide chains that form three antigen binding sites that specifically bind a CD38 polypeptide (e.g., human and/or cynomolgus monkey CD38 polypeptides), a CD28 polypeptide, and a CD3 polypeptide for expanding memory T cells (e.g., virus-specific memory T cells) and/or treating chronic viral infection.

BACKGROUND

As part of the human adaptive immunity, T cell immunity plays crucial role in controlling viral infection, eliminating infected cells which results in clearance of viral infection. In chronic infectious diseases such as Herpes viral infection (HSV, CMV, EBV, etc.), HIV, and HBV, viruses establish their persistence in humans by various mechanisms including immune suppression, T cell exhaustion, and latency establishment. Nevertheless, viral infection generally induces viral antigen specific immunity including antigen specific CD8 T cells that can readily recognize infected cells for controlling or killing through cytokine release or cytotoxic T cell (CTL) mediated killing processes.

Thus, viral antigen specific T cell activation and/or amplification in vivo and/or ex vivo may provide therapeutic strategies against chronic viral infections.

BRIEF SUMMARY

Provided herein are anti-CD38/CD28×CD3 trispecific antibodies that were developed and evaluated for their potential in activating T cells, and subsequent proliferation and/or amplification of antigen specific T cells. These trispecific Abs can effectively expand CD4 and CD8 effector and memory populations, including antigen specific CD8 T central memory and effector memory cells in vitro. Specifically, in vitro expansion of CMV, EBV, HIV-1, Influenza specific CD8 central memory and effector memory cells were demonstrated. The anti-CD38/CD28×CD3 trispecific antibodies described herein exhibited novel properties by engaging CD3/CD28/CD38, providing signaling pathways to stimulate and expand T cells, which may offer an effective strategy treating chronic infectious diseases such as HSV, CMV, EBV, HIV-1, and HBV infections.

To meet these and other needs, provided herein are binding proteins that bind a CD38 polypeptide (e.g., human and cynomolgus monkey CD38 polypeptides), a CD28 polypeptide, and a CD3 polypeptide.

In some embodiments, provided herein is a method for expanding virus-specific memory T cells, comprising contacting a virus-specific memory T cell with a binding protein, wherein the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \qquad [II]$$

and a third polypeptide chain comprises a structure represented by the formula:

$$V_{H3}\text{-}C_{H1}\text{-}\text{hinge}\text{-}C_{H2}\text{-}C_{H3} \qquad [III]$$

and a fourth polypeptide chain comprises a structure represented by the formula:

$$V_{L3}\text{-}C_L \qquad [IV]$$

wherein:
- $V_{L1}$ is a first immunoglobulin light chain variable domain;
- $V_{L2}$ is a second immunoglobulin light chain variable domain;
- $V_{L3}$ is a third immunoglobulin light chain variable domain;
- $V_{H1}$ is a first immunoglobulin heavy chain variable domain;
- $V_{H2}$ is a second immunoglobulin heavy chain variable domain;
- $V_{H3}$ is a third immunoglobulin heavy chain variable domain;
- $C_L$ is an immunoglobulin light chain constant domain;
- $C_{H1}$ is an immunoglobulin $C_{H1}$ heavy chain constant domain;
- $C_{H2}$ is an immunoglobulin $C_{H2}$ heavy chain constant domain;
- $C_{H3}$ is an immunoglobulin $C_{H3}$ heavy chain constant domain;
- hinge is an immunoglobulin hinge region connecting the $C_{H1}$ and $C_{H2}$ domains; and
- $L_1$, $L_2$, $L_3$ and $L_4$ are amino acid linkers;

wherein the polypeptide of formula I and the polypeptide of formula II form a cross-over light chain-heavy chain pair; and
wherein $V_{H1}$ and $V_{L1}$ form a first antigen binding site that binds a CD28 polypeptide,
wherein $V_{H2}$ and $V_{L2}$ form a second antigen binding site that binds a CD3 polypeptide, and
wherein $V_{H3}$ and $V_{L3}$ form a third antigen binding site that binds a CD38 polypeptide In some embodiments, provided herein is a binding protein that comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \quad [II]$$

and a third polypeptide chain comprises a structure represented by the formula:

$$V_{H3}\text{-}C_{H1}\text{-}\text{hinge}\text{-}C_{H2}\text{-}C_{H3} \quad [III]$$

and a fourth polypeptide chain comprises a structure represented by the formula:

$$V_{L3}\text{-}C_L \quad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair; and
wherein $V_{H1}$ and $V_{L1}$ form a first antigen binding site that binds a CD28 polypeptide,
wherein $V_{H2}$ and $V_{L2}$ form a second antigen binding site that binds a CD3 polypeptide, and
wherein $V_{H3}$ and $V_{L3}$ form a third antigen binding site that binds a CD38 polypeptide for use in expanding virus-specific memory T cells.

In some embodiments, the virus-specific memory T cell is contacted with the binding protein in vitro or ex vivo. In some embodiments, contacting the virus-specific memory T cell with the binding protein causes activation and/or proliferation of virus-specific memory T cells.

In some embodiments, provided herein is a method for expanding T cells, comprising contacting a T cell with a binding protein in vitro or ex vivo, wherein the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \quad [II]$$

and a third polypeptide chain comprises a structure represented by the formula:

$$V_{H3}\text{-}C_{H1}\text{-}\text{hinge}\text{-}C_{H2}\text{-}C_{H3} \quad [III]$$

and a fourth polypeptide chain comprises a structure represented by the formula:

$$V_{L3}\text{-}C_L \quad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair; and
wherein $V_{H1}$ and $V_{L1}$ form a first antigen binding site that binds a CD28 polypeptide,
wherein $V_{H2}$ and $V_{L2}$ form a second antigen binding site that binds a CD3 polypeptide, and
wherein $V_{H3}$ and $V_{L3}$ form a third antigen binding site that binds a CD38 polypeptide.

In some embodiments, provided herein is a binding protein that comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \quad [II]$$

and a third polypeptide chain comprises a structure represented by the formula:

$$V_{H3}\text{-}C_{H1}\text{-}\text{hinge}\text{-}C_{H2}\text{-}C_{H3} \quad [III]$$

and a fourth polypeptide chain comprises a structure represented by the formula:

$$V_{L3}\text{-}C_L \quad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair; and wherein $V_{H1}$ and $V_{L1}$ form a first antigen binding site that binds a CD28 polypeptide, wherein $V_{H2}$ and $V_{L2}$ form a second antigen binding site that binds a CD3 polypeptide, and wherein $V_{H3}$ and $V_{L3}$ form a third antigen binding site that binds a CD38 polypeptide for use in a method for expanding T cells.

In some embodiments, the T cell is a memory T cell or an effector T cell. In some embodiments, the T cell expresses a chimeric antigen receptor (CAR) on its cell surface or comprises a polynucleotide encoding a CAR.

In some embodiments, provided herein is a method for treating chronic viral infection, comprising administering to an individual in need thereof an effective amount of a binding protein, wherein the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \qquad [\text{I}]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \qquad [\text{II}]$$

and a third polypeptide chain comprises a structure represented by the formula:

$$V_{H3}\text{-}C_{H1}\text{-}\text{hinge}\text{-}C_{H2}\text{-}C_{H3} \qquad [\text{III}]$$

and a fourth polypeptide chain comprises a structure represented by the formula:

$$V_{L3}\text{-}C_L \qquad [\text{IV}]$$

wherein:

$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;

wherein the polypeptide of formula I and the polypeptide of formula II form a cross-over light chain-heavy chain pair; and wherein $V_{H1}$ and $V_{L1}$ form a first antigen binding site that binds a CD28 polypeptide, wherein $V_{H2}$ and $V_{L2}$ form a second antigen binding site that binds a CD3 polypeptide, and wherein $V_{H3}$ and $V_{L3}$ form a third antigen binding site that binds a CD38 polypeptide.

In some embodiments, provided herein is a binding protein that comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \qquad [\text{I}]$$

and a second polypeptide chain comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \qquad [\text{II}]$$

and a third polypeptide chain comprises a structure represented by the formula:

$$V_{H3}\text{-}C_{H1}\text{-}\text{hinge}\text{-}C_{H2}\text{-}C_{H3} \qquad [\text{III}]$$

and a fourth polypeptide chain comprises a structure represented by the formula:

$$V_{L3}\text{-}C_L \qquad [\text{IV}]$$

wherein:

$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;

wherein the polypeptide of formula I and the polypeptide of formula II form a cross-over light chain-heavy chain pair; and wherein $V_{H1}$ and $V_{L1}$ form a first antigen binding site that binds a CD28 polypeptide, wherein $V_{H2}$ and $V_{L2}$ form a second antigen binding site that binds a CD3 polypeptide, and wherein $V_{H3}$ and $V_{L3}$ form a third antigen binding site that binds a CD38 polypeptide for use in a method for treating chronic viral infection, wherein said method comprises administering to an individual in need thereof an effective amount of the binding protein. In some embodiments, provided herein is a binding protein for use in a method for treating chronic viral infection, wherein said method comprises administering to an individual in need thereof an effective amount of the binding protein, wherein the binding protein comprises four polypeptide chains that form the three antigen binding sites, wherein a first polypeptide chain of the binding protein comprises a structure represented by the formula:

$$V_{L2}\text{-}L_1\text{-}V_{L1}\text{-}L_2\text{-}C_L \qquad [\text{I}]$$

and a second polypeptide chain of the binding protein comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \qquad [\text{II}]$$

and a third polypeptide chain of the binding protein comprises a structure represented by the formula:

$$V_{H3}\text{-}C_{H1}\text{-hinge-}C_{H2}\text{-}C_{H3} \quad [III]$$

and a fourth polypeptide chain of the binding protein comprises a structure represented by the formula:

$$V_{L3}\text{-}C_L \quad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair; and
wherein $V_{H1}$ and $V_{L1}$ form a first antigen binding site that binds a CD28 polypeptide,
wherein $V_{H2}$ and $V_{L2}$ form a second antigen binding site that binds a CD3 polypeptide, and
wherein $V_{H3}$ and $V_{L3}$ form a third antigen binding site that binds a CD38 polypeptide.

In some embodiments, the individual is a human. In some embodiments, the binding protein is administered to the individual in pharmaceutical formulation comprising the binding protein and a pharmaceutically acceptable carrier. In some embodiments, administration of the binding protein results in activation and/or proliferation of virus-specific memory T cells in the individual.

In some embodiments that may be combined with any other embodiments described herein, the memory T cells are CD8+ or CD4+ memory T cells. In some embodiments, the memory T cells are central memory T cells ($T_{CM}$) or effector memory T cells ($T_{EM}$).

In some embodiments that may be combined with any other embodiments described herein, the CD28 polypeptide is a human CD28 polypeptide, wherein the CD3 polypeptide is a human CD3 polypeptide, and wherein the CD38 polypeptide is a human CD38 polypeptide.

In some embodiments that may be combined with any other embodiments described herein, the $V_{H3}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L3}$ domain comprises a CDR-$L_1$ sequence comprising the amino acid sequence of ESVDSYGNGF (SEQ ID NO:34), a CDR-$L_2$ sequence comprising the amino acid sequence of LAS (SEQ ID NO:35), and a CDR-$L_3$ sequence comprising the amino acid sequence of QQNKEDPWT (SEQ ID NO:36). In some embodiments, the $V_{H3}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the $V_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L3}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-$L_3$ sequence comprising the amino acid sequence of LQDYIYYPT (SEQ ID NO:46). In some embodiments, the $V_{H3}$ domain comprises the amino acid sequence of QVQLQQSGAELVRSGASVKMSCK-ASGYTFTSFNMHWVKETPGQGLEWIGYIYPG NGGTNYNQKFKGKATLTADTSSSTAYMQISSLTSED-SAVYFCARTGGLRRAYFTY WGQGTLVTVS (SEQ ID NO:5), and the $V_{L3}$ domain comprises the amino acid sequence of DIVLTQSPASLAVSLGQRATISCRAS-ESVDSYGNGFMHWYQQKPGQPPKLLIYLAS NLESGVPARFSGSGSRTDFTLTIDPVEADD-AATYYCQQNKEDPWTFGGGTKLEIK (SEQ ID NO:6). In some embodiments, the $V_{H3}$ domain comprises the amino acid sequence of QVQLVQSGAEVVKPGASVKVSCK-ASGYTFTSYAMHWVKEAPGQRLEWIGYIYPG QGGTNYNQKFQGRATLTADTSASTAYMELSSLRSED-TAVYFCARTGGLRRAYFTY WGQGTLVTVSS (SEQ ID NO:13), and the $V_{L3}$ domain comprises the amino acid sequence of DIVLTQSPATLSLSPGER-ATISCRASQSVSSYGQGFMHWYQQKPGQPPRLLIY-GASS RATGIPARFSGSGSGTDFTLTISPLEPED-FAVYYCQQNKEDPWTFGGGTKLEIK (SEQ ID NO:14). In some embodiments, the $V_{H3}$ domain comprises the amino acid sequence of QVQLVQSGAEVVKPGASVKVSCK-ASGYTFTSFNMHWVKEAPGQRLEWIGYIYPG NGGTNYNQKFQGRATLTADTSASTAYMELSSLRSED-TAVYFCARTGGLRRAYFTY WGQGTLVTVSS (SEQ ID NO:17), and the $V_{L3}$ domain comprises the amino acid sequence of DIVLTQSPATLSLSPGERATISCRAS-ESVDSYGNGFMHWYQQKPGQPPRLLIYLASS RAT GIPARFSGSGSGTDFTLTISPLEPED-FAVYYCQQNKEDPWTFGGGTKLEIK (SEQ ID NO:18). In some embodiments, the $V_{H3}$ domain comprises the amino acid sequence of QVQLVQSGAEVVKSGASVKVSCK-ASGYTFTSFNMHWVKEAPGQGLEWIGYIYPG NGGTNYNQKFQGRATLTADTSASTAYMEISSLRSED-TAVYFCARTGGLRRAYFTY WGQGTLVTVSS (SEQ ID NO:21), and the $V_{L3}$ domain comprises the amino acid sequence of DIVLTQSPATLSLSPGERATISCRAS-ESVDSYGNGFMHWYQQKPGQPPRLLIYLASS RAT GIPARFSGSGSGTDFTLTISPLEPED-FAVYYCQQNKEDPWTFGGGTKLEIK (SEQ ID NO:18). In some embodiments, the $V_{H3}$ domain comprises the amino acid sequence of QVQLVQSGAEVVKPGASVKMSCK-ASGYTFTSFNMHWVKEAPGQRLEWIGYIYPG NGGTNYNQKFQGRATLTADTSASTAYMEISSLRSEDTAVYFCARTGGLRRAYFTY WGQGTLVTVSS (SEQ ID NO:23), and the $V_{L3}$ domain comprises the amino acid sequence of DIVLTQSPATLSLSPGERATISCRASESVDSYGNGFMHWYQQKPGQPPRLLIYLASS RAT GIPARFSGSGSGTDFTLTISPLEPEDFAVYYCQQNKEDPWTFGGGTKLEIK (SEQ ID NO:18). In some embodiments, the $V_{H3}$ domain comprises the amino acid sequence of QVQLVESGGGVVQPGRSLRLSCAASGFTFSSYGMHWVRQAPGKGLEWVAVIWYD GSNKYYADSVKGRFTISGDNSKNTLYLQMNSLRAEDTAVYYCARMFRGAFDYWG QGTLVTVSS (SEQ ID NO:9), and the $V_{L3}$ domain comprises the amino acid sequence of AIQMTQSPSSLSASVGDRVTITCRASQGIRNDLGWYQQKPGKAPKLLIYAASSLQS GVPSRFSGSGSGTDFTLTISGLQPEDSATYYCLQDYIYYPTFGQGTKVEIK (SEQ ID NO:10).

In some embodiments that may be combined with any other embodiments described herein, the $V_{H1}$ domain comprises a CDR-H1 sequence comprising the amino acid sequence of GYTFTSYY (SEQ ID NO:108), a CDR-H2 sequence comprising the amino acid sequence of IYPGNVNT (SEQ ID NO:109), and a CDR-H3 sequence comprising the amino acid sequence of TRSHYGLDWNFDV (SEQ ID NO:110), and the $V_{L1}$ domain comprises a CDR-L1 sequence comprising the amino acid sequence of QNIYVW (SEQ ID NO:111), a CDR-L2 sequence comprising the amino acid sequence of KAS (SEQ ID NO:112), and a CDR-L3 sequence comprising the amino acid sequence of QQGQTYPY (SEQ ID NO:113). In some embodiments, the $V_{H1}$ domain comprises a CDR-H1 sequence comprising the amino acid sequence of GFSLSDYG (SEQ ID NO:114), a CDR-H2 sequence comprising the amino acid sequence of IWAGGGT (SEQ ID NO:115), and a CDR-H3 sequence comprising the amino acid sequence of ARDKGYSYYYSMDY (SEQ ID NO:116), and the $V_{L1}$ domain comprises a CDR-L1 sequence comprising the amino acid sequence of ESVEYYVTSL (SEQ ID NO:117), a CDR-L2 sequence comprising the amino acid sequence of AAS (SEQ ID NO:118), and a CDR-$L_3$ sequence comprising the amino acid sequence of QQSRKVPYT (SEQ ID NO:119). In some embodiments, the $V_{H1}$ domain comprises the amino acid sequence of QVQLVQSGAEVVKPGASVKVSCKASGYTFTSYYIHWVRQAPGQGLEWIGSIYPGN VNTNYAQKFQGRATLTVDTSISTAYMELSRLRSDDTAVYYCTRSHYGLDWNFDV WGKGTTVTVSS (SEQ ID NO:49), and the $V_{L1}$ domain comprises the amino acid sequence of DIQMTQSPSSLSASVGDRVTITCQASQNIYVWLNWYQQKPGKAPKL LIYKASNLHT GVPSRFSGSGSGTDFTLTISSLQPEDIATYYCQQGQTYPYTFGQGTKLEIK (SEQ ID NO:50). In some embodiments, the VHA domain comprises the amino acid sequence of QVQLQESGPGLVKPSQTLSLTCTVSGFSLSDYGVHWVRQPPGKGLEWLGVIWAGG GTNYNPSLKSRKTISKDTSKNQVSLKLSSVTAADTAVYYCARDKGYSYYYSMDY WGQGTTVTVS (SEQ ID NO:51), and the $V_{L1}$ domain comprises the amino acid sequence of DIVLTQSPASLAVSPGQRATITCRASESVEYYVTSLMQWYQQKPGQPPKLLIFAASN VESGVPARFSGSGSGTDFTLTINPVEANDVANYYCQQSRKVPYTFGQGTKLEIK (SEQ ID NO:52).

In some embodiments that may be combined with any other embodiments described herein, the $V_{H2}$ domain comprises a CDR-H1 sequence comprising the amino acid sequence of GFTFTKAW (SEQ ID NO:120), a CDR-H2 sequence comprising the amino acid sequence of IKDKSNSYAT (SEQ ID NO:121), and a CDR-H3 sequence comprising the amino acid sequence of RGVYYALSPFDY (SEQ ID NO:122), and the $V_{L2}$ domain comprises a CDR-L1 sequence comprising the amino acid sequence of QSLVHNNANTY (SEQ ID NO:123), a CDR-L2 sequence comprising the amino acid sequence of KVS (SEQ ID NO:124), and a CDR-L3 sequence comprising the amino acid sequence of GQGTQYPFT (SEQ ID NO:125). In some embodiments, the $V_{H2}$ domain comprises a CDR-H1 sequence comprising the amino acid sequence of GFTFTKAW (SEQ ID NO:126), a CDR-H2 sequence comprising the amino acid sequence of IKDKSNSYAT (SEQ ID NO:127), and a CDR-H3 sequence comprising the amino acid sequence of GVYYALSPFDY (SEQ ID NO:128), and the $V_{L2}$ domain comprises a CDR-L1 sequence comprising the amino acid sequence of QSLVHNNGNTY (SEQ ID NO:129), a CDR-L2 sequence comprising the amino acid sequence of KVS (SEQ ID NO:130), and a CDR-$L_3$ sequence comprising the amino acid sequence of GQGTQYPFT (SEQ ID NO:131). In some embodiments, the $V_{H2}$ domain comprises the amino acid sequence of QVQLVESGGGVVQPGRSLRLSCAASGFTFTKAWMHWVRQAPGKQLEWVAQIKD KSNSYATYYADSVKGRFTISRDDSKNTLYLQMNSLRAEDTAVYYCRGVYYALSPF DYWGQGTLVTVSS (SEQ ID NO:53), and the $V_{L2}$ domain comprises the amino acid sequence of DIVMTQTPLSLSVTPGQPASISCKSSQSLVHNNANTYLSWYLQKPGQSPQSLIYKVS NRFSGVPDRFSGSGSGTDFTLKISRVEAEDVGVYYCGQGTQYPFTFGSGTKVEIK (SEQ ID NO:54). In some embodiments, the $V_{H2}$ domain comprises the amino acid sequence of QVQLVESGGGVVQPGRSLRLSCAASGFTFTKAWMHWVRQAPGKGLEWVAQIKD KSNSYATYYADSVKGRFTISRDNSKNTLYLQMNSLRAEDTAVYYCRGVYYALSPF DYWGQGTLVTVSS (SEQ ID NO:84), and the $V_{L2}$ domain comprises the amino acid sequence of DIVMTQTPLSLSVTPGQPASISCKSSQSLVHNNGNTYLSWYLQKPGQSPQLLIYKVS NRFSGVPDRFSGSGSGTDFTLKISRVEAEDVGVYYCGQGTQYPFTFGGGTKVEIK (SEQ ID NO:85).

In some embodiments that may be combined with any other embodiments described herein, at least one of $L_1$, $L_2$, $L_3$ or $L_4$ is independently 0 amino acids in length. In some embodiments, $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO: 56), S, RT, TKGPS (SEQ ID NO: 57), GQPKAAP (SEQ ID NO: 58), and GGSGSSGSGG (SEQ ID NO: 59). In some embodiments, $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO: 58), and GGSGSSGSGG (SEQ ID NO:59). In some embodiments, $L_1$ comprises the sequence GQPKAAP (SEQ ID NO: 58), $L_2$ comprises the sequence TKGPS (SEQ ID NO:57), $L_3$ comprises the sequence S, and $L_4$ comprises the sequence RT.

In some embodiments that may be combined with any other embodiments described herein, the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 234 and 235 of human IgG4 according to EU Index, wherein the amino acid substitutions are F234A and $L_{235}A$. In some embodiments, the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 233-236 of human IgG4 according to EU Index, wherein the amino acid substitutions are E233P, F234V, L235A, and a deletion at 236. In some embodiments, the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 228 and 409 of human IgG4 according to EU Index, wherein the amino acid substitutions are S228P and R409K. In some embodiments, the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 234, 235, and 329 of human IgG1 according to EU Index, wherein the amino acid substitutions are L234A, L235A, and P329A. In some embodiments, the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 298, 299, and 300 of human IgG1 according to EU Index, wherein the amino acid substitutions are S298N, T299A, and Y300S. In some embodiments, the hinge-$C_{H2}$-$C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the hinge-$C_{H2}$-$C_{H3}$ domain of the third polypeptide chain comprises amino acid substitutions at positions corresponding to positions 354 and 366 of human IgG1 or IgG4 according to EU Index, wherein the amino acid substitutions are S354C and T366W. In some embodiments, the hinge-$C_{H2}$-$C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the hinge-$C_{H2}$-$C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V.

In certain embodiments, the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:62, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:65, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:67, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:68, and the fourth polypeptide chain comprises the amino acid sequence of SEQ ID NO:69. In certain embodiments, the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:70, and the fourth polypeptide chain comprises the amino acid sequence of SEQ ID NO:69. In certain embodiments, the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:71, and the fourth polypeptide chain comprises the amino acid sequence of SEQ ID NO:69.

In some embodiments that may be combined with any other embodiments described herein, the virus is a human immunodeficiency virus (HIV), influenza virus, cytomegalovirus (CMV), hepatitis B virus (HBV), human papillomavirus (HPV), Epstein-barr virus (EBV), human foamy virus (HFV), herpes simplex virus 1 (HSV-1), or herpes simplex virus 1 (HSV-2).

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 2 summarizes the binding affinities of indicated trispecific binding proteins against their cognate antigens (human CD3, CD28, and CD38) as measured by SPR.

FIG. 3 summarizes the binding affinity of the indicated anti-CD38xanti-CD28xanti-CD3 trispecific binding proteins for human CD38, as measured by SPR or flow cytometry (FACS).

DETAILED DESCRIPTION

Figure 1:
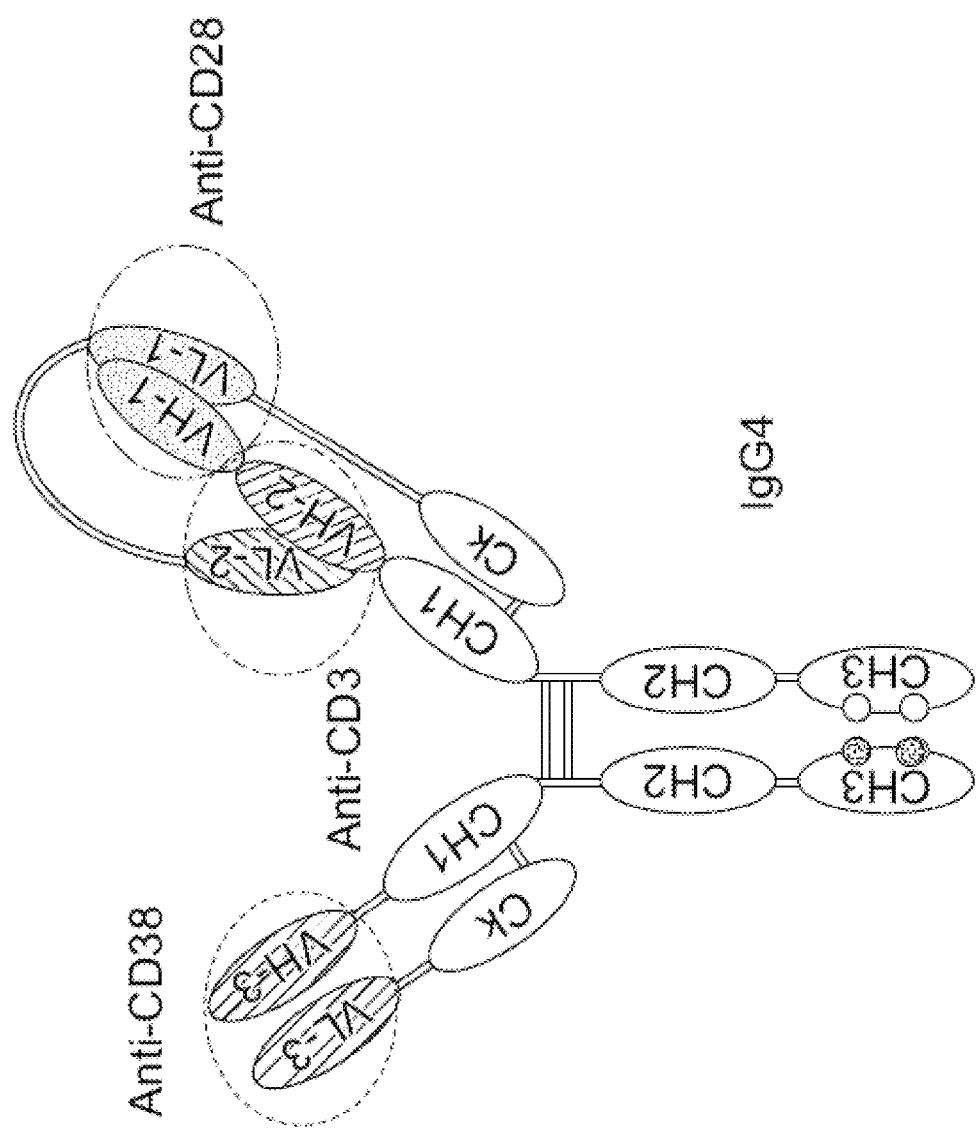
FIG. 1 provides a schematic representation of a trispecific binding protein comprising four polypeptide chains that form three antigen binding sites that binds three target proteins: CD28, CD3, and CD38. A first pair of polypeptides possess dual variable domains having a cross-over orientation (VH1-VH2 and VL2-VL1) forming two antigen binding sites that recognize CD3 and CD28, and a second pair of polypeptides possess a single variable domain (VH3 and VL3) forming a single antigen binding site that recognizes CD38. The trispecific binding protein shown in FIG. 1 uses an IgG4 constant region with a "knobs-into-holes" mutation, where the knob is on the second pair of polypeptides with a single variable domain.

The disclosure provides trispecific binding proteins comprising four polypeptide chains that form three antigen binding sites that specifically bind a CD38 polypeptide (e.g., human and cynomolgus monkey CD38 polypeptides), a CD28 polypeptide, and a CD3 polypeptide, which may find use, e.g., in expanding memory T cells (e.g., virus-specific memory T cells) and/or treating chronic viral infection.

I. General Definitions

As utilized in accordance with the present disclosure, the following terms, unless otherwise indicated, shall be understood to have the following meanings. Unless otherwise required by context, singular terms shall include pluralities and plural terms shall include the singular. As used in this specification and the appended claims, the singular forms "a", "an" and "the" include plural referents unless the content clearly dictates otherwise. Thus, for example, reference to "a molecule" optionally includes a combination of two or more such molecules, and the like.

It is understood that aspects and embodiments of the present disclosure described herein include "comprising," "consisting," and "consisting essentially of" aspects and embodiments.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phosoranilladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, *J. Mol. Biol.* 196: 901-17; Chothia et al., 1989, *Nature* 342: 877-83) found that certain subportions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, *FASEB J.* 9: 133-39; MacCallum, 1996, *J Mol. Biol.* 262(5): 732-45; and Lefranc, 2003, *Dev. Comp. Immunol.* 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," *In Antibody Engineering*, Vol. 2. Kontermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, *Nucleic Acids Res.* 22: 4673-80. Molecular models are conventionally used to correctly delineate framework and CDR regions and thus correct the sequence-based assignments.

In some embodiments, CDR/FR definition in an immunoglobulin light or heavy chain is to be determined based on IMGT definition (Lefranc et al. Dev. Comp. Immunol., 2003, 27(1):55-77; www.imgt.org).

The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins. Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, IgA2, and IgG4). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the $V_H$ and $C_{H1}$ domains of one heavy chain, wherein the $V_H$-$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a F(ab')$_2$ molecule.

The term "binding protein" as used herein refers to a non-naturally occurring (or recombinant or engineered) molecule that specifically binds to at least one target antigen, e.g., a CD38 polypeptide of the present disclosure A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "swapability" as used herein refers to the interchangeability of variable domains within the binding protein format and with retention of folding and ultimate binding affinity. "Full swapability" refers to the ability to swap the order of both $V_{H1}$ and $V_{H2}$ domains, and therefore the order of $V_{L1}$ and $V_{L2}$ domains, in the polypeptide chain of formula I or the polypeptide chain of formula II (i.e., to reverse the order) while maintaining full functionality of the binding protein as evidenced by the retention of binding affinity. Furthermore, it should be noted that the designations $V_H$ and $V_L$ refer only to the domain's location on a particular protein chain in the final format. For example, $V_{H1}$ and $V_{H2}$ could be derived from $V_{L1}$ and $V_{L2}$ domains in parent antibodies and placed into the $V_{H1}$ and $V_{H2}$ positions in the binding protein. Likewise, $V_{L1}$ and $V_{L2}$ could be derived from $V_{H1}$ and $V_{H2}$ domains in parent antibodies and placed in the $V_{H1}$ and $V_{H2}$ positions in the binding protein. Thus, the $V_H$ and $V_L$ designations refer to the present location and not the original location in a parent antibody. $V_H$ and $V_L$ domains are therefore "swappable."

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen. A target antigen may have one or more epitopes. With respect to each target antigen recognized by a binding protein, the binding protein is capable of competing with an intact antibody that recognizes the target antigen.

"CD38" is cluster of differentiation 38 polypeptide and is a glycoprotein found on the surface of many immune cells. In some embodiments, a binding protein of the present disclosure binds the extracellular domain of one or more CD38 polypeptide. Exemplary CD38 extracellular domain polypeptide sequences include, but are not limited to, the extracellular domain of human CD38 (e.g., as represented by SEQ ID NO: 1) and the extracellular domain of cynomolgus monkey CD38 (e.g., as represented by SEQ ID NO:30).

The term "T-cell engager" refers to binding proteins directed to a host's immune system, more specifically the T cells' cytotoxic activity as well as directed to a tumor target protein.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets. In some embodiments, a bispecific binding protein binds to two different antigens. In some embodiments, a bispecific binding protein binds to two different epitopes on the same antigen.

The term "bivalent binding protein" refers to a binding protein that has two binding sites.

The term "trispecific binding protein" refers to a binding protein that specifically binds to three different antigen targets. In some embodiments, a trispecific binding protein binds to three different antigens. In some embodiments, a trispecific binding protein binds to one, two, or three different epitopes on the same antigen.

The term "trivalent binding protein" refers to a binding protein that has three binding sites. In particular embodiments the trivalent binding protein can bind to one antigen target. In other embodiments, the trivalent binding protein can bind to two antigen targets. In other embodiments, the trivalent binding protein can bind to three antigen targets.

An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, N.J.). Surface plasmon analysis can also be performed by immobilizing the analyte (binding protein on a biosensor matrix) and presenting the ligand (target antigen). The term "$K_D$," as used herein refers to the dissociation constant of the interaction between a particular binding protein and a target antigen.

The term "binds to" as used herein in reference to a binding protein refers to the ability of a binding protein or an antigen-binding fragment thereof to bind to an antigen containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen. In some embodiments, a binding protein of the present disclosure binds to two or more antigens, e.g., a human and a cynomolgus monkey CD38 polypeptide.

In some embodiments, an antigen binding domain and/or binding protein of the present disclosure "cross reacts" with human and cynomolgus monkey CD38 polypeptides, e.g., CD38 extracellular domains, such as SEQ ID NO:1 (human CD38 isoform A), SEQ ID NO:105 (human CD38 isoform E) and SEQ ID NO:30 (cynomolgus monkey CD38). A binding protein binding to antigen 1 (Ag1) is "cross-reactive" to antigen 2 (Ag2) when the $EC_{50}$s are in a similar range for both antigens. In the present application, a binding protein binding to Ag1 is cross-reactive to Ag2 when the ratio of affinity of Ag2 to affinity of Ag1 is equal or less than 10 (for instance 5, 2, 1 or 0.5), affinities being measured with the same method for both antigens.

A binding protein binding to Ag1 is "not significantly cross-reactive" to Ag2 when the affinities are very different for the two antigens. Affinity for Ag2 may not be measurable if the binding response is too low. In the present application, a binding protein binding to Ag1 is not significantly cross-reactive to Ag2, when the binding response of the binding protein to Ag2 is less than 5% of the binding response of the same binding protein to Ag1 in the same experimental setting and at the same antibody concentration. In practice, the binding protein concentration used can be the $EC_{50}$ or the concentration required to reach the saturation plateau obtained with Ag1.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers described herein are referred to as $L_1$, which is located on the light chain between the C-terminus of the $V_{L2}$ and the N-terminus of the $V_{L1}$ domain; and L2, which is located on the light chain between the C-terminus of the $V_{L1}$ and the N-terminus of the CL domain. The heavy chain linkers are known as L3, which is located between the C-terminus of the $V_{H1}$ and the N-terminus of the $V_{H2}$ domain; and L4, which is located between the C-terminus of the $V_{H2}$ and the N-terminus of the $C_{H1}$ domain.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-, α-disubstituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
(1) hydrophobic: Met, Ala, Val, Leu, Ile, Phe, Trp, Tyr, Pro;
(2) polar hydrophilic: Arg, Asn, Asp, Gln, Glu, His, Lys, Ser, Thr;
(3) aliphatic: Ala, Gly, Ile, Leu, Val, Pro;
(4) aliphatic hydrophobic: Ala, Ile, Leu, Val, Pro;
(5) neutral hydrophilic: Cys, Ser, Thr, Asn, Gln;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects (e.g., mammals, such as dogs, pigs, horses, cats, cows, etc.).

The terms "treatment" or "treat" as used herein refer to both therapeutic treatment and prophylactic or preventative measures. Those in need of treatment include those having a disorder as well as those prone to have the disorder or those in which the disorder is to be prevented. In particular embodiments, binding proteins can be used to treat humans with chronic viral infection, or ameliorate chronic viral infection in a human subject.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding protein.

Trispecific Binding Proteins

Certain aspects of the present disclosure relate to trispecific binding proteins (e.g., that bind CD38, CD28, and CD3 polypeptides). Any of the CDRs or variable domains of any of the antigen binding proteins described herein may find use in a trispecific binding protein of the present disclosure.

In some embodiments, the binding protein of the disclosure is a trispecific binding protein comprising four polypeptide chains that form three antigen binding sites that bind one or more (e.g., three) different antigen targets or target proteins. In some embodiments, a first polypeptide chain comprises a structure represented by the formula:

   [I]

and a second polypeptide chain comprises a structure represented by the formula:

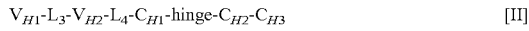   [II]

and a third polypeptide chain comprises a structure represented by the formula:

   [III]

and a fourth polypeptide chain comprises a structure represented by the formula:

   [IV]

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair. In some embodiments, the first polypeptide chain and the second polypeptide chain have a cross-over orientation that forms two distinct antigen binding sites.

In some embodiments, $V_{H1}$ and $V_{L1}$ form a first antigen binding site that binds a CD28 polypeptide, wherein $V_{H2}$ and $V_{L2}$ form a second antigen binding site that binds a CD3 polypeptide, and wherein $V_{H3}$ and $V_{L3}$ form a third antigen binding site that binds a CD38 polypeptide. In some embodiments, the CD28 polypeptide is a human CD28 polypeptide. In some embodiments, the CD3 polypeptide is a human CD3 polypeptide. In some embodiments, the CD38 polypeptide is a human CD38 polypeptide. In some embodiments, the trispecific binding protein comprises one or more antigen binding sites described infra.

The binding proteins of the disclosure may be prepared using domains or sequences obtained or derived from any human or non-human antibody, including, for example, human, murine, or humanized antibodies. In some embodiments, a binding protein of the present disclosure is an antibody. In some embodiments, the antibody is a monoclonal antibody. In some embodiments, the antibody is a chimeric, humanized, or human antibody.

Anti-CD38 Binding Sites

Certain aspects of the present disclosure relate to binding proteins that comprise an antigen binding site that binds a CD38 polypeptide (e.g., human and cynomolgus monkey CD38 polypeptides).

In some embodiments, a binding protein or antigen-binding fragment thereof cross-reacts with human CD38 (e.g., a human CD38 isoform A and/or isoform E polypeptide) and cynomolgus monkey CD38. In some embodiments, a binding protein induces apoptosis of a CD38+ cell. In some embodiments, a binding protein recruits a T cell to a CD38+ cell and optionally activates the T cell (e.g., though TCR stimulation and/or costimulation).

In some embodiments, a binding site that binds CD38 comprises: an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); and/or an antibody light chain variable (VL) domain comprising a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, a binding site that binds CD38 comprises: an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); and/or an antibody light chain variable (VL) domain comprising a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the binding proteins comprise 1, 2, 3, 4, 5, or 6 CDRs from an antibody VH and/or VL domain sequence of antiCD38_C2-CD38-1, antiCD38_C2-CD38-1_VH1-VL1, antiCD38_C2-CD38-1_VH3-VL3, antiCD38_C2-CD38-1_VH5-VL3, antiCD38_C2-CD38-1_VH6-VL3, CD38$_{HHY1370}$ (may also be referred to herein as antiCD38_1370), antiCD38_C2-CD38-1_VH1-VL1xCD28supxCD3mid IgG4 FALA, antiCD38_C2-CD38-1_VH1-VL1xCD28supxCD3mid IgG1LALA P329A, antiCD38_C2-CD38-1_VH1-VL1xCD28supxCD3mid IgG1 NNSA, CD38$_{HHY1370}$xCD28supxCD3mid IgG4 FALA, CD38$_{HHY1370}$xCD28supxCD3mid IgG1LALA P329A, or CD38$_{HHY1370}$xCD28supxCD3mid IgG1 NNSA, as shown in Table G, H, or I.

In some embodiments, a binding site that binds CD38 comprises: an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); and an antibody light chain variable (VL) domain comprising a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36).

In some embodiments, a binding site that binds CD38 comprises: an antibody heavy chain variable (VH) domain comprising a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33); and/or an antibody light chain variable (VL) domain comprising a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In other embodiments, a binding site that binds CD38 comprises: an antibody heavy chain variable (VH) domain comprising a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33); and/or an antibody light chain variable (VL) domain comprising a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, a binding site that binds CD38 comprises: an antibody heavy chain variable (VH) domain comprising a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33); and an antibody light chain variable (VL) domain comprising a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36).

In some embodiments, the VH domain comprises the sequence, from N-terminus to C-terminus, FR1-CDR-H1-FR2-CDR-H2-FR3-CDR-H3-FR4; where FR1 comprises the sequence QVQLVQSGAEVVKPGASVKVSCKAS (SEQ ID NO:86), QVQLVQSGAEVVKSGASVKVSCKAS (SEQ ID NO:87), or QVQLVQSGAEVVKPGASVKMSCKAS (SEQ ID NO:88); where FR2 comprises the sequence MHWVKEAPGQRLEWIGY (SEQ ID NO:90) or MHWVKEAPGQGLEWIGY (SEQ ID NO:91); where FR3 comprises the sequence NYNQKFQGRATLTADTSASTAYMELSSLRSEDTAVYFC (SEQ ID NO:93) or NYNQKFQGRATLTADTSASTAYMEISSLRSEDTAVYFC (SEQ ID NO:94); and where FR4 comprises the sequence WGQGTLVTVSS (SEQ ID NO:96). In some embodiments, the VL domain comprises the sequence, from N-terminus to C-terminus, FR1-CDR-L1-FR2-CDR-L2-FR3-CDR-L3-FR4; where FR1 comprises the sequence DIVLTQSPATLSLSPGERATISCRAS (SEQ ID NO:97); where FR2 comprises the sequence MHWYQQKPGQPPRLLIY (SEQ ID NO:99); where FR3 comprises the sequence SRATGIPARFSGSGSGTDFTLTISPLEPEDFAVYYC (SEQ ID NO:101); and where FR4 comprises the sequence FGGGTKLEIK (SEQ ID NO: 103).

In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:5; and/or the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:6. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 17; and/or the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:21; and/or the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:18. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:23; and/or the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 13; and/or the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:14.

In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:5; and the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:6. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 17; and the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:21; and the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:23; and the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:13; and the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 14.

In some embodiments, the VH domain comprises the amino acid sequence of SEQ ID NO:5; and the VL domain comprises the amino acid sequence of SEQ ID NO:6. In some embodiments, the VH domain comprises the amino acid sequence of SEQ ID NO: 17; and the VL domain comprises the amino acid sequence of SEQ ID NO: 18. In some embodiments, the VH domain comprises the amino acid sequence of SEQ ID NO:21; and the VL domain comprises the amino acid sequence of SEQ ID NO: 18. In some embodiments, the VH domain comprises the amino acid sequence of SEQ ID NO:23; and the VL domain comprises the amino acid sequence of SEQ ID NO: 18. In some embodiments, the VH domain comprises the amino acid sequence of SEQ ID NO: 13; and the VL domain comprises the amino acid sequence of SEQ ID NO: 14.

In some embodiments, a binding site that binds CD38 comprises: an antibody heavy chain comprising the amino acid sequence of SEQ ID NO:7 and/or an antibody light chain comprising the amino acid sequence of SEQ ID NO:8. In some embodiments, a binding protein of the present disclosure comprises an antibody heavy chain comprising the amino acid sequence of SEQ ID NO: 19 and/or an antibody light chain comprising the amino acid sequence of SEQ ID NO:20. In some embodiments, a binding protein of the present disclosure comprises an antibody heavy chain comprising the amino acid sequence of SEQ ID NO:22 and/or an antibody light chain comprising the amino acid sequence of SEQ ID NO:20. In some embodiments, a binding protein of the present disclosure comprises an antibody heavy chain comprising the amino acid sequence of SEQ ID NO:24 and/or an antibody light chain comprising the amino acid sequence of SEQ ID NO:20. In some embodiments, a binding protein of the present disclosure comprises an antibody heavy chain comprising the amino acid sequence of SEQ ID NO: 15 and/or an antibody light chain comprising the amino acid sequence of SEQ ID NO: 16.

In some embodiments, a binding protein of the present disclosure comprises an antibody heavy chain comprising the amino acid sequence of SEQ ID NO:7 and an antibody light chain comprising the amino acid sequence of SEQ ID NO: 8. In some embodiments, a binding protein of the present disclosure comprises an antibody heavy chain comprising the amino acid sequence of SEQ ID NO: 19 and an antibody light chain comprising the amino acid sequence of SEQ ID NO:20. In some embodiments, a binding protein of the present disclosure comprises an antibody heavy chain comprising the amino acid sequence of SEQ ID NO:22 and an antibody light chain comprising the amino acid sequence of SEQ ID NO:20. In some embodiments, a binding protein of the present disclosure comprises an antibody heavy chain comprising the amino acid sequence of SEQ ID NO:24 and an antibody light chain comprising the amino acid sequence of SEQ ID NO:20. In some embodiments, a binding protein of the present disclosure comprises an antibody heavy chain comprising the amino acid sequence of SEQ ID NO: 15 and an antibody light chain comprising the amino acid sequence of SEQ ID NO: 16.

In some embodiments, a binding site that binds CD38 comprises: an antibody heavy chain variable (VH) domain comprising a CDR-H1 sequence comprising the amino acid sequence of GFTFSSYG (SEQ ID NO:41), a CDR-H2 sequence comprising the amino acid sequence of IWYDG-SNK (SEQ ID NO:42), and a CDR-H3 sequence comprising the amino acid sequence of ARMFRGAFDY (SEQ ID NO:43); and/or an antibody light chain variable (VL) domain comprising a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, a binding site that binds CD38 comprises: an antibody heavy chain variable (VH) domain comprising a CDR-H1 sequence comprising the amino acid sequence of GFTFSSYG (SEQ ID NO:41), a CDR-H2 sequence comprising the amino acid sequence of IWYDG-SNK (SEQ ID NO:42), and a CDR-H3 sequence comprising the amino acid sequence of ARMFRGAFDY (SEQ ID NO:43); and an antibody light chain variable (VL) domain comprising a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46).

In some embodiments, the VH domain comprises the sequence, from N-terminus to C-terminus, FR1-CDR-H1-FR2-CDR-H2-FR3-CDR-H3-FR4; where FR1 comprises the sequence QVQLVESGGGVVQPGRSLRLSCAAS (SEQ ID NO:89); where FR2 comprises the sequence MHWVRQAPGKGLEWVAV (SEQ ID NO:92); where FR3 comprises the sequence YYADSVKGRFTISGDNSKNT-LYLQMNSLRAEDTAVYYC (SEQ ID NO:95); and where FR4 comprises the sequence WGQGTLVTVSS (SEQ ID NO:96). In some embodiments, the VL domain comprises the sequence, from N-terminus to C-terminus, FR1-CDR-L1-FR2-CDR-L2-FR3-CDR-L3-FR4; where FR1 comprises the sequence AIQMTQSPSSLSASVGDRVTIT-CRAS (SEQ ID NO:98); where FR2 comprises the sequence GWYQQKPGKAPKLLIY (SEQ ID NO: 100); where FR3 comprises the sequence SLQSGVPSRFSGSGSGTDFTLTISGLQPEDSATYYC (SEQ ID NO:102); and where FR4 comprises the sequence WGQGTLVTVSS (SEQ ID NO: 104).

In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:9; and/or the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 10.

In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:9; and the VL domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 10. In some embodiments, the VH domain comprises the amino acid sequence of SEQ ID NO:9; and the VL domain comprises the amino acid sequence of SEQ ID NO: 10.

In some embodiments, a binding protein of the present disclosure comprises an antibody heavy chain comprising the amino acid sequence of SEQ ID NO: 11 or an antibody light chain comprising the amino acid sequence of SEQ ID NO: 12. In some embodiments, a binding protein of the present disclosure comprises an antibody heavy chain comprising the amino acid sequence of SEQ ID NO: 11 and an antibody light chain comprising the amino acid sequence of SEQ ID NO: 12.

Anti-CD28 Binding Sites

Certain aspects of the present disclosure relate to binding proteins that comprise an antigen binding site that binds a CD28 polypeptide (e.g., a human CD28 polypeptide).

In some embodiments, a binding site that binds CD28 comprises: an antibody heavy chain variable (VH) domain comprising a CDR-H1 sequence comprising the amino acid sequence of GYTFTSYY (SEQ ID NO: 108), a CDR-H2 sequence comprising the amino acid sequence of IYPGNVNT (SEQ ID NO: 109), and a CDR-H3 sequence comprising the amino acid sequence of TRSHY-GLDWNFDV (SEQ ID NO: 110) and/or an antibody light chain variable (VL) domain comprising a CDR-L1 sequence comprising the amino acid sequence of QNIYVW (SEQ ID NO: 111), a CDR-L2 sequence comprising the amino acid sequence of KAS (SEQ ID NO: 112), and a CDR-L3 sequence comprising the amino acid sequence of QQGQ-TYPY (SEQ ID NO:113). In some embodiments, a binding site that binds CD28 comprises: an antibody heavy chain variable (VH) domain comprising a CDR-H1 sequence comprising the amino acid sequence of GYTFTSYY (SEQ ID NO: 108), a CDR-H2 sequence comprising the amino acid sequence of IYPGNVNT (SEQ ID NO: 109), and a CDR-H3 sequence comprising the amino acid sequence of TRSHYGLDWNFDV (SEQ ID NO: 110) and an antibody light chain variable (VL) domain comprising a CDR-L1 sequence comprising the amino acid sequence of QNIYVW (SEQ ID NO: 111), a CDR-L2 sequence comprising the amino acid sequence of KAS (SEQ ID NO: 112), and a CDR-L3 sequence comprising the amino acid sequence of QQGQTYPY (SEQ ID NO: 113).

In some embodiments, a binding site that binds CD28 comprises: an antibody heavy chain variable (VH) domain comprising a CDR-H1 sequence comprising the amino acid sequence of GFSLSDYG (SEQ ID NO: 114), a CDR-H2 sequence comprising the amino acid sequence of IWAGGGT (SEQ ID NO: 115), and a CDR-H3 sequence comprising the amino acid sequence of ARDKGYSYYYSMDY (SEQ ID NO: 116) and/or an antibody light chain variable (VL) domain comprising a CDR-L1 sequence comprising the amino acid sequence of ESVEYYVTSL (SEQ ID NO: 117), a CDR-L2 sequence comprising the amino acid sequence of AAS (SEQ ID NO: 118), and a CDR-L3 sequence comprising the amino acid sequence of QQSRKVPYT (SEQ ID NO:119). In some embodiments, a binding site that binds CD28 comprises: an antibody heavy chain variable (VH) domain comprising a CDR-H1 sequence comprising the amino acid sequence of GFSLSDYG (SEQ ID NO: 114), a CDR-H2 sequence comprising the amino acid sequence of IWAGGGT (SEQ ID NO: 115), and a CDR-H3 sequence comprising the amino acid sequence of ARDKGYSYYYSMDY (SEQ ID NO: 116) and an antibody light chain variable (VL) domain comprising a CDR-L1 sequence comprising the amino acid sequence of ESVEYYVTSL (SEQ ID NO: 117), a CDR-L2 sequence comprising the amino acid sequence of AAS (SEQ ID NO: 118), and a CDR-L3 sequence comprising the amino acid sequence of QQSRKVPYT (SEQ ID NO: 119).

Anti-CD3 Binding Sites

Certain aspects of the present disclosure relate to binding proteins that comprise an antigen binding site that binds a CD3 polypeptide (e.g., a human CD3 polypeptide).

In some embodiments, a binding site that binds CD3 comprises: an antibody heavy chain variable (VH) domain comprising a CDR-H1 sequence comprising the amino acid sequence of GFTFTKAW (SEQ ID NO: 120), a CDR-H2 sequence comprising the amino acid sequence of IKDKSNSYAT (SEQ ID NO: 121), and a CDR-H3 sequence comprising the amino acid sequence of RGVYYALSPFDY (SEQ ID NO:122) and/or an antibody light chain variable (VL) domain comprising a CDR-L1 sequence comprising the amino acid sequence of QSLVHNNANTY (SEQ ID NO: 123), a CDR-L2 sequence comprising the amino acid sequence of KVS (SEQ ID NO: 124), and a CDR-L3 sequence comprising the amino acid sequence of GQGTQYPFT (SEQ ID NO: 125). In some embodiments, a binding site that binds CD3 comprises: an antibody heavy chain variable (VH) domain comprising a CDR-H1 sequence comprising the amino acid sequence of GFTFTKAW (SEQ ID NO: 120), a CDR-H2 sequence comprising the amino acid sequence of IKDKSNSYAT (SEQ ID NO: 121), and a CDR-H3 sequence comprising the amino acid sequence of RGVYYALSPFDY (SEQ ID NO: 122) and an antibody light chain variable (VL) domain comprising a CDR-L1 sequence comprising the amino acid sequence of QSLVHNNANTY (SEQ ID NO: 123), a CDR-L2 sequence comprising the amino acid sequence of KVS (SEQ ID NO: 124), and a CDR-L3 sequence comprising the amino acid sequence of GQGTQYPFT (SEQ ID NO: 125).

In some embodiments, a binding site that binds CD3 comprises: an antibody heavy chain variable (VH) domain comprising a CDR-H1 sequence comprising the amino acid sequence of GFTFTKAW (SEQ ID NO: 126), a CDR-H2 sequence comprising the amino acid sequence of IKDKSNSYAT (SEQ ID NO: 127), and a CDR-H3 sequence comprising the amino acid sequence of GVYYALSPFDY (SEQ ID NO: 128) and/or an antibody light chain variable (VL) domain comprising a CDR-L1 sequence comprising the amino acid sequence of QSLVHNNGNTY (SEQ ID NO: 129), a CDR-L2 sequence comprising the amino acid sequence of KVS (SEQ ID NO: 130), and a CDR-L3 sequence comprising the amino acid sequence of GQGTQYPFT (SEQ ID NO: 131).

In some embodiments of any of the trispecific binding proteins of the present disclosure, one antigen binding domain binds to a CD3 polypeptide (e.g., human CD3) and one antigen binding domain binds to a CD28 polypeptide (e.g., human CD28). In some embodiments, the $V_{H1}$ domain comprises three CDRs from SEQ ID NOs:49 or 51 as shown in Table H, and the $V_{L1}$ domain comprises three CDRs from SEQ ID NOs:50 or 52 as shown in Table H. In some embodiments, the $V_{H2}$ domain comprises three CDRs from SEQ ID NOs:49 or 51 as shown in Table H, and the $V_{L2}$ domain comprises three CDRs from SEQ ID NOs:50 or 52 as shown in Table H. In some embodiments, the $V_{H1}$ domain comprises three CDRs from SEQ ID NOs:53 or 84 as shown in Table H, and the $V_{L1}$ domain comprises three CDRs from SEQ ID NOs:54 or 85 as shown in Table H. In some embodiments, the $V_{H2}$ domain comprises three CDRs from SEQ ID NOs:53 or 84 as shown in Table H, and the $V_{L2}$ domain comprises three CDRs from SEQ ID NOs:54 or 85 as shown in Table H.

In some embodiments, the $V_{H1}$ domain comprises the amino acid sequence of SEQ ID NO:49, the $V_{L1}$ domain comprises the amino acid sequence of SEQ ID NO:50, the $V_{H2}$ domain comprises the amino acid sequence of SEQ ID NO:53, and the $V_{L2}$ domain comprises the amino acid sequence of SEQ ID NO:54. In some embodiments, the $V_{H2}$ domain comprises the amino acid sequence of SEQ ID NO:49, the $V_{L2}$ domain comprises the amino acid sequence of SEQ ID NO:50, the $V_{H1}$ domain comprises the amino acid sequence of SEQ ID NO:53, and the $V_{L1}$ domain comprises the amino acid sequence of SEQ ID NO:54. In some embodiments, the $V_{H1}$ domain comprises the amino acid sequence of SEQ ID NO:51, the $V_{L1}$ domain comprises the amino acid sequence of SEQ ID NO:52, the $V_{H2}$ domain comprises the amino acid sequence of SEQ ID NO:53, and the $V_{L2}$ domain comprises the amino acid sequence of SEQ ID NO:54. In some embodiments, the $V_{H2}$ domain comprises the amino acid sequence of SEQ ID NO:51, the $V_{L2}$ domain comprises the amino acid sequence of SEQ ID NO:52, the $V_{H1}$ domain comprises the amino acid sequence of SEQ ID NO:53, and the $V_{L1}$ domain comprises the amino acid sequence of SEQ ID NO:54.

In some embodiments, the $V_{H1}$ domain comprises the amino acid sequence of SEQ ID NO:49, the $V_{L1}$ domain comprises the amino acid sequence of SEQ ID NO:50, the $V_{H2}$ domain comprises the amino acid sequence of SEQ ID NO:53, the $V_{L2}$ domain comprises the amino acid sequence of SEQ ID NO:54, the $V_{H3}$ domain comprises the amino acid sequence of SEQ ID NO: 13, and the $V_{L3}$ domain comprises the amino acid sequence of SEQ ID NO: 14. In some embodiments, the $V_{H1}$ domain comprises the amino acid sequence of SEQ ID NO:49, the $V_{L1}$ domain comprises the amino acid sequence of SEQ ID NO:50, the $V_{H2}$ domain comprises the amino acid sequence of SEQ ID NO:53, the $V_{L2}$ domain comprises the amino acid sequence of SEQ ID NO:54, the $V_{H3}$ domain comprises the amino acid sequence of SEQ ID NO:9, and the $V_{L3}$ domain comprises the amino acid sequence of SEQ ID NO:10.

In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:60, the third polypeptide chain comprises a polypeptide sequence that is at least 95% identical to the amino acid sequence of SEQ ID NO:62, and the fourth polypeptide chain comprises a polypeptide sequence that is at least 95% identical to the amino acid sequence of SEQ ID NO:63. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:64, the third polypeptide chain comprises a polypeptide sequence that is at least 95% identical to the amino acid sequence of SEQ ID NO:65, and the fourth polypeptide chain comprises a polypeptide sequence that is at least 95% identical to the amino acid sequence of SEQ ID NO:63. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:66, the third polypeptide chain comprises a polypeptide sequence that is at least 95% identical to the amino acid sequence of SEQ ID NO:67, and the fourth polypeptide chain comprises a polypeptide sequence that is at least 95% identical to the amino acid sequence of SEQ ID NO:63. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:60, the third polypeptide chain comprises a polypeptide sequence that is at least 95% identical to the amino acid sequence of SEQ ID NO:68, and the fourth polypeptide chain comprises a polypeptide sequence that is at least 95% identical to the amino acid sequence of SEQ ID NO:69. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:64, the third polypeptide chain comprises a polypeptide sequence that is at least 95% identical to the amino acid sequence of SEQ ID NO:70, and the fourth polypeptide chain comprises a polypeptide sequence that is at least 95% identical to the amino acid sequence of SEQ ID NO:69. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:66, the third polypeptide chain comprises a polypeptide sequence that is at least 95% identical to the amino acid sequence of SEQ ID NO:71, and the fourth polypeptide chain comprises a polypeptide sequence that is at least 95% identical to the amino acid sequence of SEQ ID NO:69.

In certain embodiments, the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:62, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:65, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:67, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:68, and the fourth polypeptide chain comprises the amino acid sequence of SEQ ID NO:69. In certain embodiments, the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:70, and the fourth polypeptide chain comprises the amino acid sequence of SEQ ID NO:69. In certain embodiments, the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:71, and the fourth polypeptide chain comprises the amino acid sequence of SEQ ID NO:69.

In some embodiments, a binding protein of the present disclosure comprises 1, 2, 3, 4, 5, or 6 CDR sequences of an antibody sequence shown in Table G. In some embodiments, a binding protein of the present disclosure comprises 1, 2, 3, 4, 5, or 6 CDR sequences, a VH domain sequence, and/or a VL domain sequence of an antibody sequence shown in Table H. In some embodiments, a binding protein of the present disclosure comprises 1, 2, 3, 4, 5, or 6 CDR sequences, a VH domain sequence, and/or a VL domain sequence of an antibody sequence shown in Table I. In some embodiments, a binding protein of the present disclosure comprises 1, 2, 3, or 4 polypeptide sequences shown in Table I.

TABLE G

CDR sequences of anti-CD38 binding proteins.

| Ab | CDR_H1 | CDR_H2 | CDR_H3 | CDR_L1 | CDR_L2 | CDR_L3 |
|---|---|---|---|---|---|---|
| antiCD38_C2-CD38-1 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| antiCD38_C2-CD38-1_VH1-VL1 | GYTFTSYA (SEQ ID NO: 37) | IYPGQGGT (SEQ ID NO: 38) | ARTGGLRRAYFTY (SEQ ID NO: 33) | QSVSSYGQGF (SEQ ID NO: 39) | GAS (SEQ ID NO: 40) | QQNKEDPWT (SEQ ID NO: 36) |

TABLE G-continued

CDR sequences of anti-CD38 binding proteins.

| Ab | CDR_H1 | CDR_H2 | CDR_H3 | CDR_L1 | CDR_L2 | CDR_L3 |
|---|---|---|---|---|---|---|
| antiCD38_C2-CD38-1_VH3-VL3 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| antiCD38_C2-CD38-1_VH5-VL3 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| antiCD38_C2-CD38-1_VH6-VL3 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| CD38$_{HHY1370}$ | GFTFSSYG (SEQ ID NO: 41) | IWYDGSNK (SEQ ID NO: 42) | ARMFRGAFDY (SEQ ID NO: 43) | QGIRND (SEQ ID NO: 44) | AAS (SEQ ID NO: 45) | LQDYIYYPT (SEQ ID NO: 46) |

TABLE H

Variable domain sequences of anti-CD38 and other binding proteins.

| Ab | VH (protein) | VL (protein) |
|---|---|---|
| antiCD38_C2-CD38-1 | QVQLQQSGAELVRSGASVKMSCKASGYTFTSFNMHWVKETPGQGLEWIGYIYPGNGGTNYNQKFKGKATLTADTSSSTAYMQISSLTSEDSAVYFCARTGGLRRAYFTYWGQGTLVTVSS (SEQ ID NO: 5) | DIVLTQSPASLAVSLGQRATISCRASESVDSYGNGFMHWYQQKPGQPPKLLIYL ASNLESGVPARFSGSGSRTDFTLTIDPVEADDAATYYCQQNKEDPWTFGGGTKLEIK (SEQ ID NO: 6) |
| antiCD38_C2-CD38-1_VH1-VL1 | QVQLVQSGAEVVKPGASVKVSCKASGYTFTSYAMHWVKEAPGQRLEWIGYIYPG QGGTNYNQKFQGRATLTADTSASTAYMELSSLRSEDTAVYFCARTGGLRRAYFTYWGQGTLVTVSS (SEQ ID NO: 13) | DIVLTQSPATLSLSPGERATISCRASQSVSSYGQGFMHWYQQKPGQPPRLLIYG ASSRATGIPARFSGSGSGTDFTLTISPLEPEDFAVYYCQQNKEDPWTFGGGTKLEIK (SEQ ID NO: 14) |
| antiCD38_C2-CD38-1_VH3-VL3 | QVQLVQSGAEVVKPGASVKVSCKASGYTFTSFNMHWVKEAPGQGLEWIGYIYPG NGGTNYNQKFQGRATLTADTSASTAYMELSSLRSEDTAVYFCARTGGLRRAYFTYWGQGTLVTVSS (SEQ ID NO: 17) | DIVLTQSPATLSLSPGERATISCRASESVDSYGNGFMHWYQQKPGQPPRLLIYL ASSRATGIPARFSGSGSGTDFTLTISPLEPEDFAVYYCQQNKEDPWTFGGGTKLEIK (SEQ ID NO: 18) |
| antiCD38_C2-CD38-1_VH5-VL3 | QVQLVQSGAEVVKSGASVKVSCKASGYTFTSFNMHWVKEAPGQGLEWIGYIYPG NGGTNYNQKFQGRATLTADTSASTAYMEISSLRSEDTAVYFCARTGGLRRAYFTYWGQGTLVTVSS (SEQ ID NO: 21) | DIVLTQSPATLSLSPGERATISCRASESVDSYGNGFMHWYQQKPGQPPRLLIYL ASSRATGIPARFSGSGSGTDFTLTISPLEPEDFAVYYCQQNKEDPWTFGGGTKLEIK (SEQ ID NO: 18) |
| antiCD38_C2-CD38-1_VH6-VL3 | QVQLVQSGAEVVKPGASVKMSCKASGYTFTSFNMHWVKEAPGQRLEWIGYIYPG NGGTNYNQKFQGRATLTADTSASTAYMEISSLRSEDTAVYFCARTGGLRRAYFTYWGQGTLVTVSS (SEQ ID NO: 23) | DIVLTQSPATLSLSPGERATISCRASESVDSYGNGFMHWYQQKPGQPPRLLIYL ASSRATGIPARFSGSGSGTDFTLTISPLEPEDFAVYYCQQNKEDPWTFGGGTKLEIK (SEQ ID NO: 18) |
| CD38$_{HHY1370}$ | QVQLVESGGGVVQPGRSLRLSCAASGFTFSSYGMHWVRQAPGKGLEWVAVIWYD GSNKYYADSVKGRFTISGDNSKNTLYLQMNSLRAEDTAVYYCARMFRGAFDYWGQGTLVTVSS (SEQ ID NO: 9) | AIQMTQSPSSLSASVGDRVTITCRASQGIRNDLGWYQQKPGKAPKLLIYAASSL QSGVPSRFSGSGSGTDFTLTISGLQPEDSATYYCLQDYIYYPTFGQGTKVEIK (SEQ ID NO: 10) |
| antiCD38_SB19 | QVQLVQSGAEVAKPGTSVKLSCKASGYTFTDYWMQWVKQRPGQGLEWIGTIYPGDGDTGYAQKFQGKATLTADKSSSKTVYMHLSSLASEDSAVYYCARGDYYGSNLDYWGQGTSVTVSS (SEQ ID NO: 47) | DIVMTQSHLSMSTSLGDPVSITCKASQDVSTVVAWYQQKPGQSPRRLIYSASYRYIGVPDRFTGSGAGTDFFTISSVQAEDLAVYYCQQHYSPPYTFGGGTKLEIK (SEQ ID NO: 48) |
| Anti-CD28$_{sup}$ | QVQLVQSGAEVVKPGASVKVSCKASGYTFTSYYIHWVRQAPGQGLEWIGSIYPG NVNTNYAQKFQGRATLTVDTSISTAYMELSRLRSDDTAVYYCTRSHYGLDWNFD VWGKGTTVTVSS (SEQ ID NO: 49) | DIQMTQSPSSLSASVGDRVTITCQASQNIYVWLNWYQQKPGKAPKLLIYKASNLHTGVPSRFSGSGSGTDFTLTISSLQPEDIATYYCQQ GQTYPYTFGQGTKLEIK (SEQ ID NO: 50) |
| Anti-CD28$_{cvn}$ | QVQLQESGPGLVKPSQTLSLTCTVSGFSLSDYGVHWVRQPPGKGLEWLGVIWAG GGTNYNPSLKSRKTISKDTSKNQVSLKLSSVTAADTAVYYCARDKGYSYYYSMD YWGQGTTVTVSS (SEQ ID NO: 51) | DIVLTQSPASLAVSPGQRATITCRASESVEYYVTSLMQWYQQKPGQPPKLLIFA ASNVESGVPARFSGSGSGTDFTLTINPVEANDVANYYCQQSRKVPYTFGQGTKLEIK (SEQ ID NO: 52) |
| Anti-CD3$_{mid}$ | QVQLVESGGGVVQPGRSLRLSCAASGFTFTKAWMHWVRQAPGKQLEWVAQIKDK SNSYATYYADSVKGRFTISRDDSKNTLYLQMNSLRAEDTAVYYCRGVYYALSPF DYWGQGTLVTVSS (SEQ ID NO: 53) | DIVMTQTPLSLSVTPGQPASISCKSSQSLVHNNANTYLSWYLQKPGQSPQSLIYKVSNRFSGVPDRFSGSGSGTDFTLKISRVEAEDVGVYYCGQGTQYPFTFGSGTKVEIK (SEQ ID NO: 54) |

TABLE H-continued

Variable domain sequences of anti-CD38 and other binding proteins.

| Ab | VH (protein) | VL (protein) |
|---|---|---|
| Anti-CD3$_{low}$ | QVQLVESGGGVVQPGRSLRLSCAASGFTFTKAWMHWVRQAPGKGLEWVAQIKDKSNSYATYYADSVKGRFTISRDNSKNTLYLQMNSLRAEDTAVYYCRGVYYALSPFDYWGQGTLVTVSS (SEQ ID NO: 84) | DIVMTQTPLSLSVTPGQPASISCKSSQSLVHNNGNTYLSWYLQKPGQSPQLLIYKVSNRFSGVPDRFSGSGSGTDFTLKISRVEAEDVGVYYCGQGTQYPFTFGGGTKVEIK (SEQ ID NO: 85) |

Note:
CDR sequences are bolded and underlined in amino acid sequences above.

TABLE I

Full-length sequences of binding proteins.

antiCD38_C2-CD38-1_VH1-VL1xCD28supxCD3mid IgG4 FALA

| | | |
|---|---|---|
| CD28supxCD3mid IgG4(hole) FALA Heavy Chain 1 (e.g., a second polypeptide chain of a trispecific binding protein of the present disclosure) | QVQLVQSGAEVVKPGASVKVSCKASGYTFTSYYIHWVRQAPGQGLEWIGSIYPGNVNTNYAQKFQGRATLTVDTSISTAYMELSRLRSDDTAVYYCTRSHYGLDWNFDVWGKGTTVTVSSSQVQLVESGGGVVQPGRSLRLSCAASGFTFTKAWMHWVRQAPGKQLEWVAQIKDKSNSYATYYADSVKGRFTISRDDSKNTLYLQMNSLRAEDTAVYYCRGVYYALSPFDYWGQGTLVTVSSRTASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVCTLPPSQEEMTKNQVSLSCAVKGFYPSDIAVEWESNGQPENNYKTTPPVLDSDGSFFLVSKLTVDKSRWQEGNVFSCSVMHEALHNHYTQKSLSLSLG | SEQ ID NO: 60 |
| CD28supxCD3mid Light Chain 1 (e.g., a first polypeptide chain of a trispecific binding protein of the present disclosure) | DIVMTQTPLSLSVTPGQPASISCKSSQSLVHNNANTYLSWYLQKPGQSPQSLIYKVSNRFSGVPDRFSGSGSGTDFTLKISRVEAEDVGVYYCGQGTQYPFTFGSGTKVEIKGQPKAAPDIQMTQSPSSLSASVGDRVTITCQASQNIYVWLNWYQQKPGKAPKLLIYKASNLHTGVPSRFSGSGSGTDFTLTISSLQPEDIATYYCQQGQTYPYTFGQGTKLEIKTKGPSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 61 |
| antiCD38_C2-CD38-1_VH1-VL1 IgG4(knob) FALA Heavy Chain 2 (e.g., a third polypeptide chain of a trispecific binding protein of the present disclosure) | QVQLVQSGAEVVKPGASVKVSCKASGYTFTSYAMHWVKEAPGQRLEWIGYIYPGQGTNYNQKFQGRATLTADTSASTAYMELSSLRSEDTAVYFCARTGGLRRAYFTYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPCQEEMTKNQVSLWCLVKGFYPSDIAVEWESNGQPENNYKTTPPVLDSDGSFFLYSKLTVDKSRWQEGNVFSCSVMHEALHNHYTQKSLSLSLG | SEQ ID NO: 62 |
| antiCD38_C2-CD38-1_VH1-VL1 Light Chain 2 (e.g., a fourth polypeptide chain of a trispecific binding | DIVLTQSPATLSLSPGERATISCRASQSVSSYGQGFMHWYQQKPGQPPRLLIYGASSRATGIPARFSGSGSGTDFTLTISPLEPEDFAVYYCQQNKEDPWTFGGGTKLEIKRTVAAPSVFIFPP | SEQ ID NO: 63 |

TABLE I-continued

Full-length sequences of binding proteins.

| | | |
|---|---|---|
| protein of the present disclosure) | SDEQLKSGTASVVCLLNNFYPREAKVQWK VDNALQSGNSQESVTEQDSKDSTYSLSSTL TLSKADYEKHKVYACEVTHQGLSSPVTKSF NRGEC | | antiCD38_C2-CD38-1_VH1-VL1xCD28supxCD3mid IgG1LALA P329A

| | | |
|---|---|---|
| CD28supxCD3mid IgG1(hole) LALA P329A Heavy Chain 1 (e.g., a second polypeptide chain of a trispecific binding protein of the present disclosure) | QVQLVQSGAEVVKPGASVKVSCKASGYTF TSYYIHWVRQAPGQGLEWIGSIYPGNVNTN YAQKFQGRATLTVDTSISTAYMELSRLRSD DTAVYYCTRSHYGLDWNFDVWGKGTTVT VSSSQVQLVESGGGVVQPGRSLRLSCAASG FTFTKAWMHWVRQAPGKQLEWVAQIKDK SNSYATYYADSVKGRFTISRDDSKNTLYLQ MNSLRAEDTAVYYCRGVYYALSPFDYWG QGTLVTVSSRTASTKGPSVFPLAPSSKSTSG GTAALGCLVKDYFPEPVTVSWNSGALTSG VHTFPAVLQSSGLYSLSSVVTVPSSSLGTQT YICNVNHKPSNTKVDKKVEPKSCDKTHTCP PCPAPEAAGGPSVFLFPPKPKDTLMISRTPE VTCVVVDVSHEDPEVKFNWYVDGVEVHN AKTKPREEQYNSTYRVVSVLTVLHQDWLN GKEYKCKVSNKALAAPIEKTISKAKGQPRE PQVCTLPPSRDELTKNQVSLSCAVKGFYPS DIAVEWESNGQPENNYKTTPPVLDSDGSFF LVSKLTVDKSRWQQGNVFSCSVMHEALHN HYTQKSLSLSPG | SEQ ID NO: 64 |
| CD28supxCD3mid Light Chain 1 (e.g., a first polypeptide chain of a trispecific binding protein of the present disclosure) | See above. | SEQ ID NO: 61 |
| antiCD38_C2-CD38-1_VH1- VL1 IgG1(knob) LALA P329A Heavy Chain 2 (e.g., a third polypeptide chain of a trispecific binding protein of the present disclosure) | QVQLVQSGAEVVKPGASVKVSCKASGYTF TSYAMHWVKEAPGQRLEWIGYIYPGQGGT NYNQKFQGRATLTADTSASTAYMELSSLRS EDTAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPEAAG GPSVFLFPPKPKDTLMISRTPEVTCVVVDVS HEDPEVKFNWYVDGVEVHNAKTKPREEQY NSTYRVVSVLTVLHQDWLNGKEYKCKVSN KALAAPIEKTISKAKGQPREPQVYTLPPCRD ELTKNQVSLWCLVKGFYPSDIAVEWESNG QPENNYKTTPPVLDSDGSFFLYSKLTVDKS RWQQGNVFSCSVMHEALHNHYTQKSLSLS PG | SEQ ID NO: 65 |
| antiCD38_C2-CD38-1_VH1- VL1 Light Chain 2 (e.g., a fourth polypeptide chain of a trispecific binding protein of the present disclosure) | See above. | SEQ ID NO: 63 | antiCD38_C2-CD38-1_VH1-VL1xCD28supxCD3mid IgG1 NNSA

| | | |
|---|---|---|
| CD28supxCD3mid IgG1(hole) NNSA Heavy Chain 1 (e.g., a second polypeptide chain of a trispecific binding protein of the present disclosure) | QVQLVQSGAEVVKPGASVKVSCKASGYTF TSYYIHWVRQAPGQGLEWIGSIYPGNVNTN YAQKFQGRATLTVDTSISTAYMELSRLRSD DTAVYYCTRSHYGLDWNFDVWGKGTTVT VSSSQVQLVESGGGVVQPGRSLRLSCAASG FTFTKAWMHWVRQAPGKQLEWVAQIKDK SNSYATYYADSVKGRFTISRDDSKNTLYLQ MNSLRAEDTAVYYCRGVYYALSPFDYWG QGTLVTVSSRTASTKGPSVFPLAPSSKSTSG GTAALGCLVKDYFPEPVTVSWNSGALTSG VHTFPAVLQSSGLYSLSSVVTVPSSSLGTQT YICNVNHKPSNTKVDKKVEPKSCDKTHTCP PCPAPELLGGPSVFLFPPKPKDTLMISRTPEV TCVVVDVSHEDPEVKFNWYVDGVEVHNA KTKPREEQYNNASRVVSVLTVLHQDWLNG KEYKCKVSNKALPAPIEKTISKAKGQPREPQ VCTLPPSRDELTKNQVSLSCAVKGFYPSDIA | SEQ ID NO: 66 |

TABLE I-continued

Full-length sequences of binding proteins.

| | | |
|---|---|---|
| | VEWESNGQPENNYKTTPPVLDSDGSFFLVS KLTVDKSRWQQGNVFSCSVMHEALHNHY TQKSLSLSPG | |
| CD28supxCD3mid Light Chain 1 (e.g., a first polypeptide chain of a trispecific binding protein of the present disclosure) | See above. | SEQ ID NO: 61 |
| antiCD38_C2-CD38-1_VH1-VL1 IgG1(knob) NNSA Heavy Chain 2 (e.g., a third polypeptide chain of a trispecific binding protein of the present disclosure) | QVQLVQSGAEVVKPGASVKVSCKASGYTF TSYAMHWVKEAPGQRLEWIGYIYPGQGGT NYNQKFQGRATLTADTSASTAYMELSSLRS EDTAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPELLG GPSVFLFPPKPKDTLMISRTPEVTCVVVDVS HEDPEVKFNWYVDGVEVHNAKTKPREEQY NNASRVVSVLTVLHQDWLNGKEYKCKVS NKALPAPIEKTISKAKGQPREPQVYTLPPCR DELTKNQVSLWCLVKGFYPSDIAVEWESN GQPENNYKTTPPVLDSDGSFFLYSKLTVDK SRWQQGNVFSCSVMHEALHNHYTQKSLSL SPG | SEQ ID NO: 67 |
| CD38VH1 Light Chain 2 (e.g., a fourth polypeptide chain of a trispecific binding protein of the present disclosure) | See above. | SEQ ID NO: 63 |
| CD38$_{HHY1370}$xCD28supxCD3mid IgG4 FALA | | |
| CD28supxCD3mid IgG4(hole) FALA Heavy Chain 1 (e.g., a second polypeptide chain of a trispecific binding protein of the present disclosure) | See above. | SEQ ID NO: 60 |
| CD28supxCD3mid Light Chain 1 (e.g., a first polypeptide chain of a trispecific binding protein of the present disclosure) | See above. | SEQ ID NO: 61 |
| CD38$_{HHY1370}$ IgG4(knob) FALA Heavy Chain 2 (e.g., a third polypeptide chain of a trispecific binding protein of the present disclosure) | QVQLVESGGGVVQPGRSLRLSCAASGFTFS SYGMHWVRQAPGKGLEWVAVIWYDGSNK YYADSVKGRFTISGDNSKNTLYLQMNSLRA EDTAVYYCARMFRGAFDYWGQGTLVTVSS ASTKGPSVFPLAPCSRSTSESTAALGCLVKD YFPEPVTVSWNSGALTSGVHTFPAVLQSSG LYSLSSVVTVPSSSLGTKTYTCNVDHKPSNT KVDKRVESKYGPPCPPCPAPEAAGGPSVFL FPPKPKDTLMISRTPEVTCVVVDVSQEDPEV QFNWYVDGVEVHNAKTKPREEQFNSTYRV VSVLTVLHQDWLNGKEYKCKVSNKGLPSSI EKTISKAKGQPREPQVYTLPPCQEEMTKNQ VSLWCLVKGFYPSDIAVEWESNGQPENNY KTTPPVLDSDGSFFLYSKLTVDKSRWQEGN VFSCSVMHEALHNHYTQKSLSLSLG | SEQ ID NO: 68 |
| CD38$_{HHY1370}$ Light2 (e.g., a fourth polypeptide chain of a trispecific binding protein of the present disclosure) | AIQMTQSPSSLSASVGDRVTITCRASQGIRN DLGWYQQKPGKAPKLLIYAASSLQSGVPSR FSGSGSGTDFTLTISGLQPEDSATYYCLQDY IYYPTFGQGTKVEIKRTVAAPSVFIFPPSDEQ LKSGTASVVCLLNNFYPREAKVQWKVDNA LQSGNSQESVTEQDSKDSTYSLSSTLTLSKA DYEKHKVYACEVTHQGLSSPVTKSFNRGE C | SEQ ID NO: 69 |

TABLE I-continued

Full-length sequences of binding proteins.

CD38<sub>HHY1370</sub> xCD28supxCD3mid IgG1LALA P329A

| Name | Sequence | SEQ ID |
|---|---|---|
| CD28supxCD3mid IgG1(hole) LALA P329A Heavy Chain 1 (e.g., a second polypeptide chain of a trispecific binding protein of the present disclosure) | See above. | SEQ ID NO: 64 |
| CD28supxCD3mid Light Chain 1 (e.g., a first polypeptide chain of a trispecific binding protein of the present disclosure) | See above. | SEQ ID NO: 61 |
| CD38<sub>HHY1370</sub> IgG1(knob) LALA P329A Heavy Chain 2 (e.g., a third polypeptide chain of a trispecific binding protein of the present disclosure) | QVQLVESGGGVVQPGRSLRLSCAASGFTFS SYGMHWVRQAPGKGLEWVAVIWYDGSNK YYADSVKGRFTISGDNSKNTLYLQMNSLRA EDTAVYYCARMFRGAFDYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPSN TKVDKKVEPKSCDKTHTCPPCPAPEAAGGP SVFLFPPKPKDTLMISRTPEVTCVVVDVSHE DPEVKFNWYVDGVEVHNAKTKPREEQYNS TYRVVSVLTVLHQDWLNGKEYKCKVSNK ALAAPIEKTISKAKGQPREPQVYTLPPCRDE LTKNQVSLWCLVKGFYPSDIAVEWESNGQ PENNYKTTPPVLDSDGSFFLYSKLTVDKSR WQQGNVFSCSVMHEALHNHYTQKSLSLSP G | SEQ ID NO: 70 |
| CD38<sub>HHY1370</sub>Light2 (e.g., a fourth polypeptide chain of a trispecific binding protein of the present disclosure) | See above. | SEQ ID NO: 69 |

CD38<sub>HHY1370</sub>xCD28supxCD3mid IgG1 NNSA

| Name | Sequence | SEQ ID |
|---|---|---|
| CD28supxCD3mid IgG1(hole) NNSA Heavy Chain 1 (e.g., a second polypeptide chain of a trispecific binding protein of the present disclosure) | See above. | SEQ ID NO: 66 |
| CD28supxCD3mid Light Chain 1 (e.g., a first polypeptide chain of a trispecific binding protein of the present disclosure) | See above. | SEQ ID NO: 61 |
| CD38<sub>HHY1370</sub> IgG1(knob) NNSA Heavy Chain 2 (e.g., a third polypeptide chain of a trispecific binding protein of the present disclosure) | QVQLVESGGGVVQPGRSLRLSCAASGFTFS SYGMHWVRQAPGKGLEWVAVIWYDGSNK YYADSVKGRFTISGDNSKNTLYLQMNSLRA EDTAVYYCARMFRGAFDYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPSN TKVDKKVEPKSCDKTHTCPPCPAPELLGGP SVFLFPPKPKDTLMISRTPEVTCVVVDVSHE DPEVKFNWYVDGVEVHNAKTKPREEQYN NASRVVSVLTVLHQDWLNGKEYKCKVSN KALPAPIEKTISKAKGQPREPQVYTLPPCRD ELTKNQVSLWCLVKGFYPSDIAVEWESNG QPENNYKTTPPVLDSDGSFFLYSKLTVDKS RWQQGNVFSCSVMHEALHNHYTQKSLSLS PG | SEQ ID NO: 71 |

TABLE I-continued

Full-length sequences of binding proteins.

| | | |
|---|---|---|
| CD38<sub>HHY1370</sub> Light2 (e.g., a fourth polypeptide chain of a trispecific binding protein of the present disclosure) | See above. | SEQ ID NO: 69 | antiCD38_C2-CD38-1 monovalent antibody

| | | |
|---|---|---|
| antiCD38_C2-CD38-1 heavy chain | QVQLQQSGAELVRSGASVKMSCKASGYTF TSFNMHWVKETPGQGLEWIGYIYPGNGGT NYNQKFKGKATLTADTSSSTAYMQISSLTS EDSAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPELLA GPDVFLFPPKPKDTLMISRTPEVTCVVVDVS HEDPEVKFNWYVDGVEVHNAKTKPREEQY NSTYRVVSVLTVLHQDWLNGKEYKCKVSN KALPLPEEKTISKAKGQPREPQVYTLPPSRD ELTKNQVSLTCLVKGFYPSDIAVEWESNGQ PENNYKTTPPVLDSDGSFFLYSKLTVDKSR WQQGNVFSCSVMHEALHNHYTQKSLSLSP G | SEQ ID NO: 7 |
| antiCD38_C2-CD38-1 light chain | DIVLTQSPASLAVSLGQRATISCRASESVDS YGNGFMHWYQQKPGQPPKLLIYLASNLES GVPARFSGSGSRTDFTLTIDPVEADDAATY YCQQNKEDPWTFGGGTKLEIKRTVAAPSVF IFPPSDEQLKSGTASVVCLLNNFYPREAKVQ WKVDNALQSGNSQESVTEQDSKDSTYSLSS TLTLSKADYEKHKVYACEVTHQGLSSPVTK SFNRGEC | SEQ ID NO: 8 | antiCD38_C2-CD38-1_VH1-VL1 monovalent antibody

| | | |
|---|---|---|
| antiCD38_C2-CD38-1_VH1-VL1 heavy chain | QVQLVQSGAEVVKPGASVKVSCKASGYTF TSYAMHWVKEAPGQRLEWIGYIYPGQGGT NYNQKFQGRATLTADTSASTAYMELSSLRS EDTAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPELLA GPDVFLFPPKPKDTLMISRTPEVTCVVVDVS HEDPEVKFNWYVDGVEVHNAKTKPREEQY NSTYRVVSVLTVLHQDWLNGKEYKCKVSN KALPLPEEKTISKAKGQPREPQVYTLPPSRD ELTKNQVSLTCLVKGFYPSDIAVEWESNGQ PENNYKTTPPVLDSDGSFFLYSKLTVDKSR WQQGNVFSCSVMHEALHNHYTQKSLSLSP G | SEQ ID NO: 15 |
| antiCD38_C2-CD38-1_VH1-VL1 light chain | DIVLTQSPATLSLSPGERATISCRASQSVSSY GQGFMHWYQQKPGQPPRLLIYGASSRAT GIPARFSGSGSGTDFTLTISPLEPEDFAVYYC QQNKEDPWTFGGGTKLEIKRTVAAPSVF IFPPSDEQLKSGTASVVCLLNNFYPREAKVQ WKVDNALQSGNSQESVTEQDSKDSTYSLSS TLTLSKADYEKHKVYACEVTHQGLSSPVTK SFNRGEC | SEQ ID NO: 16 | antiCD38_C2-CD38-1_VH3-VL3 monovalent antibody

| | | |
|---|---|---|
| antiCD38_C2-CD38-1_VH3-VL3 heavy chain | QVQLVQSGAEVVKPGASVKVSCKASGYTF TSFNMHWVKEAPGQRLEWIGYIYPGNGGT NYNQKFQGRATLTADTSASTAYMELSSLRS EDTAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPELLA GPDVFLFPPKPKDTLMISRTPEVTCVVVDVS HEDPEVKFNWYVDGVEVHNAKTKPREEQY NSTYRVVSVLTVLHQDWLNGKEYKCKVSN KALPLPEEKTISKAKGQPREPQVYTLPPSRD ELTKNQVSLTCLVKGFYPSDIAVEWESNGQ | SEQ ID NO: 19 |

TABLE I-continued

Full-length sequences of binding proteins.

| | | |
|---|---|---|
| | PENNYKTTPPVLDSDGSFFLYSKLTVDKSR WQQGNVFSCSVMHEALHNHYTQKSLSLSP G | |
| antiCD38_C2-CD38-1_VH3-VL3 light chain | DIVLTQSPATLSLSPGERATISCRASESVDSY GNGFMHWYQQKPGQPPRLLIYLASSRAT GIPARFSGSGSGTDFTLTISPLEPEDFAVYYC QQNKEDPWTFGGGTKLEIKRTVAAPSVF IFPPSDEQLKSGTASVVCLLNNFYPREAKVQ WKVDNALQSGNSQESVTEQDSKDSTYSLSS TLTLSKADYEKHKVYACEVTHQGLSSPVTK SFNRGEC | SEQ ID NO: 20 | antiCD38_C2-CD38-1_VH5-VL3 monovalent antibody

| | | |
|---|---|---|
| antiCD38_C2-CD38-1_VH5-VL3 heavy chain | QVQLVQSGAEVVKSGASVKVSCKASGYTF TSFNMHWVKEAPGQGLEWIGYIYPGNGGT NYNQKFQGRATLTADTSASTAYMEISSLRS EDTAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPELLA GPDVFLFPPKPKDTLMISRTPEVTCVVVDVS HEDPEVKFNWYVDGVEVHNAKTKPREEQY NSTYRVVSVLTVLHQDWLNGKEYKCKVSN KALPLPEEKTISKAKGQPREPQVYTLPPSRD ELTKNQVSLTCLVKGFYPSDIAVEWESNGQ PENNYKTTPPVLDSDGSFFLYSKLTVDKSR WQQGNVFSCSVMHEALHNHYTQKSLSLSP G | SEQ ID NO: 22 |
| antiCD38_C2-CD38-1_VH5-VL3 light chain | DIVLTQSPATLSLSPGERATISCRASESVDSY GNGFMHWYQQKPGQPPRLLIYLASSRAT GIPARFSGSGSGTDFTLTISPLEPEDFAVYYC QQNKEDPWTFGGGTKLEIKRTVAAPSVF IFPPSDEQLKSGTASVVCLLNNFYPREAKVQ WKVDNALQSGNSQESVTEQDSKDSTYSLSS TLTLSKADYEKHKVYACEVTHQGLSSPVTK SFNRGEC | SEQ ID NO: 20 | antiCD38_C2-CD38-1_VH6-VL3 monovalent antibody

| | | |
|---|---|---|
| antiCD38_C2-CD38-1_VH6-VL3 heavy chain | QVQLVQSGAEVVKPGASVKMSCKASGYTF TSFNMHWVKEAPGQRLEWIGYIYPGNGGT NYNQKFQGRATLTADTSASTAYMEISSLRS EDTAVYFCARTGGLRRAYFTYWGQGTLVT VSSASTKGPSVFPLAPSSKSTSGGTAALGCL VKDYFPEPVTVSWNSGALTSGVHTFPAVLQ SSGLYSLSSVVTVPSSSLGTQTYICNVNHKP SNTKVDKKVEPKSCDKTHTCPPCPAPELLA GPDVFLFPPKPKDTLMISRTPEVTCVVVDVS HEDPEVKFNWYVDGVEVHNAKTKPREEQY NSTYRVVSVLTVLHQDWLNGKEYKCKVSN KALPLPEEKTISKAKGQPREPQVYTLPPSRD ELTKNQVSLTCLVKGFYPSDIAVEWESNGQ PENNYKTTPPVLDSDGSFFLYSKLTVDKSR WQQGNVFSCSVMHEALHNHYTQKSLSLSP G | SEQ ID NO: 24 |
| antiCD38_C2-CD38-1_VH6-VL3 light chain | DIVLTQSPATLSLSPGERATISCRASESVDSY GNGFMHWYQQKPGQPPRLLIYLASSRAT GIPARFSGSGSGTDFTLTISPLEPEDFAVYYC QQNKEDPWTFGGGTKLEIKRTVAAPSVF IFPPSDEQLKSGTASVVCLLNNFYPREAKVQ WKVDNALQSGNSQESVTEQDSKDSTYSLSS TLTLSKADYEKHKVYACEVTHQGLSSPVTK SFNRGEC | SEQ ID NO: 20 |

CD38$_{HHY1370}$ monovalent antibody

| | | |
|---|---|---|
| CD38$_{HHY1370}$ heavy chain | QVQLVESGGGVVQPGRSLRLSCAASGFTFS SYGMHWVRQAPGKGLEWVAVIWYDGSNK YYADSVKGRFTISGDNSKNTLYLQMNSLRA EDTAVYYCARMFRGAFDYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPSN | SEQ ID NO: 11 |

TABLE I-continued

Full-length sequences of binding proteins.

| | | |
|---|---|---|
| | TKVDKKVEPKSCDKTHTCPPCPAPELLAGP<br>DVFLFPPKPKDTLMISRTPEVTCVVVDVSHE<br>DPEVKFNWYVDGVEVHNAKTKPREEQYNS<br>TYRVVSVLTVLHQDWLNGKEYKCKVSNK<br>ALPLPEEKTISKAKGQPREPQVYTLPPSRDE<br>LTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPG | |
| CD38$_{HHY1370}$ light chain | AIQMTQSPSSLSASVGDRVTITCRASQGIRN<br>DLGWYQQKPGKAPKLLIYAASSLQSGVPS<br>RFSGSGSGTDFTLTISGLQPEDSATYYCLQD<br>YIYYPTFGQGTKVEIKRTVAAPSVFIFPP<br>SDEQLKSGTASVVCLLNNFYPREAKVQWK<br>VDNALQSGNSQESVTEQDSKDSTYSLSSTL<br>TLSKADYEKHKVYACEVTHQGLSSPVTKSF<br>NRGEC | SEQ ID<br>NO: 12 | antiCD38_SB19 monovalent antibody

| | | |
|---|---|---|
| antiCD38_SB19 heavy chain | QVQLVQSGAEVAKPGTSVKLSCKASGYTFT<br>DYWMQWVKQRPGQGLEWIGTIYPGDGDT<br>GYAQKFQGKATLTADKSSKTVYMHLSSLA<br>SEDSAVYYCARGDYYGSNSLDYWGQGTSV<br>TVSSASTKGPSVFPLAPSSKSTSGGTAALGC<br>LVKDYFPEPVTVSWNSGALTSGVHTFPAVL<br>QSSGLYSLSSVVTVPSSSLGTQTYICNVNHK<br>PSNTKVDKKVEPKSCDKTHTCPPCPAPELL<br>GGPSVFLFPPKPKDTLMISRTPEVTCVVVDV<br>SHEDPEVKFNWYVDGVEVHNAKTKPREEQ<br>YNSTYRVVSVLTVLHQDWLNGKEYKCKVS<br>NKALPAPIEKTISKAKGQPREPQVYTLPPSR<br>DELTKNQVSLTCLVKGFYPSDIAVEWESNG<br>QPENNYKTTPPVLDSDGSFFLYSKLTVDKS<br>RWQQGNVFSCSVMHEALHNHYTQKSLSLS<br>PGK | SEQ ID<br>NO: 107 |
| antiCD38_SB19 light chain | DIVMTQSHLSMSTSLGDPVSITCKASQDVST<br>VVAWYQQKPGQSPRRLIYSASYRYIGVPDR<br>FTGSGAGTDFTFTISSVQAEDLAVYYCQQH<br>YSPPYTFGGGTKLEIKRTVAAPSVFIFPP<br>SDEQLKSGTASVVCLLNNFYPREAKVQWK<br>VDNALQSGNSQESVTEQDSKDSTYSLSSTL<br>TLSKADYEKHKVYACEVTHQGLSSPVTKSF<br>NRGEC | SEQ ID<br>NO: 106 |

TABLE J

Full-length polynucleotide sequences of binding proteins.

antiCD38_C2-CD38-1_VH1-VL1xCD28supxCD3mid IgG4 FALA

| | | |
|---|---|---|
| CD28supxCD3mid<br>IgG4(hole) FALA Heavy<br>Chain 1<br>(e.g., encoding a second<br>polypeptide chain of a<br>trispecific binding protein of<br>the present disclosure) | CAGGTGCAGCTGGTGCAGTCTGGCGCCGA<br>GGTCGTGAAACCTGGCGCCTCTGTGAAGG<br>TGTCCTGCAAGGCCAGCGGCTACACCTTT<br>ACCAGCTACTACATCCACTGGGTGCGCCA<br>GGCCCCTGGACAGGGACTGGAATGGATC<br>GGCAGCATCTACCCCGGCAACGTGAACA<br>CCAACTACGCCCAGAAGTTCCAGGGCAG<br>AGCCACCCTGACCGTGGACACCAGCATCA<br>GCACCGCCTACATGGAACTGAGCCGGCTG<br>AGAAGCGACGACACCGCCGTGTACTACT<br>GCACCCGGTCCCACTACGGCCTGGATTGG<br>AACTTCGACGTGTGGGGCAAGGGCACCA<br>CCGTGACAGTGTCTAGCAGCCAGGTGCAG<br>CTGGTGGAATCTGGCGGCGGAGTGGTGC<br>AGCCTGGCAGAAGCCTGAGACTGAGCTG<br>TGCCGCCAGCGGCTTCACCTTCACCAAGG<br>CCTGGATGCACTGGGTGCGCCAGGCCCCT<br>GGAAAGCAGCTGGAATGGGTGGCCCAGA<br>TCAAGGACAAGAGCAACAGCTACGCCAC<br>CTACTACGCCGACAGCGTGAAGGGCCGG<br>TTCACCATCAGCCGGGACGACAGCAAGA<br>ACACCCTGTACCTGCAGATGAACAGCCTG<br>CGGGCCGAGGACACCGCCGTGTACTACTG | SEQ ID<br>NO: 72 |

TABLE J-continued

Full-length polynucleotide sequences of binding proteins.

| | | |
|---|---|---|
| | TCGGGGCGTGTACTATGCCCTGAGCCCCT<br>TCGATTACTGGGGCCAGGGAACCCTCGTG<br>ACCGTGTCTAGTCGGACCGCCAGCACAAA<br>GGGCCCATCGGTGTTCCCTCTGGCCCCTT<br>GCAGCAGAAGCACCAGCGAATCTACAGC<br>CGCCCTGGGCTGCCTCGTGAAGGACTACT<br>TTCCCGAGCCCGTGACCGTGTCCTGGAAC<br>TCTGGCGCTCTGACAAGCGGCGTGCACAC<br>CTTTCCAGCCGTGCTCCAGAGCAGCGGCC<br>TGTACTCTCTGAGCAGCGTCGTGACAGTG<br>CCCAGCAGCAGCCTGGGCACCAAGACCT<br>ACACCTGTAACGTGGACCACAAGCCCAG<br>CAACACCAAGGTGGACAAGCGGGTGGAA<br>TCTAAGTACGGCCCTCCCTGCCCTCCTTG<br>CCCAGCCCCTGAAGCTGCCGGCGGACCCT<br>CCGTGTTCCTGTTCCCCCCAAAGCCCAAG<br>GACACCCTGATGATCAGCCGGACCCCCGA<br>AGTGACCTGCGTGGTGGTGGATGTGTCCC<br>AGGAAGATCCCGAGGTGCAGTTCAATTG<br>GTACGTGGACGGCGTGGAAGTGCACAAC<br>GCCAAGACCAAGCCCAGAGAGGAACAGT<br>TCAACAGCACCTACCGGGTGGTGTCCGTG<br>CTGACCGTGCTGCACCAGGACTGGCTGAA<br>CGGCAAAGAGTACAAGTGCAAGGTGTCC<br>AACAAGGGCCTGCCCAGCTCCATCGAGA<br>AAACCATCAGCAAGGCCAAGGGCCAGCC<br>CCGCGAGCCTCAAGTGTGTACCCTGCCCC<br>CTAGCCAGGAAGAGATGACCAAGAACCA<br>GGTGTCCCTGAGCTGTGCCGTGAAAGGCT<br>TCTACCCCAGCGACATTGCCGTGGAATGG<br>GAGAGCAACGGCCAGCCCGAGAACAACT<br>ACAAGACCACCCCCCCTGTGCTGGACAGC<br>GACGGCTCATTCTTCCTGGTGTCCAAGCT<br>GACCGTGGACAAGAGCCGGTGGCAGGAA<br>GGCAACGTGTTCAGCTGCTCCGTGATGCA<br>CGAGGCCCTGCACAACCACTACACCCAG<br>AAGTCCCTGTCTCTGTCCCTGGGC | |
| CD28supxCD3mid Light<br>Chain 1<br>(e.g., encoding a first<br>polypeptide chain of a<br>trispecific binding protein of<br>the present disclosure) | GACATCGTGATGACCCAGACCCCCCTGAG<br>CCTGAGCGTGACACCTGGACAGCCTGCCA<br>GCATCAGCTGCAAGAGCAGCCAGAGCCT<br>GGTGCACAACAACGCCAACACCTACCTG<br>AGCTGGTATCTGCAGAAGCCCGGCCAGA<br>GCCCCCAGTCCCTGATCTACAAGGTGTCC<br>AACAGATTCAGCGGCGTGCCCGACAGATT<br>CTCCGGCAGCGGCTCTGGCACCGACTTCA<br>CCCTGAAGATCAGCCGGGTGGAAGCCGA<br>GGACGTGGGCGTGTACTATTGTGGCCAGG<br>GCACCCAGTACCCCTTCACCTTTGGCAGC<br>GGCACCAAGGTGGAAATCAAGGGCCAGC<br>CCAAGGCCGCCCCCGACATCCAGATGACC<br>CAGAGCCCCAGCAGCCTGTCTGCCAGCGT<br>GGGCGACAGAGTGACCATCACCTGTCAG<br>GCCAGCCAGAACATCTACGTGTGGCTGAA<br>CTGGTATCAGCAGAAGCCCGGCAAGGCC<br>CCCAAGCTGCTGATCTACAAGGCCAGCAA<br>CCTGCACACCGGCGTGCCCAGCAGATTTT<br>CTGGCAGCGGCTCCGGCACCGACTTCACC<br>CTGACAATCAGCTCCCTGCAGCCCGAGGA<br>CATTGCCACCTACTACTGCCAGCAGGGCC<br>AGACCTACCCCTACACCTTTGGCCAGGGC<br>ACCAAGCTGGAAATCAAGACCAAGGGCC<br>CCAGCCGTACGGTGGCCGCTCCCAGCGTG<br>TTCATCTTCCCACCTAGCGACGAGCAGCT<br>GAAGTCCGGCACAGCCTCTGTCGTGTGCC<br>TGCTGAACAACTTCTACCCCCGCGAGGCC<br>AAAGTGCAGTGGAAGGTGGACAACGCCC<br>TGCAGAGCGGCAACAGCCAGGAAAGCGT<br>GACCGAGCAGGACAGCAAGGACTCCACC<br>TACAGCCTGAGCAGCACCCTGACACTGAG<br>CAAGGCCGACTACGAGAAGCACAAGGTG<br>TACGCCTGCGAAGTGACCCACCAGGGCCT<br>GTCTAGCCCCGTGACCAAGAGCTTCAACC<br>GGGGCGAGTGT | SEQ ID<br>NO: 73 |
| antiCD38_C2-CD38-1_VH1-<br>VL1 IgG4(knob) FALA<br>Heavy Chain 2 | CAGGTGCAGCTGGTGCAGTCTGGCGCCGA<br>AGTCGTGAAACCTGGCGCCTCCGTGAAGG<br>TGTCCTGCAAGGCCAGCGGCTACACCTTT | SEQ ID<br>NO: 74 |

TABLE J-continued

Full-length polynucleotide sequences of binding proteins.

| | | |
|---|---|---|
| (e.g., encoding a third polypeptide chain of a trispecific binding protein of the present disclosure) | ACCAGCTACGCCATGCACTGGGTCAAAG AGGCCCCTGGCCAGAGACTGGAATGGAT CGGCTACATCTACCCCGGCCAGGGCGGCA CCAACTACAACCAGAAGTTCCAGGGCAG AGCCACCCTGACCGCCGATACAAGCGCC AGCACCGCCTACATGGAACTGAGCAGCCT GCGGAGCGAGGATACCGCCGTGTACTTCT GTGCCAGAACAGGCGGCCTGAGGCGGGC CTACTTTACCTATTGGGGCCAGGGCACCC TCGTGACCGTGTCTAGCGCTAGCACAAAG GGCCCATCGGTGTTCCCTCTGGCCCCTTG CAGCAGAAGCACCAGCGAATCTACAGCC GCCCTGGGCTGCCTCGTGAAGGACTACTT TCCCGAGCCCGTGACCGTGTCCTGGAACT CTGGCGCTCTGACAAGCGGCGTGCACACC TTTCCAGCCGTGCTCCAGAGCAGCGGCCT GTACTCTCTGAGCAGCGTCGTGACAGTGC CCAGCAGCAGCCTGGGCACCAAGACCTA CACCTGTAACGTGGACCACAAGCCCAGC AACACCAAGGTGGACAAGGGGTGGAAT CTAAGTACGGCCCTCCCTGCCCTCCTTGC CCAGCCCCTGAAGCTGCCGGCGGACCCTC CGTGTTCCTGTTCCCCCCAAAGCCCAAGG ACACCCTGATGATCAGCCGGACCCCCGAA GTGACCTGCGTGGTGGTGGATGTGTCCCA GGAAGATCCCGAGGTGCAGTTCAATTGGT ACGTGGACGGCGTGGAAGTGCACAACGC CAAGACCAAGCCCAGAGAGGAACAGTTC AACAGCACCTACCGGGTGGTGTCCGTGCT GACCGTGCTGCACCAGGACTGGCTGAAC GGCAAAGAGTACAAGTGCAAGGTGTCCA ACAAGGGCCTGCCCAGCTCCATCGAGAA AACCATCAGCAAGGCCAAGGGCCAGCCC CGCGAGCCTCAAGTGTATACCCTGCCCCC TTGCCAGGAAGAGATGACCAAGAACCAG GTGTCCCTGTGGTGTCTCGTGAAAGGCTT CTACCCCAGCGACATTGCCGTGGAATGGG AGAGCAACGGCCAGCCCGAGAACAACTA CAAGACCACCCCCCCTGTGCTGGACAGCG ACGGCTCATTCTTCCTGTACTCCAAGCTG ACCGTGGACAAGAGCCGGTGGCAGGAAG GCAACGTGTTCAGCTGCTCCGTGATGCAC GAGGCCCTGCACAACCACTACACCCAGA AGTCCCTGTCTCTGTCCCTGGGC | |
| antiCD38_C2-CD38-1_VH1-VL1 Light Chain 2 (e.g., encoding a fourth polypeptide chain of a trispecific binding protein of the present disclosure) | GACATCGTGCTGACACAGAGCCCTGCCAC CCTGTCTCTGAGCCCTGGCGAGAGAGCCA CCATCAGCTGTAGAGCCAGCCAGAGCGT GTCCAGCTACGGCCAGGGCTTCATGCACT GGTATCAGCAGAAGCCCGGCCAGCCCCC CAGACTGCTGATCTATGGCGCCAGCAGCA GAGCCACAGGCATCCCCGCCAGATTTTCT GGCTCTGGCAGCGGCACCGACTTCACCCT GACAATCAGCCCCCTGGAACCCGAGGAC TTCGCCGTGTACTACTGCCAGCAGAACAA AGAGGACCCCTGGACCTTCGGCGGAGGC ACCAAGCTGGAAATCAAGCGTACGGTGG CCGCTCCCAGCGTGTTCATCTTCCCACCT AGCGACGAGCAGCTGAAGTCCGGCACAG CCTCTGTCGTGTGCCTGCTGAACAACTTC TACCCCCGCGAGGCCAAGGTGCAGTGGA AGGTGGACAATGCCCTGCAGAGCGGCAA CAGCCAGGAAAGCGTGACCGAGCAGGAC AGCAAGGACTCCACCTACAGCCTGAGCA GCACCCTGACCCTGTCCAAGGCCGATTAC GAGAAGCACAAGGTGTACGCCTGCGAAG TGACCCACCAGGGCCTGTCTAGCCCCGTG ACCAAGAGCTTCAACCGGGGCGAGTGC | SEQ ID NO: 75 |
| antiCD38_C2-CD38-1_VH1-VL1xCD28supxCD3mid IgG1LALA P329A | | |
| CD28supxCD3mid IgG1(hole) LALA P329A Heavy Chain 1 (e.g., encoding a second polypeptide chain of a trispecific binding protein of the present disclosure) | CAGGTGCAGCTGGTGCAGTCTGGCGCCGA GGTCGTGAAACCTGGCGCCTCTGTGAAGG TGTCCTGCAAGGCCAGCGGCTACACCTTT ACCAGCTACTACATCCACTGGGTGCGCCA GGCCCCTGGACAGGGACTGGAATGGATC GGCAGCATCTACCCCCGGCAACGTGAACA CCAACTACGCCCAGAAGTTCCAGGGCAG | SEQ ID NO: 76 |

TABLE J-continued

Full-length polynucleotide sequences of binding proteins.

| | | |
|---|---|---|
| | AGCCACCCTGACCGTGGACACCAGCATCA<br>GCACCGCCTACATGGAACTGAGCCGGCTG<br>AGAAGCGACGACACCGCCGTGTACTACT<br>GCACCCGGTCCCACTACGGCCTGGATTGG<br>AACTTCGACGTGTGGGGCAAGGGCACCA<br>CCGTGACAGTGTCTAGCAGCCAGGTGCAG<br>CTGGTGGAATCTGGCGGCGGAGTGGTGC<br>AGCCTGGCAGAAGCCTGAGACTGAGCTG<br>TGCCGCCAGCGGCTTCACCTTCACCAAGG<br>CCTGGATGCACTGGGTGCGCCAGGCCCCT<br>GGAAAGCAGCTGGAATGGGTGGCCCAGA<br>TCAAGGACAAGAGCAACAGCTACGCCAC<br>CTACTACGCCGACAGCGTGAAGGGCCGG<br>TTCACCATCAGCCGGGACGACAGCAAGA<br>ACACCCTGTACCTGCAGATGAACAGCCTG<br>CGGGCCGAGGACACCGCCGTGTACTACTG<br>TCGGGGCGTGTACTATGCCCTGAGCCCCT<br>TCGATTACTGGGGCCAGGGAACCCTCGTG<br>ACCGTGTCTAGTCGGACCGCCAGCACAAA<br>GGGCCCCAGCGTGTTCCCTCTGGCCCCTA<br>GCAGCAAGAGCACATCTGGCGGAACAGC<br>CGCCCTGGGCTGCCTCGTGAAGGACTACT<br>TTCCCGAGCCCGTGACCGTGTCCTGGAAT<br>TCTGGCGCCCTGACCAGCGGCGTGCACAC<br>CTTTCCAGCTGTGCTGCAGTCCAGCGGCC<br>TGTACAGCCTGAGCAGCGTCGTGACAGTG<br>CCCAGCAGCTCTCTGGGCACCCAGACCTA<br>CATCTGCAACGTGAACCACAAGCCCAGC<br>AACACCAAGGTGGACAAGAAGGTGGAAC<br>CCAAGAGCTGCGACAAGACCCACACCTG<br>TCCCCCTTGTCCTGCCCCGAAGCCGCCG<br>GAGGCCCTTCCGTGTTCCTGTTCCCCCCA<br>AAGCCCAAGGACACCCTGATGATCAGCC<br>GGACCCCCGAAGTGACCTGCGTGGTGGTG<br>GATGTGTCCCACGAGGACCCTGAAGTGA<br>AGTTCAATTGGTACGTGGACGGCGTGGAA<br>GTGCACAACGCCAAGACCAAGCCAAGAG<br>AGGAACAGTACAACAGCACCTACCGGGT<br>GGTGTCCGTGCTGACCGTGCTGCACCAGG<br>ACTGGCTGAACGGCAAAGAGTACAAGTG<br>CAAGGTGTCCAACAAGGCCCTGGCCGCCC<br>CCATCGAGAAAACCATCAGCAAGGCCAA<br>GGGCCAGCCCCGCGAACCCCAGGTGTGC<br>ACACTGCCCCCAAGCAGGGACGAGCTGA<br>CCAAGAACCAGGTGTCCCTGAGCTGTGCC<br>GTGAAAGGCTTCTACCCCTCCGATATCGC<br>CGTGGAATGGGAGAGCAACGGCCAGCCC<br>GAGAACAACTACAAGACCACCCCCCCTGT<br>GCTGGACAGCGACGGCTCATTCTTCCTGG<br>TGTCCAAGCTGACAGTGGACAAGTCCCGG<br>TGGCAGCAGGGCAACGTGTTCAGCTGCTC<br>CGTGATGCACGAGGCCCTGCACAACCACT<br>ACACCCAGAAGTCCCTGAGCCTGAGCCCC<br>GGC | |
| CD28supxCD3mid Light<br>Chain 1<br>(e.g., encoding a first<br>polypeptide chain of a<br>trispecific binding protein of<br>the present disclosure) | See above. | SEQ ID<br>NO: 73 |
| antiCD38_C2-CD38-1_VH1-<br>VL1 IgG1(knob) LALA<br>P329A Heavy Chain 2<br>(e.g., encoding a third<br>polypeptide chain of a<br>trispecific binding protein of<br>the present disclosure) | CAGGTGCAGCTGGTGCAGTCTGGCGCCGA<br>AGTCGTGAAACCTGGCGCCTCCGTGAAGG<br>TGTCCTGCAAGGCCAGCGGCTACACCTTT<br>ACCAGCTACGCCATGCACTGGGTCAAAG<br>AGGCCCCTGGCCAGAGACTGGAATGGAT<br>CGGCTACATCTACCCCGGCCAGGGCGGCA<br>CCAACTACAACCAGAAGTTCCAGGGCAG<br>AGCCACCCTGACCGCCGATACAAGCGCC<br>AGCACCGCCTACATGGAACTGAGCAGCCT<br>GCGGAGCGAGGATACCGCCGTGTACTTCT<br>GTGCCAGAACAGGCGGCCTGAGGCGGGC<br>CTACTTTACCTATTGGGGCCAGGGCACCC<br>TCGTGACCGTGTCTAGCGCTAGCACAAAG<br>GGCCCCAGCGTGTTCCCTCTGGCCCCTAG<br>CAGCAAGAGCACATCTGGCGGAACAGCC<br>GCCCTGGGCTGCCTCGTGAAGGACTACTT | SEQ ID<br>NO: 77 |

TABLE J-continued

Full-length polynucleotide sequences of binding proteins.

| | | |
|---|---|---|
| | TCCCGAGCCCGTGACCGTGTCCTGGAATT<br>CTGGCGCCCTGACCAGCGGCGTGCACACC<br>TTTCCAGCTGTGCTGCAGTCCAGCGGCCT<br>GTACAGCCTGAGCAGCGTCGTGACAGTGC<br>CCAGCAGCTCTCTGGGCACCCAGACCTAC<br>ATCTGCAACGTGAACCACAAGCCCAGCA<br>ACACCAAGGTGGACAAGAAGGTGGAACC<br>CAAGAGCTGCGACAAGACCCACACCTGT<br>CCCCCTTGTCCTGCCCCCGAAGCCGCCGG<br>AGGCCCTTCCGTGTTCCTGTTCCCCCCAA<br>AGCCCAAGGACACCCTGATGATCAGCCG<br>GACCCCCGAAGTGACCTGCGTGGTGGTGG<br>ATGTGTCCCACGAGGACCCTGAAGTGAA<br>GTTCAATTGGTACGTGGACGGCGTGGAAG<br>TGCACAACGCCAAGACCAAGCCAAGAGA<br>GGAACAGTACAACAGCACCTACCGGGTG<br>GTGTCCGTGCTGACCGTGCTGCACCAGGA<br>CTGGCTGAACGGCAAAGAGTACAAGTGC<br>AAGGTGTCCAACAAGGCCCTGGCCGCCCC<br>CATCGAGAAAACCATCAGCAAGGCCAAG<br>GGCCAGCCCCGCGAACCCCAGGTGTACA<br>CACTGCCCCCATGCAGGGACGAGCTGACC<br>AAGAACCAGGTGTCCCTGTGGTGTCTGGT<br>GAAAGGCTTCTACCCCTCCGATATCGCCG<br>TGGAATGGGAGAGCAACGGCCAGCCCGA<br>GAACAACTACAAGACCACCCCCCCTGTGC<br>TGGACAGCGACGGCTCATTCTTCCTGTAC<br>TCCAAGCTGACAGTGGACAAGTCCCGGTG<br>GCAGCAGGGCAACGTGTTCAGCTGCTCCG<br>TGATGCACGAGGCCCTGCACAACCACTAC<br>ACCCAGAAGTCCCTGAGCCTGAGCCCCGG<br>C | |
| antiCD38_C2-CD38-1_VH1-<br>VL1 Light Chain 2<br>(e.g., encoding a fourth<br>polypeptide chain of a<br>trispecific binding protein of<br>the present disclosure) | See above. | SEQ ID<br>NO: 75 | antiCD38_C2-CD38-1_VH1-VL1xCD28supxCD3mid IgG1 NNSA

| | | |
|---|---|---|
| CD28supxCD3mid<br>IgG1(hole) NNSA Heavy<br>Chain 1<br>(e.g., encoding a second<br>polypeptide chain of a<br>trispecific binding protein of<br>the present disclosure) | CAGGTGCAGCTGGTGCAGTCTGGCGCCGA<br>GGTCGTGAAACCTGGCGCCTCTGTGAAGG<br>TGTCCTGCAAGGCCAGCGGCTACACCTTT<br>ACCAGCTACTACATCCACTGGGTGCGCCA<br>GGCCCCTGGACAGGGACTGGAATGGATC<br>GGCAGCATCTACCCCGGCAACGTGAACA<br>CCAACTACGCCCAGAAGTTCCAGGGCAG<br>AGCCACCCTGACCGTGGACACCAGCATCA<br>GCACCGCCTACATGGAACTGAGCCGGCTG<br>AGAAGCGACGACACCGCCGTGTACTACT<br>GCACCCGGTCCCACTACGGCCTGGATTGG<br>AACTTCGACGTGTGGGGCAAGGGCACCA<br>CCGTGACAGTGTCTAGCAGCCAGGTGCAG<br>CTGGTGGAATCTGGCGGCGGAGTGGTGC<br>AGCCTGGCAGAAGCCTGAGACTGAGCTG<br>TGCCGCCAGCGGCTTCACCTTCACCAAGG<br>CCTGGATGCACTGGGTGCGCCAGGCCCCT<br>GGAAAGCAGCTGGAATGGGTGGCCCAGA<br>TCAAGGACAAGAGCAACAGCTACGCCAC<br>CTACTACGCCGACAGCGTGAAGGGCCGG<br>TTCACCATCAGCCGGGACGACAGCAAGA<br>ACACCCTGTACCTGCAGATGAACAGCCTG<br>CGGGCCGAGGACACCGCCGTGTACTACTG<br>TCGGGGCGTGTACTATGCCCTGAGCCCCT<br>TCGATTACTGGGGCCAGGGAACCCTCGTG<br>ACCGTGTCTAGTCGGACCGCCAGCACAAA<br>GGGCCCCAGCGTGTTCCCTCTGGCCCCTA<br>GCAGCAAGAGCACATCTGGCGGAACAGC<br>CGCCCTGGGCTGCCTCGTGAAGGACTACT<br>TTCCCGAGCCCGTGACCGTGTCCTGGAAT<br>TCTGGCGCCCTGACCAGCGGCGTGCACAC<br>CTTTCCAGCTGTGCTGCAGTCCAGCGGCC<br>TGTACAGCCTGAGCAGCGTCGTGACAGTG<br>CCCAGCAGCTCTCTGGGCACCCAGACCTA<br>CATCTGCAACGTGAACCACAAGCCCAGC<br>AACACCAAGGTGGACAAGAAGGTGGAAC | SEQ ID<br>NO: 78 |

TABLE J-continued

Full-length polynucleotide sequences of binding proteins.

| | | |
|---|---|---|
| | CCAAGAGCTGCGACAAGACCCACACCTG<br>TCCCCCTTGTCCTGCCCCCGAACTGCTGG<br>GAGGCCCTTCCGTGTTCCTGTTCCCCCCA<br>AAGCCCAAGGACACCCTGATGATCAGCC<br>GGACCCCCGAAGTGACCTGCGTGGTGGTG<br>GATGTGTCCCACGAGGACCCTGAAGTGA<br>AGTTCAATTGGTACGTGGACGGCGTGGAA<br>GTGCACAACGCCAAGACCAAGCCAAGAG<br>AGGAACAGTACAACAATGCCTCCCGGGT<br>GGTGTCCGTGCTGACCGTGCTGCACCAGG<br>ACTGGCTGAACGGCAAAGAGTACAAGTG<br>CAAGGTGTCCAACAAGGCCCTGCCTGCCC<br>CCATCGAGAAAACCATCAGCAAGGCCAA<br>GGGCCAGCCCCGCGAACCCCAGGTGTGC<br>ACACTGCCCCCAAGCAGGGACGAGCTGA<br>CCAAGAACCAGGTGTCCCTGAGCTGTGCC<br>GTGAAAGGCTTCTACCCCTCCGATATCGC<br>CGTGGAATGGGAGAGCAACGGCCAGCCC<br>GAGAACAACTACAAGACCACCCCCCCTGT<br>GCTGGACAGCGACGGCTCATTCTTCCTGG<br>TGTCCAAGCTGACAGTGGACAAGTCCGG<br>TGGCAGCAGGGCAACGTGTTCAGCTGCTC<br>CGTGATGCACGAGGCCCTGCACAACCACT<br>ACACCCAGAAGTCCCTGAGCCTGAGCCCC<br>GGC | |
| CD28supxCD3mid Light<br>Chain 1<br>(e.g., encoding a first<br>polypeptide chain of a<br>trispecific binding protein of<br>the present disclosure) | See above. | SEQ ID<br>NO: 73 |
| antiCD38_C2-CD38-1_VH1-<br>VL1 IgG1(knob) NNSA<br>Heavy Chain 2<br>(e.g., encoding a third<br>polypeptide chain of a<br>trispecific binding protein of<br>the present disclosure) | CAGGTGCAGCTGGTGCAGTCTGGCGCCGA<br>AGTCGTGAAACCTGGCGCCTCCGTGAAGG<br>TGTCCTGCAAGGCCAGCGGCTACACCTTT<br>ACCAGCTACGCCATGCACTGGGTCAAAG<br>AGGCCCCTGGCCAGAGACTGGAATGGAT<br>CGGCTACATCTACCCCGGCCAGGGCGGCA<br>CCAACTACAACCAGAAGTTCCAGGGCAG<br>AGCCACCCTGACCGCCGATACAAGCGCC<br>AGCACCGCCTACATGGAACTGAGCAGCCT<br>GCGGAGCGAGGATACCGCCGTGTACTTCT<br>GTGCCAGAACAGGCGGCCTGAGGCGGGC<br>CTACTTTACCTATTGGGGCCAGGGCACCC<br>TCGTGACCGTGTCTAGCGCTAGCACAAAG<br>GGCCCATCGGTCTTCCCCCTGGCACCCTC<br>CTCCAAGAGCACCTCTGGGGGCACAGCG<br>GCCCTGGGCTGCCTGGTCAAGGACTACTT<br>CCCCGAACCGGTGACGGTGTCGTGGAACT<br>CAGGCGCCCTGACCAGCGGCGTGCACAC<br>CTTCCCGGCTGTCCTACAGTCCTCAGGAC<br>TCTACTCCCTCAGCAGCGTGGTGACCGTG<br>CCCTCCAGCAGCTTGGGCACCCAGACCTA<br>CATCTGCAACGTGAATCACAAGCCCAGCA<br>ACACCAAGGTGGACAAGAAAGTTGAGCC<br>CAAATCTTGTGACAAAACTCACACATGCC<br>CACCGTGCCCAGCACCTGAACTCCTGGGG<br>GGACCGTCAGTCTTCCTCTTCCCCCCAAA<br>ACCCAAGGACACCCTCATGATCTCCCGGA<br>CCCCTGAGGTCACATGCGTGGTGGTGGAC<br>GTGAGCCACGAAGACCCTGAGGTCAAGT<br>TCAACTGGTATGTTGACGGCGTGGAGGTG<br>CATAATGCCAAGACAAAGCCGCGGGAGG<br>AGCAGTACAACAATGCCTCCCGTGTGGTC<br>AGCGTCCTCACCGTCCTGCACCAGGACTG<br>GCTGAATGGCAAGGAGTACAAGTGCAAG<br>GTCTCCAACAAAGCCCTCCCAGCCCCCAT<br>CGAGAAAACCATCTCCAAAGCCAAAGGG<br>CAGCCCCGAGAACCACAGGTGTACACCCT<br>GCCCCCATGCCGGGATGAGCTGACCAAG<br>AATCAAGTCAGCCTGTGGTGCCTGGTAAA<br>AGGCTTCTATCCCAGCGACATCGCCGTGG<br>AGTGGGAGAGCAATGGGCAGCCGGAGAA<br>CAACTACAAGACCACGCCTCCCGTGCTGG<br>ACTCCGACGGCTCCTTCTTCCTCTACTCAA<br>AACTCACCGTGGACAAGAGCAGGTGGCA<br>GCAGGGGAACGTCTTCTCATGCTCCGTGA | SEQ ID<br>NO: 79 |

TABLE J-continued

Full-length polynucleotide sequences of binding proteins.

|  |  |  |
|---|---|---|
|  | TGCATGAGGCTCTGCACAACCACTACACG CAGAAGAGCCTCTCCCTGTCTCCGGGT |  |
| antiCD38_C2-CD38-1 VH1-VL1 Light Chain 2 (e.g., encoding a fourth polypeptide chain of a trispecific binding protein of the present disclosure) | See above. | SEQ ID NO: 75 |

CD38<sub>HHY1370</sub>xCD28supxCD3mid IgG4 FALA

| CD28supxCD3mid IgG4(hole) FALA Heavy Chain 1 (e.g., encoding a second polypeptide chain of a trispecific binding protein of the present disclosure) | See above. | SEQ ID NO: 72 |
|---|---|---|
| CD28supxCD3mid Light Chain 1 (e.g., encoding a first polypeptide chain of a trispecific binding protein of the present disclosure) | See above. | SEQ ID NO: 73 |
| CD38<sub>HHY1370</sub> IgG4(knob) FALA Heavy Chain 2 (e.g., encoding a third polypeptide chain of a trispecific binding protein of the present disclosure) | CAGGTGCAGCTGGTGGAAAGCGGCGGAG GCGTGGTGCAGCCTGGCAGGTCTCTGAGA CTGAGCTGTGCCGCCAGCGGCTTCACCTT CAGCAGCTACGGAATGCACTGGGTGCGC CAGGCCCCTGGCAAAGGACTGGAATGGG TGGCCGTGATTTGGTACGACGGCAGCAAC AAGTACTACGCCGACAGCGTGAAGGGCC GGTTCACCATCAGCGGCGACAACAGCAA GAACACCCTGTACCTGCAGATGAACAGCC TGCGGGCCGAGGACACCGCCGTGTACTAC TGCGCCAGAATGTTCAGAGGCGCCTTCGA CTACTGGGGCCAGGGCACACTCGTGACCG TGTCTAGTGCGTCGACCAAGGGCCCATCG GTGTTCCCTCTGGCCCCTTGCAGCAGAAG CACCAGCGAATCTACAGCCGCCCTGGGCT GCCTCGTGAAGGACTACTTTCCCGAGCCC GTGACCGTGTCCTGGAACTCTGGCGCTCT GACAAGCGGCGTGCACACCTTTCCAGCCG TGCTCCAGAGCAGCGGCCTGTACTCTCTG AGCAGCGTCGTGACAGTGCCCAGCAGCA GCCTGGGCACCAAGACCTACACCTGTAAC GTGGACCACAAGCCCAGCAACACCAAGG TGGACAAGCGGGTGGAATCTAAGTACGG CCCTCCCTGCCCTCCTTGCCCAGCCCCTG AAGCTGCCGGCGGACCCTCCGTGTTCCTG TTCCCCCCAAAGCCCAAGGACACCCTGAT GATCAGCCGGACCCCCGAAGTGACCTGC GTGGTGGTGGATGTGTCCCAGGAAGATCC CGAGGTGCAGTTCAATTGGTACGTGGACG GCGTGGAAGTGCACAACGCCAAGACCAA GCCCAGAGAGGAACAGTTCAACAGCACC TACCGGGTGGTGTCCGTGCTGACCGTGCT GCACCAGGACTGGCTGAACGGCAAAGAG TACAAGTGCAAGGTGTCCAACAAGGGCC TGCCCAGCTCCATCGAGAAAACCATCAGC AAGGCCAAGGGCCAGCCCCGCGAGCCTC AAGTGTATACCCTGCCCCCTTGCCAGGAA GAGATGACCAAGAACCAGGTGTCCCTGT GGTGTCTCGTGAAAGGCTTCTACCCCAGC GACATTGCCGTGGAATGGGAGAGCAACG GCCAGCCCGAGAACAACTACAAGACCAC CCCCCCTGTGCTGGACAGCGACGGCTCAT TCTTCCTGTACTCCAAGCTGACCGTGGAC AAGAGCCGGTGGCAGGAAGGCAACGTGT TCAGCTGCTCCGTGATGCACGAGGCCCTG CACAACCACTACACCCAGAAGTCCCTGTC TCTGTCCCTGGGC | SEQ ID NO: 80 |

TABLE J-continued

Full-length polynucleotide sequences of binding proteins.

| | | |
|---|---|---|
| CD38<sub>HHY1370</sub> Light2 (e.g., encoding a fourth polypeptide chain of a trispecific binding protein of the present disclosure) | GCCATCCAGATGACCCAGAGCCCCAGCA GCCTGTCTGCCAGCGTGGGCGACAGAGTG ACCATCACCTGTAGAGCCAGCCAGGGCAT CCGGAACGACCTGGGCTGGTATCAGCAG AAGCCTGGCAAGGCCCCCAAGCTGCTGAT CTACGCCGCTAGCTCTCTGCAGTCCGGCG TGCCCAGCAGATTTTCTGGCAGCGGCTCC GGCACCGACTTCACCCTGACAATCTCTGG CCTGCAGCCCGAGGACAGCGCCACCTACT ACTGTCTGCAAGACTACATCTACTACCCC ACCTTCGGCCAGGGCACCAAGGTGGAAA TCAAGCGTACGGTGGCCGCTCCCAGCGTG TTCATCTTCCCACCTAGCGACGAGCAGCT GAAGTCCGGCACAGCCTCTGTCGTGTGCC TGCTGAACAACTTCTACCCCCGCGAGGCC AAAGTGCAGTGGAAGGTGGACAACGCCC TGCAGAGCGGCAACAGCCAGGAAAGCGT GACCGAGCAGGACAGCAAGGACTCCACC TACAGCCTGAGCAGCACCCTGACACTGAG CAAGGCCGACTACGAGAAGCACAAGGTG TACGCCTGCGAAGTGACCCACCAGGGCCT GTCTAGCCCCGTGACCAAGAGCTTCAACC GGGGCGAGTGT | SEQ ID NO: 81 |
| CD38<sub>HHY1370</sub>xCD28supxCD3mid IgG1LALA P329A | | |
| CD28supxCD3mid IgG1(hole) LALA P329A Heavy Chain 1 (e.g., encoding a second polypeptide chain of a trispecific binding protein of the present disclosure) | See above. | SEQ ID NO: 76 |
| CD28supxCD3mid Light Chain 1 (e.g., encoding a first polypeptide chain of a trispecific binding protein of the present disclosure) | See above. | SEQ ID NO: 73 |
| CD38<sub>HHY1370</sub> IgG1(knob) LALA P329A Heavy Chain 2 (e.g., encoding a third polypeptide chain of a trispecific binding protein of the present disclosure) | CAGGTGCAGCTGGTGGAAAGCGGCGGAG GCGTGGTGCAGCCTGGCAGGTCTCTGAGA CTGAGCTGTGCCGCCAGCGGCTTCACCTT CAGCAGCTACGGAATGCACTGGGTGCGC CAGGCCCCTGGCAAAGGACTGGAATGGG TGGCCGTGATTTGGTACGACGGCAGCAAC AAGTACTACGCCGACAGCGTGAAGGGCC GGTTCACCATCAGCGGCGACAACAGCAA GAACACCCTGTACCTGCAGATGAACAGCC TGCGGGCCGAGGACACCGCCGTGTACTAC TGCGCCAGAATGTTCAGAGGCGCCTTCGA CTACTGGGGCCAGGGCACACTCGTGACCG TGTCTAGTGCGTCGACCAAGGGCCCCAGC GTGTTCCCTCTGGCCCCTAGCAGCAAGAG CACATCTGGCGGAACAGCCGCCCTGGGCT GCCTCGTGAAGGACTACTTTCCCGAGCCC GTGACCGTGTCCTGGAATTCTGGCGCCCT GACCAGCGGCGTGCACACCTTTCCAGCTG TGCTGCAGTCCAGCGGCCTGTACAGCCTG AGCAGCGTCGTGACAGTGCCCAGCAGCTC TCTGGGCACCCAGACCTACATCTGCAACG TGAACCACAAGCCCAGCAACACCAAGGT GGACAAGAAGGTGGAACCCAAGAGCTGC GACAAGACCCACACCTGTCCCCCTTGTCC TGCCCCCGAAGCCGCCGGAGGCCCTTCCG TGTTCCTGTTCCCCCCAAAGCCCAAGGAC ACCCTGATGATCAGCCGGACCCCCGAAGT GACCTGCGTGGTGGTGGATGTGTCCCACG AGGACCCTGAAGTGAAGTTCAATTGGTAC GTGGACGGCGTGGAAGTGCACAACGCCA AGACCAAGCCAAGAGAGGAACAGTACAA CAGCACCTACCGGGTGGTGTCCGTGCTGA CCGTGCTGCACCAGGACTGGCTGAACGGC AAAGAGTACAAGTGCAAGGTGTCCAACA AGGCCCTGGCCGCCCCCATCGAGAAAAC CATCAGCAAGGCCAAGGGCCAGCCCCGC | SEQ ID NO: 82 |

TABLE J-continued

Full-length polynucleotide sequences of binding proteins.

| | | |
|---|---|---|
| | GAACCCCAGGTGTACACACTGCCCCCATG<br>CAGGGACGAGCTGACCAAGAACCAGGTG<br>TCCCTGTGGTGTCTGGTGAAAGGCTTCTA<br>CCCCTCCGATATCGCCGTGGAATGGGAGA<br>GCAACGGCCAGCCCGAGAACAACTACAA<br>GACCACCCCCCCTGTGCTGGACAGCGACG<br>GCTCATTCTTCCTGTACTCCAAGCTGACA<br>GTGGACAAGTCCCGGTGGCAGCAGGGCA<br>ACGTGTTCAGCTGCTCCGTGATGCACGAG<br>GCCCTGCACAACCACTACACCCAGAAGTC<br>CCTGAGCCTGAGCCCCGGC | |
| CD38$_{HHY1370}$ Light2<br>(e.g., encoding a fourth<br>polypeptide chain of a<br>trispecific binding protein of<br>the present disclosure) | See above. | SEQ ID<br>NO: 81 |

CD38$_{HHY1370}$xCD28supxCD3mid IgG1 NNSA

| | | |
|---|---|---|
| CD28supxCD3mid<br>IgG1(hole) NNSA Heavy<br>Chain 1<br>(e.g., encoding a second<br>polypeptide chain of a<br>trispecific binding protein of<br>the present disclosure) | See above. | SEQ ID<br>NO: 78 |
| CD28supxCD3mid Light<br>Chain 1<br>(e.g., encoding a first<br>polypeptide chain of a<br>trispecific binding protein of<br>the present disclosure) | See above. | SEQ ID<br>NO: 73 |
| CD38$_{HHY1370}$ IgG1(knob)<br>NNSA Heavy Chain 2<br>(e.g., encoding a third<br>polypeptide chain of a<br>trispecific binding protein of<br>the present disclosure) | CAGGTGCAGCTGGTGGAAAGCGGCGGAG<br>GCGTGGTGCAGCCTGGCAGGTCTCTGAGA<br>CTGAGCTGTGCCGCCAGCGGCTTCACCTT<br>CAGCAGCTACGGAATGCACTGGGTGCGC<br>CAGGCCCCTGGCAAAGGACTGGAATGGG<br>TGGCCGTGATTTGGTACGACGGCAGCAAC<br>AAGTACTACGCCGACAGCGTGAAGGGCC<br>GGTTCACCATCAGCGGCGACAACAGCAA<br>GAACACCCTGTACCTGCAGATGAACAGCC<br>TGCGGGCCGAGGACACCGCCGTGTACTAC<br>TGCGCCAGAATGTTCAGAGGCGCCTTCGA<br>CTACTGGGGCCAGGGCACACTCGTGACCG<br>TGTCTAGTGCGTCGACCAAGGGCCCATCG<br>GTCTTCCCCCTGGCACCCTCCTCCAAGAG<br>CACCTCTGGGGGCACAGCGGCCCTGGGCT<br>GCCTGGTCAAGGACTACTTCCCCGAACCG<br>GTGACGGTGTCGTGGAACTCAGGCGCCCT<br>GACCAGCGGCGTGCACACCTTCCCGGCTG<br>TCCTACAGTCCTCAGGACTCTACTCCCTC<br>AGCAGCGTGGTGACCGTGCCCTCCAGCAG<br>CTTGGGCACCCAGACCTACATCTGCAACG<br>TGAATCACAAGCCCAGCAACACCAAGGT<br>GGACAAGAAAGTTGAGCCCAAATCTTGT<br>GACAAAACTCACACATGCCCACCGTGCCC<br>AGCACCTGAACTCCTGGGGGGACCGTCA<br>GTCTTCCTCTTCCCCCCAAAACCCAAGGA<br>CACCCTCATGATCTCCCGGACCCCTGAGG<br>TCACATGCGTGGTGGTGGACGTGAGCCAC<br>GAAGACCCTGAGGTCAAGTTCAACTGGTA<br>TGTTGACGGCGTGGAGGTGCATAATGCCA<br>AGACAAAGCCGCGGGAGGAGCAGTACAA<br>CAATGCCTCCCGTGTGGTCAGCGTCCTCA<br>CCGTCCTGCACCAGGACTGGCTGAATGGC<br>AAGGAGTACAAGTGCAAGGTCTCCAACA<br>AAGCCCTCCCAGCCCCCATCGAGAAAACC<br>ATCTCCAAAGCCAAAGGGCAGCCCCGAG<br>AACCACAGGTGTACACCCTGCCCCCATGC<br>CGGGATGAGCTGACCAAGAATCAAGTCA<br>GCCTGTGGTGCCTGGTAAAAGGCTTCTAT<br>CCCAGCGACATCGCCGTGGAGTGGGAGA<br>GCAATGGGCAGCCGGAGAACAACTACAA<br>GACCACGCCTCCCGTGCTGGACTCCGACG<br>GCTCCTTCTTCCTCTACTCAAAACTCACCG | SEQ ID<br>NO: 83 |

TABLE J-continued

Full-length polynucleotide sequences of binding proteins.

```
                          TGGACAAGAGCAGGTGGCAGCAGGGGAA
                          CGTCTTCTCATGCTCCGTGATGCATGAGG
                          CTCTGCACAACCACTACACGCAGAAGAG
                          CCTCTCCCTGTCTCCGGGT
```

CD38<sub>HHY1370</sub> Light2  See above.  SEQ ID NO: 81
(e.g., encoding a fourth
polypeptide chain of a
trispecific binding protein of
the present disclosure)

CD38 polypeptides

In some embodiments, a binding protein of the present disclosure comprises an antigen binding site that binds an extracellular domain of a human CD38 polypeptide and an extracellular domain of a cynomolgus monkey CD38 polypeptide. Exemplary assays for determining whether an antigen binding site binds an antigen are described herein and known in the art. In some embodiments, binding is determined by ELISA assay, e.g., as described infra. In some embodiments, binding is determined by SPR assay, e.g., as described infra. In some embodiments, binding is determined by flow cytometry assay using cells expressing a CD38 polypeptide on their cell surface, e.g., as described infra.

In some embodiments, a binding protein of the present disclosure binds a purified polypeptide or fragment thereof comprising the amino acid sequence of SEQ ID NO: 1 and/or 30 (e.g., as measured by ELISA or SPR). In some embodiments, a binding protein of the present disclosure binds a polypeptide or comprising the amino acid sequence of SEQ ID NO:1 and/or 30 when expressed on the surface of a cell (e.g., as measured by flow cytometry).

In some embodiments, a binding protein of the present disclosure binds to a CD38 isoform A polypeptide (e.g., comprising the amino acid sequence of SEQ ID NO: 1). In some embodiments, a binding protein of the present disclosure binds to a CD38 isoform E polypeptide (e.g., comprising the amino acid sequence of SEQ ID NO: 105 and not comprising the full amino acid sequence of SEQ ID NO: 1, consisting of the amino acid sequence of SEQ ID NO: 105, or consisting essentially of the amino acid sequence of SEQ ID NO: 105). In some embodiments, a binding protein of the present disclosure binds to a CD38 isoform A polypeptide (e.g., comprising the amino acid sequence of SEQ ID NO: 1) and a CD38 isoform E polypeptide (e.g., comprising the amino acid sequence of SEQ ID NO: 105 and not comprising the full amino acid sequence of SEQ ID NO: 1, consisting of the amino acid sequence of SEQ ID NO: 105, or consisting essentially of the amino acid sequence of SEQ ID NO: 105). Without wishing to be bound to theory, it is thought that binding to a CD38 isoform E polypeptide can be advantageous, e.g., in targeting a binding protein of the present disclosure to cell(s) expressing a CD38 isoform E polypeptide.

Human CD38 Isoform A Extracellular Domain Polypeptide Sequence (SEQ ID NO: 1)
RWRQQWSGPGTTKRFPETVLARCVKYTEIHPEMRHVDCQSVWDAFKGAF

ISKHPCNITEEDYQPLMKLGTQTVPCNKILLWSRIKDLAHQFTQVQRDM

-continued
FTLEDTLLGYLADDLTWCGEFNTSKINYQSCPDWRKDCSNNPVSVFWKT

VSRRFAEAACDVVHVMLNGSRSKIFDKNSTFGSVEVHNLQPEKVQTLEA

WVIHGGREDSRDLCQDPTIKELESIISKRNIQFSCKNIYRPDKFLQCVK

NPEDSSCTSEI

Human CD38 Isoform E Polypeptide Sequence (SEQ ID NO: 105)
RWRQQWSGPGTTKRFPETVLARCVKYTEIHPEMRHVDCQSVWDAFKGAF

ISKHPCNITEEDYQPLMKLGTQTVPCNKILLWSRIKDLAHQFTQVQRDM

FTLEDTLLGYLADDLTWCGEFNTSKINYQSCPDWRKDCSNNPVSVFWKT

VSRRHFWECGSP

In some embodiments, the extracellular domain of a human CD38 polypeptide comprises the amino acid sequence of SEQ ID NO: 1. In some embodiments, the extracellular domain of a cynomolgus monkey CD38 polypeptide comprises the amino acid sequence of SEQ ID NO:30.

Cynomolgus Monkey CD38 Polypeptide Sequence (SEQ ID NO: 30)
RWRQQWSGSGTTSRFPETVLARCVKYTEVHPEMRHVDCQSVWDAFKGAF

ISKYPCNITEEDYQPLVKLGTQTVPCNKTLLWSRIKDLAHQFTQVQRDM

FTLEDMLLGYLADDLTWCGEFNTFEINYQSCPDWRKDCSNNPVSVFWKT

VSRRFAETACGVVHVMLNGSRSKIFDKNSTFGSVEVHNLQPEKVQALEA

WVIHGGREDSRDLCQDPTIKELESIISKRNIRFFCKNIYRPDKFLQCVK

NPEDSSCLSGI

Linkers

In some embodiments, the linkers $L_1$, $L_2$, $L_3$ and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$ and $L_4$ in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues; a peptide with five glycine residues; a peptide with six glycine residues; a peptide with seven glycine residues; and a peptide with eight glycine residues. Other combinations of amino acid residues may be used such as the peptide GGGGSGGGGS (SEQ ID NO: 55), the peptide GGGGSGGGGSGGGGS (SEQ ID NO: 56), the peptide TKGPS (SEQ ID NO: 57), the peptide GQPKAAP (SEQ ID NO:58), and the peptide GGSGSSGSGG (SEQ ID NO:59). The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345 and International Application No. PCT/US2017/027488.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In some embodiments, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, the length of $L_1$ is at least twice the length of $L_3$. In some embodiments, the length of $L_2$ is at least twice the length of $L_4$. In some embodiments, the length of $L_1$ is at least twice the length of $L_3$, and the length of $L_2$ is at least twice the length of $L_4$. In some embodiments, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In some embodiments, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In some embodiments, $L_1$ is 7 amino acid residues in length, $L_2$ is 5 amino acid residues in length, $L_3$ is 1 amino acid residue in length, and $L_4$ is 2 amino acid residues in length. In some embodiments, $L_1$ is 10 amino acid residues in length, $L_2$ is 10 amino acid residues in length, $L_3$ is 0 amino acid residue in length, and $L_4$ is 0 amino acid residues in length. In some embodiments, $L_1$, $L_2$, $L_3$, and $L_4$ each have an independently selected length from 0 to 15 amino acids (e.g., 0, 1, 2, 3, 4, 5, 6, 7, 8, 9, 10, 11, 12, 13, 14, or 15 amino acids), wherein at least two of the linkers have a length of 1 to 15 amino acids (e.g., 1, 2, 3, 4, 5, 6, 7, 8, 9, 10, 11, 12, 13, 14, or 15 amino acids). In some embodiments, $L_1$, $L_2$, $L_3$, and $L_4$ are each 0 amino acids in length.

In some embodiments, $L_1$, $L_2$, $L_3$, and/or $L_4$ comprise a sequence derived from a naturally occurring sequence at the junction between an antibody variable domain and an antibody constant domain (e.g., as described in WO2012/135345). For example, in some embodiments, the linker comprises a sequence found at the transition between an endogenous $V_H$ and $C_{H1}$ domain, or between an endogenous $V_L$ and $C_L$ domain (e.g., kappa or lambda). In some embodiments, the linker comprises a sequence found at the transition between an endogenous human $V_H$ and $C_{H1}$ domain, or between an endogenous human $V_L$ and $C_L$ domain (e.g., human kappa or lambda).

In some embodiments, $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO: 58), and GGSGSSGSGG (SEQ ID NO:59). In some embodiments, $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO: 58), and GGSGSSGSGG (SEQ ID NO:59).

In some embodiments, $L_1$ comprises the sequence GQPKAAP (SEQ ID NO: 58), $L_2$ comprises the sequence TKGPS (SEQ ID NO:57), $L_3$ comprises the sequence S, and $L_4$ comprises the sequence RT. In some embodiments, $L_1$ comprises the sequence GGGGSGGGGS (SEQ ID NO:55), $L_2$ comprises the sequence GGGGSGGGGS (SEQ ID NO:55), $L_3$ is 0 amino acids in length, and $L_4$ is 0 amino acids in length. In some embodiments, $L_1$ comprises the sequence GGSGSSGSGG (SEQ ID NO:59), $L_2$ comprises the sequence GGSGSSGSGG (SEQ ID NO:59), $L_3$ is 0 amino acids in length, and $L_4$ is 0 amino acids in length. In some embodiments, $L_1$ comprises the sequence GGGGSGGGGSGGGGS (SEQ ID NO:56), $L_2$ is 0 amino acids in length, $L_3$ comprises the sequence GGGGSGGGGSGGGGS (SEQ ID NO:56), and $L_4$ is 0 amino acids in length.

Fc Regions and Constant Domains

In some embodiments, a binding protein of the present disclosure comprises a full-length antibody heavy chain or a polypeptide chain comprising an Fc region. In some embodiments, the Fc region is a human Fc region, e.g., a human IgG1, IgG2, IgG3, or IgG4 Fc region. In some embodiments, the Fc region includes an antibody hinge, $C_{H1}$, $C_{H2}$, $C_{H3}$, and optionally $C_{H4}$ domains. In some embodiments, the Fc region is a human IgG1 Fc region. In some embodiments, the Fc region is a human IgG4 Fc region. In some embodiments, the Fc region includes one or more of the mutations described infra.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

In some embodiments, the Fc region comprises one or more mutations that reduce or eliminate Fc receptor binding and/or effector function of the Fc region (e.g., Fc receptor-mediated antibody-dependent cellular phagocytosis (ADCP), complement-dependent cytotoxicity (CDC), and/or antibody-dependent cellular cytotoxicity (ADCC)).

In some embodiments, the Fc region is a human IgG1 Fc region comprising one or more amino acid substitutions at positions corresponding to positions 234, 235, and/or 329 of human IgG1 according to EU Index. In some embodiments, the amino acid substitutions are L234A, L235A, and/or P329A. In some embodiments, the Fc region is a human IgG1 Fc region comprising amino acid substitutions at positions corresponding to positions 298, 299, and/or 300 of human IgG1 according to EU Index. In some embodiments, the amino acid substitutions are S298N, T299A, and/or Y300S.

In some embodiments, the Fc region is a human IgG4 Fc region comprising one or more mutations that reduce or eliminate FcγI and/or FcγII binding. In some embodiments, the Fc region is a human IgG4 Fc region comprising one or more mutations that reduce or eliminate FcγI and/or FcγII binding but do not affect FcRn binding. In some embodiments, the Fc region is a human IgG4 Fc region comprising amino acid substitutions at positions corresponding to positions 228 and/or 409 of human IgG4 according to EU Index. In some embodiments, the amino acid substitutions are S228P and/or R409K. In some embodiments, the Fc region is a human IgG4 Fc region comprising amino acid substitutions at positions corresponding to positions 234 and/or 235 of human IgG4 according to EU Index. In some embodiments, the amino acid substitutions are F234A and/or L235A. In some embodiments, the Fc region is a human IgG4 Fc region comprising amino acid substitutions at positions corresponding to positions 228, 234, 235, and/or 409 of human IgG4 according to EU Index. In some embodiments, the amino acid substitutions are S228P, F234A, L235A, and/or R409K. In some embodiments, the Fc region is a human IgG4 Fc region comprising amino acid substitutions at positions corresponding to positions 233-236 of human IgG4 according to EU Index. In some embodiments, the amino acid substitutions are E233P, F234V, L235A, and a deletion at 236. In some embodiments, the Fc region is a human IgG4 Fc region comprising amino acid mutations at substitutions corresponding to positions 228, 233-236, and/or 409 of human IgG4 according to EU Index. In some embodiments, the amino acid mutations are S228P; E233P, F234V, L235A, and a deletion at 236; and/or R409K.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) *Sci. Rep.* 5:17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and hole mutations and one or more mutations to improve purification. In some embodiments, the first and/or second Fc regions are human IgG1 Fc regions. In some embodiments, the first and/or second Fc regions are human IgG4 Fc regions.

In some embodiments, one or both Fc regions are human IgG4 Fc regions comprising amino acid substitutions at positions corresponding to positions 233-236 of human IgG4 according to EU Index. In some embodiments, the amino acid substitutions are E233P, F234V, L235A, and a deletion at 236. In some embodiments, the Fc regions are human IgG4 Fc regions comprising amino acid mutations at substitutions corresponding to positions 228, 233-236, and/or 409 of human IgG4 according to EU Index. In some embodiments, the amino acid mutations are S228P; E233P, F234V, L235A, and a deletion at 236; and/or R409K. In some embodiments, one or both Fc regions are human IgG1 Fc regions comprising one or more amino acid substitutions at positions corresponding to positions 234, 235, and/or 329 of human IgG1 according to EU Index. In some embodiments, the amino acid substitutions are L234A, L235A, and/or P329A. In some embodiments, the Fc regions are human IgG1 Fc regions comprising amino acid substitutions at positions corresponding to positions 298, 299, and/or 300 of human IgG1 according to EU Index. In some embodiments, the amino acid substitutions are S298N, T299A, and/or Y300S.

To improve the yields of some binding proteins (e.g., bispecific or trispecific binding proteins), the $C_{H3}$ domains can be altered by the "knob-into-holes" technology which is described in detail with several examples in, for example, International Publication No. WO 96/027011, Ridgway et al., 1996, Protein Eng. 9: 617-21; and Merchant et al., 1998, Nat. Biotechnol. 16: 677-81. Specifically, the interaction surfaces of the two $C_{H3}$ domains are altered to increase the heterodimerisation of both heavy chains containing these two $C_{H3}$ domains. Each of the two $C_{H3}$ domains (of the two heavy chains) can be the "knob," while the other is the "hole." The introduction of a disulfide bridge further stabilizes the heterodimers (Merchant et al., 1998; Atwell et al., 1997, *J. Mol. Biol.* 270: 26-35) and increases the yield. In particular embodiments, the knob is on the second pair of polypeptides with a single variable domain. In other embodiments, the knob is on the first pair of polypeptides having the cross-over orientation. In yet other embodiments, the $C_{H3}$ domains do not include a knob in hole.

In some embodiments, a binding protein of the present disclosure (e.g., a trispecific binding protein) comprises a "knob" mutation on the second polypeptide chain and a "hole" mutation on the third polypeptide chain. In some embodiments, a binding protein of the present disclosure comprises a "knob" mutation on the third polypeptide chain and a "hole" mutation on the second polypeptide chain. In some embodiments, the "knob" mutation comprises substitution(s) at positions corresponding to positions 354 and/or 366 of human IgG1 or IgG4 according to EU Index. In some embodiments, the amino acid substitutions are S354C, T366W, T366Y, S354C and T366W, or S354C and T366Y. In some embodiments, the "knob" mutation comprises substitutions at positions corresponding to positions 354 and 366 of human IgG1 or IgG4 according to EU Index. In some embodiments, the amino acid substitutions are S354C and T366W. In some embodiments, the "hole" mutation comprises substitution(s) at positions corresponding to positions 407 and, optionally, 349, 366, and/or 368 and of human IgG1 or IgG4 according to EU Index. In some embodiments, the amino acid substitutions are Y407V or Y407T and optionally Y349C, T366S, and/or L368A. In some embodiments, the "hole" mutation comprises substitutions at positions corresponding to positions 349, 366, 368, and 407 of human IgG1 or IgG4 according to EU Index. In some embodiments, the amino acid substitutions are Y349C, T366S, L368A, and Y407V.

In some embodiments, the second polypeptide chain further comprises a first Fc region linked to $C_{H1}$, the first Fc region comprising an immunoglobulin hinge region and CH2 and CH3 immunoglobulin heavy chain constant domains, wherein the first Fc region comprises amino acid substitution(s) at positions corresponding to positions 366 and optionally 354 of human IgG1 or IgG4 according to EU Index, wherein the amino acid substitutions are T366W or T366Y and optionally S354C; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366 and optionally 354 of human IgG1 or IgG4 according to EU Index, wherein the amino acid substitutions are T366W or T366Y and optionally S354C.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution at position corresponding to position 366 of human IgG1 or IgG4 according to EU Index, wherein the amino acid substitution is T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366, 368, and/or 407 and of human IgG1 or IgG4 according to EU Index, wherein the amino acid substitutions are T366S, L368A, and/or Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366, 368, and/or 407 and of human IgG1 or IgG4 according to EU Index, wherein the amino acid substitutions are T366S, L368A, and/or Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution at position corresponding to position 366 of human IgG1 or IgG4 according to EU Index, wherein the amino acid substitution is T366W.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W. In some embodiments, the first and/or second Fc regions are human IgG1 Fc regions. In some embodiments, the first and/or second Fc regions are human IgG4 Fc regions.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 354, 366, and 409 of human IgG4 according to EU Index, wherein the amino acid substitutions are S228P, S354C, T366W, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 349, 366, 368, 407, and 409 of human IgG4 according to EU Index, wherein the amino acid substitutions are S228P, Y349C, T366S, L368A, Y407V, and R409K. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 349, 366, 368, 407, and 409 of human IgG4 according to EU Index, wherein the amino acid substitutions are S228P, Y349C, T366S, L368A, Y407V, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 354, 366, and 409 of human IgG4 according to EU Index, wherein the amino acid substitutions are S228P, S354C, T366W, and R409K.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 234, 235, 354, and 366 of human IgG4 according to EU Index, wherein the amino acid substitutions are F234A, L235A, S354C, and T366W; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 234, 235, 349, 366, 368, and 407 of human IgG4 according to EU Index, wherein the amino acid substitutions are F234A, L235A, Y349C, T366S, L368A, and Y407V. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 234, 235, 349, 366, 368, and 407 of human IgG4 according to EU Index, wherein the amino acid substitutions are F234A, L235A, Y349C, T366S, L368A, and Y407V; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 234, 235, 354, and 366 of human IgG4 according to EU Index, wherein the amino acid substitutions are F234A, L235A, S354C, and T366W.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 234, 235, 354, 366, and 409 of human IgG4 according to EU Index, wherein the amino acid substitutions are S228P, F234A, L235A, S354C, T366W, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 234, 235, 349, 366, 368, 407, and 409 of human IgG4 according to EU Index, wherein the amino acid substitutions are S228P, F234A, L235A, Y349C, T366S, L368A, Y407V, and R409K. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 234, 235, 349, 366, 368, 407, and 409 of human IgG4 according to EU Index, wherein the amino acid substitutions are S228P, F234A, L235A, Y349C, T366S, L368A, Y407V, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 234, 235, 354, 366, and 409 of human IgG4 according to EU Index, wherein the amino acid substitutions are S228P, F234A, L235A, S354C, T366W, and R409K.

In some embodiments, a binding protein of the present disclosure comprises one or more mutations to improve serum half-life (See e.g., Hinton, P. R. et al. (2006) J. Immunol. 176(1):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve stability, e.g., of the hinge region and/or dimer interface of IgG4 (See e.g., Spiess, C. et al. (2013) J. Biol. Chem. 288:26583-26593). In some embodiments, the mutation comprises substitutions at positions corresponding to positions 228 and 409 of human IgG4 according to EU Index, wherein the amino acid substitutions are S228P and R409K. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, a binding protein of the present disclosure comprises knob and hole mutations and one or more mutations to improve stability. In some embodiments, the first and/or second Fc regions are human IgG4 Fc regions.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) *Sci. Rep.* 5:17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and hole mutations and one or more mutations to improve purification. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve serum half-life (See e.g., Hinton, P. R. et al. (2006) J. Immunol. 176(1):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG4 Fc regions, and the Fc regions each comprise amino acid substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A.

In some embodiments, a binding protein of the present disclosure comprises knob and hole mutations and one or more mutations to reduce effector function. In some embodiments, the first and/or second Fc regions are human IgG1 Fc regions. In some embodiments, the first and/or second Fc regions are human IgG4 Fc regions. For further description of Fc mutations at position 329, see, e.g., Shields, R. L. et al. (2001) *J. Biol. Chem.* 276:6591-6604 and WO1999051642.

In some embodiments, the types of mutations described supra can be combined in any order or combination. For example, a binding protein of the present disclosure can comprise two or more of the "knob" and "hole" mutations, the one or more mutations to improve serum half-life, the one or more mutations to improve IgG4 stability, the one or more mutations to improve purification, and/or the one or more mutations to reduce effector function described supra.

Nucleic Acids

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins described herein. In some embodiments, the isolated nucleic acid molecules comprise a sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NOs:60-83 and/or shown in Table J.

Certain aspects of the present disclosure relate to kits of polynucleotides. In some embodiments, one or more of the polynucleotides is a vector (e.g., an expression vector). The kits may find use, inter alia, in producing one or more of the binding proteins described herein, e.g., a trispecific binding protein of the present disclosure. In some embodiments, the kit comprises one, two, three, or four polynucleotides shown in Table J (e.g., of antiCD38_C2-CD38-1_VH1-VL1xCD28supxCD3mid IgG4 FALA, antiCD38_C2-CD38-1_VH1-VL1xCD28supxCD3mid IgG1LALA P329A, antiCD38_C2-CD38-1_VH1-VL1xCD28supxCD3mid IgG1 NNSA, CD38$_{HH\gamma1370}$xCD28supxCD3mid IgG4 FALA, CD38$_{HH\gamma1370}$xCD28supxCD3mid IgG1LALA P329A, or CD38$_{HH\gamma1370}$CD28supxCD3mid IgG1 NNSA). In some embodiments, a kit of polynucleotides comprises: a first polynucleotide comprising the sequence of SEQ ID NO:73, a second polynucleotide comprising the sequence of SEQ ID NO:72, a third polynucleotide comprising the sequence of SEQ ID NO:74, and a fourth polynucleotide comprising the sequence of SEQ ID NO:75. In some embodiments, a kit of polynucleotides comprises: a first polynucleotide comprising the sequence of SEQ ID NO:73, a second polynucleotide comprising the sequence of SEQ ID NO:76, a third polynucleotide comprising the sequence of SEQ ID NO:77, and a fourth polynucleotide comprising the sequence of SEQ ID NO:75. In some embodiments, a kit of polynucleotides comprises: a first polynucleotide comprising the sequence of SEQ ID NO:73, a second polynucleotide comprising the sequence of SEQ ID NO:78, a third polynucleotide comprising the sequence of SEQ ID NO:79, and a fourth polynucleotide comprising the sequence of SEQ ID NO:75. In some embodiments, a kit of polynucleotides comprises: a first polynucleotide comprising the sequence of SEQ ID NO:73, a second polynucleotide comprising the sequence of SEQ ID NO:72, a third polynucleotide comprising the sequence of SEQ ID NO:80, and a fourth polynucleotide comprising the sequence of SEQ ID NO:81. In some embodiments, a kit of polynucleotides comprises: a first polynucleotide comprising the sequence of SEQ ID NO:73, a second polynucleotide comprising the sequence of SEQ ID NO:76, a third polynucleotide comprising the sequence of SEQ ID NO:82, and a fourth polynucleotide comprising the sequence of SEQ ID NO:81. In some embodiments, a kit of polynucleotides comprises: a first polynucleotide comprising the sequence of SEQ ID NO:73, a second polynucleotide comprising the sequence of SEQ ID NO:78, a third polynucleotide comprising the sequence of SEQ ID NO:83, and a fourth polynucleotide comprising the sequence of SEQ ID NO:81.

In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2): 193-9, 1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art, and can be used to transfect any cell of interest.

Other aspects of the present disclosure relate to a vector system comprising one or more vectors encoding a first, second, third, and fourth polypeptide chain of any of the binding proteins described herein. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the vector system comprises a first vector encoding the first and third polypeptide chains of the binding protein, and a second vector encoding the second and fourth polypeptide chains of the binding protein. In some embodiments, the vector system comprises a first vector encoding the first and fourth polypeptide chains of the binding protein, and a second vector encoding the second and third polypeptide chains of the binding protein. In some embodiments, the vector system comprises a first vector encoding the first, second, third, and fourth polypeptide chains of the binding protein. The one or more vectors of the vector system may be any of the vectors described herein. In some embodiments, the one or more vectors are expression vectors.

Isolated Host Cells

Other aspects of the present disclosure relate to an isolated host cell comprising one or more isolated polynucleotides, polynucleotide kits, vectors, and/or vector systems described herein. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frugiperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), Expi293™ cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NSO and Sp2/0 cells).

Methods and Uses for Binding Proteins

Certain aspects of the present disclosure relate to methods for expanding virus-specific memory T cells. In some embodiments, the methods comprise contacting a virus-specific memory T cell with a binding protein of the present disclosure, e.g., a trispecific binding protein that comprises a first antigen binding site that binds a CD28 polypeptide, a second antigen binding site that binds a CD3 polypeptide, and a third antigen binding site that binds a CD38 polypeptide.

In some embodiments, the virus-specific memory T cell is contacted with the binding protein in vitro or ex vivo.

In some embodiments, contacting the virus-specific memory T cell with the binding protein causes activation and/or proliferation of virus-specific memory T cells.

Other aspects of the present disclosure relate to methods for expanding T cells. In some embodiments, the methods comprise contacting a T cell with a binding protein of the present disclosure, e.g., a trispecific binding protein that comprises a first antigen binding site that binds a CD28 polypeptide, a second antigen binding site that binds a CD3 polypeptide, and a third antigen binding site that binds a CD38 polypeptide.

In some embodiments, the T cell is a memory T cell or an effector T cell.

In some embodiments, the T cell expresses a chimeric antigen receptor (CAR) on its cell surface or comprises a polynucleotide encoding a CAR.

Other aspects of the present disclosure relate to methods for treating chronic viral infection, e.g., in an individual in need thereof. In some embodiments, the methods comprise administering to an individual in need thereof an effective amount of a binding protein of the present disclosure, e.g., a trispecific binding protein that comprises a first antigen binding site that binds a CD28 polypeptide, a second antigen binding site that binds a CD3 polypeptide, and a third antigen binding site that binds a CD38 polypeptide.

In some embodiments, the individual is a human.

In some embodiments, the binding protein is administered to the individual in pharmaceutical formulation comprising the binding protein and a pharmaceutically acceptable carrier.

In some embodiments, administration of the binding protein results in activation and/or proliferation of virus-specific memory T cells in the individual.

In any of the above methods, memory T cells can be CD8+ or CD4+ memory T cells. In any of the above methods, memory T cells can be central memory T cells ($T_{CM}$) or effector memory T cells ($T_{EM}$).

Any of the binding proteins described herein may find use in the methods of the present disclosure.

The binding proteins can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

For diagnostic applications, in certain embodiments, binding proteins can be labeled with a detectable moiety. The detectable moiety can be any one that is capable of producing, either directly or indirectly, a detectable signal. For example, the detectable moiety can be a radioisotope, such as $^{3}H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, preferably into the bloodstream, and the presence and location of the labeled antibody in the host assayed. The binding protein can be labeled with any moiety that is detectable in an animal, whether by nuclear magnetic resonance, radiology, or other detection means known in the art.

For clinical or research applications, in certain embodiments, binding proteins can be conjugated to a cytotoxic agent. A variety of antibodies coupled to cytotoxic agents (i.e., antibody-drug conjugates) have been used to target cytotoxic payloads to specific tumor cells. Cytotoxic agents and linkers that conjugate the agents to an antibody are known in the art; see, e.g., Parslow, A. C. et al. (2016) *Biomedicines* 4:14 and Kalim, M. et al. (2017) *Drug Des. Devel. Ther.* 11:2265-2276.

The disclosure also relates to a kit comprising a binding protein and other reagents useful for detecting target antigen levels in biological samples. Such reagents can include a detectable label, blocking serum, positive and negative control samples, and detection reagents. In some embodiments, the kit comprises a composition comprising any binding protein, polynucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper pierceable by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Binding Protein Therapeutic Compositions and Administration Thereof

Therapeutic or pharmaceutical compositions comprising binding proteins are within the scope of the disclosure. Such therapeutic or pharmaceutical compositions can comprise a therapeutically effective amount of a binding protein, or binding protein-drug conjugate, in admixture with a pharmaceutically or physiologically acceptable formulation agent selected for suitability with the mode of administration. These pharmaceutical compositions may find use in any of the methods and uses described herein (e.g., ex vivo, in vitro, and/or in vivo).

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, binding protein compositions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

The pharmaceutical compositions of the disclosure can be selected for parenteral delivery or subcutaneous. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry powder for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

EXAMPLES

The Examples that follow are illustrative of specific embodiments of the disclosure, and various uses thereof. They are set forth for explanatory purposes only, and should not be construed as limiting the scope of the invention in any way.

The following terminology may be used interchangeably in the Examples and Drawings herein to refer to specific anti-CD38 antigen binding domains or antibodies:
 antiCD38_C2-CD38-1_VH1-VL1 or $CD38_{VH1}$
 antiCD38_1370 or $CD38_{HHY1370}$
 antiCD38_SB19 or isatuximab Example 1: Cross-Reactivity and Apoptosis Induction of Anti-CD38 Antibodies Humanized anti-CD38 variants were characterized for binding to human and cynomolgus CD38 polypeptides and for induction of apoptosis.

Materials and Methods

Binding Affinity to Soluble CD38 Extracellular Domains

The binding properties of the anti-CD38 mAbs were evaluated using a BIAcore 2000 (BIAcore Inc., Uppsala, N.J.). Briefly, a CM5 BIAcore biosensor chip was docked into the instrument and activated with 250 µL of 1:1 NHS/EDC at room temperature. A mouse anti-human Fc IgG1 (GE Healthcare # BR-1008-39) (13.5 µg/mL in 0.05M acetate buffer, pH5) was immobilized on the activated chips in flow cells 1. The immobilization was carried out at a flow rate of 5 µL/min. The chip was then blocked by injection of 55 µL of ethanolamine-HCL, pH8.5, followed by five washes with 50 mM NaOH, 1M NaCl. To measure the binding of anti-CD38 mAbs to the human CD38 protein or cyno CD38 protein, antibodies were used at 2 µg/mL in BIAcore running buffer (HBS-EP). Antigens (human CD38-histag (ID2) or cyno CD38-histag (ID3)) were injected from 3 to 1000 nM. Following completion of the injection phase, dissociation was monitored in a BIAcore running buffer at the same flow rate for 360 sec. The surface was regenerated between injections using 30 µL of 50 mM NaOH-1 M NaCl. Individual sensorgrams were analyzed using BIAsimulation software.

Binding Affinity to Human CD38-Expressing Pre-B Cells

The binding of anti-CD38 antibodies to CD38 expressed on the surface of recombinant murine preB::300.19 cells was determined by flow cytometry. The recombinant cell line was described by J. Deckket et al. 2014 Clin. Cancer Res 20:4574-4583. Murine preB::300.19 CD38-expressing cells were coated at 40,000 cells/well on 96-well High Bind plate (MSD L15XB-3) and 100 µL/well of anti-CD38 antibodies were added for 45 min at 4° C. and washed three times with PBS 1% BSA. 100 µL/well of goat anti-human IgG conjugated with Alexa488 (Jackson ImmunoResearch; #109-545-098) was added for 45 min at 4° C. and washed three times with PBS 1% BSA. Antibody binding was evaluated after centrifugation and resuspension of cells by adding 200 µl/well PBS 1% BSA and read using Guava® easyCyte™ 8HT Flow Cytometry System. Apparent KD and EC50 values were estimated using BIOST@T-BINDING and BIOST@T-SPEED software, respectively.

Recombinant CD38 Proteins

Various recombinant CD38 proteins derived from isoform A with different tag and point mutations were used (SEQ ID NOs:2, 3, 4, and 28), and a tagged version of CD38 isoform E (SEQ ID NO: 105) encompassing CD38 extracellular domain from R45-P203. The proteins were produced by transient expression in mammalian cells. Coding DNA sequences were cloned into mammalian expression plasmids under CMV enhancer/promoter and SV40 polyA signals. HEK293 cells (Invitrogen; # K9000-10) were transiently transfected with the expression plasmids using FreeStyle™ MAX 293 Expression System according to the manufacturer's instructions.

Apoptosis Induction Assay

Cells were incubated at $2 \times 10^5$ cells/mL in complete medium (RPMI-1640, 10% FBS, 2 mM L-glutamine) with 1.5 µg/mL (10 nM) of indicated antibodies for 20 hours at 37° C. with 5% CO2. Cells were stained with AnnexinV-FITC in accordance with the manufacturer's instructions (Life Technologies). Samples were analyzed by flow cytometry on a BD FACSAria™ flow cytometer with BD FACS-Diva software for acquisition control and data analysis (both BD Biosciences).

ELISA Assays 96-well plates were coated with CD38 at 0.5 µg/well in PBS and 100 µL/well of antibodies were added to the plate. The plate was incubated at 37° C. for 1 h and washed five times with PBS containing 0.05% Tween-20 (PBS-T). Then, 100 µL of a 1:25,000 dilution of Anti-human IgG, conjugated with horseradish peroxidase, (Jackson Ref: 109-035-098) was added to each well. Following incubation at 37° C. for 1 h in darkness, plates were washed with PBS-T five times. Antibody binding was visualized by adding TMB-$H_2O_2$ buffer and read at a wavelength of 450 nm. EC50 values were estimated using BIOST@T-SPEED software.

Results

Binding properties of selected anti-human CD38 antibodies to soluble human CD38 and cynomolgus monkey CD38 was examined using ELISA, and surface plasmon resonance (SPR) assay using the BIAcore system (Pharmacia Biosensor; Piscataway, N.J.). ELISA data were used to determine the EC50 of antibody binding to human and cynomolgus monkey CD38 for humanized anti-CD38 antibodies antiCD38_C2-CD38-1_VH1-VL1, antiCD38_C2-CD38-1_VH3-VL3, antiCD38_C2-CD38-1_VH5-VL3, antiCD38_C2-CD38-1_VH6-VL3, and human anti-CD38 antibody antiCD38_1370.

The binding of the humanized anti-CD38 variants or human anti-CD38 mAb to CD38 was also evaluated using SPR assays. SPR data were used to determine the $K_D$ and $k_{off}$ of antibody binding to human and cynomolgus monkey CD38 for humanized anti-CD38 antibodies antiCD38_C2-CD38-1_VH1-VL1, antiCD38_C2-CD38-1_VH3-VL3, antiCD38_C2-CD38-1_VH5-VL3, antiCD38_C2-CD38-1_VH6-VL3, and human anti-CD38 antibody antiCD38_1370. The binding data, summarized in Table K, show that all the anti-CD38 mAbs bind to CD38 with similar binding characteristics.

TABLE K

Binding affinity of anti-CD38 mAbs to the soluble extracellular domain of humanCD38 and cynomolgusCD38 as determined by surface plasmon resonance assay.

| | hCD38-his (SEQ ID NO: 2) | | cCD38-his (SEQ ID NO: 4) | |
|---|---|---|---|---|
| | Kd (s−1) | KD (M) | Kd (s−1) | KD (M) |
| antiCD38_C2-CD38-1 | 2.66E−04 | 3.36E−10 | 9.85E−05 | 3.90E−10 |
| antiCD38_C2-CD38-1_VH1-VL1 | 3.90E−04 | 3.32E−10 | 7.84E−04 | 3.44E−09 |
| antiCD38_C2-CD38-1_VH3-VL3 | 2.83E−04 | 4.83E−10 | 1.29E−04 | 7.10E−10 |
| antiCD38_C2-CD38-1_VH5-VL3 | 5.29E−04 | 8.22E−10 | 2.01E−04 | 1.14E−09 |
| antiCD38_C2-CD38-1_VH6-VL3 | 3.33E−04 | 3.12E−10 | 1.25E−04 | 5.63E−10 |
| antiCD38_1370 | 2.03E−04 | 1.44E−09 | 1.90E−04 | 1.38E−09 |

The ability of the humanized anti-CD38 variants to bind to CD38-expressing cells was assessed using the FACS-based binding assay described above. FACS data were used to determine the EC50 of antibody binding to human and cynomolgus monkey CD38 for humanized anti-CD38 antibodies antiCD38_C2-CD38-1_VH1-VL1, antiCD38_C2-CD38-1_VH3-VL3, antiCD38_C2-CD38-1_VH5-VL3, antiCD38_C2-CD38-1_VH6-VL3, and human anti-CD38 antibody antiCD38_1370. The binding data, set forth in Table L, shows that all humanized anti-CD38 variants exhibited similar binding affinities for cell surface CD38.

TABLE L

Binding affinity of anti-CD38 mAbs to CD38 expressing murine preB::300.19 cells.

| | Apparent KD FACS (M) | |
|---|---|---|
| | hCD38-expressing cells | cCD38-expressing cells |
| antiCD38_C2-CD38-1 | 2.80E−10 | 2.20E−10 |
| antiCD38_C2-CD38-1_VH1-VL1 | 3.30E−10 | 7.50E−10 |
| antiCD38_C2-CD38-1_VH3-VL3 | 7.80E−10 | 1.31E−09 |
| antiCD38_C2-CD38-1_VH5-VL3 | 5.50E−10 | 1.15E−09 |
| antiCD38_C2-CD38-1_VH6-VL3 | 6.80E−10 | 1.07E−09 |
| antiCD38 1370 | 2.07E−09 | 1.14E−09 |

Binding data from the ELISA, SPR, and FACS assays above are summarized in Table L2, along with sequence identity of the VH and VL domains to human V regions.

TABLE L2

Summary of ELISA, SPR, and FACS assays characterizing the binding of the indicated antibodies to human (Hu) and cynomolgus (Cyno) monkey CD38 polypeptides.

| | INN | ELISA EC50 nM | | SPR KD nM | | FACS EC50 nM | | Human V region identity | |
|---|---|---|---|---|---|---|---|---|---|
| | Nomenclature | Hu | Cyno | Hu | Cyno | Hu | Cyno | Hu | Cyno |
| antiCD38_C2-CD38-1_VH1-VL1 | -zumAb | 0.11 | 0.10 | 0.33 | 3.44 | 0.33 | 0.76 | 84.7% | 87.1% |
| antiCD38_C2-CD38-1_VH3-VL3 | -zumAb | 0.16 | 0.15 | 0.48 | 0.71 | 0.78 | 1.31 | 83.7% | 83.9% |
| antiCD38_C2-CD38-1_VH5-VL3 | -zumAb | 0.16 | 0.17 | 0.82 | 1.14 | 0.55 | 1.15 | 80.6% | 83.9% |
| antiCD38_C2-CD38-1_VH6-VL3 | -zumAb | 0.14 | 0.14 | 0.31 | 0.56 | 0.68 | 1.06 | 81.6% | 83.9% |
| antiCD38_1370 | -umAb | 0.05 | 0.09 | 1.44 | 1.38 | 2.00 | 1.14 | 99.0% | 95.8% |

The ability of anti-CD38 antibodies to bind to both human CD38 isoforms A and E was also examined. For evaluating binding to CD38 isoform A and isoform E, an Enzyme-linked immunosorbent assay (ELISA) was performed by using isoform A and isoform E proteins (prepared as described above) as capturing antigen. 96-well plates were coated with either isoform at 0.5 µg/well in PBS and 100 µL/well of antibodies were added to the plate. The plate was incubated at 37° C. for 1 h and washed five times with PBS containing 0.05% Tween-20 (PBS-T). Then, 100 µL of a 1:25,000 dilution of Anti-human IgG, conjugated with horseradish peroxidase, (Jackson Ref: 109-035-098) was added to each well. Following incubation at 37° C. for 1 h in darkness, plates were washed with PBS-T five times. Antibody binding was visualized by adding TMB-$H_2O_2$ buffer and read at a wavelength of 450 nm. EC50 values were estimated using BIOST@T-SPEED software.

The binding affinity of various antibodies to CD38 isoform A (SEQ ID NO:1) and isoform E (SEQ ID NO: 105) was determined, as shown in Table L3. Table M provides a comparison of binding properties for various anti-CD38 antibodies.

TABLE L3

Binding affinity of anti-CD38 antibodies for CD38 isoforms A and E, based on EC50 as determined by ELISA.

| Antibody | CD38 isoform A EC50 (nM) | CD38 isoform E EC50 (nM) |
|---|---|---|
| antiCD38_C2-CD38-1 | 0.11 (CV 9%) | 0.08 (CV 7%) |
| antiCD38_C2-CD38-1_VH1-VL1 | 0.14 (CV 13%) | 0.10 (CV 12%) |
| antiCD38_1370 | 0.47 (CV 3.7%) | 0.32 (CV 5%) |
| antiCD38_SB19 | 0.10 (CV 7.1%) | No binding |

TABLE M

Binding characteristics of various anti-CD38 antibodies.

| Anti-CD38 | H11 (Santa Cruz) | Daratumumab | antiCD38_SB19 | antiCD38_C2-CD38-1 | antiCD38_1370 |
|---|---|---|---|---|---|
| Binding to huCD38 isoform A | + | + | + | + | + |
| Binding to huCD38 isoform E | + | − | − | + | + |
| Binding to cyno CD38 | + | − | − | + | + |

In conclusion, only antiCD38_C2-CD38-1 bound to both human and cynomolgus monkey CD38 with sub-nanomolar affinity and bound to CD38 isoforms A and E.

Example 2: Generation of Trispecific Anti-CD38 Binding Proteins

Next, binding properties of the antigen binding domains of selected anti-CD38 antibodies described in Example 1 were analyzed in the trispecific format depicted in FIG. 1.

Materials and Methods

Production and Purification of Trispecific Binding Proteins

Trispecific binding proteins were produced by transient transfection of 4 expression plasmids into Expi293 cells using ExpiFectamine™ 293 Transfection Kit (Thermo Fisher Scientific) according to manufacturer's protocol. Briefly, 25% (w/w) of each plasmid was diluted into Opti-MEM, mixed with pre-diluted ExpiFectamine reagent for 20-30 minutes at room temperature (RT), and added into Expi293 cells ($2.5 \times 10^6$ cells/ml). An optimization of transfection to determine the best ratio of plasmids was often used in order to produce the trispecific binding protein with good yield and purity.

4-5 days post transfection, the supernatant from transfected cells was collected and filtered through 0.45 μm filter unit (Nalgene). The trispecific binding protein in the supernatant was purified using a 3-step procedure. First, protein A affinity purification was used, and the bound Ab was eluted using "IgG Elution Buffer" (Thermo Fisher Scientific). Second, product was dialyzed against PBS (pH7.4) overnight with 2 changes of PBS buffer. Any precipitate was cleared by filtration through 0.45 μm filter unit (Nalgene) before next step. Third, size-exclusion chromatography (SEC) purification (Hiload 16/600 Superdex 200 pg, or Hiload 26/600 Superdex 200 pg, GE Healthcare) was used to remove aggregates and different species in the prep. The fractions were analyzed on reduced and non-reduced SDS-PAGE to identify the fractions that contained the monomeric trispecific binding protein before combining them. The purified antibody can be aliquoted and stored at −80° C. long term.

ELISA Assays

The binding properties of the purified antibodies were analyzed either using ELISA or SPR methods. For ELISA, corresponding antigens for each binding site in the trispecific binding protein were used to coat a 96-well Immuno Plate (Nunc 439454, Thermo Fisher Scientific) overnight at 4° C. using 2 μg/ml each antigen in PBS (pH7.4). The coated plate was blocked using 5% skim milk+2% BSA in PBS for one hour at RT, followed by washing with PBS+0.25% Tween 20 three times (Aqua Max 400, Molecular Devices). Serial dilution of antibodies (trispecific and control Abs) were prepared and added onto the ELISA plates (100 μl/well in duplicate), incubated at RT for one hour, followed by washing 5 times with PBS+0.25% Tween 20.

After washing, the HRP conjugated secondary anti-human Fab (1:5000, Cat. No. 109-035-097, Jackson ImmunoResearch Inc) was added to each well and incubated at RT for 30 minutes. After washing 5 times with PBS+0.25% Tween 20, 100 μl of TMB Microwell Peroxidase Substrate (KPL, Gaithersburg, Md., USA) was added to each well. The reaction was terminated by adding 50 μl 1M $H_2SO_4$, and $OD_{450}$ was measured using SpectraMax M5 (Molecular Devices) and analyzed using SoftMax Pro6.3 software (Molecular Devices). The final data was transferred to GraphPad Prism software (GraphPad Software, CA, USA), and plotted as shown. EC50 was calculated using the same software.

ELISA assay was used to determine the binding of an anti-CD38xCD28xCD3 trispecific antibodies or isotype control antibody (human IgG4) to human CD3 (Cambridge Biologics LLC Cat #03-01-0051), CD28 (Cambridge Biologics LLC Cat #03-01-0303), and CD38 (Cambridge Biologics LLC Cat #03-01-0369). The bound antibodies were detected using a horseradish peroxidase (HRP)-conjugated anti-Fab secondary antibody (Jackson ImmunoResearch Inc #109-035-097).

Results

Anti-CD38 antigen binding domains were tested in trispecific format (anti-CD38xanti-CD28xanti-CD3) for ability to bind CD38 when other antigen binding domains are bound to their cognate ligands using SPR. For sequential binding of the three antigens to each trispecific Ab, saturating concentration (>10 KD) of each antigen was injected for 8 min followed by 5 min dissociation. Surface regenerate was conducted by injecting 10 mM Glycine-HCl pH 2.5 for 60 sec at 30 μl/min. Data were fitted with 1:1 kinetic binding model and analyzed using Biacore S200 Evaluation Software v 1.0. Equilibrium dissociation constant ($K_D$) was calculated using association rate constant ($k_{on}$) and dissociation rate constant ($k_{off}$).

This SPR-based assay showed that trispecific binding proteins were able to bind CD38 regardless of whether the CD3 and/or CD28 antigen binding domains were also bound to their cognate antigen. Kinetic parameters as measured by SPR are provided in Table M2.

TABLE M2

Binding of trispecific anti-CD38xanti-CD28xanti-CD3 binding proteins to 1, 2, or 3 cognate antigens.

| Binding protein state prior to CD38 binding | $k_a$ (M$^{-1}$s$^{-1}$) | $k_d$ (s$^{-1}$) | $K_D$ (M) |
|---|---|---|---|
| No prebound | 9.02E+05 | 1.42E-03 | 1.57E-09 |
| Prebound CD3 | 8.35E+05 | 1.24E-03 | 1.48E-09 |
| Prebound CD28 | 7.39E+05 | 1.32E-03 | 1.79E-09 |
| Prebound CD3 then CD28 | 8.18E+05 | 1.23E-03 | 1.50E-09 |
| Prebound CD28 then CD3 | 8.37E+05 | 1.23E-03 | 1.47E-09 |

These results demonstrate that all three targets can bind to the trispecific binding proteins simultaneously. Pre-binding the trispecific binding proteins with CD28, CD3, or both (in either order) did not alter binding kinetics or binding affinity to CD38.

Next, each antigen binding domain of the CD38$_{SB19}$xCD28$_{sup}$xCD3$_{mid}$ trispecific binding protein was evaluated by SPR for the ability to bind cognate antigen with and without the other two antigen binding domains in saturation. Tables M3 and M4 show the results of these assays.

TABLE M3

Target binding without other targets present.

| Target | ka (M$^{-1}$s$^{-1}$) | $k_d$ (s$^{-1}$) | $K_d$ (M) |
|---|---|---|---|
| CD38 | 8.04E+05 | 1.41E-03 | 1.75E-09 |
| CD28 | 1.16E+05 | 3.14E-04 | 2.71E-09 |
| CD3 | 2.90E+04 | 6.73E-04 | 2.32E-08 |

TABLE M4

Target binding with other targets in saturation.

| Target | ka (M$^{-1}$s$^{-1}$) | $k_d$ (s$^{-1}$) | $K_d$ (M) |
|---|---|---|---|
| CD38 | 5.93E+05 | 1.44E-03 | 2.42E-09 |
| CD28 | 1.05E+05 | 3.96E-04 | 3.77E-09 |
| CD3 | 1.27E+05 | 2.36E-03 | 1.86E-08 |

As demonstrated in Tables M3 and M4, having two targets saturated by pre-binding with antigen did not impact the kinetics or binding affinity of the third target for CD38 or CD28. In the case of CD3 binding, prebound CD38 and/or CD28 resulted in faster kinetics (approximately 4-fold impact on $k_{on}$ and $k_{off}$ values).

Anti-CD38 antigen binding domains were tested in trispecific format with two anti-CD28 antigen binding domains (super agonist, "sup," and conventional agonist, "cvn") and two anti-CD3 antigen binding domains ("mid" and "low"). Variable domain sequences for these antigen binding domains are provided as follows: anti-CD28$_{sup}$: SEQ ID NO:49 (VH) and SEQ ID NO:50 (VL); anti-CD28$_{cvn}$: SEQ ID NO:51 (VH) and SEQ ID NO:52 (VL); anti-CD3$_{mid}$: SEQ ID NO:53 (VH) and SEQ ID NO:54 (VL); anti-CD3$_{low}$: SEQ ID NO:84 (VH) and SEQ ID NO:85 (VL). The results of SPR assays examining binding of trispecific binding proteins are shown in FIG. 2. Three anti-CD38 binding domains had roughly the same binding affinity in the trispecific binding protein format as in a monospecific format. Both CD3 binding domains had approximately the same binding affinity in mono-, bi-, and trispecific formats. CD28 binding domains showed slightly lower (but still nanomolar) binding affinity in bi- or trispecific format as compared with monospecific. When the other two antigen binding domains were saturated, anti-CD38$_{SB19}$ and anti-CD28$_{sup}$ binding domains had similar binding affinities, compared with when the other two antigen binding domains are not bound to antigen. However, the anti-CD3$_{mid}$ binding domain showed faster kinetics when the other two antigen binding domains were saturated. These results demonstrate that anti-CD38, anti-CD28, and anti-CD3 binding domains are compatible for use with the trispecific binding protein format.

The anti-CD38 antigen binding domains generated herein were also compared against the existing anti-CD38 antigen binding domain of antiCD38_SB19 (see SEQ ID NO:47 for VH and SEQ ID NO:48 for VL sequences, respectively). The binding of trispecific molecules to CD38 expressed on the surface of recombinant murine preB::300.19 cells was determined by flow cytometry and the corresponding anti-CD38 monovalent antibodies were assayed in parallel. The recombinant cell line was described by J. Deckket et al. 2014 Clin. Cancer Res 20:4574-4583. Murine preB::300.19 CD38-expressing cells were coated at 40,000 cells/well on 96-well High Bind plate (MSD L15XB-3) and 100 µL/well of trispecific molecules were added for 45 min at 4° C. and washed three times with PBS 1% BSA. 100 µL/well of goat anti-human IgG conjugated with Alexa488 (Jackson ImmunoResearch; #109-545-098) was added for 45 min at 4° C. and washed three times with PBS 1% BSA. Antibody binding was evaluated after centrifugation and resuspension of cells by adding 200 µl/well PBS 1% BSA and read using Guava® easyCyte™ 8HT Flow Cytometry System. Apparent KD and EC50 values were estimated using BIOST@T-BINDING and BIOST@T-SPEED software, respectively.

Flow cytometry was used as described above to examine binding of antiCD38_SB19 antibody or the trispecific binding protein with the antiCD38_SB19 anti-CD38 antigen binding domain to murine pre-B cells expressing human or cynomolgus monkey CD38 polypeptide on their cell surface. The CD38xCD28$_{sup}$xCD3$_{mid}$ trispecific binding protein with the antiCD38_SB19 anti-CD38 antigen binding domain bound to cells expressing human CD38 with 8-fold lower apparent affinity (EC50=4 nM) than antiCD38_SB19 monospecific antibody (EC50=0.5 nM). Neither antiCD38_SB19 monospecific antibody or the trispecific binding protein with the antiCD38_SB19 anti-CD38 antigen binding domain bound to cells expressing cynomolgus CD38.

The binding domain of humanized anti-CD38 antibody antiCD38_C2-CD38-1_VH1-VL1 was also tested in trispecific formats for binding to cells expressing human or cynomolgus CD38 polypeptides. Unlike antiCD38_SB19, CD38xCD28$_{sup}$xCD3$_{mid}$ and CD38xCD28$_{cvn}$xCD3mid trispecific binding proteins with antiCD38_C2-CD38-1_VH1-VL1 anti-CD38 antigen binding domain, as well as the antiCD38_C2-CD38-1_VH1-VL1 monospecific antibody, were able to bind both human and cynomolgus monkey CD38 polypeptides. The CD38xCD28$_{cvn}$xCD3$_{mid}$ trispecific binding protein with the antiCD38_C2-CD38-1_VH1-VL1 anti-CD38 antigen binding domain bound to cells expressing human CD38 with 9-fold lower apparent affinity (EC50=4.4 nM) than the parental antiCD38_C2-CD38-1_VH1-VL1 antibody (EC50=0.5 nM). The CD38xCD28$_{cvn}$xCD3$_{mid}$ trispecific binding protein with the antiCD38_C2-CD38-1_VH1-VL1 anti-CD38 antigen binding domain bound to cells expressing cynomolgus CD38 with 7.5-fold lower apparent affinity (EC50=7.5 nM) than the parental antiCD38_C2-CD38-1_VH1-VL1 antibody (EC50=1 nM). The CD38xCD28$_{sup}$xCD3$_{mid}$ trispecific binding protein with the antiCD38_C2-CD38-1_VH1-VL1 anti-CD38 antigen binding domain bound to cells expressing human CD38 with a 2.5-fold lower apparent affinity (EC50=11 nM) than the CD38xCD28$_{cvn}$xCD3$_{mid}$ trispecific binding protein with the antiCD38_C2-CD38-1_VH1-VL1 anti-CD38 antigen binding domain (EC50=4.4 nM).

The binding domain of humanized anti-CD38 antibody antiCD38_1370 was also compared against the antiCD38_1370 monospecific antibody for binding to cells expressing human or cynomolgus CD38 polypeptides. While the antiCD38_1370 monospecific antibody bound to cells expressing human (EC50=11.2 nM) or cynomolgus monkey (EC50=6.6 nM) CD38 polypeptides in the nM range, the CD38xCD28$_{sup}$xCD3$_{mid}$ trispecific binding protein with the antiCD38_1370 anti-CD38 antigen binding domain bound to cells expressing human or cynomolgus monkey CD38 polypeptides without saturation.

In conclusion, the affinity for CD38SB19xCD28$_{sup}$xCD3$_{mid}$ trispecific binding protein (antiCD38_SB19 anti-CD38 binding domain) binding to human CD38 was found to be in the same range, whether examining binding to recombinant human CD38 by SPR or to human CD38 expressed on a cell surface by flow cytometry (FIG. 3). Similarly, the affinity of CD38$_{VH1}$xCD28$_{sup}$xCD3$_{mid/low}$ (antiCD38_C2-CD38-1_VH1-VL1 anti-CD38 binding domain) and CD38$_{VH1}$xCD28$_{cvn}$xCD3$_{mid/low}$ trispecific binding proteins (antiCD38_C2-CD38-1_VH1-VL1 anti-CD38 binding domain) for binding to human CD38 was also in the same range in both assays. For CD38$_{HHY1370}$xCD28$_{sup}$xCD3mid (antiCD38_1370 anti-CD38 binding domain), the K$_D$ for binding human CD38 was determined by SPR to be 1 nM, whereas no accurate EC50 value could be estimated by flow cytometry (FIG. 3). A summary of apparent KD values (obtained by FACS analyses) of trispecific binding proteins with various anti-CD38 binding domains is provided in Table M5.

TABLE M5

Summary of apparent KD values obtained by flow cytometry assays.

| | Apparent KD FACS (M) | |
|---|---|---|
| | hCD38-expressing cells | cCD38-expressing cells |
| Trispecific with antiCD38_C2-CD38-1_VH1-VL1 anti-CD38 binding domain | 4.4 nM | 7.5 nM |
| Trispecific with antiCD38_1370 anti-CD38 binding domain | No saturation | No saturation |
| Trispecific with antiCD38_SB19 anti-CD38 binding domain | 4 nM | No binding |
| antiCD38_C2-CD38-1_VH1-VL1 | 0.5 nM | 1 nM |
| antiCD38 1370 | 11.2 nM | 6.6 nM |
| antiCD38_SB19 | 0.5 nM | No binding |

As expected, ΔCD38xCD28$_{sup}$xCD3$_{mid}$ trispecific binding protein lacking the anti-CD38 binding domain did not bind to cells expressing human or cynomolgus monkey CD38 polypeptides. This indicates that the binding observed in this assay was specific for the CD38 antigen binding domains.

Example 3: CD38/CD3xCD28 Ab Stimulates Central Memory CD4 and CD8, Th1 and Antigen-Specific Responses To determine whether the CD38/CD3xCD28 trispecific Ab could enhance cellular immune function, the phenotype of expanded T cells in vitro was evaluated.

Materials and Methods

Peripheral blood mononuclear cells were isolated from blood of healthy human donors collected by Research Blood Components, LLC (Boston, Mass.). The PBMC were added to antibody-coated plates (350 ng/well) (5×10$^5$ cells/mL), as previously described above, and incubated at 37° C. for 3 and 7 days. The cells were collected at specific time points and analyzed by flow cytometry for T cell subsets: naïve (CCR7+CD45RO−), Tcm (CCR7+CD45RO+), T$_{em}$ (CCR7−CD45RO+), Tregs (CD4+Foxp3+CD25hi). Cells were also treated with monensin (GolgiStop) (BD Biosciences, CA) for at least 6 hours before flow staining to determine intracellular cytokine expression: Th1 (CD4+IFN-γ+), Th2 (CD4+IL-4+), and Th17 (CD4+IL-17+). CMV pp65-specific CD8+ T cells were detected using fluorescent-conjugated pentamer restricted to the PBMC donors' HLA (A*02:01/NLVPMVATV) (ProImmune, Oxford, UK). PBMC was obtained from HemaCare (Van Nuys, CA) from donors with known CMV positive populations and HLA types. PMBC from donors negative for the restricting HLA type was used as negative control. Staining was done as per manufacturer's protocol.

Results

Figure 4A:
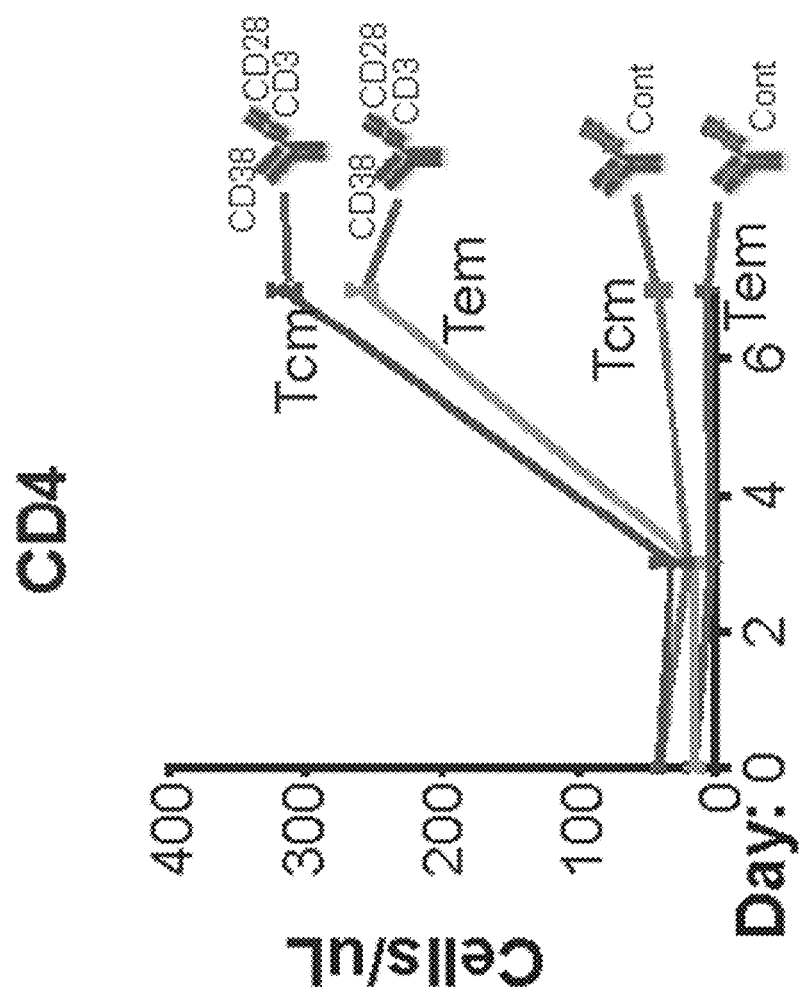
FIGS. 4A-4D show the characterization of in vitro T cell subset expansion in response to CD38VH1/CD3midxCD28sup trispecific antibodies. Evaluation of T cell subset expansion was performed by coating wells with 350 ng/well of the CD38 trispecific Ab in the absence of exogenous cytokines. T cell populations were measured at indicated time points. A trispecific Ab having three mutated antigen binding domains was used as negative control. Flow cytometry was used to determine central ($T_{cm}$) and effector memory ($T_{em}$) CD4 T cells (FIG. 4A), T helper cells (Th1, Th17, Th2) (FIG. 4B), central ($T_{cm}$) and effector memory ($T_{em}$) CD8 T cells (FIG. 4C), and cytomegalovirus (CMV) pp65-specific CD8 cells (FIG. 4D) as described in Example 3. Analysis of CMV-specific pp65 effector cells was performed by pentamer staining of peripheral blood mononuclear cells (PBMCs) from HLA-A2 CMV+ donors treated with the CD38 trispecific or the triple negative control antibodies.
Figure 4B:
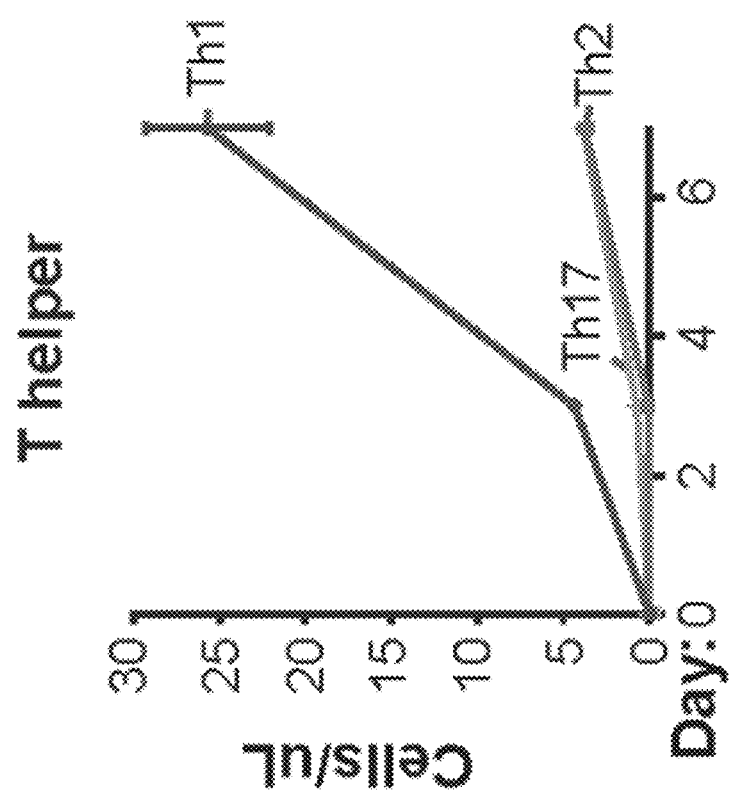
Figure 4C:
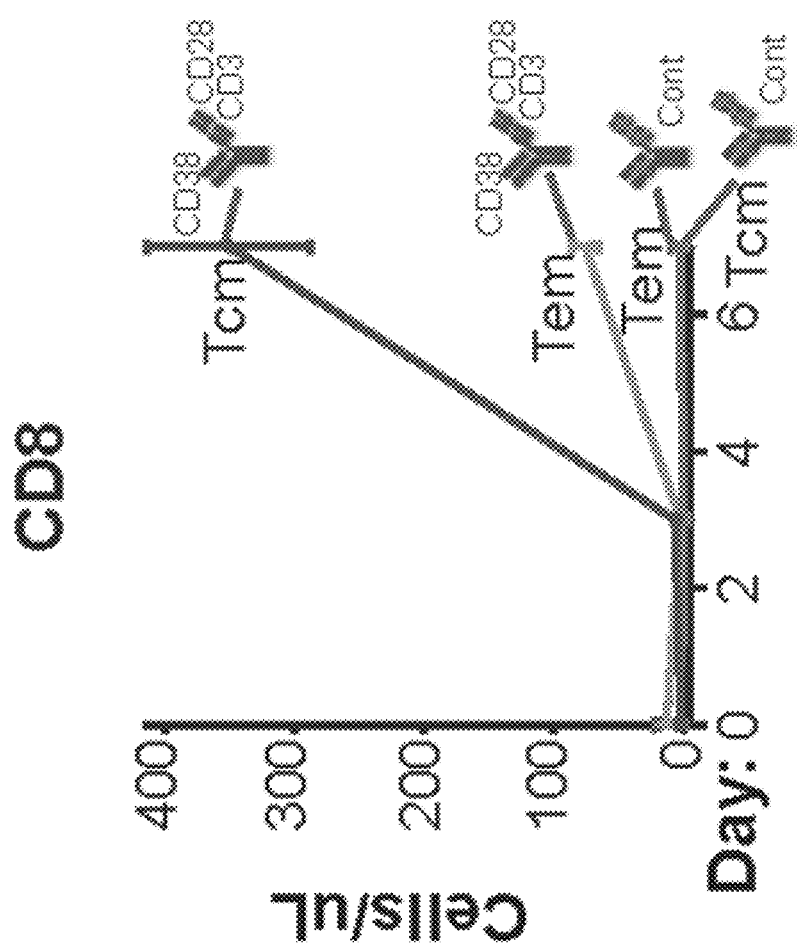
Figure 4D:
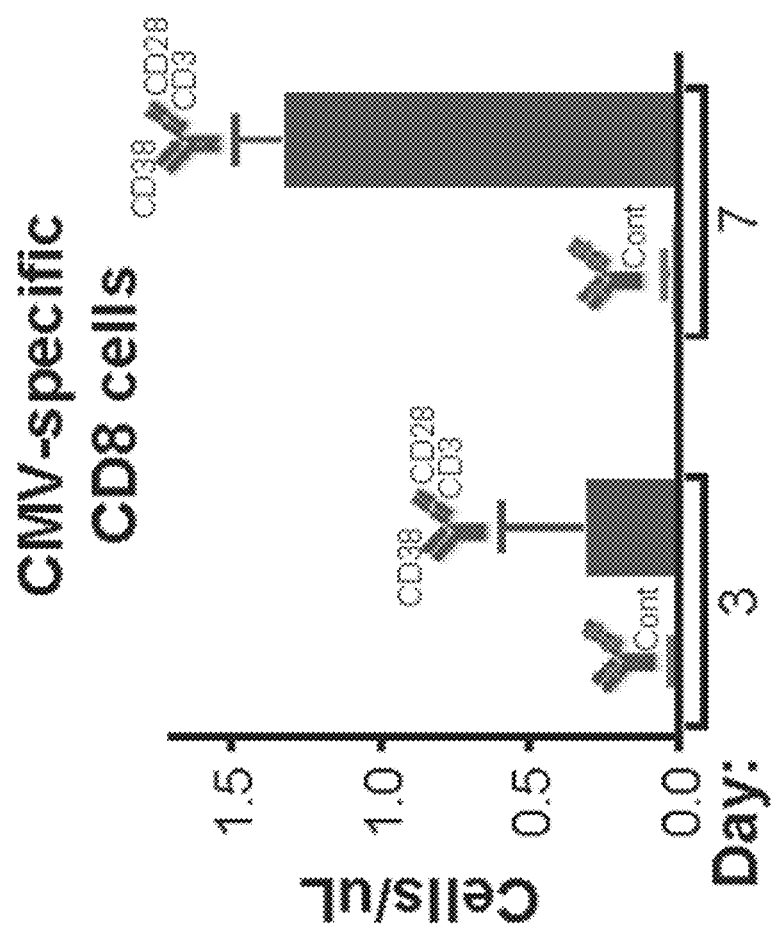

Human PBMCs from CMV-infected donors were incubated for 7 days with the trispecific Ab or a negative control trispecific antibody with three mutated antigen binding sites in the absence of cytokines. Analysis of the CD4 subsets revealed the greatest proliferation in the central memory pool, with a smaller increase in effector memory cells (FIG. 4A). Analysis of the CD4 subset also revealed the greatest proliferation of Th1 cells (>6-fold) compared to Th2 or Th17 cells (FIG. 4B). In the CD8 subset, there was a >150-fold increase in the central memory CD8 subset by day 7, with a lesser increase in effector memory cells (FIG. 4C). Importantly, pre-existing antigen-specific CD8 responses to CMV, directed to the pp65 epitope in seropositive HLA-A2 donors using tetramer staining (Gratama J W, van Esser J W, et al. *Blood* 98:1358-1364(2001)), increased >44-fold in the presence of the CD38 trispecific compared to negative control (FIG. 4D).

Taken together, these data indicate that the CD38 trispecific Ab stimulates Th1 function and protective CD8 memory T cell responses that are likely to enhance anti-tumor and anti-viral immunity in vivo.

Example 4: CD38/CD28xCD3 Trispecific Antibodies Promote CMV-Specific Immune Response The activation and/or proliferation of viral antigen specific T cells could provide a therapeutic strategy against viral infections, such as infections of Cytomegalovirus (CMV). The ability of CD38/CD28xCD3 trispecific antibodies to promote activation and expansion of CMV-specific T cells was determined.

Materials and Methods

ELISA Assays

Binding affinities to each target antigen by the CD38/CD28xCD3 T cell engagers were measured by ELISA. Briefly, each antigen was used to coat the 96-well Immuno Plate (Thermo Fisher Scientific) overnight at 4° C. using 200 ng/well in PBS (pH7.4) of each antigen. The coated plate was blocked using 5% skim milk+2% BSA in PBS for one hour at RT, followed by washing with PBS+0.25% Tween 20 three times (Aqua Max 400, Molecular Devices). Serial dilution of antibodies (trispecific and control Abs) were prepared and added onto the ELISA plates (100 µl/well in duplicate), incubated at RT for one hour, followed by washing 5 times with PBS+0.25% Tween 20. After washing, the HRP conjugated secondary anti-human Fab (1:5000, Cat. No. 109-035-097, Jackson ImmunoResearch Inc) was added to each well and incubated at RT for 30 minutes. After washing 5 times with PBS+0.25% Tween 20, 100 µl of TMB Microwell Peroxidase Substrate (KPL, Gaithersburg, Md., USA) was added to each well. The reaction was terminated by adding 50 µl 1M H2SO4, and OD450 was measured using SpectraMax M5 (Molecular Devices) and analyzed using SoftMax Pro6.3 software (Molecular Devices). The final data was transferred to GraphPad Prism software (GraphPad Software, CA, USA), and plotted. EC50 was calculated using the same software.

SPR Assays

Human CD38-His antigens were used (Cambridge Biologics, Cambridge, Mass.) for full kinetic analysis. Kinetic characterization of purified antibodies was performed using SPR technology on a BIACORE 3000 (GE Healthcare). A capture assay using human IgG1 specific antibody capture and orientation of the investigated antibodies was used. For capture of Fc containing protein constructs the human antibody capture kit (GE Healthcare) was used. For capture of His-tagged antigen, anti-His antibody capture kit (GE Healthcare) was used. The capture antibody was immobilized via primary amine groups (11000 RU) on a research grade CM5 chip (GE Life Sciences) using standard procedures. The analyzed antibody was captured at a flow rate of 10 µL/min with an adjusted RU value that would result in maximal analyte binding signal of typically 30 RU. Binding kinetics was measured against the trispecific antibodies. As assay buffer HBS EP (10 mM HEPES, pH 7.4, 150 mM NaCl, 3 mM EDTA, and 0.005% Surfactant P20) was used at a flow rate of 30 µl/min. Chip surfaces were regenerated with the regeneration solution of the respective capture kit. Kinetic parameters were analyzed and calculated in the BIA evaluation program package v4.1 using a flow cell without captured antibody as reference and the 1:1 Langmuir binding model with mass transfer.

In Vitro T Cell Proliferation Measurement

T cells were isolated from human Peripheral blood mononuclear cell (PBMC) donors by negative selection using a magnetic Pan T Cell Isolation Kit (Miltenyi Biotec GmbH, Germany). Antibodies were coated onto 96-well cell culture plates by preparing the antibodies in sterile PBS and dispensing 50 uL into each well (350 ng/well). The plates were then incubated at 37° C. for at least 2 hours and then washed with sterile PBS. The untouched T cells were added to the antibody-coated plates ($5\times10^5$ cells/mL) and incubated at 37° C. for multiple days. The cells were passaged with new cell culture media onto fresh antibody-coated plates on day 4. In certain experiments with 7 days incubation, only fresh medium was added w/o changing to fresh antibody-coated plate. The cells were collected at specific time points and cell numbers calculated using CountBright™ counting beads.

In Vitro T Cell Proliferation Assay and T Cell Subset Determination

Peripheral blood mononuclear cells were isolated from blood of healthy human donors collected by Research Blood Components, LLC (Boston, Mass.). The PBMCs were added to antibody-coated plates (350 ng/well) ($5\times10^5$ cells/mL), as previously described above, and incubated at 37° C. for 3 and 7 days. The cells were collected at specific time points and analyzed by flow cytometry for T cell subsets: naïve (CCR7+CD45RO−), $T_{cm}$ (CCR7+CD45RO+), $T_{em}$ (CCR7−CD45RO+), $T_{regs}$ (CD4+Foxp3+CD25hi). Cells were also treated with monensin (GolgiStop) (BD Biosciences, CA) for at least 6 hours before flow staining to determine intracellular cytokine expression: Th1 (CD4+IFN-γ+), Th2 (CD4+IL-4+), and Th17 (CD4+IL-17+). CMV pp65-specific, EBV BMLF-specific, Influenza A MP-specific and HIV-1 Gag-specific CD8+ T cells were detected using fluorescent-conjugated pentamer restricted to the PBMC donors' HLA/viral peptide (A*02:01/NLVPMVATV; SEQ ID NO:26), (A*02:01/GLCTLVAML; SEQ ID NO:27), (A*02:01/GILGFVFTL; SEQ ID NO:28), and (A*02:01/SLYNTVATL; SEQ ID NO:25) respectively (ProImmune, Oxford, UK). PBMC was obtained from HemaCare (Van Nuys, CA) for donors with known CMV, EBV, or Influenza A, and from BioIVT (Westbury, N.Y.) for donors with known HIV-1 positivity and HLA types. PMBC from donors negative for the restricting HLA type was used as negative control. Staining was done as per manufacturer's protocol.

Quantification of CMV-Specific T-Cells

As described above, PBMCs were isolated from blood of known CMV-infected human donors and added to plates containing the trispecific antibody or control antibody. The plates were incubated at 37° C. The cells were collected at the indicated time points and analyzed as described above.

Results

Figure 5A:
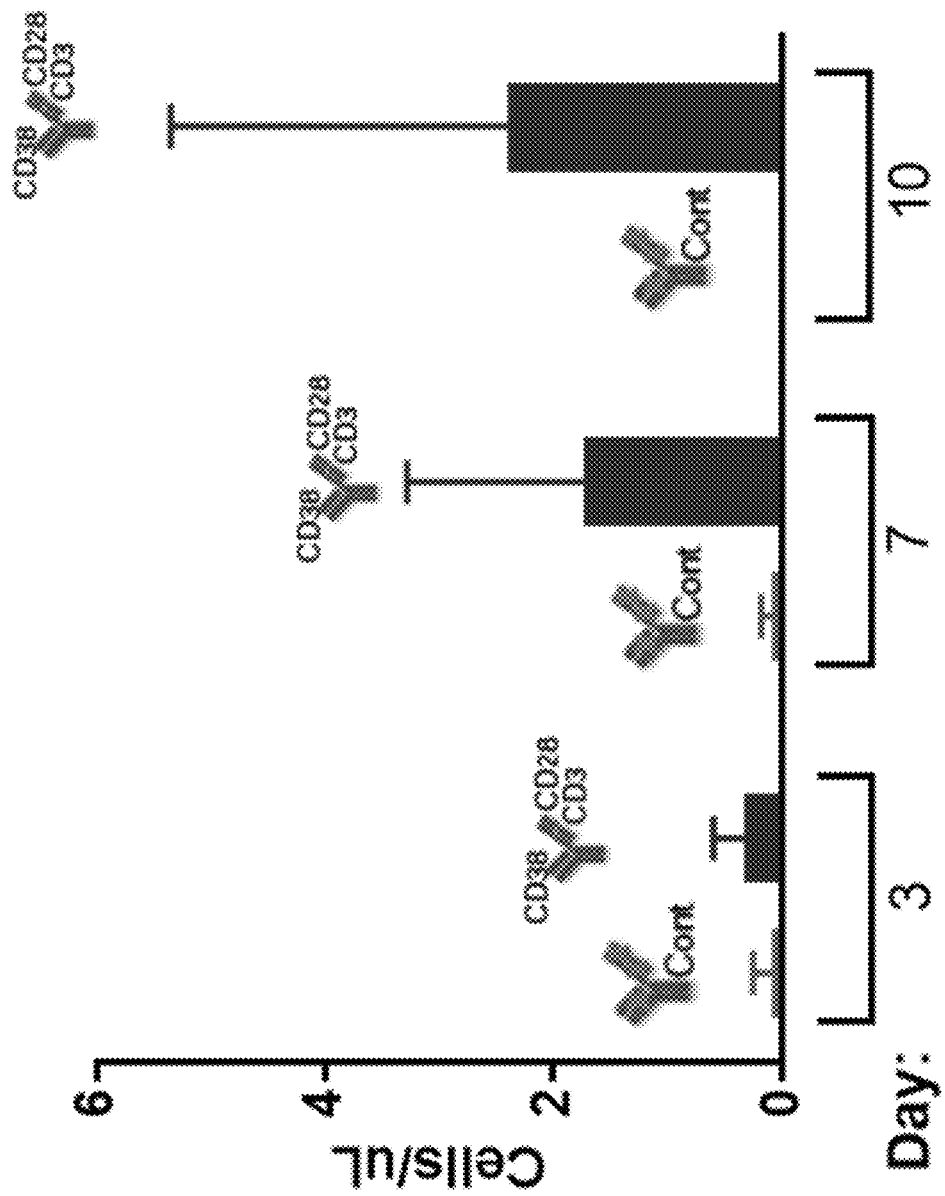
FIGS. 5A-5B show the characterization of in vitro T cell subset expansion in PBMCs collected from CMV-infected Donor B in response to $CD38_{VH1}$/CD28sup x CD3mid trispecific antibody. T cell populations were measured at indicated time points. The triple mutant trispecific antibody was used as negative control. Flow cytometry was used to quantify CMV-specific memory CD8+ T cells (FIG. 5A), as well as CMV-specific central memory ($T_{cm}$) and effector memory ($T_{em}$) CD8+ T cells (FIG. 5B). $CD38_{VH1}$/CD28sup x CD3mid trispecific antibody activated T cells and promoted the proliferation of CMV-specific memory CD8+ T cells.
Figure 5B:
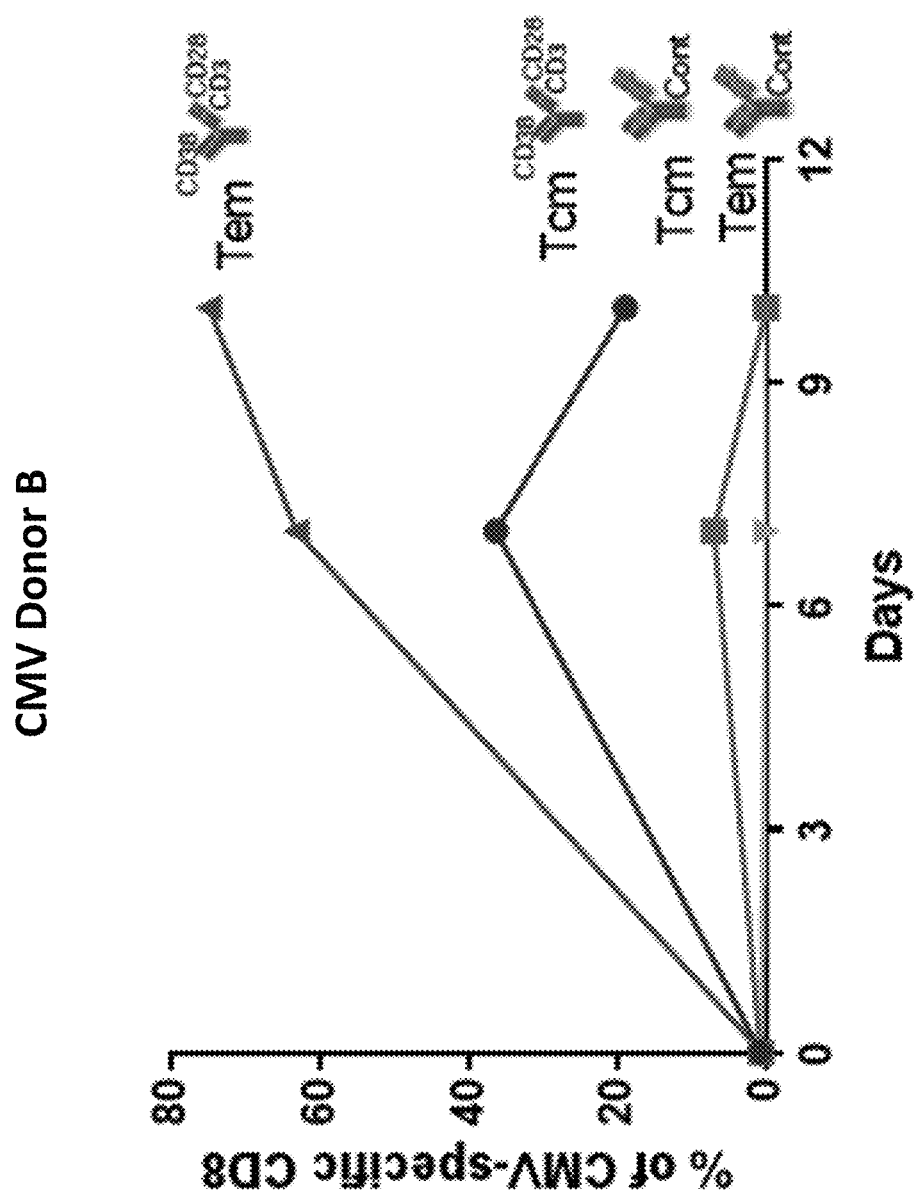
Figure 6A:
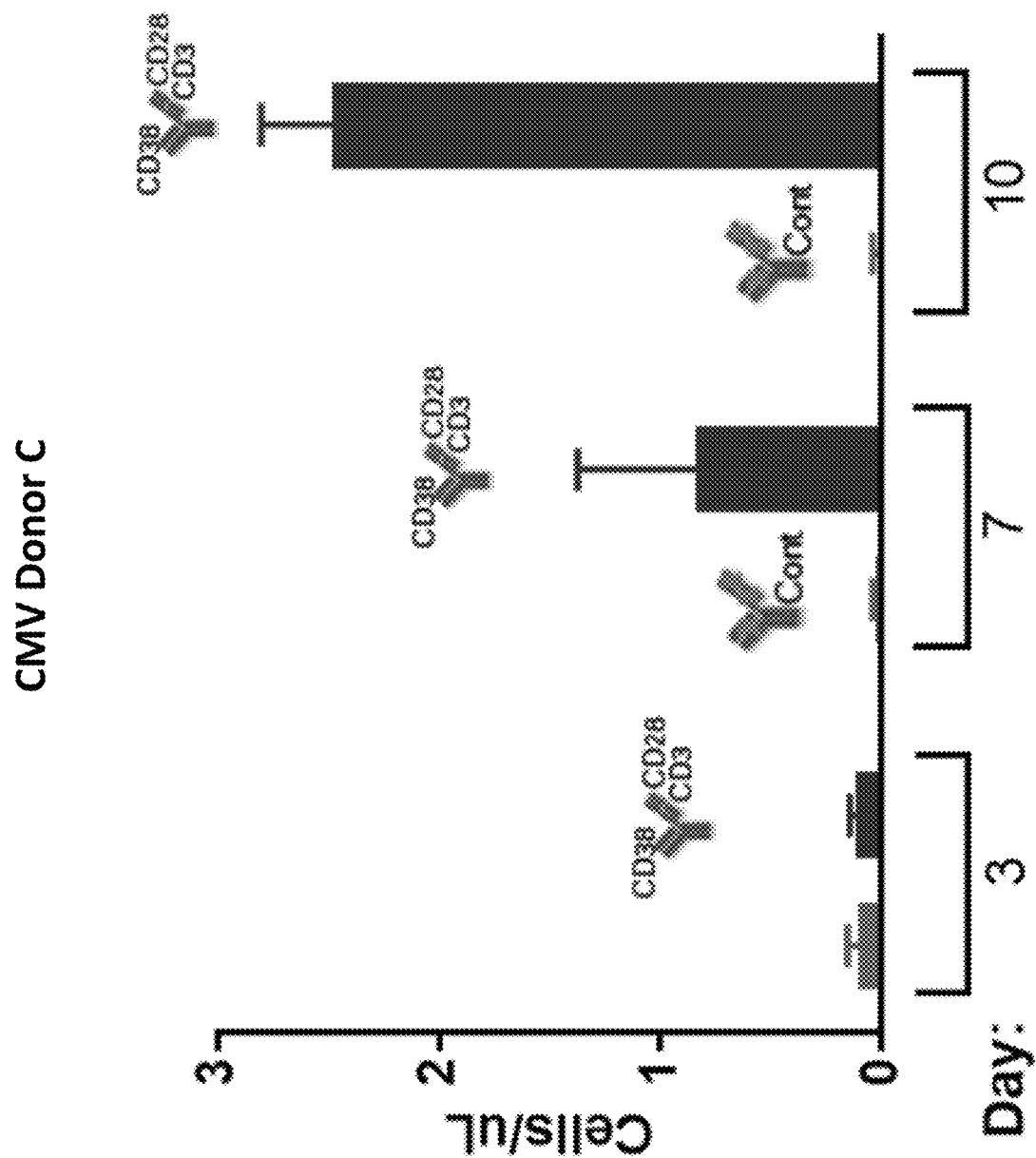
FIGS. 6A-6B show the characterization of in vitro T cell subset expansion in PBMCs collected from CMV-infected Donor C in response to $CD38_{VH1}$/CD28sup x CD3mid trispecific antibody. T cell populations were measured at indicated time points. The triple mutant trispecific antibody was used as negative control. Flow cytometry was used to quantify CMV-specific memory CD8+ T cells (FIG. 6A), as well as CMV-specific central memory ($T_{cm}$) and effector memory ($T_{em}$) CD8+ T cells (FIG. 6B). $CD38_{VH1}$/CD28sup x CD3mid trispecific antibody activated T cells and promoted the proliferation of CMV-specific memory CD8+ T cells.
Figure 6B:
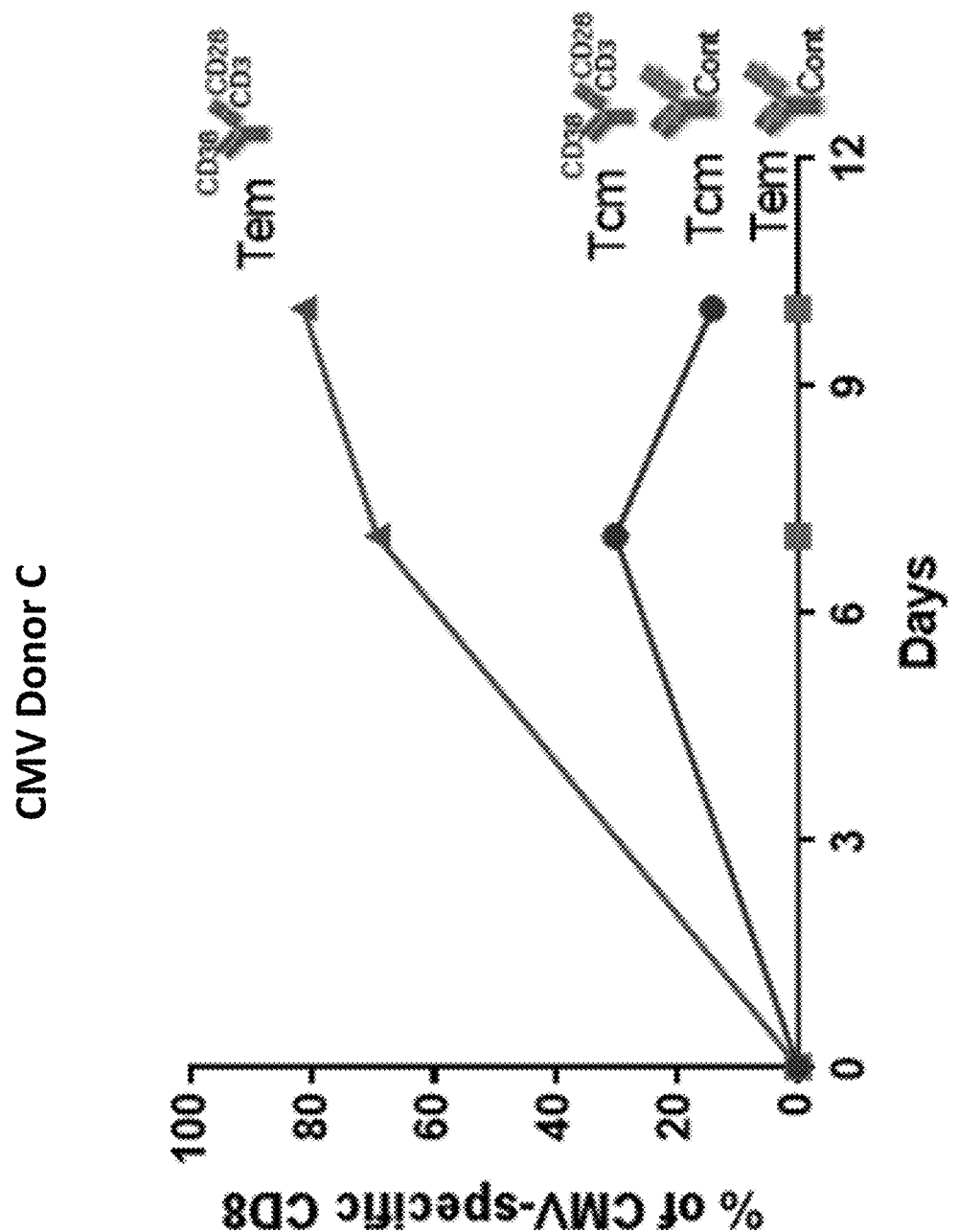

The $CD38_{VH1}$/CD28sup x CD3mid trispecific antibody activated T cells and promoted the proliferation of CMV-specific memory CD8+ T cells following incubation for up to 10 days with PBMCs isolated from CMV-infected human donor B (FIGS. 5A-5B) and CMV-infected human donor C (FIGS. 6A-6B). As shown in FIG. 5A (CMV Donor B) and FIG. 6A (CMV Donor C), the $CD38_{VH1}$/CD28sup x CD3mid trispecific antibody led to increases in CMV-specific memory CD8+ T cells (cells/µl) relative to a the triple mutant control antibody. In addition, $CD38_{VH1}$/CD28sup x CD3mid trispecific antibody increased the percentage of CMV-specific CD8+ effector memory ($T_{em}$) and central memory ($T_{cm}$) cells relative to the triple mutant control antibody (CMV Donor B, FIG. 5B; CMV Donor C, FIG. 6B).

Taken together, these data indicate that CD38/CD28xCD3 trispecific antibodies promote activation and expansion of CMV-specific T cells, such as CMV-specific CD8+ T cells, CMV-specific effector memory ($T_{em}$) CD8+ T cells, and CMV-specific central memory ($T_{cm}$) CD8+ T cells.

Example 5: CD38/CD28xCD3 Trispecific Antibodies Promote EBV-Specific Immune Response Next, the ability of CD38/CD28xCD3 trispecific antibodies to promote activation and expansion of Epstein-Barr virus (EBV)-specific T cells was determined.

Materials and Methods

Quantification of EBV-Specific T-Cells

As described above, PBMCs were isolated from blood of known EBV-infected human donors and added to plates containing the trispecific antibody or control antibody. The plates were incubated at 37° C. The cells were collected at the indicated time points and analyzed as described above.

Results

Figure 7A:
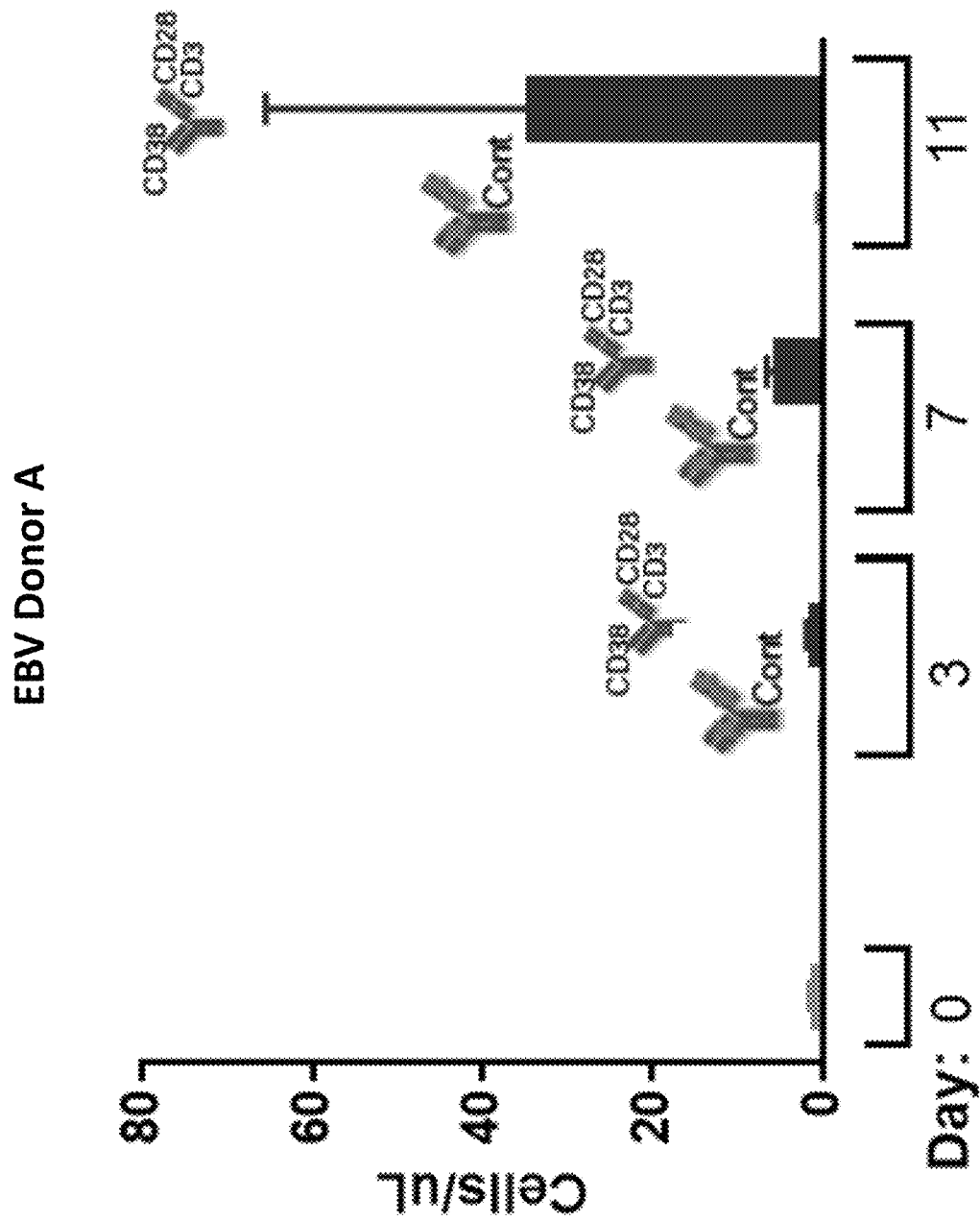
FIGS. 7A-7B show the characterization of in vitro T cell subset expansion in PBMCs collected from Epstein-barr virus (EBV)-infected Donor A in response to $CD38_{VH1}$/CD28sup x CD3mid trispecific antibody. T cell populations were measured at indicated time points. The triple mutant trispecific antibody was used as negative control. Flow cytometry was used to quantify EBV-specific memory CD8+ T cells (FIG. 7A), as well as EBV-specific central memory ($T_{cm}$) and effector memory ($T_{em}$) CD8+ T cells (FIG. 7B). $CD38_{VH1}$/CD28sup x CD3mid trispecific antibody activated T cells and promoted the proliferation of EBV-specific memory CD8+ T cells.
Figure 7B:
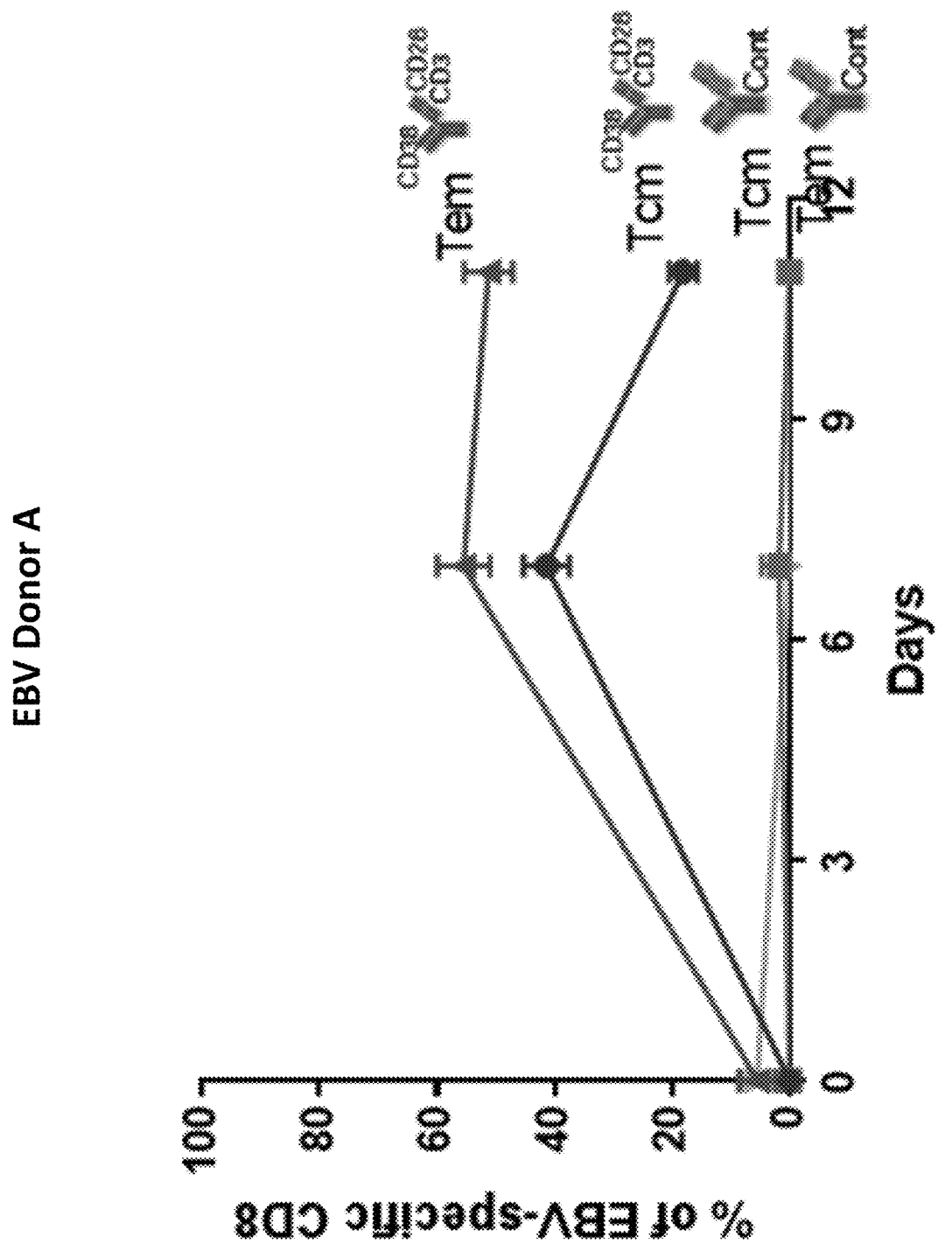
Figure 8A:
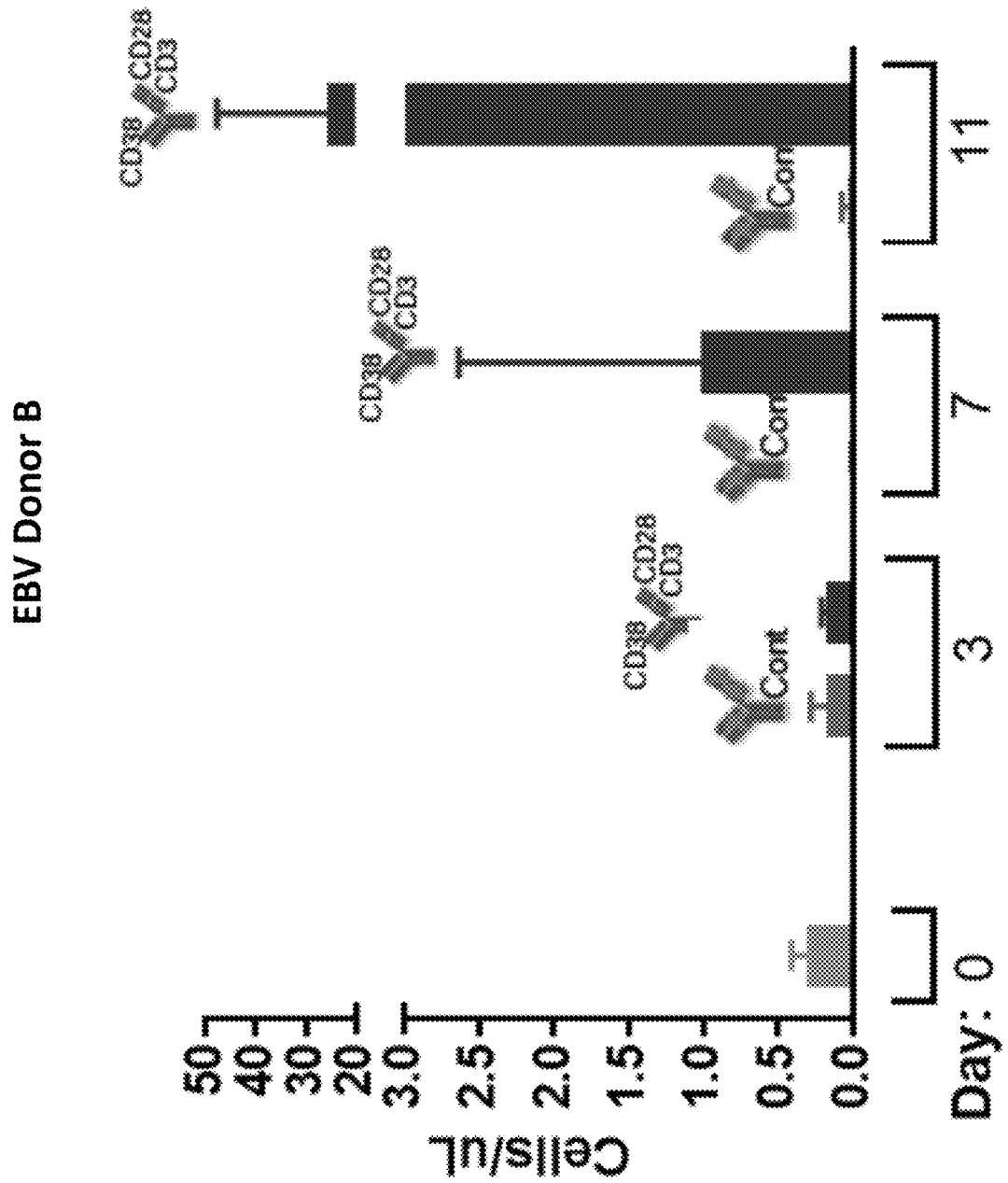
FIGS. 8A-8B show the characterization of in vitro T cell subset expansion in PBMCs collected from EBV-infected Donor B in response to $CD38_{VH1}$/CD28sup x CD3mid trispecific antibody. T cell populations were measured at indicated time points. The triple mutant trispecific antibody was used as negative control. Flow cytometry was used to quantify EBV-specific memory CD8+ T cells (FIG. 8A), as well as EBV-specific central memory ($T_{cm}$) and effector memory ($T_{em}$) CD8+ T cells (FIG. 8B). $CD38_{VH1}$/CD28sup x CD3mid trispecific antibody activated T cells and promoted the proliferation of EBV-specific memory CD8+ T cells.
Figure 8B:
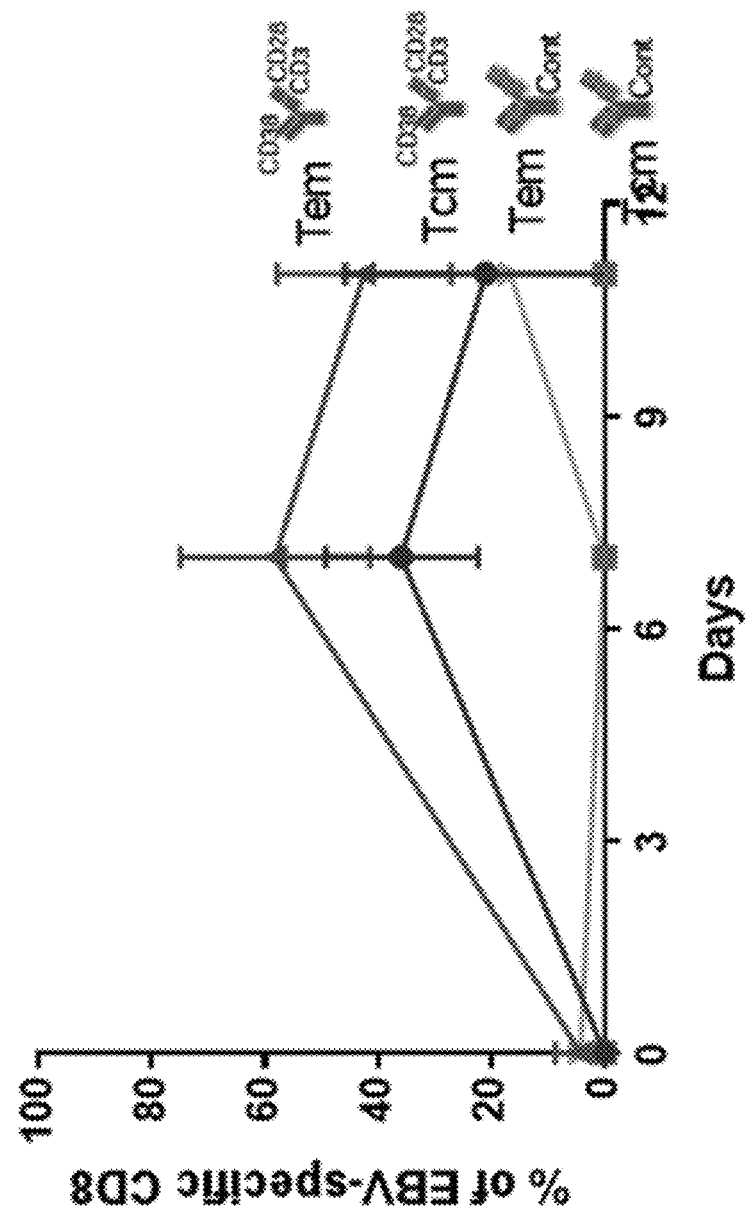

The CD38$_{VH1}$/CD28sup × CD3mid trispecific antibody activated T cells and promoted the proliferation of EBV-specific memory CD8+ T cells following incubation for up to 11 days with PBMCs isolated from EBV-infected human donor A (FIGS. 7A-7B) and EBV-infected human donor B (FIGS. 8A-8B). As shown in FIG. 7A (EBV Donor A) and FIG. 8A (EBV Donor B), the CD38$_{VH1}$/CD28sup × CD3mid trispecific antibody led to increases in EBV-specific memory CD8+ T cells (cells/μl) relative to the triple mutant control antibody. In addition, CD38$_{VH1}$/CD28sup × CD3mid trispecific antibody increased the percentage of EBV-specific CD8+T$_{em}$ cells and T$_{cm}$ cells relative to the triple mutant control antibody (EBV Donor A, FIG. 7B; EBV Donor B, FIG. 8B, e.g. see day 7).

Taken together, these data indicate that CD38/CD28×CD3 trispecific antibodies promote activation and expansion of EBV-specific T cells, such as EBV-specific CD8+ T cells, EBV-specific effector memory (T$_{em}$) CD8+ T cells, and EBV-specific central memory (T$_{cm}$) CD8+ T cells.

Example 6: CD38/CD28×CD3 Trispecific Antibodies Promote HIV-Specific Immune Response Next, the ability of CD38/CD28×CD3 trispecific antibodies to promote activation and expansion of Human Immunodeficiency Virus (HIV)-specific T cells was determined.

Materials and Methods

Quantification of HIV-Specific T-Cells

As described above, PBMCs were isolated from blood of known HIV-infected human donors and added to plates containing the trispecific antibody or control antibody. The plates were incubated at 37° C. The cells were collected at the indicated time points and analyzed as described above.

Results

Figure 9:
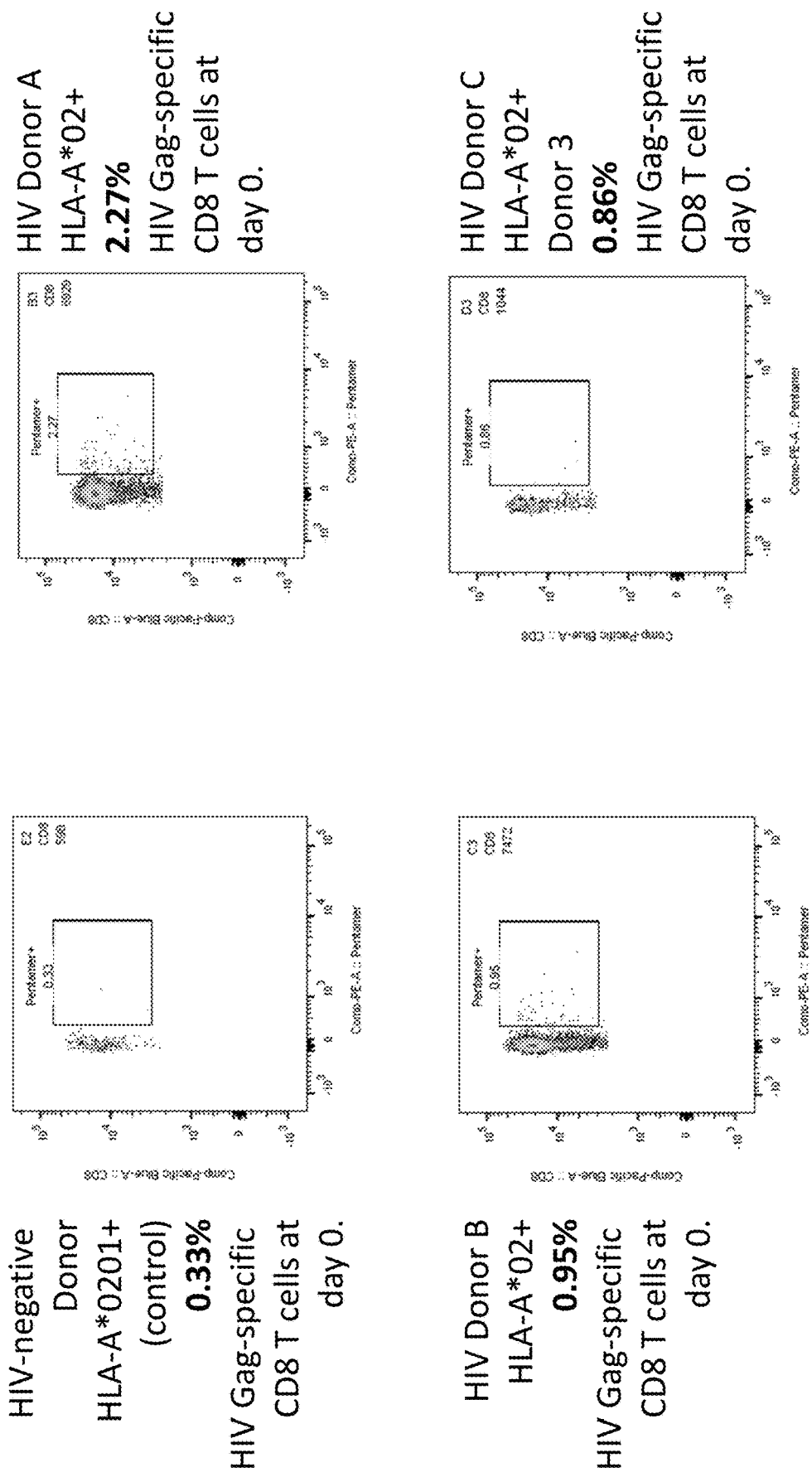
FIG. 9 shows flow cytometry profiles of PBMCs from the indicated human immunodeficiency virus (HIV)-positive donors (bottom panels and top right panel) assayed for HIV Gag-specific CD8+ T cells (A*02:01—SLYNTVATL (HIV-1 gag p17 76-84) Pentamer conjugated to PE, ProImmune) at baseline (day 0; prior to incubation with trispecific antibodies). PBMCs from an HIV-negative donor were used as negative control (top left panel). The percentages of Gag-specific CD8+ T cell population are provided and shown as inset boxes. At baseline PBMCs from HIV-positive donors contain HIV Gag-specific CD8+ T cells. Donors A-C in FIG. 9 are the same as donors D-F shown in FIGS. 10A-12B.

On day 0 (prior to incubation with trispecific antibodies), PBMCs from HIV-positive donors exhibit HIV Gag-specific CD8 T cells (A*02:01—SLYNTVATL (HIV-1 gag p17 76-84) Pentamer conjugated to PE, ProImmune) (FIG. 9). For example, three HIV-positive PBMC donors had 0.86% (HIV Donor A), 0.95% (HIV Donor B), and 2.27% (HIV Donor C) Gag-specific CD8 T cells compared to 0.33% in PBMCs from an HIV-negative donor.

Figure 10A:
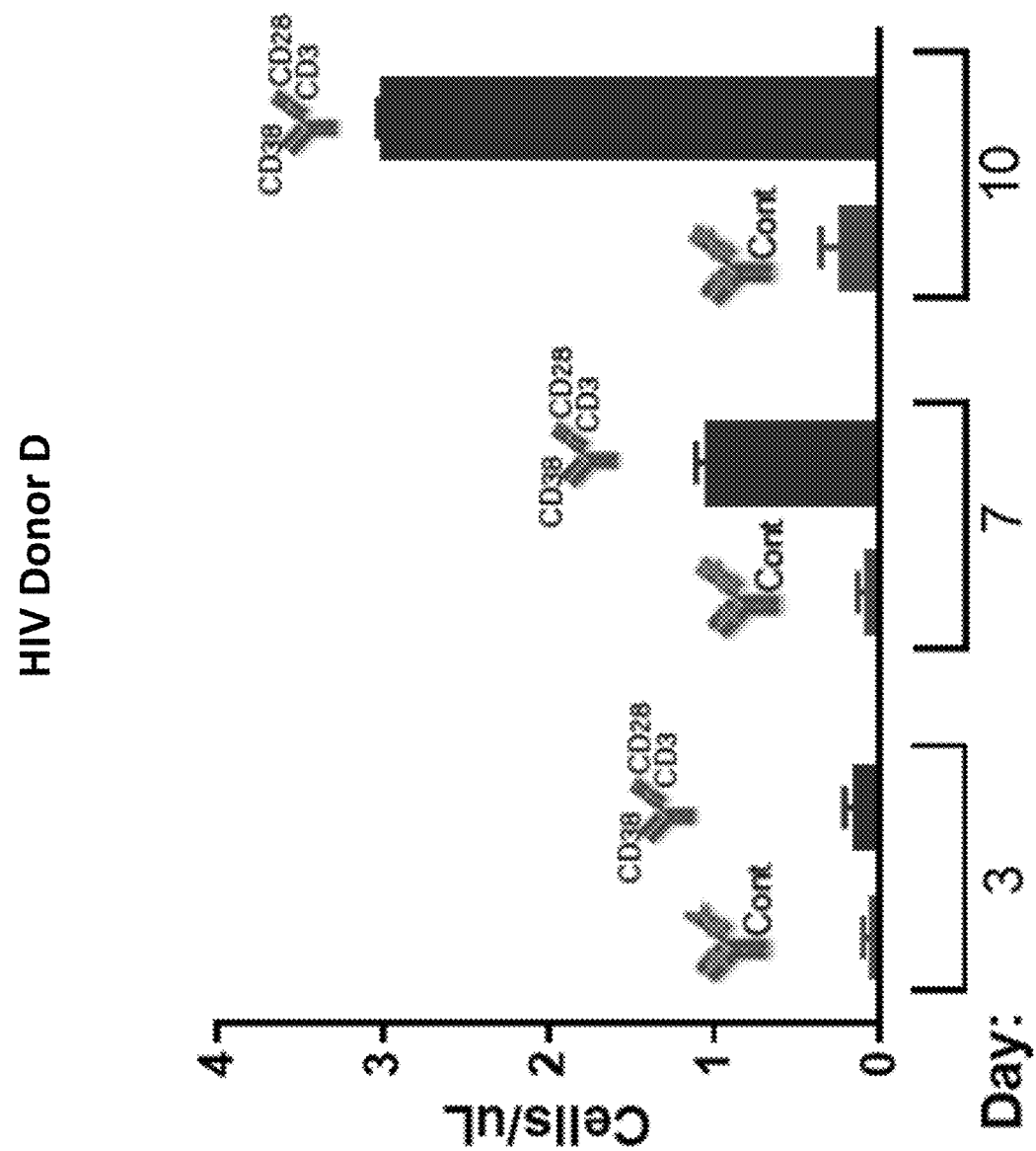
FIGS. 10A-10B show the characterization of in vitro T cell subset expansion in PBMCs collected from HIV-positive Donor D in response to $CD38_{VH1}$/CD28sup x CD3mid trispecific antibody. T cell populations were measured at indicated time points. The triple mutant trispecific antibody was used as negative control. Flow cytometry was used to quantify HIV-specific memory CD8+ T cells (FIG. 10A), as well as HIV-specific central memory ($T_{cm}$) and effector memory ($T_{em}$) CD8+ T cells (FIG. 10B). $CD38_{VH1}$/CD28sup x CD3mid trispecific antibody activated T cells and promoted the proliferation of effector memory ($T_{em}$) CD8+ T cells.
Figure 10B:
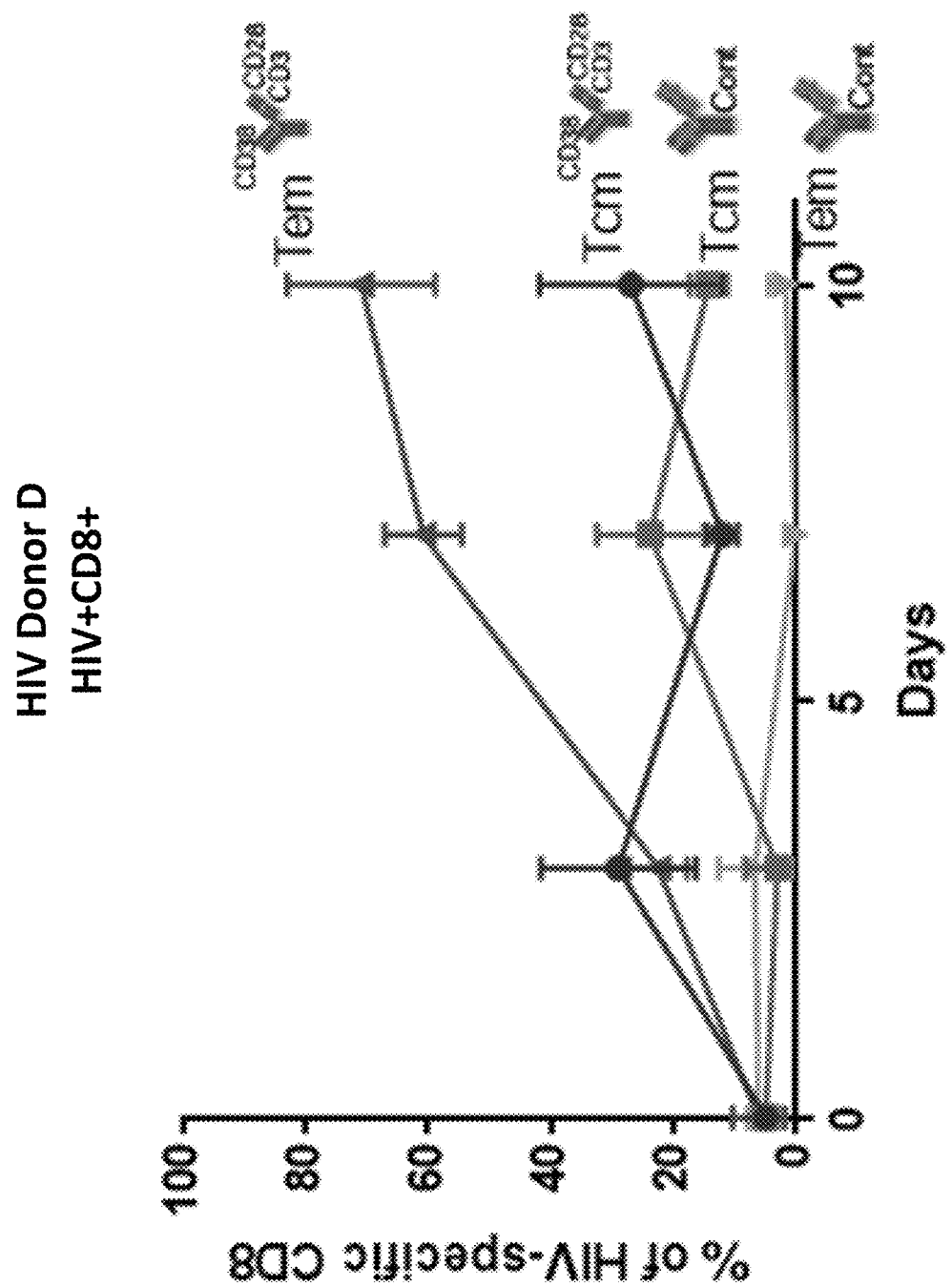
Figure 11A:
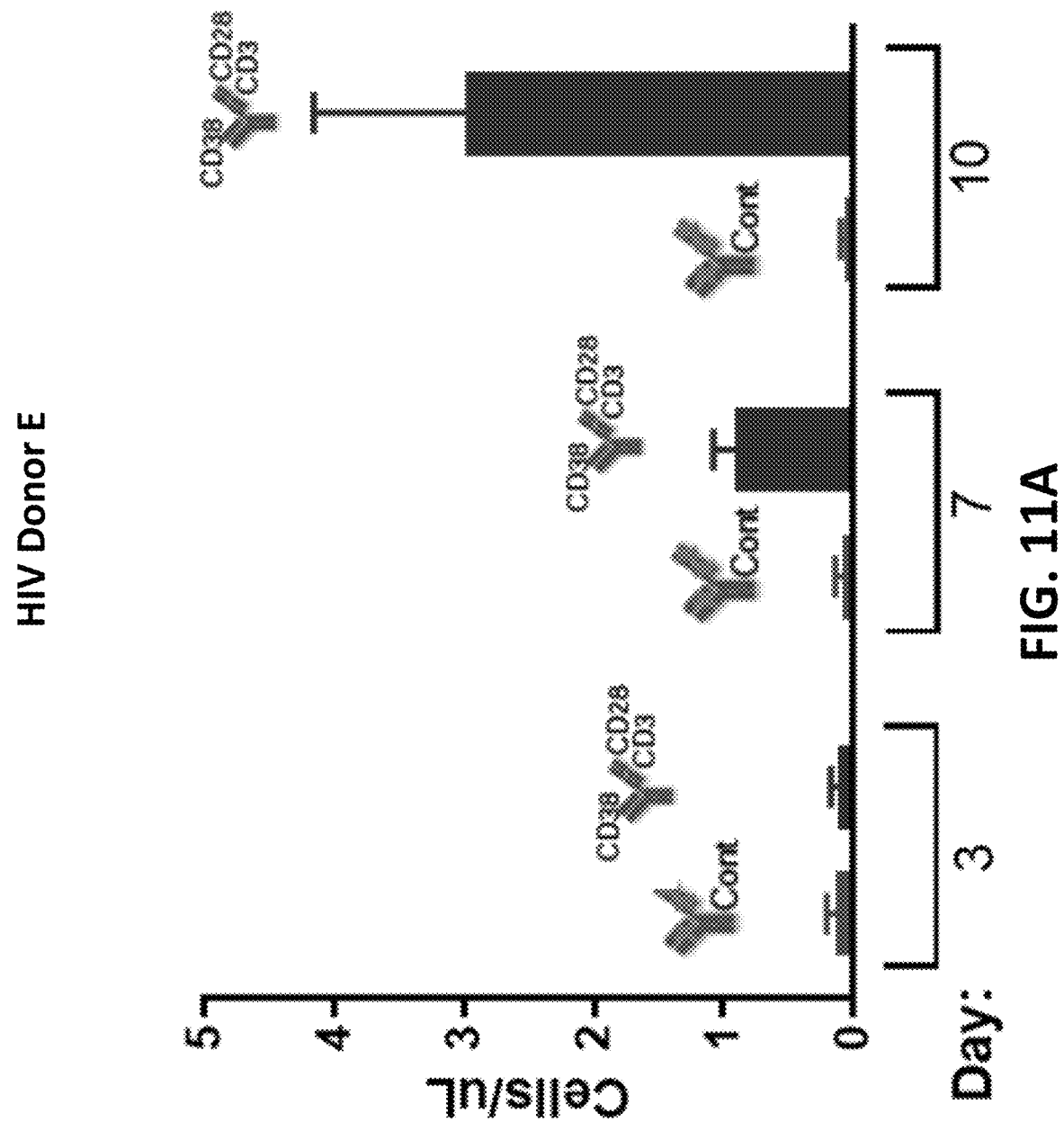
FIGS. 11A-11B show the characterization of in vitro T cell subset expansion in PBMCs collected from HIV-positive Donor E in response to $CD38_{VH1}$/CD28sup x CD3mid trispecific antibody. T cell populations were measured at indicated time points. The triple mutant trispecific antibody was used as negative control. Flow cytometry was used to quantify HIV-specific memory CD8+ T cells (FIG. 11A), as well as HIV-specific central memory ($T_{cm}$) and effector memory ($T_{em}$) CD8+ T cells (FIG. 11B). $CD38_{VH1}$/CD28sup x CD3mid trispecific antibody activated T cells and promoted the proliferation of effector memory ($T_{em}$) CD8+ T cells.
Figure 11B:
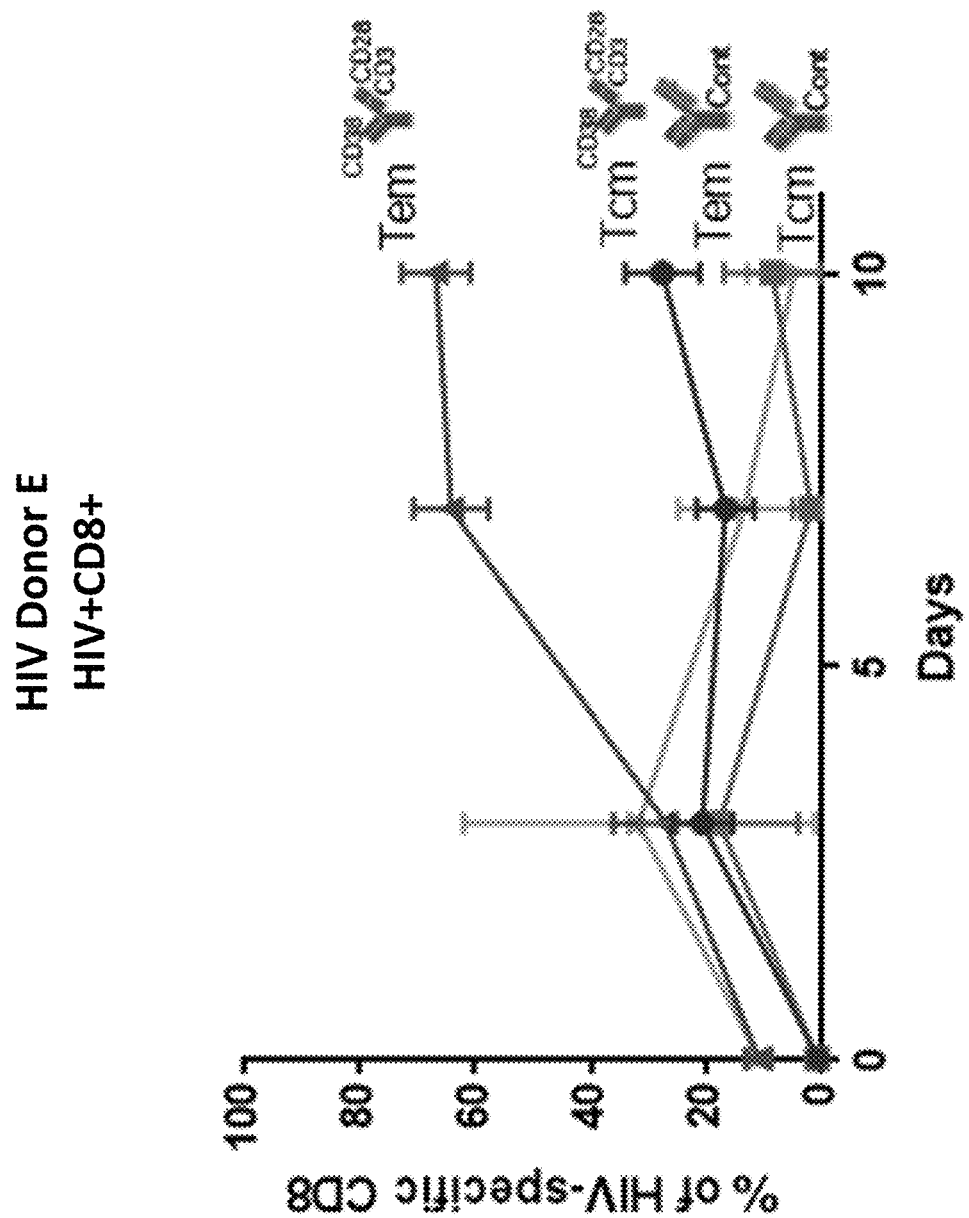
Figure 12A:
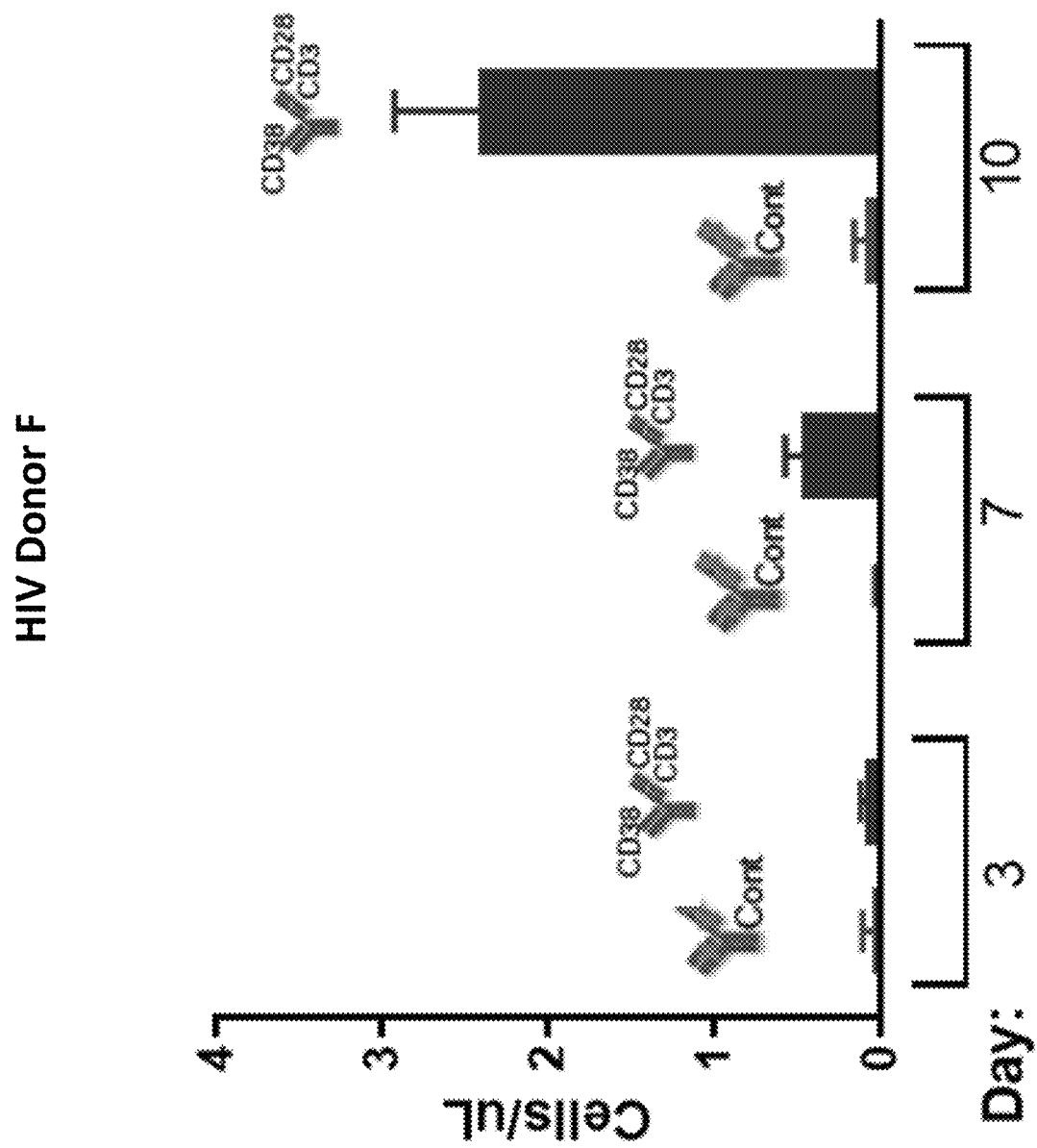
FIGS. 12A-12B show the characterization of in vitro T cell subset expansion in PBMCs collected from HIV-positive Donor F in response to $CD38_{VH1}$/CD28sup x CD3mid trispecific antibody. T cell populations were measured at indicated time points. The triple mutant trispecific antibody was used as negative control. Flow cytometry was used to quantify HIV-specific memory CD8+ T cells (FIG. 12A), as well as HIV-specific central memory ($T_{cm}$) and effector memory ($T_{em}$) CD8+ T cells (FIG. 12B). $CD38_{VH1}$/CD28sup x CD3mid trispecific antibody activated T cells and promoted the proliferation of effector memory ($T_{em}$) CD8+ T cells.
Figure 12B:
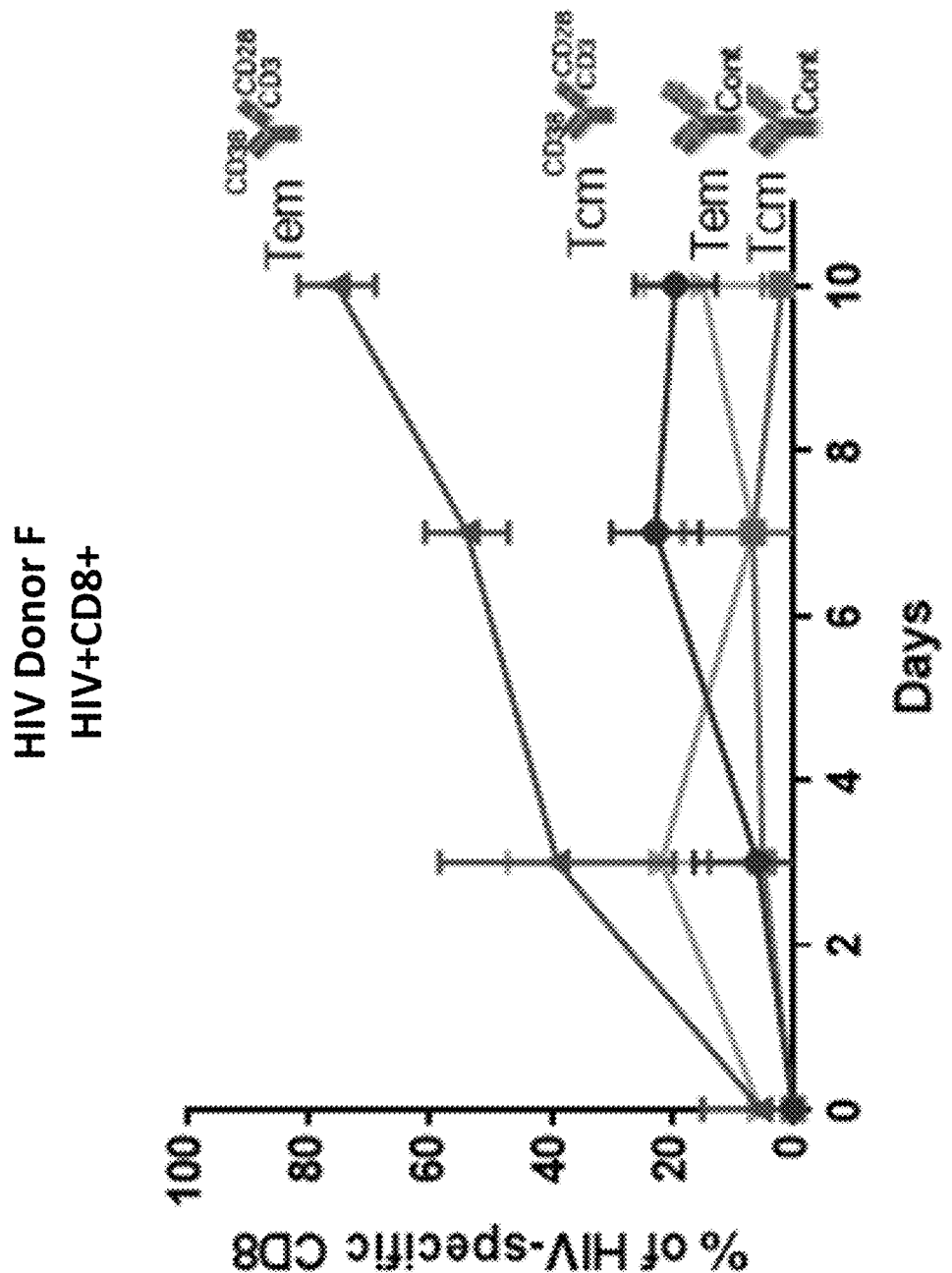

Incubation of PBMCs for up to 10 days with CD38$_{VH1}$/CD28sup × CD3mid trispecific antibody activated T cells and promoted proliferation of HIV-specific T cells. As shown in FIG. 10A (HIV Donor D), FIG. 11A (HIV Donor E), and FIG. 12A (HIV Donor F), the CD38$_{VH1}$/CD28sup × CD3mid trispecific antibody led to increases in HIV-specific memory CD8+ T cells (cells/μl) relative to the triple mutant control antibody. In addition, CD38$_{VH1}$/CD28sup × CD3mid trispecific antibody increased the percentage of HIV-specific CD8+ effector memory (T$_{em}$) cells (e.g., see days 7 and 10), and also to a lesser degree CD8+ central memory (T$_{cm}$) cells, relative to the triple mutant control antibody (HIV Donor D, FIG. 10B; HIV Donor E, FIG. 11B; HIV Donor F, FIG. 12B).

Example 7: CD38/CD28×CD3 Trispecific Antibodies Promote Influenza-Specific Immune Response The ability of CD38/CD28×CD3 trispecific antibodies to promote activation and expansion of influenza-specific T cells was determined.

Materials and Methods

Quantification of Influenza-Specific T-Cells

As described above, PBMCs were isolated from blood of known influenza A-infected human donors and added to plates containing the trispecific antibody or control antibody. The plates were incubated at 37° C. The cells were collected at the indicated time points and analyzed as described above.

Results

Figure 13A:
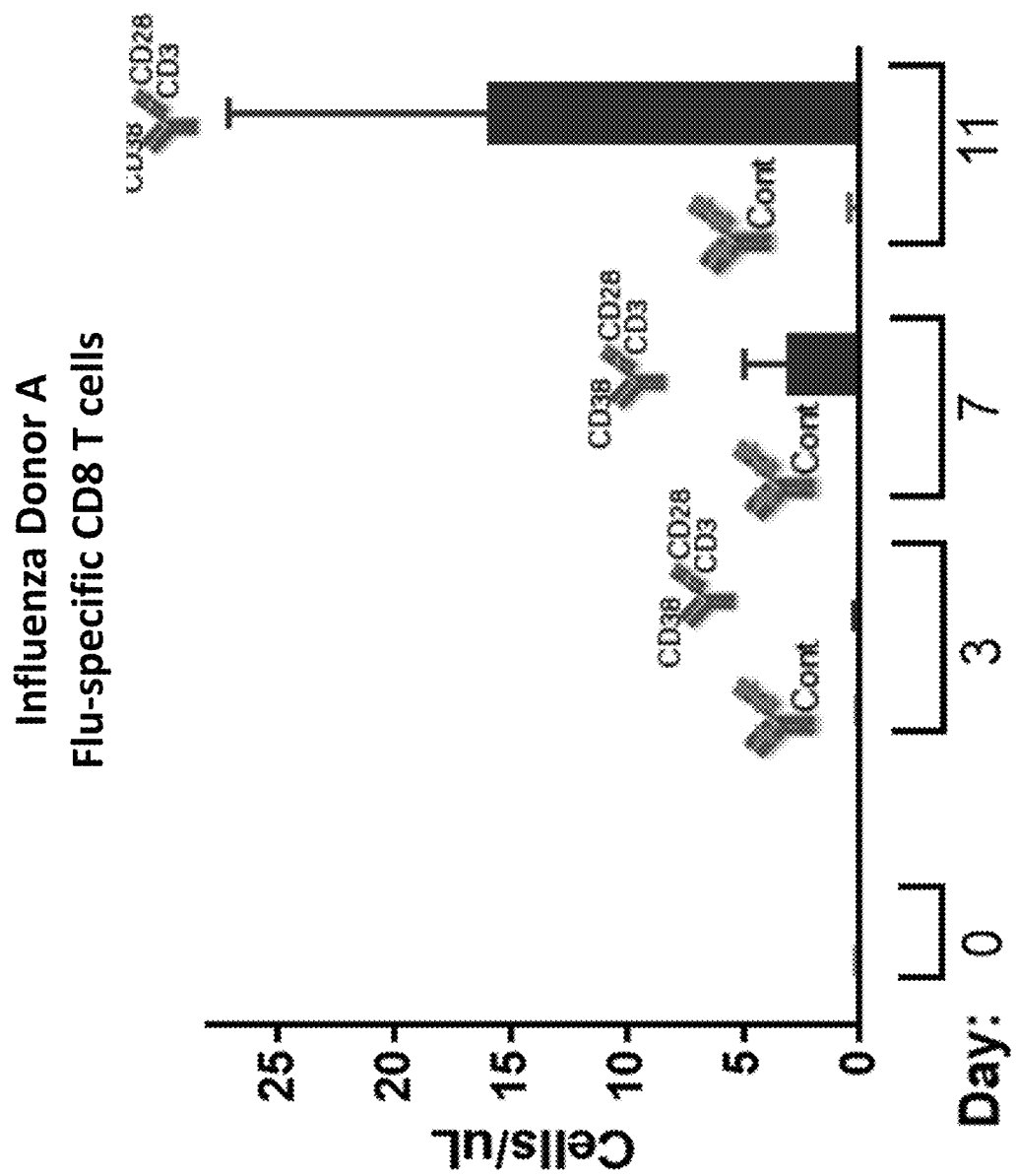
FIGS. 13A-13B show the characterization of in vitro T cell subset expansion in PBMCs collected from influenza-infected Donor A in response to $CD38_{VH1}$/CD28sup x CD3mid trispecific antibody. T cell populations were measured at indicated time points. The triple mutant trispecific antibody was used as negative control. Flow cytometry was used to quantify influenza (Flu)-specific memory CD8+ T cells (FIG. 13A), as well as Flu-specific central memory ($T_{cm}$) and effector memory ($T_{em}$) CD8+ T cells (FIG. 13B). $CD38_{VH1}$/CD28sup x CD3mid trispecific antibody activated T cells and promoted the proliferation of $T_{em}$ CD8+ T cells (e.g., see days 7, 11) and $T_{cm}$ CD8+ T cells (e.g., see day 7).
Figure 13B:
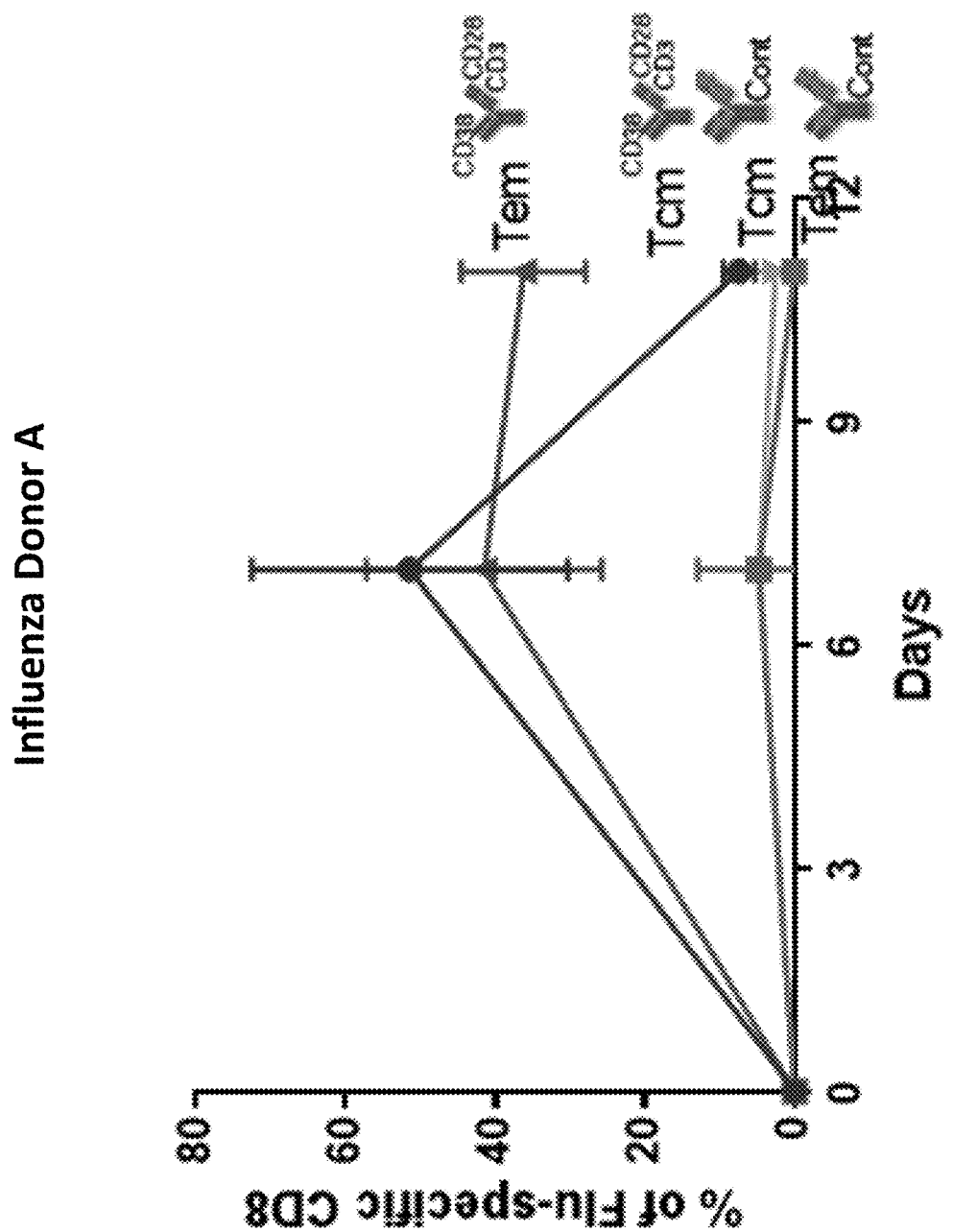

The CD38$_{VH1}$/CD28sup × CD3mid trispecific antibody activated T cells and promoted the proliferation of influenza-specific memory CD8+ T cells following incubation for up to 11 days with PBMCs isolated from a known influenza-infected human donor FIGS. 13A-13B (Influenza Donor A). As shown in FIG. 13A, the CD38$_{VH1}$/CD28sup × CD3mid trispecific antibody led to increases in influenza-specific memory CD8+ T cells (cells/μl) relative to the triple mutant control antibody. In addition, CD38$_{VH1}$/CD28sup × CD3mid trispecific antibody increased the percentage of influenza (Flu)-specific CD8+T$_{em}$ cells (e.g., see days 7 and 11) and T$_{cm}$ cells (e.g., see day 7) relative to the triple mutant control antibody (FIG. 13B).

Taken together, the data presented in Examples 1-7 demonstrate trispecific anti-CD38/CD3/CD28 antibodies stimulate potent anti-viral immunity against diverse viruses. Without wishing to be bound by theory, it is believed that CD38/CD3/CD28 trispecific antibodies can activate and promote the proliferation of T cells by engaging all three ligands on T cells. In particular, it is believed that engagement of CD3/CD28 on T cells by CD38/CD3/CD28 trispecific antibodies initiates T cell activation, proliferation, and differentiation into memory T cells. Further, without wishing to be bound by theory, it is believed that engagement of CD28 provides an advantageous co-stimulatory signal which enhances the duration and magnitude of the immune response, and promotes T cell proliferation and survival.

While the disclosure includes various embodiments, it is understood that variations and modifications will occur to those skilled in the art. Therefore, it is intended that the appended claims cover all such equivalent variations that come within the scope of the disclosure. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

What is claimed is:

1. A method for expanding virus-specific memory T cells, comprising contacting a virus-specific memory T cell with a binding protein, wherein the binding protein comprises four polypeptide chains that form three antigen binding sites, wherein the first polypeptide chain of the binding protein comprises a structure represented by the formula:

$$V_{L2}\text{-}L_1\text{-}V_{L1}\text{-}L_2\text{-}C_L \qquad [I]$$

and the second polypeptide chain of the binding protein comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \qquad [II]$$

and the third polypeptide chain of the binding protein comprises a structure represented by the formula:

$$V_{H3}\text{-}C_{H1}\text{-}\text{hinge}\text{-}C_{H2}\text{-}C_{H3} \qquad [III]$$

and the fourth polypeptide chain of the binding protein comprises a structure represented by the formula:

$$V_{L3}\text{-}C_L \qquad [IV]$$

wherein:
$V_{L1}$ is a first immunoglobulin light chain variable domain;
$V_{L2}$ is a second immunoglobulin light chain variable domain;

$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair;
wherein $V_{H1}$ and $V_{L1}$ form a first antigen binding site that binds a CD28 polypeptide, wherein $V_{H2}$ and $V_{L2}$ form a second antigen binding site that binds a CD3 polypeptide, and wherein $V_{H3}$ and $V_{L3}$ form a third antigen binding site that binds a CD38 polypeptide;
wherein:
(i) the VHA domain comprises a CDR-H1 sequence comprising the amino acid sequence of GYTFTSYY (SEQ ID NO:108), a CDR-H2 sequence comprising the amino acid sequence of IYPGNVNT (SEQ ID NO:109), and a CDR-H3 sequence comprising the amino acid sequence of TRSHYGLDWNFDV (SEQ ID NO:110), and the $V_{L1}$ domain comprises a CDR-L1 sequence comprising the amino acid sequence of QNIYVW (SEQ ID NO:111), a CDR-L2 sequence comprising the amino acid sequence of KAS (SEQ ID NO:112), and a CDR-L3 sequence comprising the amino acid sequence of QQGQTYPY (SEQ ID NO:113); or the $V_{H1}$ domain comprises a CDR-H1 sequence comprising the amino acid sequence of GFSLSDYG (SEQ ID NO:114), a CDR-H2 sequence comprising the amino acid sequence of IWAGGGT (SEQ ID NO:115), and a CDR-H3 sequence comprising the amino acid sequence of ARDKGYSYYYSMDY (SEQ ID NO:116), and the $V_{L1}$ domain comprises a CDR-L1 sequence comprising the amino acid sequence of ESVEYYVTSL (SEQ ID NO:117), a CDR-L2 sequence comprising the amino acid sequence of AAS (SEQ ID NO:118), and a CDR-L3 sequence comprising the amino acid sequence of QQSRKVPYT (SEQ ID NO:119);
(ii) the $V_{H2}$ domain comprises a CDR-H1 sequence comprising the amino acid sequence of GFTFTKAW (SEQ ID NO:120), a CDR-H2 sequence comprising the amino acid sequence of IKDKSNSYAT (SEQ ID NO:121), and a CDR-H3 sequence comprising the amino acid sequence of RGVYYALSPFDY (SEQ ID NO:122), and the $V_{L2}$ domain comprises a CDR-L1 sequence comprising the amino acid sequence of QSLVHNNANTY (SEQ ID NO:123), a CDR-L2 sequence comprising the amino acid sequence of KVS (SEQ ID NO:124), and a CDR-L3 sequence comprising the amino acid sequence of GQGTQYPFT (SEQ ID NO:125); or the $V_{H2}$ domain comprises a CDR-H1 sequence comprising the amino acid sequence of GFTFTKAW (SEQ ID NO:126), a CDR-H2 sequence comprising the amino acid sequence of IKDKSNSYAT (SEQ ID NO:127), and a CDR-H3 sequence comprising the amino acid sequence of GVYYALSPFDY (SEQ ID NO:128), and the $V_{L2}$ domain comprises a CDR-L1 sequence comprising the amino acid sequence of QSLVHNNGNTY (SEQ ID NO:129), a CDR-L2 sequence comprising the amino acid sequence of KVS (SEQ ID NO:130), and a CDR-L3 sequence comprising the amino acid sequence of GQGTQYPFT (SEQ ID NO:131); and (iii) the $V_{H3}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L3}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36); the $V_{H3}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36); or the $V_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L3}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46).

2. The method of claim 1, wherein the virus-specific memory T cell is contacted with the binding protein in vitro or ex vivo.

3. The method of claim 1, wherein contacting the virus-specific memory T cell with the binding protein causes activation and/or proliferation of virus-specific memory T cells.

4. A method for expanding T cells, comprising contacting a T cell with a binding protein in vitro or ex vivo, wherein the binding protein comprises four polypeptide chains that form three antigen binding sites, wherein the first polypeptide chain of the binding protein comprises a structure represented by the formula:

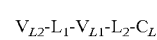

$$V_{L2}\text{-}L_1\text{-}V_{L1}\text{-}L_2\text{-}C_L \qquad [I]$$

and the second polypeptide chain of the binding protein comprises a structure represented by the formula:

$$V_{H1}\text{-}L_3\text{-}V_{H2}\text{-}L_4\text{-}C_{H1}\text{-hinge-}C_{H2}\text{-}C_{H3} \qquad [II]$$

and the third polypeptide chain of the binding protein comprises a structure represented by the formula:

$$V_{H3}\text{-}C_{H1}\text{-hinge-}C_{H2}\text{-}C_{H3} \quad [\text{III}]$$

and the fourth polypeptide chain of the binding protein comprises a structure represented by the formula:

$$V_{L3}\text{-}C_L \quad [\text{IV}]$$

wherein:
- $V_{L1}$ is a first immunoglobulin light chain variable domain;
- $V_{L2}$ is a second immunoglobulin light chain variable domain;
- $V_{L3}$ is a third immunoglobulin light chain variable domain;
- $V_{H1}$ is a first immunoglobulin heavy chain variable domain;
- $V_{H2}$ is a second immunoglobulin heavy chain variable domain;
- $V_{H3}$ is a third immunoglobulin heavy chain variable domain;
- $C_L$ is an immunoglobulin light chain constant domain;
- $C_{H1}$ is an immunoglobulin $C_{H1}$ heavy chain constant domain;
- $C_{H2}$ is an immunoglobulin $C_{H2}$ heavy chain constant domain;
- $C_{H3}$ is an immunoglobulin $C_{H3}$ heavy chain constant domain;
- hinge is an immunoglobulin hinge region connecting the $C_{H1}$ and $C_{H2}$ domains; and
- $L_1$, $L_2$, $L_3$ and $L_4$ are amino acid linkers;

wherein the polypeptide of formula I and the polypeptide of formula II form a cross-over light chain-heavy chain pair;

wherein $V_{H1}$ and $V_{L1}$ form a first antigen binding site that binds a CD28 polypeptide, wherein $V_{H2}$ and $V_{L2}$ form a second antigen binding site that binds a CD3 polypeptide, and wherein $V_{H3}$ and $V_{L3}$ form a third antigen binding site that binds a CD38 polypeptide;

wherein:
(i) the $V_{H1}$ domain comprises a CDR-H1 sequence comprising the amino acid sequence of GYTFTSYY (SEQ ID NO:108), a CDR-H2 sequence comprising the amino acid sequence of IYPGNVNT (SEQ ID NO:109), and a CDR-H3 sequence comprising the amino acid sequence of TRSHYGLDWNFDV (SEQ ID NO:110), and the $V_{L1}$ domain comprises a CDR-L1 sequence comprising the amino acid sequence of QNIYVW (SEQ ID NO:111), a CDR-L2 sequence comprising the amino acid sequence of KAS (SEQ ID NO:112), and a CDR-L3 sequence comprising the amino acid sequence of QQGQTYPY (SEQ ID NO:113); or the $V_{H1}$ domain comprises a CDR-H1 sequence comprising the amino acid sequence of GFSLSDYG (SEQ ID NO:114), a CDR-H2 sequence comprising the amino acid sequence of IWAGGGT (SEQ ID NO:115), and a CDR-H3 sequence comprising the amino acid sequence of ARDKGYSYYYSMDY (SEQ ID NO:116), and the $V_{L1}$ domain comprises a CDR-L1 sequence comprising the amino acid sequence of ESVEYYVTSL (SEQ ID NO:117), a CDR-L2 sequence comprising the amino acid sequence of AAS (SEQ ID NO:118), and a CDR-L3 sequence comprising the amino acid sequence of QQSRKVPYT (SEQ ID NO:119);

(ii) the $V_{H2}$ domain comprises a CDR-H1 sequence comprising the amino acid sequence of GFTFTKAW (SEQ ID NO:120), a CDR-H2 sequence comprising the amino acid sequence of IKDKSNSYAT (SEQ ID NO:121), and a CDR-H3 sequence comprising the amino acid sequence of RGVYYALSPFDY (SEQ ID NO:122), and the $V_{L2}$ domain comprises a CDR-L1 sequence comprising the amino acid sequence of QSLVHNNANTY (SEQ ID NO:123), a CDR-L2 sequence comprising the amino acid sequence of KVS (SEQ ID NO:124), and a CDR-L3 sequence comprising the amino acid sequence of GQGTQYPFT (SEQ ID NO:125); or the $V_{H2}$ domain comprises a CDR-H1 sequence comprising the amino acid sequence of GFTFTKAW (SEQ ID NO:126), a CDR-H2 sequence comprising the amino acid sequence of IKDKSNSYAT (SEQ ID NO:127), and a CDR-H3 sequence comprising the amino acid sequence of GVYYALSPFDY (SEQ ID NO:128), and the $V_{L2}$ domain comprises a CDR-L1 sequence comprising the amino acid sequence of QSLVHNNGNTY (SEQ ID NO:129), a CDR-L2 sequence comprising the amino acid sequence of KVS (SEQ ID NO:130), and a CDR-L3 sequence comprising the amino acid sequence of GQGTQYPFT (SEQ ID NO:131); and (iii) the $V_{H3}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L3}$ domain comprises a CDR-L1 sequence comprising the amino acid sequence of ESVDSYG-NGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36); the $V_{H3}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36); or the $V_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L3}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46).

5. The method of claim 4, wherein the T cell is a memory T cell or an effector T cell.

6. The method of claim 4, wherein the T cell expresses a chimeric antigen receptor (CAR) on its cell surface or comprises a polynucleotide encoding a CAR.

7. The method of claim 1, wherein the memory T cells are CD8+ or CD4+ memory T cells.

8. The method of claim 1, wherein the memory T cells are central memory T cells ($T_{CM}$) or effector memory T cells ($T_{EM}$).

9. The method of claim 1, wherein the CD28 polypeptide is a human CD28 polypeptide, wherein the CD3 polypeptide is a human CD3 polypeptide, and wherein the CD38 polypeptide is a human CD38 polypeptide.

10. The method of claim 1, wherein:
(a) the $V_{H3}$ domain comprises the amino acid sequence of QVQLQQSGAELVRSGASVKMSCKASGYTFTSFNMHWVKETPGQGLEWIGYIYPGNGG TNYNQKFKGKATLTADTSSSTAYMQISSLTSEDSAVYFCARTGGLRRAYFTYWGQGTL VTVS (SEQ ID NO:5), and the $V_{L3}$ domain comprises the amino acid sequence of DIVLTQSPASLAVSLGQRATISCRASESVDSYGNGFMHWYQQKPGQPPKWYLASNLES GVPARFSGSGSRTDFTLTIDPVEADDAATYYCQQNKEDPWTFGGGTKLEIK (SEQ ID NO:6);
(b) the $V_{H3}$ domain comprises the amino acid sequence of QVQLVQSGAEVVKPGASVKVSCKASGYTFTSYAMHWVKEAPGQRLEWIGYIYPGQGG TNYNQKFQGRATLTADTSASTAYMELSSLRSEDTAVYFCARTGGLRRAYFTYWGQGTL VTVSS (SEQ ID NO:13), and the $V_{L3}$ domain comprises the amino acid sequence of DIVLTQSPATLSLSPGERATISCRASQSVSSYGQGFMHWYQQKPGQPPRLLIYGASSRAT GIPARFSGSGSGTDFTLTISPLEPEDFAVYYCQQNKEDPWTFGGGTKLEIK (SEQ ID NO:14);
(c) the $V_{H3}$ domain comprises the amino acid sequence of QVQLVQSGAEVVKPGASVKVSCKASGYTFTSFNMHWVKEAPGQRLEWIGYIYPGNGG TNYNQKFQGRATLTADTSASTAYMELSSLRSEDTAVYFCARTGGLRRAYFTYWGQGTL VTVSS (SEQ ID NO:17), and the $V_{L3}$ domain comprises the amino acid sequence of DIVLTQSPATLSLSPGERATISCRASESVDSYGNGFMHWYQQKPGQPPRLLIYLASSRAT GIPARFSGSGSGTDFTLTISPLEPEDFAVYYCQQNKEDPWTFGGGTKLEIK (SEQ ID NO:18);
(d) the $V_{H3}$ domain comprises the amino acid sequence of QVQLVQSGAEVVKSGASVKVSCKASGYTFTSFNMHWVKEAPGQGLEWIGYIYPGNGG TNYNQKFQGRATLTADTSASTAYMEISSLRSEDTAVYFCARTGGLRRAYFTYWGQGTL VTVSS (SEQ ID NO:21), and the $V_{L3}$ domain comprises the amino acid sequence of DIVLTQSPATLSLSPGERATISCRASESVDSYGNGFMHWYQQKPGQPPRLLIYLASSRAT GIPARFSGSGSGTDFTLTISPLEPEDFAVYYCQQNKEDPWTFGGGTKLEIK (SEQ ID NO:18);
(e) the $V_{H3}$ domain comprises the amino acid sequence of QVQLVQSGAEVVKPGASVKMSCKASGYTFTSFNMHWVKEAPGQRLEWIGYIYPGNGG TNYNQKFQGRATLTADTSASTAYMEISSLRSEDTAVYFCARTGGLRRAYFTYWGQGTL VTVSS (SEQ ID NO:23), and the $V_{L3}$ domain comprises the amino acid sequence of DIVLTQSPATLSLSPGERATISCRASESVDSYGNGFMHWYQQKPGQPPRLLIYLASSRAT GIPARFSGSGSGTDFTLTISPLEPEDFAVYYCQQNKEDPWTFGGGTKLEIK (SEQ ID NO:18); or
(f) the $V_{H3}$ domain comprises the amino acid sequence of QVQLVESGGGVVQPGRSLRLSCAASGFTFSSYGMHWVRQAPGKGLEWVAVIWYDGSN KYYADSVKGRFTISGDNSKNTLYLQMNSLRAEDTAVYYCARMFRGAFDYWGQ GTLVT VSS (SEQ ID NO:9), and the $V_{L3}$ domain comprises the amino acid sequence of AIQMTQSPSSLSASVGDRVTITCRASQGIRNDLGWYQQKPGKAPKLLIYAASSLQSGVPS RFSGSGSGTDFTLTISGLQPEDSATYYCLQDYIYYPTFGQGTKVEIK (SEQ ID NO:10).

11. The method of claim 1, wherein:
(a) the $V_{H1}$ domain comprises the amino acid sequence of QVQLVQSGAEVVKPGASVKVSCKASGYTFTSYYIHWVRQAPGQGLEWIGSWPGNVNT NYAQKFQGRATLTVDTSISTAYMELSRLRSDDTAVYYCTRSHYGLDWNFDVWGKGTT VTVSS (SEQ ID NO:49), and the $V_{L1}$ domain comprises the amino acid sequence of DIQMTQSPSSLSASVGDRVTITCQASQNIYVWLNWYQQKPGKAPKWYKASNLHTGVP SRFSGSGSGTDFTLTISSLQPEDIATYYCQQGQTYPYTFGQGTKLEIK (SEQ ID NO:50); or
(b) the $V_{H1}$ domain comprises the amino acid sequence of QVQLQESGPGLVKPSQTLSLTCTVSGFSLSDYGVHWVRQPPGKGLEWLGVIWAGGGTN YNPSLKSRKTISKDTSKNQVSLKLSSVTAADTAVYYCARDKGYSYYYSMDYWGQGTT VTVS (SEQ ID NO:51), and the $V_{L1}$ domain comprises the amino acid sequence of DIVLTQSPASLAVSPGQRATITCRASESVEYYVTSLMQWYQQKPGQPPKLLIFAASNVES GVPARFSGSGSGTDFTLTINPVEANDVANYYCQQSRKVPYTFGQGTKLEIK (SEQ ID NO:52).

12. The method of claim 1, wherein:
(a) the $V_{H2}$ domain comprises the amino acid sequence of QVQLVESGGGVVQPGRSLRLSCAASGFTFTKAWMHWVRQAPGKQLEWVAQIK DKSNS YATYYADSVKGRFTISRDDSKNTLYLQMNSLRAEDTAVYYCRGVYYALSPFDYWGQG TLVTVSS (SEQ ID NO:53), and the $V_{L2}$ domain comprises the amino acid sequence of DIVMTQTPLSLSVTPGQPASISCKSSQSLVHNNANTYLSWYLQKPGQSPQSLIYKVSNRF SGVPDRFSGSGSGTDFTLKISRVEAEDVGVYYCGQGTQYPFTFGSGTKVEIK (SEQ ID NO:54); or
(b) the $V_{H2}$ domain comprises the amino acid sequence of QVQLVESGGGVVQPGRSLRLSCAASGFTFTKAWMHWVRQAPGKGLEWVAQIKDKSNS YATYYADSVKGRFTISRDNSKNTLYLQMNSLRAEDTAVYYCRGVYYAL SPFDYWGQG TLVTVSS (SEQ ID NO:84), and the $V_{L2}$ domain comprises the amino acid sequence of DIVMTQTPLSLSVTPGQPASISCKSSQSLVHNNGNTYLSWYLQKPGQSPQLLIYKVSNRF SGVPDRFSGSGSGTDFTLKISRVEAEDVGVYYCGQGTQYPFTFGGGTKVEIK (SEQ ID NO:85).

13. The method of claim 1, wherein at least one of $L_1$, $L_2$, $L_3$ or $L_4$ is independently 0 amino acids in length.

14. The method of claim 1, wherein (a) $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO: 56), S, RT, TKGPS (SEQ ID NO: 57), GQPKAAP (SEQ ID NO: 58), and GGSGSSGSGG (SEQ ID NO: 59); or (b) $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO: 58), and GGSGSSGSGG (SEQ ID NO:59).

15. The method of claim 1, wherein $L_1$ comprises the sequence GQPKAAP (SEQ ID NO: 58), $L_2$ comprises the sequence TKGPS (SEQ ID NO:57), $L_3$ comprises the sequence S, and $L_4$ comprises the sequence RT.

16. The method of claim 1, wherein the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 234 and 235 of human IgG4 according to EU Index, wherein the amino acid substitutions are F234A and L235A.

17. The method of claim 1, wherein the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 233-236 of human IgG4 according to EU Index, wherein the amino acid substitutions are E233P, F234V, L235A, and a deletion at 236.

18. The method of claim 1, wherein the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 228 and 409 of human IgG4 according to EU Index, wherein the amino acid substitutions are S228P and R409K.

19. The method of claim 1, wherein the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 234, 235, and 329 of human IgG1 according to EU Index, wherein the amino acid substitutions are L234A, L235A, and P329A.

20. The method of claim 1, wherein the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 298, 299, and 300 of human IgG1 according to EU Index, wherein the amino acid substitutions are S298N, T299A, and Y300S.

21. The method of claim 1, wherein the hinge-$C_{H2}$-$C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the hinge-$C_{H2}$-$C_{H3}$ domain of the third polypeptide chain comprises amino acid substitutions at positions corresponding to positions 354 and 366 of human IgG1 or IgG4 according to EU Index, wherein the amino acid substitutions are S354C and T366W.

22. The method of claim 1, wherein the hinge-$C_{H2}$-$C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the hinge-$C_{H2}$-$C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V.

23. The method of claim 1, wherein:
(a) the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:62, and the fourth polypeptide chain comprises the amino acid sequence of SEQ ID NO:63;
(b) the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:65, and the fourth polypeptide chain comprises the amino acid sequence of SEQ ID NO:63;
(c) the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:67, and the fourth polypeptide chain comprises the amino acid sequence of SEQ ID NO:63;
(d) the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:68, and the fourth polypeptide chain comprises the amino acid sequence of SEQ ID NO:69;
(e) the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:70, and the fourth polypeptide chain comprises the amino acid sequence of SEQ ID NO:69; or
(f) the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:71, and the fourth polypeptide chain comprises the amino acid sequence of SEQ ID NO:69.

24. The method of claim 1, wherein the virus is a human immunodeficiency virus (HIV), influenza virus, cytomegalovirus (CMV), hepatitis B virus (HBV), human papillomavirus (HPV), Epstein-barr virus (EBV), human foamy virus (HFV), herpes simplex virus 1 (HSV-1), or herpes simplex virus 1 (HSV-2).

25. The method of claim 4, wherein the CD28 polypeptide is a human CD28 polypeptide, wherein the CD3 polypeptide is a human CD3 polypeptide, and wherein the CD38 polypeptide is a human CD38 polypeptide.

26. The method of claim 4, wherein:
(a) the $V_{H3}$ domain comprises the amino acid sequence of QVQLQQSGAELVRSGASVKMSCK-ASGYTFTSFNMHWVKETPGQGLEWI-GYIYPGNGG TNYNQKFKGKATL-TADTSSSTAYMQISSLTSEDSAVYFCARTGGLRR AYFTYWGQGTL VTVS (SEQ ID NO:5), and the $V_{L3}$ domain comprises the amino acid sequence of DIVLTQSPASLAVSLGQRATISCRASESVDSYG-NGFMHWYQQKPGQPPKWYLASNLES GVPARFSGSGSRTDFTLTIDPVEADD-
AATYYCQQNKEDPWTFGGGTKLEIK (SEQ ID NO:6);
(b) the $V_{H3}$ domain comprises the amino acid sequence of QVQLVQSGAEVVKPGASVKVSCKASGYTFTSY-AMHWVKEAPGQRLEWIGYIYPGQGG TNYNQKFQGRATLTADTSASTAYMELSSLRSED-TAVYFCARTGGLRRAYFTYWGQGTL VTVSS (SEQ ID NO:13), and the $V_{L3}$ domain comprises the amino acid sequence of DIVLTQSPATLSLSPGER-ATISCRASQSVSSYGQGFMHWYQQKPGQP-PRLLIYGASSRAT GIPARFSGSGSGTDFTLTISPLEPED-FAVYYCQQNKEDPWTFGGGTKLEIK (SEQ ID NO:14);
(c) the $V_{H3}$ domain comprises the amino acid sequence of QVQLVQSGAEVVKPGASVKVSCK-ASGYTFTSFNMHWVKEAPGQRLEWI-GYIYPGNGG TNYNQKFQGRATLTADTSAS-TAYMELSSLRSEDTAVYFCARTGGLRRAYFTYW GQGTL VTVSS (SEQ ID NO:17), and the $V_{L3}$ domain comprises the amino acid sequence of DIVLTQSPATLSLSPGERATISCRASESVDSYG-NGFMHWYQQKPGQPPRLLIYLASSRAT GIPARFSGSGSGTDFTLTISPLEPED-FAVYYCQQNKEDPWTFGGGTKLEIK (SEQ ID NO:18);
(d) the $V_{H3}$ domain comprises the amino acid sequence of QVQLVQSGAEVVKSGASVKVSCK-ASGYTFTSFNMHWVKEAPGQGLEWI-GYIYPGNGG TNYNQKFQGRATLTADTSAS-TAYMEISSLRSEDTAVYFCARTGGLRRAYFTYW GQGTL VTVSS (SEQ ID NO:21), and the $V_{L3}$ domain comprises the amino acid sequence of DIVLTQSPATLSLSPGERATISCRASESVDSYG-NGFMHWYQQKPGQPPRLLIYLASSRAT GIPARFSGSGSGTDFTLTISPLEPED-FAVYYCQQNKEDPWTFGGGTKLEIK (SEQ ID NO:18);
(e) the $V_{H3}$ domain comprises the amino acid sequence of QVQLVQSGAEVVKPGASVKMSCK-ASGYTFTSFNMHWVKEAPGQRLEWI-GYIYPGNGG TNYNQKFQGRATLTADTSAS-TAYMEISSLRSEDTAVYFCARTGGLRRAYFTYW GQGTL VTVSS (SEQ ID NO:23), and the $V_{L3}$ domain comprises the amino acid sequence of DIVLTQSPATLSLSPGERATISCRASESVDSYG-NGFMHWYQQKPGQPPRLLIYLASSRAT GIPARFSGSGSGTDFTLTISPLEPED-FAVYYCQQNKEDPWTFGGGTKLEIK (SEQ ID NO:18); or
(f) the $V_{H3}$ domain comprises the amino acid sequence of QVQLVESGGGVVQPGRSLRLS-CAASGFTFSSYGMHWVRQAPGKGLEWVAVI-WYDGSN KYYADSVKGRFTISGDNSKNT-LYLQMNSLRAEDTAVYYCARMFRGAFDYWGQ GTLVT VSS (SEQ ID NO:9), and the $V_{L3}$ domain comprises the amino acid sequence of AIQMTQSPSSLSASVGDRVTITCRASQ-GIRNDLGWYQQKPGKAPKLLIYAASSLQSGVPS RFSGSGSGTDFTLTISGLQPEDSATYY-CLQDYIYYPTFGQGTKVEIK (SEQ ID NO:10).
27. The method of claim 4, wherein:
(a) the $V_{H1}$ domain comprises the amino acid sequence of QVQLVQSGAEVVKPGASVKVSCKASGYTFT-SYYIHWVRQAPGQGLEWIGSIYPGNVNT NYAQKFQGRATLTVDTSISTAYMELSRLRSDD-TAVYYCTRSHYGLDWNFDVWGKGTT VTVSS (SEQ ID NO:49), and the $V_{L1}$ domain comprises the amino acid sequence of DIQMTQSPSSL-SASVGDRVTITCQASQNIYVWLNWYQQKPGKA PKLLIYKASNLHTGVP SRFSGSGSGTDFTLTISSLQPEDIATYYCQQGQ-TYPYTFGQGTKLEIK (SEQ ID NO:50); or
(b) the $V_{H1}$ domain comprises the amino acid sequence of QVQLQESGPGLVKP-SQTLSLTCTVSGFSLSDYGVHWVRQPPGK-GLEWLGVIWAGGGTN YNPSLKSRKTISKDTSKNQVSLKLSSVTAAD-TAVYYCARDKGYSYYYSMDYWGQGTT VTVS (SEQ ID NO:51), and the $V_{L1}$ domain comprises the amino acid sequence of DIVLTQSPASLAVSPGQRATITCRASESVEYYVT-SLMQWYQQKPGQPPKLLIFAASNVES GVPARFSGSGSGTDFTLTINPVEAND-VANYYCQQSRKVPYTFGQGTKLEIK (SEQ ID NO:52).
28. The method of claim 4, wherein:
(a) the $V_{H2}$ domain comprises the amino acid sequence of QVQLVESGGGVVQPGRSLRLS-CAASGFTFTKAWMHWVRQAPGKQLEWVAQIK DKSNS YATYYADSVKGRFTISRDDSKNT-LYLQMNSLRAEDTAVYYCRGVYYAL-SPFDYWGQG TLVTVSS (SEQ ID NO:53), and the $V_{L2}$ domain comprises the amino acid sequence of DIVMTQTPLSLSVTPGQPASISCKSSQSLVHN-NANTYLSWYLQKPGQSPQSLIYKVSNRF SGVPDRFSGSGSGTDFTLKISRVEAE-DVGVYYCGQGTQYPFTFGSGTKVEIK (SEQ ID NO:54); or
(b) the $V_{H2}$ domain comprises the amino acid sequence of QVQLVESGGGVVQPGRSLRLS-CAASGFTFTKAWMHWVRQAPGK-GLEWVAQIKDKSNS YATYYADSVKGRFTIS-RDNSKNTLYLQMNSLRAEDTAVYYCRGVYYAL SPFDYWGQG TLVTVSS (SEQ ID NO:84), and the $V_{L2}$ domain comprises the amino acid sequence of DIVMTQTPLSLSVTPGQPASISCKSSQSLVHNNG-NTYLSWYLQKPGQSPQLLIYKVSNRF SGVPDRFSGSGSGTDFTLKISRVEAE-DVGVYYCGQGTQYPFTFGGGTKVEIK (SEQ ID NO:85).
29. The method of claim 4, wherein (a) $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO: 56), S, RT, TKGPS (SEQ ID NO: 57), GQPKAAP (SEQ ID NO: 58), and GGSGSSGSGG (SEQ ID NO: 59); or (b) $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO: 58), and GGSGSSGSGG (SEQ ID NO:59).
30. The method of claim 4, wherein $L_1$ comprises the sequence GQPKAAP (SEQ ID NO: 58), $L_2$ comprises the sequence TKGPS (SEQ ID NO:57), $L_3$ comprises the sequence S, and $L_4$ comprises the sequence RT.
31. The method of claim 4, wherein the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 234 and 235 of human IgG4 according to EU Index, wherein the amino acid substitutions are F234A and L235A.

32. The method of claim 4, wherein the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 228 and 409 of human IgG4 according to EU Index, wherein the amino acid substitutions are S228P and R409K.

33. The method of claim 4, wherein the hinge-$C_{H2}$-$C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the hinge-$C_{H2}$-$C_{H3}$ domain of the third polypeptide chain comprises amino acid substitutions at positions corresponding to positions 354 and 366 of human IgG1 or IgG4 according to EU Index, wherein the amino acid substitutions are S354C and T366W.

34. The method of claim 4, wherein:
(a) the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:62, and the fourth polypeptide chain comprises the amino acid sequence of SEQ ID NO:63;
(b) the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:65, and the fourth polypeptide chain comprises the amino acid sequence of SEQ ID NO:63;
(c) the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:67, and the fourth polypeptide chain comprises the amino acid sequence of SEQ ID NO:63;
(d) the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:68, and the fourth polypeptide chain comprises the amino acid sequence of SEQ ID NO:69;
(e) the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:70, and the fourth polypeptide chain comprises the amino acid sequence of SEQ ID NO:69; or
(f) the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:71, and the fourth polypeptide chain comprises the amino acid sequence of SEQ ID NO:69.

* * * * *

UNITED STATES PATENT AND TRADEMARK OFFICE
CERTIFICATE OF CORRECTION

| | | Page 1 of 3 |
|---|---|---|
| PATENT NO. | : 11,530,268 B2 | |
| APPLICATION NO. | : 16/596474 | |
| DATED | : December 20, 2022 | |
| INVENTOR(S) | : Lan Wu et al. | |

It is certified that error appears in the above-identified patent and that said Letters Patent is hereby corrected as shown below:

On the Title Page

Left-hand column, under item (30) under Foreign Application Priority Data please insert --Oct. 9, 2018 (US) PCT/US2018/055084--.

In the Claims

In Claim 1, Column 217, Line 28: please replace "the VHA domain" with --the $V_{H1}$ domain--;
In Claim 10, Column 221, Line 12: please replace "GNGG TNYN" with --GNGGTNYN--;
In Claim 10, Column 221, Lines 13-14: please replace "GGLR RAYF" with --GGLRRAYF--;
In Claim 10, Column 221, Lines 17-18: please replace "NLES GVPA" with --NLESGVPA--;
In Claim 10, Column 221, Lines 24-25: please replace "GQGG TNYN" with --GQGGTNYN--;
In Claim 10, Column 221, Lines 25-26: please replace "QGTL VTVS" with --QGTLVTVS--;
In Claim 10, Column 221, Lines 30-31: please replace "SRAT GIPA" with --SRATGIPA--;
In Claim 10, Column 221, Line 37: please replace "GNGG TNYN" with --GNGGTNYN--;
In Claim 10, Column 221, Lines 39-40: please replace "TYW GQG" with --TYWGQG--;
In Claim 10, Column 221, Line 40: please replace "TL VTV" with --TLVTV--;
In Claim 10, Column 221, Lines 43-44: please replace "SRAT GIPA" with --SRATGIPA--;
In Claim 10, Column 221, Line 50: please replace "GNGG TNYN" with --GNGGTNYN--;
In Claim 10, Column 221, Lines 51-52: please replace "TYW GQG" with --TYWWGQG--;
In Claim 10, Column 221, Line 52: please replace "TL VTV" with --TLVTV--;
In Claim 10, Column 221, Lines 55-56: please replace "SRAT GIPA" with --SRATGIPA--;
In Claim 10, Column 221, Line 62: please replace "GNGG TNYN" with --GNGGTNYN--;
In Claim 10, Column 221, Lines 63-64: please replace "FTYW GQGT" with --FTYWGQGT--;
In Claim 10, Column 221, Line 67-Column 222, Line 1: please replace "SRAT GIPA" with --SRATGIPA--;
In Claim 10, Column 222, Line 7: please replace "DGSN KYYA" with --DGSNKYYA--;
In Claim 10, Column 222, Lines 8-9: please replace "YWGQ GTL" with --YWGQGTL--;

Signed and Sealed this
Fifth Day of March, 2024

*Katherine Kelly Vidal*
Katherine Kelly Vidal
*Director of the United States Patent and Trademark Office*

CERTIFICATE OF CORRECTION (continued)
U.S. Pat. No. 11,530,268 B2

In Claim 10, Column 222, Line 9: please replace "VT VSS" with --VTVSS--;
In Claim 10, Column 222, Lines 12-13: please replace "GVPS RFSG" with --GVPSRFSG--;
In Claim 11, Column 222, Line 17: please replace "GSWPG" with --GSIYPG--;
In Claim 11, Column 222, Lines 17-18: please replace "NVNT NYAQ" with --NVNTNYAQ--;
In Claim 11, Column 222, Line 19: please replace "KGTT VTVS" with --KGTTVTVS--;
In Claim 11, Column 222, Lines 22-23: please replace "PGKA PK" with --PGKAPK--;
In Claim 11, Column 222, Line 23: please replace "WYK" with --LLIYK--;
In Claim 11, Column 222, Lines 23-24: please replace "TGVP SRFS" with --TGVPSRFS--;
In Claim 11, Column 222, Lines 29-30: please replace "GGTN YNPS" with --GGTNYNPS--;
In Claim 11, Column 222, Line 31: please replace "QGTT VTVS" with --QGTTVTVS--;
In Claim 11, Column 222, Lines 35-36: please replace "NVES GVPA" with --NVESGVPA--;
In Claim 12, Column 222, Lines 42-43: please replace "AQIK DKSNS YATY" with --AQIKDKSNSYATY--;
In Claim 12, Column 222, Line 45: please replace "WGQG TLVT" with --WGQGTLVT--;
In Claim 12, Column 222, Lines 48-49: please replace "SNRF SGVP" with --SNRFSGVP--;
In Claim 12, Column 222, Line 55: please replace "KSNS YATY" with --KSNSYATY--;
In Claim 12, Column 222, Lines 56-57: please replace "YYAL SPFD" with --YYALSPFD--;
In Claim 12, Column 222, Lines 60-61: please replace "SNRF SGVP" with --SNRFSGVP--;
In Claim 24, Column 224, Lines 52-53: please replace "herpes simplex virus 1 (HSV-2)" with --herpes simplex virus 2 (HSV-2)--;
In Claim 26, Column 224, Line 62: please replace "GNGG TNYN" with --GNGGTNYN--;
In Claim 26, Column 224, Lines 63-64: please replace "GLRR AYFT" with --GLRRAYFT--;
In Claim 26, Column 224, Line 67: please replace "PKWYL" with --PKLLIYL--;
In Claim 26, Column 224, Line 67-Column 225, Line 1: please replace "NLES GVPA" with --NLESGVPA--;
In Claim 26, Column 225, Lines 6-7: please replace "GQGG TNYN" with --GQGGTNYN--;
In Claim 26, Column 225, Line 8: please replace "QGTL VTVS" with --QGTLVTVS--;
In Claim 26, Column 225, Lines 12-13: please replace "SRAT GIPA" with --SRATGIPA--;
In Claim 26, Column 225, Line 19: please replace "GNGG TNYN" with --GNGGTNYN--;
In Claim 26, Column 225, Lines 20-21: please replace "FTYW GQGT" with --FTYWGQGT--;
In Claim 26, Column 225, Line 21: please replace "QGTL VTVS" with --QGTLVTVS--;
In Claim 26, Column 225, Lines 24-25: please replace "SRAT GIPA" with --SRATGIPA--;
In Claim 26, Column 225, Line 31: please replace "GNGG TNYN" with --GNGGTNYN--;
In Claim 26, Column 225, Lines 32-33: please replace "FTYW GQGTL VTVSS" with --FTYWGQGTLVTVSS--;
In Claim 26, Column 225, Lines 36-37: please replace "SRAT GIPA" with --SRATGIPA--;
In Claim 26, Column 225, Line 43: please replace "GNGG TNYN" with --GNGGTNYN--;
In Claim 26, Column 225, Lines 44-45: please replace "FTYW GQGT" with --FTYWGQGT--;
In Claim 26, Column 225, Lines 48-49: please replace "SRAT GIPA" with --SRATGIPA--;
In Claim 26, Column 225, Line 55: please replace "DGSN KYYA" with --DGSNKYYA--;
In Claim 26, Column 225, Lines 56-57: please replace "YWGQ GTLVT VSS" with --YWGQGTLVTVSS--;
In Claim 26, Column 225, Lines 60-61: please replace "GVPS RFSG" with --GVPSRFSG--;
In Claim 27, Column 225, Lines 66-67: please replace "NVNT NYAQ" with --NVNTNYAQ--;
In Claim 27, Column 226, Line 1: please replace "KGTT VTVS"with --KGTTVTVS--;
In Claim 27, Column 226, Lines 4-5: please replace "PGKA PKLL" with --PGKAPKLL--;

CERTIFICATE OF CORRECTION (continued)
U.S. Pat. No. 11,530,268 B2

In Claim 27, Column 226, Lines 5-6: please replace "TGVP SRFS" with --TGVPSRFS--;
In Claim 27, Column 226, Lines 11-12: please replace "GGTN YNPS" with --GGTNYNPS--;
In Claim 27, Column 226, Line 13: please replace "QGTT VTVS" with --QGTTVTVS--;
In Claim 27, Column 226, Lines 16-17: please replace "NVES GVPA" with --NVESGVPA--;
In Claim 28, Column 226, Lines 23-24: please replace "AQIK DKSNS YATY" with --AQIKDKSNSYATY--;
In Claim 28, Column 226, Line 26: please replace "WGQG TLVT" with --WGQGTLVT--;
In Claim 28, Column 226, Lines 29-30: please replace "SNRF SGVP" with --SNRFSGVP--;
In Claim 28, Column 226, Line 36: please replace "KSNS YATY" with --KSNSYATY--;
In Claim 28, Column 226, Lines 37-38: please replace "YYAL SPFD" with --YYALSPFD--;
In Claim 28, Column 226, Line 38: please replace "WGQG TLVT" with --WGQGTLVT--; and
In Claim 28, Column 226, Lines 41-42: please replace "SNRF SGVP" with --SNRFSGVP--.

SEQUENCE LISTING

```
<160> NUMBER OF SEQ ID NOS: 132

<210> SEQ ID NO 1
<211> LENGTH: 256
<212> TYPE: PRT
<213> ORGANISM: Homo sapiens
```

```
<400> SEQUENCE: 1

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asn Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Asn Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Ala Ala Cys Asp Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

<210> SEQ ID NO 2
<211> LENGTH: 265
<212> TYPE: PRT
<213> ORGANISM: Homo sapiens

<400> SEQUENCE: 2

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asn Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110
```

```
Leu Thr Trp Cys Gly Glu Phe Asn Thr Ser Lys Ile Asn Tyr Gln Ser
            115                 120                 125

Cys Pro Asp Trp Arg Lys Asp Cys Ser Asn Asn Pro Val Ser Val Phe
            130                 135                 140

Trp Lys Thr Val Ser Arg Arg Phe Ala Glu Ala Ala Cys Asp Val Val
145                 150                 155                 160

His Val Met Leu Asn Gly Ser Arg Ser Lys Ile Phe Asp Lys Asn Ser
            165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
            195                 200                 205

Leu Cys Gln Asp Pro Thr Ile Lys Glu Leu Glu Ser Ile Ile Ser Lys
            210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
            245                 250                 255

Ser Ala Ser His His His His His
            260                 265

<210> SEQ ID NO 3

<400> SEQUENCE: 3

000

<210> SEQ ID NO 4
<211> LENGTH: 265
<212> TYPE: PRT
<213> ORGANISM: Macaca fascicularis

<400> SEQUENCE: 4

Arg Trp Arg Gln Gln Trp Ser Gly Ser Gly Thr Thr Ser Arg Phe Pro
1               5                   10                  15

Glu Thr Val Leu Ala Arg Cys Val Lys Tyr Thr Glu Val His Pro Glu
            20                  25                  30

Met Arg His Val Asp Cys Gln Ser Val Trp Asp Ala Phe Lys Gly Ala
            35                  40                  45

Phe Ile Ser Lys Tyr Pro Cys Asn Ile Thr Glu Glu Asp Tyr Gln Pro
    50                  55                  60

Leu Val Lys Leu Gly Thr Gln Thr Val Pro Cys Asn Lys Thr Leu Leu
65                  70                  75                  80

Trp Ser Arg Ile Lys Asp Leu Ala His Gln Phe Thr Gln Val Gln Arg
            85                  90                  95

Asp Met Phe Thr Leu Glu Asp Met Leu Leu Gly Tyr Leu Ala Asp Asp
            100                 105                 110

Leu Thr Trp Cys Gly Glu Phe Asn Thr Phe Glu Ile Asn Tyr Gln Ser
            115                 120                 125

Cys Pro Asp Trp Arg Lys Asp Cys Ser Asn Asn Pro Val Ser Val Phe
            130                 135                 140

Trp Lys Thr Val Ser Arg Arg Phe Ala Glu Thr Ala Cys Gly Val Val
145                 150                 155                 160

His Val Met Leu Asn Gly Ser Arg Ser Lys Ile Phe Asp Lys Asn Ser
            165                 170                 175
```

Thr Phe Gly Ser Val Glu Val His Asn Leu Gln Pro Glu Lys Val Gln
            180                 185                 190

Ala Leu Glu Ala Trp Val Ile His Gly Gly Arg Glu Asp Ser Arg Asp
            195                 200                 205

Leu Cys Gln Asp Pro Thr Ile Lys Glu Leu Glu Ser Ile Ile Ser Lys
210                 215                 220

Arg Asn Ile Arg Phe Phe Cys Lys Asn Ile Tyr Arg Pro Asp Lys Phe
225                 230                 235                 240

Leu Gln Cys Val Lys Asn Pro Glu Asp Ser Ser Cys Leu Ser Gly Ile
            245                 250                 255

Ser Ala Ser His His His His His His
            260                 265

<210> SEQ ID NO 5
<211> LENGTH: 119
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Phe
            20                  25                  30

Asn Met His Trp Val Lys Glu Thr Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Lys Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser
        115

<210> SEQ ID NO 6
<211> LENGTH: 111
<212> TYPE: PRT
<213> ORGANISM: Artificial Sequence
<220> FEATURE:
<223> OTHER INFORMATION: Synthetic Construct

<400> SEQUENCE: 6

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 7
<211> LENGTH: 449
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Phe
            20                  25                  30

Asn Met His Trp Val Lys Glu Thr Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Lys Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 8
<211> LENGTH: 218
<212> TYPE: PRT
<213> ORGANISM: Artificial Sequence
<220> FEATURE:
<223> OTHER INFORMATION: Synthetic Construct

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Lys
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 9
<211> LENGTH: 117
<212> TYPE: PRT
<213> ORGANISM: Artificial Sequence
<220> FEATURE:

<223> OTHER INFORMATION: Synthetic Construct

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Met Phe Arg Gly Ala Phe Asp Tyr Trp Gly Gln Gly Thr Leu
            100                 105                 110

Val Thr Val Ser Ser
            115

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
            85                  90                  95

Thr Phe Gly Gln Gly Thr Lys Val Glu Ile Lys
            100                 105

<210> SEQ ID NO 11
<211> LENGTH: 446
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val

```
            50                  55                  60
Lys Gly Arg Phe Thr Ile Ser Gly Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Phe Arg Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Ala Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 12
<211> LENGTH: 214
<212> TYPE: PRT
<213> ORGANISM: Artificial Sequence
```

<220> FEATURE:
<223> OTHER INFORMATION: Synthetic Construct

<400> SEQUENCE: 12

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser

<210> SEQ ID NO 14
<211> LENGTH: 111
<212> TYPE: PRT
<213> ORGANISM: Artificial Sequence
<220> FEATURE:
<223> OTHER INFORMATION: Synthetic Construct

<400> SEQUENCE: 14

```
Asp Ile Val Leu Thr Gln Ser Pro Ala Thr Leu Ser Leu Ser Pro Gly
1               5                   10                  15

Glu Arg Ala Thr Ile Ser Cys Arg Ala Ser Gln Ser Val Ser Ser Tyr
            20                  25                  30

Gly Gln Gly Phe Met His Trp Tyr Gln Gln Lys Pro Gly Gln Pro Pro
        35                  40                  45

Arg Leu Leu Ile Tyr Gly Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys
            100                 105                 110
```

<210> SEQ ID NO 15
<211> LENGTH: 449
<212> TYPE: PRT
<213> ORGANISM: Artificial Sequence
<220> FEATURE:
<223> OTHER INFORMATION: Synthetic Construct

<400> SEQUENCE: 15

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Ala Gly
225                 230                 235                 240
Pro Asp Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Leu Pro Glu Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly

<210> SEQ ID NO 16
<211> LENGTH: 218
<212> TYPE: PRT
<213> ORGANISM: Artificial Sequence
<220> FEATURE:
<223> OTHER INFORMATION: Synthetic Construct

<400> SEQUENCE: 16

Asp Ile Val Leu Thr Gln Ser Pro Ala Thr Leu Ser Leu Ser Pro Gly
1               5                   10                  15
Glu Arg Ala Thr Ile Ser Cys Arg Ala Ser Gln Ser Val Ser Ser Tyr
            20                  25                  30
Gly Gln Gly Phe Met His Trp Tyr Gln Gln Lys Pro Gly Gln Pro Pro
        35                  40                  45
Arg Leu Leu Ile Tyr Gly Ala Ser Ser Arg Ala Thr Gly Ile Pro Ala
    50                  55                  60
Arg Phe Ser Gly Ser Gly Ser Gly Thr Asp Phe Thr Leu Thr Ile Ser
65                  70                  75                  80
Pro Leu Glu Pro Glu Asp Phe Ala Val Tyr Tyr Cys Gln Gln Asn Lys
                85                  90                  95
Glu Asp Pro Trp Thr Phe Gly Gly Gly Thr Lys Leu Glu Ile Lys Arg
```

```
                100             105             110
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 17
<211> LENGTH: 120
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Arg Leu Glu Trp Ile
            35                  40                  45

Gly Tyr Ile Tyr Pro Gly Asn Gly Gly Thr Asn Tyr Asn Gln Lys Phe
        50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
            85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
            115                 120

<210> SEQ ID NO 18
<211> LENGTH: 111
<212> TYPE: PRT
<213> ORGANISM: Artificial Sequence
<220> FEATURE:
<223> OTHER INFORMATION: Synthetic Construct

<400> SEQUENCE: 18

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
            35                  40                  45

Arg Leu Leu Ile Tyr Leu Ala Ser Ser Arg Ala Thr Gly Ile Pro Ala
        50                  55                  60
```

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 19
<211> LENGTH: 449
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Phe
                20                  25                  30

Asn Met His Trp Val Lys Glu Ala Pro Gly Gln Arg Leu Glu Trp Ile
            35                  40                  45

Gly Tyr Ile Tyr Pro Gly Asn Gly Gly Thr Asn Tyr Asn Gln Lys Phe
50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Leu Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 20
<211> LENGTH: 218
<212> TYPE: PRT
<213> ORGANISM: Artificial Sequence
<220> FEATURE:
<223> OTHER INFORMATION: Synthetic Construct

<400> SEQUENCE: 20

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Arg Leu Leu Ile Tyr Leu Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 21
<211> LENGTH: 120
<212> TYPE: PRT
<213> ORGANISM: Artificial Sequence
<220> FEATURE:
<223> OTHER INFORMATION: Synthetic Construct

<400> SEQUENCE: 21

```
Gln Val Gln Leu Val Gln Ser Gly Ala Glu Val Val Lys Ser Gly Ala
1               5                   10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Ile Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
        115                 120
```

<210> SEQ ID NO 22
<211> LENGTH: 449
<212> TYPE: PRT
<213> ORGANISM: Artificial Sequence
<220> FEATURE:
<223> OTHER INFORMATION: Synthetic Construct

<400> SEQUENCE: 22

```
Gln Val Gln Leu Val Gln Ser Gly Ala Glu Val Val Lys Ser Gly Ala
1               5                   10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Ile Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 23
<211> LENGTH: 120
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Phe
            20                  25                  30

Asn Met His Trp Val Lys Glu Ala Pro Gly Gln Arg Leu Glu Trp Ile
        35                  40                  45

Gly Tyr Ile Tyr Pro Gly Asn Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Ile Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln

```
                100                 105                 110
Gly Thr Leu Val Thr Val Ser Ser
        115                 120

<210> SEQ ID NO 24
<211> LENGTH: 449
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Phe
                20                  25                  30

Asn Met His Trp Val Lys Glu Ala Pro Gly Gln Arg Leu Glu Trp Ile
            35                  40                  45

Gly Tyr Ile Tyr Pro Gly Asn Gly Gly Thr Asn Tyr Asn Gln Lys Phe
        50                  55                  60

Gln Gly Arg Ala Thr Leu Thr Ala Asp Thr Ser Ala Ser Thr Ala Tyr
65                  70                  75                  80

Met Glu Ile Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Lys Thr Ile Ser Lys Ala Lys Gly Gln Pro Arg Glu Pro Gln Val Tyr
```

```
                    340                 345                 350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Ser Leu Tyr Asn Thr Val Ala Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Asn Leu Val Pro Met Val Ala Thr Val
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Gly Leu Cys Thr Leu Val Ala Met Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gly Ile Leu Gly Phe Val Phe Thr Leu
1               5

<210> SEQ ID NO 29

<400> SEQUENCE: 29
```

<210> SEQ ID NO 30
<211> LENGTH: 256
<212> TYPE: PRT
<213> ORGANISM: Macaca fascicularis

<400> SEQUENCE: 30

Arg Trp Arg Gln Gln Trp Ser Gly Ser Gly Thr Thr Ser Arg Phe Pro
1               5                   10                  15

Glu Thr Val Leu Ala Arg Cys Val Lys Tyr Thr Glu Val His Pro Glu
            20                  25                  30

Met Arg His Val Asp Cys Gln Ser Val Trp Asp Ala Phe Lys Gly Ala
        35                  40                  45

Phe Ile Ser Lys Tyr Pro Cys Asn Ile Thr Glu Glu Asp Tyr Gln Pro
    50                  55                  60

Leu Val Lys Leu Gly Thr Gln Thr Val Pro Cys Asn Lys Thr Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Met Leu Leu Gly Tyr Leu Ala Asp Asp
            100                 105                 110

Leu Thr Trp Cys Gly Glu Phe Asn Thr Phe Glu Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Thr Ala Cys Gly Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Ala Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220

Arg Asn Ile Arg Phe Phe Cys Lys Asn Ile Tyr Arg Pro Asp Lys Phe
225                 230                 235                 240

Leu Gln Cys Val Lys Asn Pro Glu Asp Ser Ser Cys Leu Ser Gly Ile
                245                 250                 255

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Gly Tyr Thr Phe Thr Ser Phe Asn
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 32

Ile Tyr Pro Gly Asn Gly Gly Thr
1               5

<210> SEQ ID NO 33
<211> LENGTH: 13
<212> TYPE: PRT
<213> ORGANISM: Artificial Sequence
<220> FEATURE:
<223> OTHER INFORMATION: Synthetic Construct

<400> SEQUENCE: 33

Ala Arg Thr Gly Gly Leu Arg Arg Ala Tyr Phe Thr Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Glu Ser Val Asp Ser Tyr Gly Asn Gly Phe
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Synthetic Construct

<400> SEQUENCE: 35

Leu Ala Ser
1

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Gln Gln Asn Lys Glu Asp Pro Trp Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gly Tyr Thr Phe Thr Ser Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38
```

```
Ile Tyr Pro Gly Gln Gly Gly Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Gln Ser Val Ser Ser Tyr Gly Gln Gly Phe
1               5                   10

<210> SEQ ID NO 40
<211> LENGTH: 3
<212> TYPE: PRT
<213> ORGANISM: Artificial Sequence
<220> FEATURE:
<223> OTHER INFORMATION: Synthetic Construct

<400> SEQUENCE: 40

Gly Ala Ser
1

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Gly Phe Thr Phe Ser Ser Tyr Gly
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Ile Trp Tyr Asp Gly Ser Asn Lys
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Ala Arg Met Phe Arg Gly Ala Phe Asp Tyr
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44
```

Gln Gly Ile Arg Asn Asp
1               5

<210> SEQ ID NO 45
<211> LENGTH: 3
<212> TYPE: PRT
<213> ORGANISM: Artificial Sequence
<220> FEATURE:
<223> OTHER INFORMATION: Synthetic Construct

<400> SEQUENCE: 45

Ala Ala Ser
1

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Leu Gln Asp Tyr Ile Tyr Tyr Pro Thr
1               5

<210> SEQ ID NO 47
<211> LENGTH: 120
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: Synthetic Construct

<400> SEQUENCE: 48

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Leu Ile
                35                  40                  45

Tyr Ser Ala Ser Tyr Arg Tyr Ile Gly Val Pro Asp Arg Phe Thr Gly
 50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys
                100                 105

<210> SEQ ID NO 49
<211> LENGTH: 120
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
                35                  40                  45

Gly Ser Ile Tyr Pro Gly Asn Val Asn Thr Asn Tyr Ala Gln Lys Phe
 50                  55                  60

Gln Gly Arg Ala Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Ser His Tyr Gly Leu Asp Trp Asn Phe Asp Val Trp Gly Lys
                100                 105                 110

Gly Thr Thr Val Thr Val Ser Ser
            115                 120

<210> SEQ ID NO 50
<211> LENGTH: 107
<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asn Ile Tyr Val Trp
                20                  25                  30

Leu Asn Trp Tyr Gln Gln Lys Pro Gly Lys Ala Pro Lys Leu Leu Ile
                35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Gly Gln Thr Tyr Pro Tyr
                 85                  90                  95

Thr Phe Gly Gln Gly Thr Lys Leu Glu Ile Lys
                100                 105

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Asp Tyr
            20                  25                  30

Gly Val His Trp Val Arg Gln Pro Pro Gly Lys Gly Leu Glu Trp Leu
        35                  40                  45

Gly Val Ile Trp Ala Gly Gly Thr Asn Tyr Asn Pro Ser Leu Lys
    50                  55                  60

Ser Arg Lys Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Lys Gly Tyr Ser Tyr Tyr Ser Met Asp Tyr Trp Gly Gln
            100                 105                 110

Gly Thr Thr Val Thr Val Ser
        115

<210> SEQ ID NO 52
<211> LENGTH: 111
<212> TYPE: PRT
<213> ORGANISM: Artificial Sequence
<220> FEATURE:
<223> OTHER INFORMATION: Synthetic Construct

<400> SEQUENCE: 52

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Val Ala Asn Tyr Tyr Cys Gln Gln Ser Arg
                85                  90                  95

Lys Val Pro Tyr Thr Phe Gly Gln Gly Thr Lys Leu Glu Ile Lys
            100                 105                 110

<210> SEQ ID NO 53
<211> LENGTH: 121
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
            35                  40                  45

Ala Gln Ile Lys Asp Lys Ser Asn Ser Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120

<210> SEQ ID NO 54
<211> LENGTH: 112
<212> TYPE: PRT
<213> ORGANISM: Artificial Sequence
<220> FEATURE:
<223> OTHER INFORMATION: Synthetic Construct

<400> SEQUENCE: 54

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Ala Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
            100                 105                 110

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Gly Gly Gly Ser Gly Gly Gly Gly Ser
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 5
<212> TYPE: PRT
<213> ORGANISM: Artificial Sequence
<220> FEATURE:
<223> OTHER INFORMATION: Synthetic Construct

<400> SEQUENCE: 57

```
Thr Lys Gly Pro Ser
1               5
```

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

```
Gly Gln Pro Lys Ala Ala Pro
1               5
```

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

```
Gly Gly Ser Gly Ser Ser Gly Ser Gly Gly
1               5                   10
```

<210> SEQ ID NO 60
<211> LENGTH: 570
<212> TYPE: PRT
<213> ORGANISM: Artificial Sequence
<220> FEATURE:
<223> OTHER INFORMATION: Synthetic Construct

<400> SEQUENCE: 60

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Ala Gln Lys Phe
    50                  55                  60

Gln Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser His Tyr Gly Leu Asp Trp Asn Phe Asp Val Trp Gly Lys
            100                 105                 110

Gly Thr Thr Val Thr Val Ser Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Thr Lys Ala Trp Met His Trp Val Arg Gln
145                 150                 155                 160

Ala Pro Gly Lys Gln Leu Glu Trp Val Ala Gln Ile Lys Asp Lys Ser
```

```
                165                 170                 175
Asn Ser Tyr Ala Thr Tyr Tyr Ala Asp Ser Val Lys Gly Arg Phe Thr
            180                 185                 190

Ile Ser Arg Asp Asp Ser Lys Asn Thr Leu Tyr Leu Gln Met Asn Ser
            195                 200                 205

Leu Arg Ala Glu Asp Thr Ala Val Tyr Tyr Cys Arg Gly Val Tyr Tyr
            210                 215                 220

Ala Leu Ser Pro Phe Asp Tyr Trp Gly Gln Gly Thr Leu Val Thr Val
225                 230                 235                 240

Ser Ser Arg Thr Ala Ser Thr Lys Gly Pro Ser Val Phe Pro Leu Ala
            245                 250                 255

Pro Cys Ser Arg Ser Thr Ser Glu Ser Thr Ala Ala Leu Gly Cys Leu
            260                 265                 270

Val Lys Asp Tyr Phe Pro Glu Pro Val Thr Val Ser Trp Asn Ser Gly
            275                 280                 285

Ala Leu Thr Ser Gly Val His Thr Phe Pro Ala Val Leu Gln Ser Ser
            290                 295                 300

Gly Leu Tyr Ser Leu Ser Ser Val Val Thr Val Pro Ser Ser Ser Leu
305                 310                 315                 320

Gly Thr Lys Thr Tyr Thr Cys Asn Val Asp His Lys Pro Ser Asn Thr
                325                 330                 335

Lys Val Asp Lys Arg Val Glu Ser Lys Tyr Gly Pro Pro Cys Pro Pro
            340                 345                 350

Cys Pro Ala Pro Glu Ala Ala Gly Gly Pro Ser Val Phe Leu Phe Pro
            355                 360                 365

Pro Lys Pro Lys Asp Thr Leu Met Ile Ser Arg Thr Pro Glu Val Thr
370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
            435                 440                 445

Asn Lys Gly Leu Pro Ser Ser Ile Glu Lys Thr Ile Ser Lys Ala Lys
            450                 455                 460

Gly Gln Pro Arg Glu Pro Gln Val Cys Thr Leu Pro Pro Ser Gln Glu
465                 470                 475                 480

Glu Met Thr Lys Asn Gln Val Ser Leu Ser Cys Ala Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Val Ser Lys Leu Thr Val Asp Lys Ser Arg Trp Gln Glu Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly
            565                 570

<210> SEQ ID NO 61
```

<211> LENGTH: 338
<212> TYPE: PRT
<213> ORGANISM: Artificial Sequence
<220> FEATURE:
<223> OTHER INFORMATION: Synthetic Construct

<400> SEQUENCE: 61

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Ala Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gly
                85                  90                  95

Thr Gln Tyr Pro Phe Thr Phe Gly Ser Gly Thr Lys Val Glu Ile Lys
            100                 105                 110

Gly Gln Pro Lys Ala Ala Pro Asp Ile Gln Met Thr Gln Ser Pro Ser
        115                 120                 125

Ser Leu Ser Ala Ser Val Gly Asp Arg Val Thr Ile Thr Cys Gln Ala
145                 150                 155                 160

Ser Gln Asn Ile Tyr Val Trp Leu Asn Trp Tyr Gln Gln Lys Pro Gly
145                 150                 155                 160

Lys Ala Pro Lys Leu Leu Ile Tyr Lys Ala Ser Asn Leu His Thr Gly
            165                 170                 175

Val Pro Ser Arg Phe Ser Gly Ser Gly Ser Gly Thr Asp Phe Thr Leu
        180                 185                 190

Thr Ile Ser Ser Leu Gln Pro Glu Asp Ile Ala Thr Tyr Tyr Cys Gln
    195                 200                 205

Gln Gly Gln Thr Tyr Pro Tyr Thr Phe Gly Gln Gly Thr Lys Leu Glu
210                 215                 220

Ile Lys Thr Lys Gly Pro Ser Arg Thr Val Ala Ala Pro Ser Val Phe
225                 230                 235                 240

Ile Phe Pro Pro Ser Asp Glu Gln Leu Lys Ser Gly Thr Ala Ser Val
            245                 250                 255

Val Cys Leu Leu Asn Asn Phe Tyr Pro Arg Glu Ala Lys Val Gln Trp
        260                 265                 270

Lys Val Asp Asn Ala Leu Gln Ser Gly Asn Ser Gln Glu Ser Val Thr
    275                 280                 285

Glu Gln Asp Ser Lys Asp Ser Thr Tyr Ser Leu Ser Ser Thr Leu Thr
290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
            325                 330                 335

Glu Cys

<210> SEQ ID NO 62
<211> LENGTH: 446
<212> TYPE: PRT
<213> ORGANISM: Artificial Sequence
<220> FEATURE:

<223> OTHER INFORMATION: Synthetic Construct

<400> SEQUENCE: 62

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 63
<211> LENGTH: 218
<212> TYPE: PRT
<213> ORGANISM: Artificial Sequence
<220> FEATURE:
<223> OTHER INFORMATION: Synthetic Construct

<400> SEQUENCE: 63

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Gln Ser Val Ser Ser Tyr
            20                  25                  30

Gly Gln Gly Phe Met His Trp Tyr Gln Gln Lys Pro Gly Gln Pro Pro
        35                  40                  45

Arg Leu Leu Ile Tyr Gly Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 573
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

```
Gly Ser Ile Tyr Pro Gly Asn Val Asn Thr Asn Tyr Ala Gln Lys Phe
    50                  55                  60
Gln Gly Arg Ala Thr Leu Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Thr Arg Ser His Tyr Gly Leu Asp Trp Asn Phe Asp Val Trp Gly Lys
            100                 105                 110
Gly Thr Thr Val Thr Val Ser Ser Gln Val Gln Leu Val Glu Ser
            115                 120                 125
Gly Gly Gly Val Val Gln Pro Gly Arg Ser Leu Arg Leu Ser Cys Ala
    130                 135                 140
Ala Ser Gly Phe Thr Phe Thr Lys Ala Trp Met His Trp Val Arg Gln
145                 150                 155                 160
Ala Pro Gly Lys Gln Leu Glu Trp Val Ala Gln Ile Lys Asp Lys Ser
                165                 170                 175
Asn Ser Tyr Ala Thr Tyr Tyr Ala Asp Ser Val Lys Gly Arg Phe Thr
            180                 185                 190
Ile Ser Arg Asp Asp Ser Lys Asn Thr Leu Tyr Leu Gln Met Asn Ser
    195                 200                 205
Leu Arg Ala Glu Asp Thr Ala Val Tyr Tyr Cys Arg Gly Val Tyr Tyr
210                 215                 220
Ala Leu Ser Pro Phe Asp Tyr Trp Gly Gln Gly Thr Leu Val Thr Val
225                 230                 235                 240
Ser Ser Arg Thr Ala Ser Thr Lys Gly Pro Ser Val Phe Pro Leu Ala
                245                 250                 255
Pro Ser Ser Lys Ser Thr Ser Gly Gly Thr Ala Ala Leu Gly Cys Leu
            260                 265                 270
Val Lys Asp Tyr Phe Pro Glu Pro Val Thr Val Ser Trp Asn Ser Gly
    275                 280                 285
Ala Leu Thr Ser Gly Val His Thr Phe Pro Ala Val Leu Gln Ser Ser
290                 295                 300
Gly Leu Tyr Ser Leu Ser Ser Val Val Thr Val Pro Ser Ser Ser Leu
305                 310                 315                 320
Gly Thr Gln Thr Tyr Ile Cys Asn Val Asn His Lys Pro Ser Asn Thr
                325                 330                 335
Lys Val Asp Lys Lys Val Glu Pro Lys Ser Cys Asp Lys Thr His Thr
            340                 345                 350
Cys Pro Pro Cys Pro Ala Pro Glu Ala Ala Gly Gly Pro Ser Val Phe
    355                 360                 365
Leu Phe Pro Pro Lys Pro Lys Asp Thr Leu Met Ile Ser Arg Thr Pro
370                 375                 380
Glu Val Thr Cys Val Val Val Asp Val Ser His Glu Asp Pro Glu Val
385                 390                 395                 400
Lys Phe Asn Trp Tyr Val Asp Gly Val Glu Val His Asn Ala Lys Thr
                405                 410                 415
Lys Pro Arg Glu Glu Gln Tyr Asn Ser Thr Tyr Arg Val Val Ser Val
            420                 425                 430
Leu Thr Val Leu His Gln Asp Trp Leu Asn Gly Lys Glu Tyr Lys Cys
    435                 440                 445
Lys Val Ser Asn Lys Ala Leu Ala Ala Pro Ile Glu Lys Thr Ile Ser
450                 455                 460
```

```
Lys Ala Lys Gly Gln Pro Arg Glu Pro Gln Val Cys Thr Leu Pro Pro
465                 470                 475                 480

Ser Arg Asp Glu Leu Thr Lys Asn Gln Val Ser Leu Ser Cys Ala Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Val Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly
                565                 570

<210> SEQ ID NO 65
<211> LENGTH: 449
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 66
<211> LENGTH: 573
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Ala Gln Lys Phe
    50                  55                  60

Gln Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser His Tyr Gly Leu Asp Trp Asn Phe Asp Val Trp Gly Lys
            100                 105                 110

Gly Thr Thr Val Thr Val Ser Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Thr Lys Ala Trp Met His Trp Val Arg Gln
145                 150                 155                 160

Ala Pro Gly Lys Gln Leu Glu Trp Val Ala Gln Ile Lys Asp Lys Ser
```

```
            165                 170                 175
Asn Ser Tyr Ala Thr Tyr Tyr Ala Asp Ser Val Lys Gly Arg Phe Thr
            180                 185                 190

Ile Ser Arg Asp Asp Ser Lys Asn Thr Leu Tyr Leu Gln Met Asn Ser
            195                 200                 205

Leu Arg Ala Glu Asp Thr Ala Val Tyr Tyr Cys Arg Gly Val Tyr Tyr
            210                 215                 220

Ala Leu Ser Pro Phe Asp Tyr Trp Gly Gln Gly Thr Leu Val Thr Val
225                 230                 235                 240

Ser Ser Arg Thr Ala Ser Thr Lys Gly Pro Ser Val Phe Pro Leu Ala
            245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
            275                 280                 285

Ala Leu Thr Ser Gly Val His Thr Phe Pro Ala Val Leu Gln Ser Ser
            290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
            325                 330                 335

Lys Val Asp Lys Lys Val Glu Pro Lys Ser Cys Asp Lys Thr His Thr
            340                 345                 350

Cys Pro Pro Cys Pro Ala Pro Glu Leu Leu Gly Gly Pro Ser Val Phe
            355                 360                 365

Leu Phe Pro Pro Lys Pro Lys Asp Thr Leu Met Ile Ser Arg Thr Pro
370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
            405                 410                 415

Lys Pro Arg Glu Glu Gln Tyr Asn Asn Ala Ser Arg Val Val Ser Val
            420                 425                 430

Leu Thr Val Leu His Gln Asp Trp Leu Asn Gly Lys Glu Tyr Lys Cys
            435                 440                 445

Lys Val Ser Asn Lys Ala Leu Pro Ala Pro Ile Glu Lys Thr Ile Ser
450                 455                 460

Lys Ala Lys Gly Gln Pro Arg Glu Pro Gln Val Cys Thr Leu Pro Pro
465                 470                 475                 480

Ser Arg Asp Glu Leu Thr Lys Asn Gln Val Ser Leu Ser Cys Ala Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Leu Val Ser Lys Leu Thr Val Asp Lys Ser Arg Trp
530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly
            565                 570

<210> SEQ ID NO 67
```

```
<211> LENGTH: 449
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Lys Glu Ala Pro Gly Gln Arg Leu Glu Trp Ile
            35                  40                  45

Gly Tyr Ile Tyr Pro Gly Gln Gly Gly Thr Asn Tyr Asn Gln Lys Phe
        50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Asn Ala Ser Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 68
<211> LENGTH: 443
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285
```

-continued

```
Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Cys Gln
            340                 345                 350

Glu Glu Met Thr Lys Asn Gln Val Ser Leu Trp Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
            435                 440

<210> SEQ ID NO 69
<211> LENGTH: 214
<212> TYPE: PRT
<213> ORGANISM: Artificial Sequence
<220> FEATURE:
<223> OTHER INFORMATION: Synthetic Construct

<400> SEQUENCE: 69

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210
```

<210> SEQ ID NO 70
<211> LENGTH: 446
<212> TYPE: PRT
<213> ORGANISM: Artificial Sequence
<220> FEATURE:
<223> OTHER INFORMATION: Synthetic Construct

<400> SEQUENCE: 70

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Ala Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 71
<211> LENGTH: 446
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

```
Val Lys Phe Asn Trp Tyr Val Asp Gly Val Glu Val His Asn Ala Lys
            275                 280                 285

Thr Lys Pro Arg Glu Glu Gln Tyr Asn Asn Ala Ser Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 72
<211> LENGTH: 1710
<212> TYPE: DNA
<213> ORGANISM: Artificial Sequence
<220> FEATURE:
<223> OTHER INFORMATION: Synthetic Construct

<400> SEQUENCE: 72
caggtgcagc tggtgcagtc tggcgccgag gtcgtgaaac ctggcgcctc tgtgaaggtg     60
tcctgcaagg ccagcggcta cacctttacc agctactaca tccactgggt gcgccaggcc    120
cctggacagg gactggaatg gatcggcagc atctaccccg caacgtgaa caccaactac    180 gcccagaagt tccagggcag agccaccctg accgtgaca ccagcatcag caccgcctac    240
atggaactga gccggctgag aagcgacgac accgccgtgt actactgcac ccggtcccac    300
tacggcctgg attggaactt cgacgtgtgg ggcaagggca ccaccgtgac agtgtctagc    360
agccaggtgc agctggtgga atctggcggc ggagtggtgc agcctggcag aagcctgaga    420
ctgagctgtg ccgccagcgg cttcaccttc accaaggcct ggatgcactg ggtgcgccag    480
gcccctggaa agcagctgga atgggtggcc cagatcaagg acaagagcaa cagctacgcc    540
acctactacg ccgacagcgt gaagggccgg ttcaccatca gccgggacga cagcaagaac    600
accctgtacc tgcagatgaa cagcctgcgg gccgaggaca ccgccgtgta ctactgtcgg    660
ggcgtgtact atgccctgag ccccttcgat tactggggcc agggaaccct cgtgaccgtg    720
tctagtcgga ccgccagcac aaagggccca tcggtgttcc ctctggcccc ttgcagcaga    780
agcaccagcg aatctacagc cgccctgggc tgcctcgtga aggactactt ccccgagccc    840
gtgaccgtgt cctggaactc tggcgctctg acaagcggcg tgcacacctt ccagccgtg    900 ctccagagca gcggcctgta ctctctgagc agcgtcgtga cagtgcccag cagcagcctg    960
ggcaccaaga cctacacctg taacgtggac cacaagccca gcaacaccaa ggtggacaag   1020
cgggtggaat ctaagtacgg ccctccctgc cctccttgcc cagccctga agctgccggc   1080
```

```
ggaccctccg tgttcctgtt ccccccaaag cccaaggaca ccctgatgat cagccggacc    1140
cccgaagtga cctgcgtggt ggtggatgtg tcccaggaag atcccgaggt gcagttcaat    1200
tggtacgtgg acggcgtgga agtgcacaac gccaagacca agcccagaga ggaacagttc    1260
aacagcacct accgggtggt gtccgtgctg accgtgctgc accaggactg gctgaacggc    1320
aaagagtaca agtgcaaggt gtccaacaag ggcctgccca gctccatcga gaaaaccatc    1380
agcaaggcca agggccagcc ccgcgagcct caagtgtgta ccctgccccc tagccaggaa    1440
gagatgacca agaaccaggt gtccctgagc tgtgccgtga aaggcttcta ccccagcgac    1500
attgccgtgg aatgggagag caacggccag cccgagaaca actacaagac cacccccct     1560 gtgctggaca gcgacggctc attcttcctg gtgtccaagc tgaccgtgga caagagccgg    1620
tggcaggaag gcaacgtgtt cagctgctcc gtgatgcacg aggccctgca caaccactac    1680
acccagaagt ccctgtctct gtccctgggc                                     1710

<210> SEQ ID NO 73
<211> LENGTH: 1014
<212> TYPE: DNA
<213> ORGANISM: Artificial Sequence
<220> FEATURE:
<223> OTHER INFORMATION: Synthetic Construct

<400> SEQUENCE: 73
gacatcgtga tgacccagac cccctgagc ctgagcgtga cacctggaca gcctgccagc      60
atcagctgca agagcagcca gagcctggtg cacaacaacg ccaacaccta cctgagctgg    120
tatctgcaga agcccggcca gagccccag tccctgatct acaaggtgtc caacagattc     180
agcggcgtgc ccgacagatt ctccggcagc ggctctggca ccgacttcac cctgaagatc    240
agccgggtgg aagccgagga cgtgggcgtg tactattgtg gccagggcac ccagtacccc    300
ttcacctttg gcagcggcac caaggtggaa atcaagggcc agcccaaggc cgcccccgac    360
atccagatga cccagagccc cagcagcctg tctgccagcg tgggcgacag agtgaccatc    420
acctgtcagg ccagccagaa catctacgtg tggctgaact ggtatcagca gaagcccggc    480
aaggccccca gctgctgat ctacaaggcc agcaacctgc acaccggcgt gcccagcaga    540 tttctggca gcggctccgg caccgacttc accctgacaa tcagctccct gcagcccgag    600
gacattgcca cctactactg ccagcagggc cagacctacc cctacacctt ggccagggc     660 accaagctgg aaatcaagac caagggcccc agccgtacgg tggccgctcc cagcgtgttc    720
atcttcccac ctagcgacga gcagctgaag tccggcacag cctctgtcgt gtgcctgctg    780
aacaacttct accccgcga ggccaaagtg cagtggaagg tggacaacgc cctgcagagc    840
ggcaacagcc aggaaagcgt gaccgagcag gacagcaagg actccaccta cagcctgagc    900
agcaccctga cactgagcaa ggccgactac gagaagcaca aggtgtacgc ctgcgaagtg    960
acccaccagg gcctgtctag ccccgtgacc aagagcttca ccggggcga gtgt           1014

<210> SEQ ID NO 74
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 74
caggtgcagc tggtgcagtc tggcgccgaa gtcgtgaaac tggcgcctc cgtgaaggtg      60 tcctgcaagg ccagcggcta cacctttacc agctacgcca tgcactgggt caaagaggcc    120
```

```
cctggccaga gactggaatg gatcggctac atctaccccg gccagggcgg caccaactac    180
aaccagaagt tccagggcag agccaccctg accgccgata caagcgccag caccgcctac    240
atggaactga gcagcctgcg gagcgaggat accgccgtgt acttctgtgc cagaacaggc    300
ggcctgaggc gggcctactt tacctattgg ggccagggca ccctcgtgac cgtgtctagc    360
gctagcacaa agggcccatc ggtgttccct ctggccccct tgcagcagaag caccagcgaa    420 tctacagccg ccctgggctg cctcgtgaag gactactttc ccgagcccgt gaccgtgtcc    480
tggaactctg gcgctctgac aagcggcgtg cacacctttc cagccgtgct ccagagcagc    540
ggcctgtact ctctgagcag cgtcgtgaca gtgcccagca gcagcctggg caccaagacc    600
tacacctgta acgtggacca caagcccagc aacaccaagg tggacaagcg ggtggaatct    660
aagtacggcc ctcccctgcccc tccttgccca gcccctgaag ctgccggcgg accctccgtg    720
ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac cgtgctgcac caggactggc tgaacggcaa agagtacaag    960
tgcaaggtgt ccaacaaggg cctgcccagc tccatcgaga aaaccatcag caaggccaag    1020
ggccagcccc gcgagcctca agtgtatacc ctgccccctt gccaggaaga tgaccaag    1080 aaccaggtgt ccctgtggtg tctcgtgaaa ggcttctacc ccagcgacat tgccgtggaa    1140
tgggagagca acggccagcc cgagaacaac tacaagacca ccccccctgt gctggacagc    1200
gacggctcat tcttcctgta ctccaagctg accgtggaca agagccggtg gcaggaaggc    1260
aacgtgttca gctgctccgt gatgcacgag gccctgcaca accactacac ccagaagtcc    1320
ctgtctctgt ccctgggc    1338
```

<210> SEQ ID NO 75
<211> LENGTH: 654
<212> TYPE: DNA
<213> ORGANISM: Artificial Sequence
<220> FEATURE:
<223> OTHER INFORMATION: Synthetic Construct

<400> SEQUENCE: 75

```
gacatcgtgc tgacacagag ccctgccacc ctgtctctga gccctggcga gagagccacc    60
atcagctgta gagccagcca gagcgtgtcc agctacggcc agggcttcat gcactggtat    120
cagcagaagc ccggccagcc ccccagactg ctgatctatg cgccagcag cagagccaca    180 ggcatccccg ccagatttc tggctctggc agcggcaccg acttcaccct gacaatcagc    240
cccctggaac ccgaggactt cgccgtgtac tactgccagc agaacaaaga ggaccccctgg    300 accttcggcg gaggcaccaa gctggaaatc aagcgtacgg tggccgctcc cagcgtgttc    360
atcttcccac ctagcgacga gcagctgaag tccggcacag cctctgtcgt gtgcctgctg    420
aacaacttct acccccgcga ggccaaggtg cagtggaagg tggacaatgc cctgcagagc    480
ggcaacagcc aggaaagcgt gaccgagcag gacagcaagg actccaccta cagcctgagc    540
agcaccctga ccctgtccaa ggccgattac gagaagcaca aggtgtacgc ctgcgaagtg    600
acccaccagg gcctgtctag ccccgtgacc aagagcttca accggggcga gtgc    654
```

<210> SEQ ID NO 76
<211> LENGTH: 1719
<212> TYPE: DNA

<213> ORGANISM: Artificial Sequence
<220> FEATURE:
<223> OTHER INFORMATION: Synthetic Construct

<400> SEQUENCE: 76

```
caggtgcagc tggtgcagtc tggcgccgag gtcgtgaaac ctggcgcctc tgtgaaggtg      60
tcctgcaagg ccagcggcta caccttttacc agctactaca tccactgggt gcgccaggcc    120
cctggacagg gactggaatg gatcggcagc atctacccg gcaacgtgaa caccaactac      180
gcccagaagt tccagggcag agccaccctg accgtggaca ccagcatcag caccgcctac    240
atggaactga gccggctgag aagcgacgac accgccgtgt actactgcac ccggtcccac    300
tacggcctgg attggaactt cgacgtgtgg ggcaagggca ccaccgtgac agtgtctagc    360
agccaggtgc agctggtgga atctggcggc ggagtggtgc agcctggcag aagcctgaga    420
ctgagctgtg ccgccagcgg cttcaccttc accaaggcct ggatgcactg ggtgcgccag    480
gcccctggaa agcagctgga atgggtggcc cagatcaagg acaagagcaa cagctacgcc    540
acctactacg ccgacagcgt gaagggccgg ttcaccatca gccgggacga cagcaagaac    600
accctgtacc tgcagatgaa cagcctgcgg gccgaggaca ccgccgtgta ctactgtcgg    660
ggcgtgtact atgccctgag ccccttcgat tactggggcc agggaaccct cgtgaccgtg    720
tctagtcgga ccgccagcac aaagggcccc agcgtgttcc ctctggcccc tagcagcaag    780
agcacatctg gcggaacagc cgccctgggc tgcctcgtga aggactactt ccccgagccc    840
gtgaccgtgt cctggaattc tggcgccctg accagcggcg tgcacacctt tccagctgtg    900
ctgcagtcca gcgcctgta cagcctgagc agcgtcgtga cagtgcccag cagctctctg    960
ggcacccaga cctacatctg caacgtgaac cacaagccca gcaacaccaa ggtggacaag   1020
aaggtggaac ccaagagctg cgacaagacc cacacctgtc ccccttgtcc tgccccgaa    1080
gccgccggag cccttccgt gttcctgttc cccccaaagc ccaaggacac cctgatgatc   1140
agccggaccc ccgaagtgac ctgcgtggtg gtggatgtgt cccacgagga ccctgaagtg   1200
aagttcaatt ggtacgtgga cggcgtggaa gtgcacaacg ccaagaccaa gccaagagag   1260
gaacagtaca acagcaccta ccgggtggtg tccgtgctga ccgtgctgca ccaggactgg   1320
ctgaacggca aagagtacaa gtgcaaggtg tccaacaagg ccctggccgc ccccatcgag   1380
aaaaccatca gcaaggccaa gggccagccc cgcgaacccc aggtgtgcac actgccccca   1440
agcagggacg agctgaccaa gaaccaggtg tccctgagct gtgccgtgaa aggcttctac   1500
ccctccgata tcgccgtgga atgggagagc aacggccagc ccgagaacaa ctacaagacc   1560
accccccctg tgctggacag cgacggctca ttcttcctgg tgtccaagct gacagtggac   1620
aagtcccggt ggcagcaggg caacgtgttc agctgctccg tgatgcacga ggccctgcac   1680
aaccactaca cccagaagtc cctgagcctg agccccggc                           1719
```

<210> SEQ ID NO 77
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 77

```
caggtgcagc tggtgcagtc tggcgccgaa gtcgtgaaac ctggcgcctc cgtgaaggtg      60
tcctgcaagg ccagcggcta cacctttacc agctacgcca tgcactgggt caaagaggcc    120
cctggccaga gactggaatg gatcggctac atctacccg gccagggcgg caccaactac     180
```

| | |
|---|---|
| aaccagaagt tccagggcag agccaccctg accgccgata caagcgccag caccgcctac | 240 |
| atggaactga gcagcctgcg gagcgaggat accgccgtgt acttctgtgc cagaacaggc | 300 |
| ggcctgaggc gggcctactt tacctattgg ggccagggca ccctcgtgac cgtgtctagc | 360 |
| gctagcacaa agggccccag cgtgttccct ctggccccta gcagcaagag cacatctggc | 420 |
| ggaacagccg ccctgggctg cctcgtgaag gactactttc ccgagcccgt gaccgtgtcc | 480 |
| tggaattctg gcgccctgac cagcggcgtg cacacctttc cagctgtgct gcagtccagc | 540 |
| ggcctgtaca gcctgagcag cgtcgtgaca gtgcccagca gctctctggg cacccagacc | 600 |
| tacatctgca acgtgaacca caagcccagc aacaccaagg tggacaagaa ggtggaaccc | 660 |
| aagagctgcg acaagaccca cacctgtccc ccttgtcctg cccccgaagc cgccggaggc | 720 |
| ccttccgtgt tcctgttccc cccaaagccc aaggacaccc tgatgatcag ccggaccccc | 780 |
| gaagtgacct gcgtggtggt ggatgtgtcc cacgaggacc ctgaagtgaa gttcaattgg | 840 |
| tacgtggacg gcgtggaagt gcacaacgcc aagaccaagc caagagagga acagtacaac | 900 |
| agcacctacc gggtggtgtc cgtgctgacc gtgctgcacc aggactggct gaacggcaaa | 960 |
| gagtacaagt gcaaggtgtc caacaaggcc ctggccgccc catcgagaa aaccatcagc | 1020 |
| aaggccaagg gccagccccg cgaaccccag gtgtacacac tgcccccatg cagggacgag | 1080 |
| ctgaccaaga accaggtgtc cctgtggtgt ctggtgaaag gcttctaccc ctccgatatc | 1140 |
| gccgtggaat gggagagcaa cggccagccc gagaacaact acaagaccac ccccctgtg | 1200 |
| ctggacagcg acggctcatt cttcctgtac tccaagctga cagtggacaa gtcccggtgg | 1260 |
| cagcagggca acgtgttcag ctgctccgtg atgcacgagg ccctgcacaa ccactacacc | 1320 |
| cagaagtccc tgagcctgag ccccggc | 1347 |

<210> SEQ ID NO 78
<211> LENGTH: 1719
<212> TYPE: DNA
<213> ORGANISM: Artificial Sequence
<220> FEATURE:
<223> OTHER INFORMATION: Synthetic Construct

<400> SEQUENCE: 78

| | |
|---|---|
| caggtgcagc tggtgcagtc tggcgccgag gtcgtgaaac ctggcgcctc tgtgaaggtg | 60 |
| tcctgcaagg ccagcggcta cacctttacc agctactaca tccactgggt gcgccaggcc | 120 |
| cctggacagg gactggaatg gatcggcagc atctaccccg gcaacgtgaa caccaactac | 180 |
| gcccagaagt tccagggcag agccaccctg accgtgaca ccagcatcag caccgcctac | 240 |
| atggaactga gccggctgag aagcgacgac accgccgtgt actactgcac ccggtcccac | 300 |
| tacggcctga ttggaacttt cgacgtgtgg ggcaagggca ccaccgtgac agtgtctagc | 360 |
| agccaggtgc agctggtgga atctggcggc ggagtggtgc agcctggcag aagcctgaga | 420 |
| ctgagctgtg ccgccagcgg cttcaccttc accaaggcct ggatgcactg ggtgcgccag | 480 |
| gcccctggaa agcagctgga atgggtggcc cagatcaagg acaagagcaa cagctacgcc | 540 |
| acctactacg ccgacagcgt gaagggccgg ttcaccatca gccgggacga cagcaagaac | 600 |
| accctgtacc tgcagatgaa cagcctgcgg gccgaggaca ccgccgtgta ctactgtcgg | 660 |
| ggcgtgtact atgccctgag ccccttcgat tactgggccc agggaaccct cgtgaccgtg | 720 |
| tctagtcgga ccgccagcac aaagggcccc agcgtgttcc ctctggcccc tagcagcaag | 780 |
| agcacatctg gcggaacagc cgccctgggc tgcctcgtga aggactactt tcccgagccc | 840 |

```
gtgaccgtgt cctggaattc tggcgccctg accagcggcg tgcacacctt ccagctgtg     900 ctgcagtcca gcggcctgta cagcctgagc agcgtcgtga cagtgcccag cagctctctg    960
ggcacccaga cctacatctg caacgtgaac cacaagccca gcaacaccaa ggtggacaag   1020
aaggtggaac ccaagagctg cgacaagacc cacacctgtc cccttgtcc tgccccgaa     1080 ctgctgggag gccttccgt gttcctgttc ccccaaagc ccaaggacac cctgatgatc     1140
agccggaccc ccgaagtgac ctgcgtggtg gtggatgtgt cccacgagga ccctgaagtg   1200
aagttcaatt ggtacgtgga cggcgtggaa gtgcacaacg ccaagaccaa gccaagagag   1260
gaacagtaca acaatgcctc ccgggtggtg tccgtgctga ccgtgctgca ccaggactgg   1320
ctgaacggca aagagtacaa gtgcaaggtg tccaacaagg ccctgcctgc ccccatcgag   1380
aaaaccatca gcaaggccaa gggccagccc cgcgaacccc aggtgtgcac actgccccca   1440
agcagggacg agctgaccaa gaaccaggtg tccctgagct gtgccgtgaa aggcttctac   1500
ccctccgata tcgccgtgga atgggagagc aacggccagc ccgagaacaa ctacaagacc   1560
accccccctg tgctggacag cgacggctca ttcttcctgg tgtccaagct gacagtggac   1620
aagtcccggt ggcagcaggg caacgtgttc agctgctccg tgatgcacga ggccctgcac   1680
aaccactaca cccagaagtc cctgagcctg agccccggc                          1719
```

<210> SEQ ID NO 79
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 79

```
caggtgcagc tggtgcagtc tggcgccgaa gtcgtgaaac tggcgcctc cgtgaaggtg     60 tcctgcaagg ccagcggcta cacctttacc agctacgcca tgcactgggt caaagaggcc    120
cctggccaga gactggaatg gatcggctac atctaccccg gccagggcgg caccaactac    180
aaccagaagt tccagggcag agccacccctg accgccgata agcgccag caccgcctac     240 atggaactga gcagcctgcg gagcgaggat accgccgtgt acttctgtgc cagaacaggc    300
ggcctgaggc gggcctactt tacctattgg ggccagggca cctcgtgac cgtgtctagc     360 gctagcacaa agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggga    720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tatgttgacg gcgtggaggt gcataatgcc aagacaaagc cgcgggagga gcagtacaac    900
aatgcctccc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatg ccgggatgag   1080
ctgaccaaga atcaagtcag cctgtggtgc ctggtaaaag gcttctatcc cagcgacatc   1140
gccgtggagt gggagagcaa tgggcagccg gagaacaact acaagaccac gcctcccgtg   1200
```

```
ctggactccg acggctcctt cttcctctac tcaaaactca ccgtggacaa gagcaggtgg   1260
cagcagggga acgtcttctc atgctccgtg atgcatgagg ctctgcacaa ccactacacg   1320
cagaagagcc tctccctgtc tccgggt                                       1347

<210> SEQ ID NO 80
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 80
caggtgcagc tggtggaaag cggcggaggc gtggtgcagc ctggcaggtc tctgagactg    60
agctgtgccg ccagcggctt caccttcagc agctacggaa tgcactgggt gcgccaggcc   120
cctggcaaag gactggaatg ggtggccgtg atttggtacg acggcagcaa caagtactac   180
gccgacagcg tgaagggccg gttccacatc agcggcgaca acagcaagaa caccctgtac   240
ctgcagatga acagcctgcg ggccgaggac accgccgtgt actactgcgc cagaatgttc   300
agaggcgcct tcgactactg gggccagggc acactcgtga ccgtgtctag tgcgtcgacc   360
aagggcccat cggtgttccc tctggcccct gcagcagaa gcaccagcga atctacagcc   420
gccctgggct gcctcgtgaa ggactacttt cccgagcccg tgaccgtgtc ctggaactct   480
ggcgctctga caagcggcgt gcacaccttt ccagccgtgc tccagagcag cggcctgtac   540
tctctgagca gcgtcgtgac agtgccagca gcagcctgg gcaccaagac ctacacctgt   600
aacgtggacc acaagcccag caacaccaag gtggacaagc gggtggaatc taagtacggc   660
cctccctgcc ctccttgccc agcccctgaa gctgccggcg gaccctccgt gttcctgttc   720
cccccaaagc ccaaggacac cctgatgatc agccggaccc ccgaagtgac ctgcgtggtg   780
gtggatgtgt cccaggaaga tcccgaggtg cagttcaatt ggtacgtgga cggcgtggaa   840
gtgcacaacg ccaagaccaa gcccagagag gaacagttca acagcaccta ccgggtggtg   900
tccgtgctga ccgtgctgca ccaggactgg ctgaacggca agagtacaa gtgcaaggtg   960 tccaacaagg gcctgcccag ctccatcgag aaaaccatca gcaaggccaa gggccagccc  1020
cgcgagcctc aagtgtatac cctgccccct tgccaggaag atgaccaa gaaccaggtg   1080 tccctgtggt gtctcgtgaa aggcttctac cccagcgaca ttgccgtgga atgggagagc  1140
aacggccagc ccgagaacaa ctacaagacc acccccctg tgctggacag cgacggctca  1200
ttcttcctgt actccaagct gaccgtggac aagagccggt ggcaggaagg caacgtgttc   1260
agctgctccg tgatgcacga ggccctgcac aaccactaca cccagaagtc cctgtctctg  1320
tccctgggc                                                          1329

<210> SEQ ID NO 81
<211> LENGTH: 642
<212> TYPE: DNA
<213> ORGANISM: Artificial Sequence
<220> FEATURE:
<223> OTHER INFORMATION: Synthetic Construct

<400> SEQUENCE: 81
gccatccaga tgacccagag ccccagcagc ctgtctgcca gcgtgggcga cagagtgacc    60
atcacctgta gagccagcca gggcatccgg aacgacctgg ctggtatca gcagaagcct   120 ggcaaggccc ccaagctgct gatctacgcc gctagctctc tgcagtccgg cgtgcccagc   180
```

| | |
|---|---|
| agattttctg gcagcggctc cggcaccgac ttcaccctga caatctctgg cctgcagccc | 240 |
| gaggacagcg ccacctacta ctgtctgcaa gactacatct actacccac cttcggccag | 300 |
| ggcaccaagg tggaaatcaa gcgtacggtg ccgctccca gcgtgttcat cttcccacct | 360 |
| agcgacgagc agctgaagtc cggcacagcc tctgtcgtgt gcctgctgaa caacttctac | 420 |
| ccccgcgagg ccaaagtgca gtggaaggtg gacaacgccc tgcagagcgg caacagccag | 480 |
| gaaagcgtga ccgagcagga cagcaaggac tccacctaca gcctgagcag caccctgaca | 540 |
| ctgagcaagg ccgactacga aagcacaag gtgtacgcct gcgaagtgac ccaccagggc | 600 |
| ctgtctagcc ccgtgaccaa gagcttcaac cggggcgagt gt | 642 |

<210> SEQ ID NO 82
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 82

| | |
|---|---|
| caggtgcagc tggtggaaag cggcggaggc gtggtgcagc ctggcaggtc tctgagactg | 60 |
| agctgtgccg ccagcggctt caccttcagc agctacggaa tgcactgggt gcgccaggcc | 120 |
| cctggcaaag gactggaatg ggtggccgtg atttggtacg acggcagcaa caagtactac | 180 |
| gccgacagcg tgaagggccg gttcaccatc agcggcgaca cagcaagaa caccctgtac | 240 |
| ctgcagatga acagcctgcg ggccgaggac accgccgtgt actactgcgc cagaatgttc | 300 |
| agaggcgcct tcgactactg gggccaggc acactcgtga ccgtgtctag tgcgtcgacc | 360 |
| aagggcccca gcgtgttccc tctggcccct agcagcaaga gcacatctgg cggaacagcc | 420 |
| gccctgggct gcctcgtgaa ggactacttt cccgagcccg tgaccgtgtc ctggaattct | 480 |
| ggcgccctga ccagcggcgt gcacaccttt ccagctgtgc tgcagtccag cggcctgtac | 540 |
| agcctgagca gcgtcgtgac agtgcccagc agctctctgg caccagac ctacatctgc | 600 |
| aacgtgaacc acaagcccag caacaccaag gtggacaaga aggtggaacc caagagctgc | 660 |
| gacaagaccc acacctgtcc cccttgtcct gccccgaag ccgccggagg ccttccgtg | 720 |
| ttcctgttcc ccccaaagcc caaggacacc ctgatgatca gccggacccc cgaagtgacc | 780 |
| tgcgtggtgg tggatgtgtc ccacgaggac cctgaagtga agttcaattg gtacgtggac | 840 |
| ggcgtggaag tgcacaacgc caagaccaag ccaagagagg aacagtacaa cagcacctac | 900 |
| cgggtggtgt ccgtgctgac cgtgctgcac caggactggc tgaacggcaa agagtacaag | 960 |
| tgcaaggtgt ccaacaaggc cctggccgcc cccatcgaga aaaccatcag caaggccaag | 1020 |
| ggccagcccc gcgaaccca ggtgtacaca ctgcccccat gcaggacga gctgaccaag | 1080 |
| aaccaggtgt ccctgtggtg tctggtgaaa ggcttctacc cctccgatat cgccgtggaa | 1140 |
| tgggagagca acggccagcc cgagaacaac tacaagacca ccccccctgt gctggacagc | 1200 |
| gacggctcat tcttcctgta ctccaagctg acagtggaca agtccggtg gcagcaggc | 1260 |
| aacgtgttca gctgctccgt gatgcacgag gccctgcaca accactacac ccagaagtcc | 1320 |
| ctgagcctga gccccggc | 1338 |

<210> SEQ ID NO 83
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 83

```
caggtgcagc tggtggaaag cggcggaggc gtggtgcagc ctggcaggtc tctgagactg      60
agctgtgccg ccagcggctt caccttcagc agctacggaa tgcactgggt gcgccaggcc     120
cctggcaaag actggaatgg ggtggccgtg atttggtacg acggcagcaa caagtactac     180
gccgacagcg tgaagggccg gttcaccatc agcggcgaca acagcaagaa caccctgtac     240
ctgcagatga acagcctgcg ggccgaggac accgccgtgt actactgcgc cagaatgttc     300
agaggcgcct tcgactactg gggccagggc acactcgtga ccgtgtctag tgcgtcgacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtatgttgac     840
ggcgtggagg tgcataatgc caagacaaag ccgcgggagg agcagtacaa caatgcctcc     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat gccgggatga gctgaccaag    1080
aatcaagtca gcctgtggtg cctggtaaaa ggcttctatc ccagcgacat cgccgtggag    1140
tgggagagca atgggcagcc ggagaacaac tacaagacca cgcctcccgt gctggactcc    1200
gacggctcct tcttcctcta ctcaaaactc accgtggaca gagcaggtg gcagcagggg    1260
aacgtcttct catgctccgt gatgcatgag gctctgcaca accactacac gcagaagagc    1320
ctctccctgt ctccgggt                                                   1338
```

<210> SEQ ID NO 84
<211> LENGTH: 121
<212> TYPE: PRT
<213> ORGANISM: Artificial Sequence
<220> FEATURE:
<223> OTHER INFORMATION: Synthetic Construct

<400> SEQUENCE: 84

```
Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Ala Leu Ser Pro Phe Asp Tyr Trp Gly
            100                 105                 110
```

```
Gln Gly Thr Leu Val Thr Val Ser Ser
        115                 120
```

<210> SEQ ID NO 85
<211> LENGTH: 112
<212> TYPE: PRT
<213> ORGANISM: Artificial Sequence
<220> FEATURE:
<223> OTHER INFORMATION: Synthetic Construct

<400> SEQUENCE: 85

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gly Gly Thr Lys Val Glu Ile Lys
            100                 105                 110
```

<210> SEQ ID NO 86
<211> LENGTH: 25
<212> TYPE: PRT
<213> ORGANISM: Artificial Sequence
<220> FEATURE:
<223> OTHER INFORMATION: Synthetic Construct

<400> SEQUENCE: 86

```
Gln Val Gln Leu Val Gln Ser Gly Ala Glu Val Val Lys Pro Gly Ala
1               5                   10                  15

Ser Val Lys Val Ser Cys Lys Ala Ser
            20                  25
```

<210> SEQ ID NO 87
<211> LENGTH: 25
<212> TYPE: PRT
<213> ORGANISM: Artificial Sequence
<220> FEATURE:
<223> OTHER INFORMATION: Synthetic Construct

<400> SEQUENCE: 87

```
Gln Val Gln Leu Val Gln Ser Gly Ala Glu Val Val Lys Ser Gly Ala
1               5                   10                  15

Ser Val Lys Val Ser Cys Lys Ala Ser
            20                  25
```

<210> SEQ ID NO 88
<211> LENGTH: 25
<212> TYPE: PRT
<213> ORGANISM: Artificial Sequence
<220> FEATURE:
<223> OTHER INFORMATION: Synthetic Construct

<400> SEQUENCE: 88

```
Gln Val Gln Leu Val Gln Ser Gly Ala Glu Val Val Lys Pro Gly Ala
1               5                   10                  15
```

Ser Val Lys Met Ser Cys Lys Ala Ser
            20                  25

<210> SEQ ID NO 89
<211> LENGTH: 25
<212> TYPE: PRT
<213> ORGANISM: Artificial Sequence
<220> FEATURE:
<223> OTHER INFORMATION: Synthetic Construct

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 90
<211> LENGTH: 17
<212> TYPE: PRT
<213> ORGANISM: Artificial Sequence
<220> FEATURE:
<223> OTHER INFORMATION: Synthetic Construct

<400> SEQUENCE: 90

Met His Trp Val Lys Glu Ala Pro Gly Gln Arg Leu Glu Trp Ile Gly
1               5                   10                  15

Tyr

<210> SEQ ID NO 91
<211> LENGTH: 17
<212> TYPE: PRT
<213> ORGANISM: Artificial Sequence
<220> FEATURE:
<223> OTHER INFORMATION: Synthetic Construct

<400> SEQUENCE: 91

Met His Trp Val Lys Glu Ala Pro Gly Gln Gly Leu Glu Trp Ile Gly
1               5                   10                  15

Tyr

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct

<400> SEQUENCE: 92

Met His Trp Val Arg Gln Ala Pro Gly Lys Gly Leu Glu Trp Val Ala
1               5                   10                  15

Val

<210> SEQ ID NO 93
<211> LENGTH: 38
<212> TYPE: PRT
<213> ORGANISM: Artificial Sequence
<220> FEATURE:
<223> OTHER INFORMATION: Synthetic Construct

<400> SEQUENCE: 93

Asn Tyr Asn Gln Lys Phe Gln Gly Arg Ala Thr Leu Thr Ala Asp Thr
1               5                   10                  15

Ser Ala Ser Thr Ala Tyr Met Glu Leu Ser Ser Leu Arg Ser Glu Asp

Thr Ala Val Tyr Phe Cys
        35

<210> SEQ ID NO 94
<211> LENGTH: 38
<212> TYPE: PRT
<213> ORGANISM: Artificial Sequence
<220> FEATURE:
<223> OTHER INFORMATION: Synthetic Construct

<400> SEQUENCE: 94

Asn Tyr Asn Gln Lys Phe Gln Gly Arg Ala Thr Leu Thr Ala Asp Thr
1               5                   10                  15

Ser Ala Ser Thr Ala Tyr Met Glu Ile Ser Ser Leu Arg Ser Glu Asp
            20                  25                  30

Thr Ala Val Tyr Phe Cys
        35

<210> SEQ ID NO 95
<211> LENGTH: 38
<212> TYPE: PRT
<213> ORGANISM: Artificial Sequence
<220> FEATURE:
<223> OTHER INFORMATION: Synthetic Construct

<400> SEQUENCE: 95

Tyr Tyr Ala Asp Ser Val Lys Gly Arg Phe Thr Ile Ser Gly Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 96
<211> LENGTH: 11
<212> TYPE: PRT
<213> ORGANISM: Artificial Sequence
<220> FEATURE:
<223> OTHER INFORMATION: Synthetic Construct

<400> SEQUENCE: 96

Trp Gly Gln Gly Thr Leu Val Thr Val Ser Ser
1               5                   10

<210> SEQ ID NO 97
<211> LENGTH: 26
<212> TYPE: PRT
<213> ORGANISM: Artificial Sequence
<220> FEATURE:
<223> OTHER INFORMATION: Synthetic Construct

<400> SEQUENCE: 97

Asp Ile Val Leu Thr Gln Ser Pro Ala Thr Leu Ser Leu Ser Pro Gly
1               5                   10                  15

Glu Arg Ala Thr Ile Ser Cys Arg Ala Ser
            20                  25

<210> SEQ ID NO 98
<211> LENGTH: 26
<212> TYPE: PRT
<213> ORGANISM: Artificial Sequence
<220> FEATURE:
<223> OTHER INFORMATION: Synthetic Construct

<400> SEQUENCE: 98

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 99
<211> LENGTH: 17
<212> TYPE: PRT
<213> ORGANISM: Artificial Sequence
<220> FEATURE:
<223> OTHER INFORMATION: Synthetic Construct

<400> SEQUENCE: 99

Met His Trp Tyr Gln Gln Lys Pro Gly Gln Pro Pro Arg Leu Leu Ile
1               5                   10                  15

Tyr

<210> SEQ ID NO 100
<211> LENGTH: 16
<212> TYPE: PRT
<213> ORGANISM: Artificial Sequence
<220> FEATURE:
<223> OTHER INFORMATION: Synthetic Construct

<400> SEQUENCE: 100

Gly Trp Tyr Gln Gln Lys Pro Gly Lys Ala Pro Lys Leu Leu Ile Tyr
1               5                   10                  15

<210> SEQ ID NO 101
<211> LENGTH: 36
<212> TYPE: PRT
<213> ORGANISM: Artificial Sequence
<220> FEATURE:
<223> OTHER INFORMATION: Synthetic Construct

<400> SEQUENCE: 101

Ser Arg Ala Thr Gly Ile Pro Ala Arg Phe Ser Gly Ser Gly Ser Gly
1               5                   10                  15

Thr Asp Phe Thr Leu Thr Ile Ser Pro Leu Glu Pro Glu Asp Phe Ala
            20                  25                  30

Val Tyr Tyr Cys
        35

<210> SEQ ID NO 102
<211> LENGTH: 36
<212> TYPE: PRT
<213> ORGANISM: Artificial Sequence
<220> FEATURE:
<223> OTHER INFORMATION: Synthetic Construct

<400> SEQUENCE: 102

Ser Leu Gln Ser Gly Val Pro Ser Arg Phe Ser Gly Ser Gly Ser Gly
1               5                   10                  15

Thr Asp Phe Thr Leu Thr Ile Ser Gly Leu Gln Pro Glu Asp Ser Ala
            20                  25                  30

Thr Tyr Tyr Cys
        35

<210> SEQ ID NO 103
<211> LENGTH: 10
<212> TYPE: PRT

```
<213> ORGANISM: Artificial Sequence
<220> FEATURE:
<223> OTHER INFORMATION: Synthetic Construct

<400> SEQUENCE: 103

Phe Gly Gly Gly Thr Lys Leu Glu Ile Lys
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Construct

<400> SEQUENCE: 104

Trp Gly Gln Gly Thr Leu Val Thr Val Ser Ser
1               5                   10

<210> SEQ ID NO 105
<211> LENGTH: 159
<212> TYPE: PRT
<213> ORGANISM: Artificial Sequence
<220> FEATURE:
<223> OTHER INFORMATION: Synthetic Construct

<400> SEQUENCE: 105

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asn Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Asn Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg His Phe Trp Glu Cys Gly Ser Pro
145                 150                 155

<210> SEQ ID NO 106
<211> LENGTH: 214
<212> TYPE: PRT
<213> ORGANISM: Artificial Sequence
<220> FEATURE:
<223> OTHER INFORMATION: Synthetic Construct

<400> SEQUENCE: 106

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
```

```
                35                  40                  45
Tyr Ser Ala Ser Tyr Arg Tyr Ile Gly Val Pro Asp Arg Phe Thr Gly
 50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 107
<211> LENGTH: 450
<212> TYPE: PRT
<213> ORGANISM: Artificial Sequence
<220> FEATURE:
<223> OTHER INFORMATION: Synthetic Construct

<400> SEQUENCE: 107

Gln Val Gln Leu Val Gln Ser Gly Ala Glu Val Ala Lys Pro Gly Thr
 1               5                  10                  15

Ser Val Lys Leu Ser Cys Lys Ala Ser Gly Tyr Thr Phe Thr Asp Tyr
                 20                  25                  30

Trp Met Gln Trp Val Lys Gln Arg Pro Gly Gln Gly Leu Glu Trp Ile
             35                  40                  45

Gly Thr Ile Tyr Pro Gly Asp Gly Asp Thr Gly Tyr Ala Gln Lys Phe
 50                  55                  60

Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180             185              190
        Ser Ser Leu Gly Thr Gln Thr Tyr Ile Cys Asn Val Asn His Lys
            195                 200             205

Pro Ser Asn Thr Lys Val Asp Lys Val Glu Pro Lys Ser Cys Asp
            210                 215             220

Lys Thr His Thr Cys Pro Cys Pro Ala Pro Glu Leu Leu Gly Gly
        225                 230             235                 240

Pro Ser Val Phe Leu Phe Pro Pro Lys Pro Lys Asp Thr Leu Met Ile
                        245             250                 255

Ser Arg Thr Pro Glu Val Thr Cys Val Val Val Asp Val Ser His Glu
                        260             265             270

Asp Pro Glu Val Lys Phe Asn Trp Tyr Val Asp Gly Val Glu Val His
                        275             280             285

Asn Ala Lys Thr Lys Pro Arg Glu Glu Gln Tyr Asn Ser Thr Tyr Arg
                        290             295             300

Val Val Ser Val Leu Thr Val Leu His Gln Asp Trp Leu Asn Gly Lys
        305                 310             315                 320

Glu Tyr Lys Cys Lys Val Ser Asn Lys Ala Leu Pro Ala Pro Ile Glu
                            325             330             335

Lys Thr Ile Ser Lys Ala Lys Gly Gln Pro Arg Glu Pro Gln Val Tyr
                        340             345             350

Thr Leu Pro Pro Ser Arg Asp Glu Leu Thr Lys Asn Gln Val Ser Leu
                        355             360             365

Thr Cys Leu Val Lys Gly Phe Tyr Pro Ser Asp Ile Ala Val Glu Trp
                370             375             380

Glu Ser Asn Gly Gln Pro Glu Asn Asn Tyr Lys Thr Thr Pro Pro Val
        385                 390             395                 400

Leu Asp Ser Asp Gly Ser Phe Phe Leu Tyr Ser Lys Leu Thr Val Asp
                            405             410             415

Lys Ser Arg Trp Gln Gln Gly Asn Val Phe Ser Cys Ser Val Met His
                        420             425             430

Glu Ala Leu His Asn His Tyr Thr Gln Lys Ser Leu Ser Leu Ser Pro
                        435             440             445

Gly Lys
            450

<210> SEQ ID NO 108
<211> LENGTH: 8
<212> TYPE: PRT
<213> ORGANISM: Artificial Sequence
<220> FEATURE:
<223> OTHER INFORMATION: Synthetic Construct

<400> SEQUENCE: 108

Gly Tyr Thr Phe Thr Ser Tyr Tyr
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Ile Tyr Pro Gly Asn Val Asn Thr
1               5
```

```
<210> SEQ ID NO 110
<211> LENGTH: 13
<212> TYPE: PRT
<213> ORGANISM: Artificial Sequence
<220> FEATURE:
<223> OTHER INFORMATION: Synthetic Construct

<400> SEQUENCE: 110

Thr Arg Ser His Tyr Gly Leu Asp Trp Asn Phe Asp Val
1               5                   10

<210> SEQ ID NO 111
<211> LENGTH: 6
<212> TYPE: PRT
<213> ORGANISM: Artificial Sequence
<220> FEATURE:
<223> OTHER INFORMATION: Synthetic Construct

<400> SEQUENCE: 111

Gln Asn Ile Tyr Val Trp
1               5

<210> SEQ ID NO 112
<211> LENGTH: 3
<212> TYPE: PRT
<213> ORGANISM: Artificial Sequence
<220> FEATURE:
<223> OTHER INFORMATION: Synthetic Construct

<400> SEQUENCE: 112

Lys Ala Ser
1

<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113

Gln Gln Gly Gln Thr Tyr Pro Tyr
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic Construct

<400> SEQUENCE: 114

Gly Phe Ser Leu Ser Asp Tyr Gly
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic Construct

<400> SEQUENCE: 115

Ile Trp Ala Gly Gly Gly Thr
1               5
```

```
<210> SEQ ID NO 116
<211> LENGTH: 14
<212> TYPE: PRT
<213> ORGANISM: Artificial Sequence
<220> FEATURE:
<223> OTHER INFORMATION: Synthetic Construct

<400> SEQUENCE: 116

Ala Arg Asp Lys Gly Tyr Ser Tyr Tyr Tyr Ser Met Asp Tyr
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Glu Ser Val Glu Tyr Tyr Val Thr Ser Leu
1               5                   10

<210> SEQ ID NO 118
<211> LENGTH: 3
<212> TYPE: PRT
<213> ORGANISM: Artificial Sequence
<220> FEATURE:
<223> OTHER INFORMATION: Synthetic Construct

<400> SEQUENCE: 118

Ala Ala Ser
1

<210> SEQ ID NO 119
<211> LENGTH: 9
<212> TYPE: PRT
<213> ORGANISM: Artificial Sequence
<220> FEATURE:
<223> OTHER INFORMATION: Synthetic Construct

<400> SEQUENCE: 119

Gln Gln Ser Arg Lys Val Pro Tyr Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic Construct

<400> SEQUENCE: 120

Gly Phe Thr Phe Thr Lys Ala Trp
1               5

<210> SEQ ID NO 121
<211> LENGTH: 10
<212> TYPE: PRT
<213> ORGANISM: Artificial Sequence
<220> FEATURE:
<223> OTHER INFORMATION: Synthetic Construct

<400> SEQUENCE: 121

Ile Lys Asp Lys Ser Asn Ser Tyr Ala Thr
1               5                   10

<210> SEQ ID NO 122
```

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 122

Arg Gly Val Tyr Tyr Ala Leu Ser Pro Phe Asp Tyr
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic Construct

<400> SEQUENCE: 123

Gln Ser Leu Val His Asn Asn Ala Asn Thr Tyr
1               5                   10

<210> SEQ ID NO 124
<211> LENGTH: 3
<212> TYPE: PRT
<213> ORGANISM: Artificial Sequence
<220> FEATURE:
<223> OTHER INFORMATION: Synthetic Construct

<400> SEQUENCE: 124

Lys Val Ser
1

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gly Gln Gly Thr Gln Tyr Pro Phe Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 126

Gly Phe Thr Phe Thr Lys Ala Trp
1               5

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct

<400> SEQUENCE: 127

Ile Lys Asp Lys Ser Asn Ser Tyr Ala Thr
1               5                   10

<210> SEQ ID NO 128
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 128

Gly Val Tyr Tyr Ala Leu Ser Pro Phe Asp Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic Construct

<400> SEQUENCE: 129

Gln Ser Leu Val His Asn Asn Gly Asn Thr Tyr
1               5                   10

<210> SEQ ID NO 130
<211> LENGTH: 3
<212> TYPE: PRT
<213> ORGANISM: Artificial Sequence
<220> FEATURE:
<223> OTHER INFORMATION: Synthetic Construct

<400> SEQUENCE: 130

Lys Val Ser
1

<210> SEQ ID NO 131
<211> LENGTH: 9
<212> TYPE: PRT
<213> ORGANISM: Artificial Sequence
<220> FEATURE:
<223> OTHER INFORMATION: Synthetic Construct

<400> SEQUENCE: 131

Gly Gln Gly Thr Gln Tyr Pro Phe Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic Construct

<400> SEQUENCE: 132

Gln Ser Val Ser Ser Tyr Gly Gln Gly
1               5
```